US010201604B2

(12) United States Patent
Gelb, Jr. et al.

(10) Patent No.: US 10,201,604 B2
(45) Date of Patent: Feb. 12, 2019

(54) LIVE ATTENUATED INFECTIOUS LARYNGOTRACHEITIS VIRUS (ILTV) VACCINES AND PREPARATION THEREOF

(71) Applicants: UNIVERSITY OF DELAWARE, Newark, DE (US); Jack Gelb, Jr., Landenberg, PA (US); Brian S. Ladman, Landenberg, PA (US); Miguel Ruano, Newark, DE (US)

(72) Inventors: Jack Gelb, Jr., Landenberg, PA (US); Brian S. Ladman, Landenberg, PA (US); Miguel Ruano, Newark, DE (US)

(73) Assignee: UNIVERSITY OF DELAWARE, Newark, DE (US)

( * ) Notice: Subject to any disclaimer, the term of this patent is extended or adjusted under 35 U.S.C. 154(b) by 0 days.

(21) Appl. No.: 15/032,338

(22) PCT Filed: Oct. 29, 2014

(86) PCT No.: PCT/US2014/062823
§ 371 (c)(1),
(2) Date: Apr. 27, 2016

(87) PCT Pub. No.: WO2015/066130
PCT Pub. Date: May 7, 2015

(65) Prior Publication Data
US 2016/0263210 A1 Sep. 15, 2016

Related U.S. Application Data

(60) Provisional application No. 61/896,729, filed on Oct. 29, 2013.

(51) Int. Cl.
| | |
|---|---|
| *A61K 39/245* | (2006.01) |
| *C12N 7/00* | (2006.01) |
| *A61K 39/12* | (2006.01) |
| *A61K 39/00* | (2006.01) |

(52) U.S. Cl.
CPC .......... *A61K 39/245* (2013.01); *A61K 39/12* (2013.01); *C12N 7/00* (2013.01); *A61K 2039/5254* (2013.01); *A61K 2039/552* (2013.01); *C12N 2710/16034* (2013.01); *C12N 2710/16064* (2013.01); *C12N 2710/16334* (2013.01); *C12N 2710/16362* (2013.01); *C12N 2710/16364* (2013.01)

(58) Field of Classification Search
None
See application file for complete search history.

(56) References Cited

U.S. PATENT DOCUMENTS

| | | | | |
|---|---|---|---|---|
| 3,331,736 A | * | 7/1967 | Gelenczei | ............ A61K 39/245 424/229.1 |
| 4,867,975 A | * | 9/1989 | Gelb, Jr. | .............. A61K 39/215 424/222.1 |
| 5,250,298 A | | 10/1993 | Gelb, Jr. | |

FOREIGN PATENT DOCUMENTS

WO    WO 2012/018813 A2    2/2012

OTHER PUBLICATIONS

Garcia et al., "Genomic sequence analysis of the United States infectious laryngotracheitis vaccine strains checking embryo origin (CEO) and tissue culture origin (TCO)" Mar. 26, 2013 *Virology*, 440(1):64-74.
National Center for Biotechnology Information, GenBank Accession No. JN580312.1, "Gallid herpesvirus 1 strain TCO IVAX, complete genome," [online]. Bethesda, MD [retrieved on Jan. 16, 2015]. Retrieved from the Internet <http://www.ncbi.nlm.nih.gov/nuccore/390987536/>; 240 pages.
[Korea] PCT Application No. PCT/US2014/062823, filed Oct. 29, 2014; [International Search Report / Written Opinion] dated Feb. 16, 2015; 16 pages.
Mahmoudian et al., "Kinetics of transportation of infectious laryngotracheitis virus genes" 2011 *Comparative Immunology, Microbiology and Infectious Diseases*, 35(2):103-115.
Majid et al., "Differentiation of field isolates and vaccine strains of infectious laryngotracheitis virus by DNA sequencing" Oct. 30, 2011 *African Journal of Microbiology Research*, 5(24):4112-17.
Office of Economic Innovation & Partnerships, University of Delware "Improved Laryngotracheitis Vaccine for Avian Species (UD14-01)" Sep. 2, 2014 *Agriculture/Earth, Ocean and Environment*, <http://sites.udel.edu/techtransfer/2014/09/02/improved-laryngotracheitis-viacine-for-avian-species-ud14-01/.>.
Ou et al., "Infectious laryngotracheitis virus in chickens" Oct. 12, 2012 *World of Journal Virology*, 1(5):142-49.
[WIPO] ] PCT Application No. PCT/US2014/062823, filed Oct. 29, 2014; [International Preliminary Report on Patentability] dated May 3, 2016; 9 pages.

* cited by examiner

*Primary Examiner* — Stacy B Chen
(74) *Attorney, Agent, or Firm* — Mueting, Raasch & Gebhardt, P.A.

(57) ABSTRACT

This disclosure describes a modified live infectious laryngotracheitis virus (ILTV) developed from a strain of ILTV grown at a reduced incubation temperature, vaccines that include the modified live ILTV, methods for producing the live modified ILTV, and methods that include administering the modified ILTV to a subject.

4 Claims, 1 Drawing Sheet
Specification includes a Sequence Listing.

LIVE ATTENUATED INFECTIOUS LARYNGOTRACHEITIS VIRUS (ILTV) VACCINES AND PREPARATION THEREOF

CROSS-REFERENCE TO RELATED APPLICATION

This application is the § 371 U.S. National Stage of International Application No. PCT/US2014/062823, filed 29 Oct. 2014, which claims priority to U.S. Provisional Patent Application No. 61/896,729, filed Oct. 29, 2013, each of which is incorporated herein by reference.

GOVERNMENT FUNDING

This invention was made with government support under 2013-31100-0610 awarded by the U.S. Department of Agriculture. The government has certain rights in the invention.

SEQUENCE LISTING

This application contains a Sequence Listing electronically submitted to the United States Patent and Trademark Office via EFS-Web as an ASCII text file entitled "458-00060201_SequenceListing_ST25.txt" having a size of 272 KB and created on Oct. 29, 2014. Due to the electronic filing of the Sequence Listing, the electronically submitted Sequence Listing serves as both the paper copy required by 37 CFR § 1.821(c) and the CRF required by § 1.821(e). The information contained in the Sequence Listing is incorporated by reference herein.

SUMMARY

This disclosure describes, in one aspect a modified live infectious laryngotracheitis virus (ILTV) developed from a strain of ILTV grown at a reduced incubation temperature. The ILTV strain may be of tissue culture origin (TCO) or chick embryo origin (CEO). In particular embodiments, the strain of ILTV can be tissue culture origin (TCO). The modified live strain is serially passaged at a temperature in the range of 28° C. to 31° C., which is lower than the typical growth temperature (37° C.) for producing ILTV, for about 30-50 passages through a suitable culture medium. In some embodiments, the modified strain is generated by serially passaging at a temperature of 30° C. In some embodiments, the strain is produced through 34-44 serial passages. In some embodiments, the culture medium may be chicken embryos or cell culture. In some of these embodiments, the culture medium is cell culture.

In some embodiments, the attenuated ILTV can possess at least one genetic modification compared to the starting ILTV and/or a wild-type ILTV. In some embodiments, the genetic modification can include deletion of a thymine in the coding region for UL50. Such a deletion can result in a frame shift at Asn10 of UL50.

In another aspect, this disclosure describes a vaccine for poultry. The vaccine includes an effective amount of a modified live ILTV. The vaccine may further include a pharmaceutically acceptable diluent, carrier, and/or adjuvant. The vaccine may be useful for immunizing poultry. In some embodiments, the poultry can include a chicken. The vaccine may be formulated for administering to poultry by any suitable route. In some embodiments, the vaccine may be administered via an oral, an ocular (eye drop), an intranasal, an aerosol (spray), or an ingestion (drinking water) route. In particular embodiments, the vaccine may be administered via an aerosol (spray) or drinking water administration, which can be more cost effective for commercial poultry production than other routes of administration. In some embodiments, oral administration of the modified live ILTV to a subject produces increased weight gain and/or decreased sign of infectious laryngotracheitis disease following challenge with a virulent ILTV, compared with an unvaccinated control subject.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

DETAILED DESCRIPTION OF ILLUSTRATIVE EMBODIMENTS

Figure 1A:
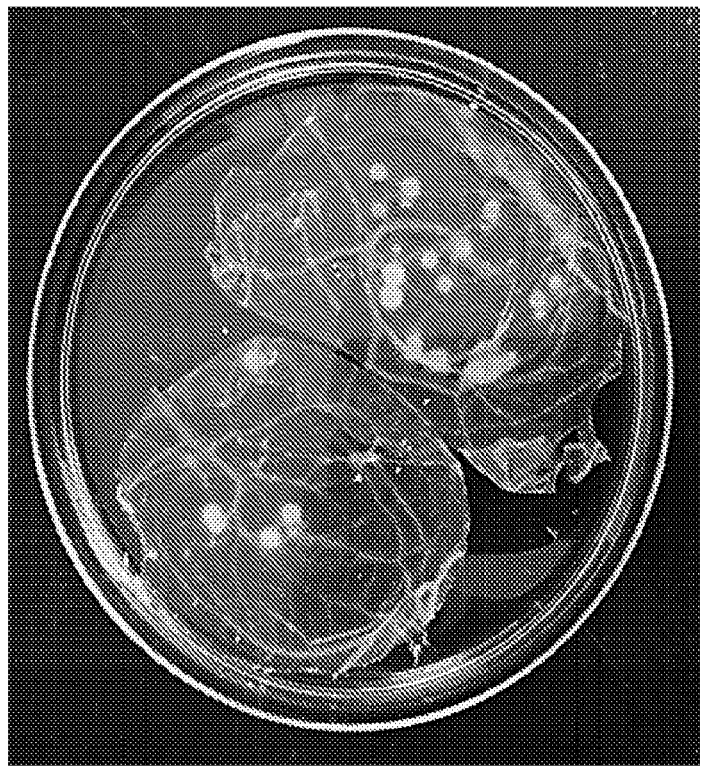
FIG. 1. ILTV lesions, also referred to as plaques or pocks, on the chorioallantoic membrane (CAM) of the embryonating chicken egg at five days following inoculation. (A) Appearance of unique ILTV lesions on the CAM following inoculation with clone 5-7. Note the small well defined plaques. (B) Appearance of a typical ILTV plaque on the CAM. Note diffuse spreading lesion following inoculation with experimental vaccine P32 37C.
Figure 1B:
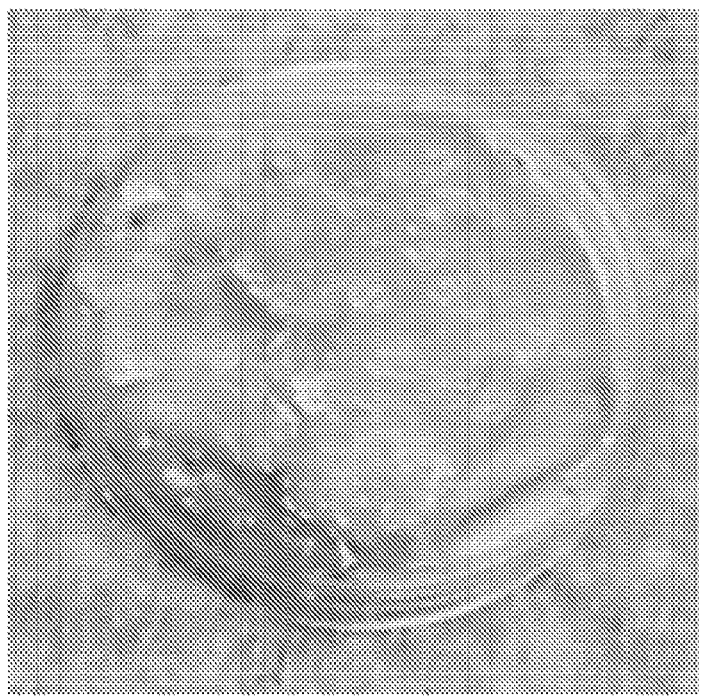

The disclosure relates to live attenuated infectious laryngotracheitis viruses (ILTVs) and the use of the live attenuated ILTVs as vaccines for poultry. Poultry such as, for example, broiler chickens, vaccinated with the vaccine may have a lower incidence of clinical disease signs and/or increased growth (as measured, for example, by greater weight gain), than poultry vaccinated with chick embryo origin (CEO) vaccines. Also, poultry vaccinated using the methods and vaccines described herein can have improved weight gain compared an unvaccinated poultry after being challenged with a virulent challenge strain of ILTV.

Modified live vaccines of two types have been available for many years to control infectious laryngotracheitis (ILT): vaccines of chick embryo origin (CEO) and vaccines of tissue culture origin (TCO). The CEO products often exhibit negative side effects such as, for example, causing disease, reducing growth rates (exhibited as reduce weight gain), and reducing feed efficiency. Because of the side effect produced by the CEO vaccines, poultry producers may prefer not to use them unless it becomes absolutely necessary to do so. Thus, many flocks go unvaccinated and are susceptible to the disease.

There are limited options for commercially available TCO vaccines. A TCO product is typically milder than a CEO vaccine, but is typically administered via the ocular route. This severely limits its practical commercial use by poultry producers because the vaccine must be instilled into the conjunctiva of each individual bird of a flock. This "eye drop" application can be laborious and expensive. Thus, poultry producers disfavor the process and, consequently, TCO vaccines.

More recently, a third type of vaccine, a recombinant ILTV vaccine, has been commercialized. A recombinant ILTV product can express one or more immunogenic proteins, but not the complete virus, and thus fail to produce side effects associated with CEO vaccines. A disadvantage of recombinant vaccines, however, is that they can be expensive to purchase compared to live vaccines, and are only partially effective. If a safer and effective live vaccine could be developed, the cost of vaccine production would dramatically reduce costs to control ILT.

The new vaccine described herein can replace the use of existing modified live and recombinant vaccines. For example, in commercial use with broiler chicken production, a vaccine prepared with the live attenuated ILTV described herein can offer a cheaper alternative to recombinant vaccines and be safer than current modified live vaccines. As another example, in commercial production of breeder chickens and/or layer chickens, the live attenuated ILTV described herein can be a component of a primary vaccine could be used for primary vaccination, which can be followed with one or more booster vaccinations using, for example, currently available CEO vaccines.

In one embodiment, a commercially available vaccine referred to as a tissue culture origin (TCO) vaccine (LT-IVAX, Merck Animal Health, Summit, N.J.), was serially passaged up to approximately 40 times in successive cultures of chicken kidney cells (CKC) in cell culture maintained at 30° C., an incubation temperature lower than the typical culture temperature used to grow ILTV (37° C.). The virus was then cloned in CKC culture at 30° C. by limiting dilution to obtain a more homogeneous virus population than is typically produced without limiting dilution. The more homogeneous virus population can produce more consistent vaccine characteristics when administered to poultry.

Most poultry vaccines are grown at 37° C. As just discussed above, the ILTV described herein (P32 30C) was produced serially passaging the virus in culture at a temperature of 30° C. A corresponding ILTV (P32 37C) was prepared similarly to the P32 30C ILTV except that it was generated by serially passaging the virus in a culture maintained at 37° C. The resulting experimental vaccines were tested in chickens and found to be safe and efficacious by the ocular/eye drop and oral routes of administration.

TABLE 1

Post-vaccination assessment of ILTV commercial and experimental vaccines in two-week-old broiler chickens vaccinated by the ocular or oral routes.

| Group | Treatment | Weight Gain From 1-6 Days Post Vaccination As a % of Non-Vacc. Weight Gain | Clinical Disease Signs Associated With Vaccination |
|---|---|---|---|
| | Combined Bodyweight & Clinical Disease Signs Data Following Ocular or Oral Vaccination | | |
| 1 | TCO[A] Commercial | 94 | 6/15 |
| 2 | CEO[B] Commercial | 92 | 12/15 |
| 3 | P32 37 C.[C] | 87 | 4/15 |
| 4 | P32 30 C.[D] | 92 | 1/15 |
| 5 | No Vaccine | 100 | 0/15 |
| | Bodyweight & Clinical Disease Signs Data Post Ocular Vaccination | | |
| 1 | TCO Commercial | 89 | 2/5 |
| 2 | CEO Commercial | 93 | 5/5 |
| 3 | P32 37 C. | 105 | 1/5 |
| 4 | P32 30 C. | 103 | 0/5 |
| 5 | No Vaccine | 100 | 0/5 |
| | Bodyweight & Clinical Disease Signs Data Post Oral Vaccination | | |
| 1 | TCO Commercial | 96 | 4/10 |
| 2 | CEO Commercial | 92 | 7/10 |
| 3 | P32 37 C. | 78 | 3/10 |
| 4 | P32 30 C. | 87 | 1/10 |
| 5 | No Vaccine | 100 | 0/10 |

[A]TCO = Tissue culture origin (LT-IVAX, Merck Animal Health, Summit, NJ).
[B]CEO = Chicken embryo origin (TRACHIVAX, Merck Animal Health, Summit, NJ).
[C]P32 37 C. = 32 tissue culture passages performed at 37° C.
[D]P32 30 C. = 32 tissue culture passages performed at 30° C.

Vaccination with commercial (TCO Commercial and CEO Commercial) and experimental (P32 37C and P32 30C) vaccines exhibited somewhat reduced growth of broiler chickens as measured by bodyweight gain (Table 1). The negative effect of vaccination on bodyweight gain is a general drawback to the use of modified live vaccines for controlling ILTV infections. The negative effect on bodyweight gain is typically offset by improved health of vaccinated birds compared to non-vaccinated birds beyond the period reflected in Table 1.

Another disadvantage to using modified live vaccines is their tendency to produce clinical disease signs following vaccination. The P32 30C vaccine produced the fewest number of chickens with clinical disease signs. Clinical disease signs include, for example, conjunctival swelling and/or reddening, presence of an ocular and/or nasal (nares) exudate, nasal sinus swelling, labored breathing, and/or coughing, and in severe cases, a bloody expectoration.

TABLE 2

Post-vaccination assessment of ILTV commercial and experimental vaccines in two-week-old broiler chickens vaccinated by the ocular or oral routes. Q-PCR and ILT Serum Antibody Data Following Ocular or Oral Vaccination

| Group | Treatment | Q-PCR Values-Day 6 Post Vaccination | | | ILTV Serology-Day 14 Post Vaccination | |
|---|---|---|---|---|---|---|
| | | Total Group Combined | Ocular | Oral | ILTV Antibody Titers | #of Chickens with Positive Titer/Total |
| 1 | TCO Commercial | 31.6 | 35.2 | 29.8 | 184 | 3/15 |
| 2 | CEO Commercial | 29.0 | 27.3 | 29.9 | 1003 | 12/15 |
| 3 | P32 37C | 33.2 | 34.1 | 35.9 | 1301 | 12/15 |
| 4 | P32 30C | 36.5 | 39.4 | 35.1 | 15 | 6/15 |
| 5 | No Vaccine | 46.0 | 46.0 | 46.0 | 0 | 0/15 |

Quantitative (Q)-PCR values are an indication of the presence of ILTV vaccine in the oral/pharyngeal cavity, a body site where the vaccine may be detected. Values are inversely related to virus levels; Lower Q-PCR values equate to the presence of higher virus genome levels. Regardless of the type of vaccine tested, ILTV was not detected in great quantities on Day 6 post-vaccination.

The findings indicate that chickens given the CEO Commercial vaccine had the highest levels of ILTV-specific genome based on Q-PCR. A difference of 3.0 between Q-PCR values represents a 10-fold difference in the level of detectable viral genome. Chickens vaccinated with the P32 30C vaccine showed the lowest level of ILTV in the oral/pharyngeal cavity, suggesting that the vaccine is more attenuated than the other vaccines tested.

Serum antibody titers for ILTV were measured on day 14 post-vaccination using a commercial ELISA kit (Synbiotics Corp., Kansas City, Mo.). The CEO Commercial and P32 37C vaccines induced the highest antibody titers, detected in 12/15 chickens. This finding, along with the higher incidence of clinical disease signs and weight suppression suggest that the CEO Commercial and P32 37C experimental vaccines were not attenuated—i.e., they were more invasive than the TCO Commercial and P32 30C vaccines. Moreover, ELISA serum antibody titers may not correlate well with protection (Fahey et al. 1990. *J. Gen. Virol.* 71:2401-2405). Thus, a more attenuated vaccine like the P32 30C vaccine can induce protection (Table 3) even when producing low serum antibody titers.

All vaccines induced protection as measured by weight gain from days 1-6 after challenge, the lack of clinical disease signs, and microscopic pathology observed after ocular and intratracheal route challenge with the virulent USDA challenge strain of ILTV. The Animal and Plant Health Inspection Service of the USDA provides the challenge strain to researchers for the purpose of evaluating immunity of chickens following vaccination with experimental and/or commercial vaccines. It is thus a "standard" strain used for challenge purposes.

Chickens vaccinated with the P32 30C vaccine showed the greatest weight gain, indicating that the broilers were protected. Clinical disease signs observed only in the broilers in the No Vaccine treatment included conjunctival swelling and reddening, presence of an ocular and/or nasal (nares) exudate, labored breathing and coughing. Microscopic pathology of eyelid and trachea was performed to determine whether clinical signs of ILTV infection associated with the virulent challenge were present in these tissues.

Thus, the data in Tables 1-3 demonstrate that the P32 30C vaccine is more attenuated than the other vaccines, based on its ability to produce milder clinical signs. The P32 30C vaccine, however, produced body weight suppression when administered by the oral route, the most common method of vaccine application in commercial practice. For this reason, we decided to clone the P32 30C vaccine using a limit dilution procedure. The limit dilution procedure (Example 2) produced Clone 5-7. Clone 5-7 was evaluated and the results are provided in Tables 4-6. Three serial ten-fold dilutions ($10^{-1}$, $10^{-2}$, and $10^{-3}$) of the virus stock were used to vaccinate broiler chickens at two weeks of age. Vaccines were administered by the ocular or oral route.

TABLE 3

Post-challenge assessment of ILTV commercial and experimental vaccines in two-week-old broiler chickens vaccinated by the ocular or oral routes.

| Group | Treatment | Weight Gain From 1-6 Days Post Challenge As a % of Non-Vacc. Weight Gain | Clinical Disease Signs Associated With ILTV Infection | Birds with Microscopic Pathology Eyelid | Trachea |
|---|---|---|---|---|---|
| Bodyweight and Protection (Clinical Signs and Microscopic Pathology) Data After Challenge of Chickens Vaccinated via the Ocular or Oral Routes-Combined Data ||||||
| 1 | TCO Commercial | 678 | 0/13 | 0/13 | 0/13 |
| 2 | CEO Commercial | 711 | 0/13 | 0/13 | 0/13 |
| 3 | P32 37 C. | 677 | 0/13 | 0/13 | 0/13 |
| 4 | P32 30 C. | 741 | 0/12 | 0/13 | 0/13 |
| 5 | No Vaccine | 100 | 12/12 | 12/12 | 5/12 |
| Bodyweight and Protection (Clinical Signs and Microscopic Pathology) Data After Challenge of Chickens Vaccinated via the Ocular Route ||||||
| 1 | TCO Commercial | 618 | 0/5 | 0/5 | 0/5 |
| 2 | CEO Commercial | 704 | 0/5 | 0/5 | 0/5 |
| 3 | P32 37 C. | 626 | 0/5 | 0/5 | 0/5 |
| 4 | P32 30 C. | 716 | 0/5 | 0/5 | 0/5 |
| 5 | No Vaccine | 100 | 12/12 | 12/12 | 5/12 |
| Bodyweight and Protection (Clinical Signs and Microscopic Pathology) Data After Challenge of Chickens Vaccinated via the Oral Route ||||||
| 1 | TCO Commercial | 716 | 0/8 | 0/8 | 0/8 |
| 2 | CEO Commercial | 715 | 0/8 | 0/8 | 0/8 |
| 3 | P32 37 C. | 708 | 0/8 | 0/8 | 0/8 |
| 4 | P32 30 C. | 753 | 0/7 | 0/8 | 0/8 |
| 5 | No Vaccine | 100 | 12/12 | 12/12 | 5/12 |

TABLE 4

Post-vaccination assessment of varying dilutions ($10^{-1}$-$10^{-3}$) of ILTV experimental vaccine Clone 5-7 in two-week-old broiler chickens vaccinated by the ocular or oral route.

| Group | Treatment | Weight Gain From 1-6 Days Post Vaccination as a % of Non-Vacc. Weight Gain | Clinical Disease Signs Associated With Vaccination |
|---|---|---|---|
| Combined Bodyweight Data Following Ocular or Oral Vaccination | | | |
| 1 | Clone 5-7 Dilution $10^{-1}$ | 94 | 2/10 |
| 2 | Clone 5-7 Dilution $10^{-2}$ | 92 | 0/12 |
| 3 | Clone 5-7 Dilution $10^{-3}$ | 101 | 0/12 |
| 4 | No Vaccine/Challenge | Not Applicable | Not Applicable |
| 5 | No Vaccine/No Challenge | 100 | Not Applicable |
| Bodyweight Data Post Ocular Vaccination | | | |
| 1 | Clone 5-7 Dilution $10^{-1}$ | 103 | 0/5 |
| 2 | Clone 5-7 Dilution $10^{-2}$ | 94 | 0/5 |
| 3 | Clone 5-7 Dilution $10^{-3}$ | 100 | 0/5 |
| 4 | No Vaccine/Challenge | Not Applicable | Not Applicable |
| 5 | No Vaccine/No Challenge | 100 | Not Applicable |
| Bodyweight Data Post Oral Vaccination | | | |
| 1 | Clone 5-7 Dilution $10^{-1}$ | 85 | 2/5 |
| 2 | Clone 5-7 Dilution $10^{-2}$ | 86 | 0/5 |
| 3 | Clone 5-7 Dilution $10^{-3}$ | 101 | 0/5 |
| 4 | No Vaccine/Challenge | Not Applicable | Not Applicable |
| 5 | No Vaccine/No Challenge | 100 | Not Applicable |

Clone 5-7 dilutions given ocularly had minimal impact on chickens 1-6 days post vaccination. Oral administration reduced weight gain at the 10-1 and 10-2 dilutions, but not at the 10-3 dilution. Clinical disease signs were only observed at the highest oral dose ($10^{-1}$ dilution.

Chickens receiving the $10^{-3}$ dilution of the vaccine were free of clinical signs and gained bodyweight at the same rate as chickens not receiving the vaccine or the virulent challenge ("No Vaccine/No Challenge" treatment). Thus, Clone 5-7 demonstrated the potential to be a safe and economically desirable vaccine candidate.

TABLE 5

Post-vaccination assessment of dilutions $10^{-1}$ to $10^{-3}$ of ILTV experimental vaccine Clone 5-7 in two-week-old broiler chickens vaccinated by the ocular or oral routes.

| | | Q-PCR Values- Day 6 Post Vaccination | | | LT Antibody Serology- Day 14 Post Vaccination | | | | | |
|---|---|---|---|---|---|---|---|---|---|---|
| Group | Treatment | Combined Group | Ocular | Oral | ELISA Titers: Combined Group | # of Birds w/Positive Titer: Combined Group | ELISA Titers: Ocular | # of Birds w/Positive Titer: Ocular | ELISA Titers: Oral | # of Birds w/Positive Titer: Oral |
| 1 | Clone 5-7 Dilution $10^{-1}$ | 39.2 | 41.8 | 36.7 | 894 | 6/9 | 451 | 2/4 | 1211 | 4/5 |
| 2 | Clone 5-7 Dilution $10^{-2}$ | 37.4 | 40.9 | 32.7 | 786 | 9/12 | 584 | 4/7 | 1189 | 4/5 |
| 3 | Clone 5-7 Dilution $10^{-3}$ | 37.8 | 37.0 | 41.4 | 368 | 6/12 | 334 | 2/7 | 295 | 2/5 |
| 4 | No Vaccine/Challenge | Not Detected | Not Detected | Not Detected | 17 | 0/14 | 17 | 0/14 | 17 | 0/14 |
| 5 | No Vaccine/No Challenge | N/A | N/A | N/A | N/A | N/A | N/A | N/A | N/A | N/A |

N/A = Not Applicable

Again, quantitative (Q)-PCR values are an indication of the presence of ILTV vaccine in the oral/pharyngeal cavity, a site where the vaccine may be detected. Values are inversely related to virus genome levels; Lower Q-PCR values equate to the presence of higher virus genome levels. Regardless of the type of vaccine tested, ILTV was not detected in great quantities on Day 6 post-vaccination. A difference of 3.0 between Q-PCR values represents a 10-fold difference in the level of detectable viral genome. Chickens vaccinated with the dilutions of the Clone 5-7 vaccine showed a low level of ILTV in the oral/pharyngeal cavity suggesting the vaccine is attenuated.

Serum antibody titers for ILTV were measured on day 14 post-vaccination using a commercial ELISA kit (Synbiotics Corp., Kansas City, Mo.). Fifty percent or more of chickens vaccinated with the Clone 5-7 vaccine via the ocular or oral route (see Combined Group) produced an ILTV serum antibody response. In each vaccine dilution treatment group, ILTV antibodies were detected in the majority of birds. The data show a greater antibody response in birds receiving the $10^{-1}$ and $10^{-2}$ dilution vaccines orally compared to chickens given the vaccines via the ocular route. Chickens not given the vaccine (No Vaccine/Challenge treatment) did not produce ILTV serum antibody responses. Once again, however, ELISA titers may not correlate well with protection (Fahey et al. 1990. *J. Gen. Virol.* 71:2401-2405).

TABLE 6

Post-challenge assessment of dilutions $10^{-1}$ to $10^{-3}$ of ILTV Clone 5-7 vaccine in two-week-old broiler chickens vaccinated by the ocular or oral route.

| Group | Treatment | Weight Gain From 1-6 Days Post Vaccination As a % of Non-Vacc. Weight Gain | Clinical Disease Signs Associated With ILTV Infection |
|---|---|---|---|
| | Combined Bodyweight & Clinical Disease Signs Data Following Ocular or Oral Vaccination | | |
| 1 | Clone 5-7 Dilution $10^{-1}$ | 99 | 1/8 |
| 2 | Clone 5-7 Dilution $10^{-2}$ | 92 | 0/10 |
| 3 | Clone 5-7 Dilution $10^{-3}$ | 105 | 1/8 |
| 4 | No Vaccine/ Challenge | 61 | 5/5 |
| 5 | No Vaccine/ No Challenge | 100 | 0/10 |
| | Combined Bodyweight & Clinical Disease Signs Data Following Ocular Vaccination | | |
| 1 | Clone 5-7 Dilution $10^{-1}$ | 123 | 1/3 |
| 2 | Clone 5-7 Dilution $10^{-2}$ | 94 | 0/5 |
| 3 | Clone 5-7 Dilution $10^{-3}$ | 140 | 1/4 |
| 4 | No Vaccine/ Challenge | 61 | 5/5 |
| 5 | No Vaccine/ No Challenge | 100 | 0/10 |
| | Combined Bodyweight & Clinical Disease Signs Data Following Oral Vaccination | | |
| 1 | Clone 5-7 Dilution $10^{-1}$ | 97 | 0/5 |
| 2 | Clone 5-7 Dilution $10^{-2}$ | 106 | 0/5 |
| 3 | Clone 5-7 Dilution $10^{-3}$ | 99 | 0/4 |
| 4 | No Vaccine/ Challenge | 61 | 5/5 |
| 5 | No Vaccine/ No Challenge | 100 | 0/10 |

After challenge with virulent USDA challenge strain of ILTV, chickens receiving any ILTV Clone 5-7 vaccine dilution had higher weight gain than non-vaccinated/challenged chickens (No Vaccine/Challenge treatment). Following challenge, chickens vaccinated via the ocular or oral routes had fewer clinical disease signs compared to chickens not receiving a vaccination. All chickens vaccinated via the ocular route were protected against clinical disease signs after challenge.

TABLE 7

Post-vaccination assessment of $10^{-2}$ dilution of ILTV experimental vaccine Clone 5-7 in five-week-old specific pathogen-free (SPF) chickens vaccinated by the ocular route. Passage 1 and Passage 2.

| Bird Number | Vaccinated | Clinical Disease Signs Observed During 14 Days Before Challenge | Q-PCR Ct Value: Oral Swabs 5 DPV |
|---|---|---|---|
| Passage 1. Oral Vaccine Shed Following Ocular Vaccination | | | |
| Y41 | Yes | None | 32.7* |
| Y42 | Yes | None | 32.5* |
| Y43 | Yes | None | 33* |
| Y44 | Yes | None | Undetermined |
| Y45 | Yes | None | 35.3 |
| Y46 | Yes | None | 34.5 |
| Y47 | Yes | None | 30.1* |
| Y48 | Yes | None | 35.0 |
| Y49 | Yes | None | 32.4* |
| Y50 | Yes | None | Undetermined |
| Passage 2. Oral Vaccine Shed Following Ocular Vaccination | | | |
| G61 | Yes | None | Undetermined |
| G62 | Yes | None | Undetermined |
| G63 | Yes | None | Undetermined |
| G64 | Yes | None | Undetermined |
| G65 | Yes | None | Undetermined |
| G66 | Yes | None | Undetermined |
| G67 | Yes | None | Undetermined |
| G68 | Yes | None | Undetermined |
| G69 | Yes | None | Undetermined |
| G70 | Yes | None | Undetermined |

Inoculum Ct Value of 28 (Clone 5-7 diluted $10^{-2}$ or 1:100).
*Used in pool for Passage 2 inoculum.

In Passage 1, five days post ocular vaccination with the ILTV Clone 5-7 vaccine, minimal shedding was observed in oral swabbings. In Passage 2, virus was not detected five days post vaccination with material collected from Passage 1 birds.

TABLE 8

Post-challenge assessment of $10^{-2}$ dilution of ILTV experimental vaccine Clone 5-7 in five-week-old specific pathogen-free (SPF) chickens vaccinated by the ocular route. Passage 1 and Passage 2.

| Bird Number | Vacc. | Clinical Disease Signs Observed: Days Post Challenge | | | | | | | | | |
|---|---|---|---|---|---|---|---|---|---|---|---|
| | | 1 | 2 | 3 | 4 | 5 | 6 | 7 | 8 | 9 | 10 |
| Passage 1. Post Challenge Data | | | | | | | | | | | |
| Y41 | Yes | None | None | None | None | None | None | None | None | None | None |
| Y42 | Yes | None | None | None | None | None | None | None | None | None | None |
| Y43 | Yes | None | None | None | None | None | None | None | None | None | None |
| Y44 | Yes | None | None | None | None | None | None | None | None | None | None |
| Y45 | Yes | None | None | None | None | None | None | None | None | None | None |
| Y46 | Yes | None | None | None | None | None | None | None | None | None | None |

TABLE 8-continued

Post-challenge assessment of $10^{-2}$ dilution of ILTV experimental vaccine Clone 5-7 in five-week-old specific pathogen-free (SPF) chickens vaccinated by the ocular route. Passage 1 and Passage 2.

| Bird Number | Vacc. | Clinical Disease Signs Observed: Days Post Challenge | | | | | | | | | |
|---|---|---|---|---|---|---|---|---|---|---|---|
| | | 1 | 2 | 3 | 4 | 5 | 6 | 7 | 8 | 9 | 10 |
| Y47 | Yes | None | None | None | None | None | None | None | None | None | None |
| Y48 | Yes | None | None | None | None | None | None | None | None | None | None |
| Y49 | Yes | None | None | None | None | None | None | None | None | None | None |
| Y50 | Yes | None | None | None | None | None | None | None | None | None | None |
| B26 | No | None | None | None | Wet Eye (+1)[A] | Conj. (+3)[B] | Conj. (+3) | Wet Eye (+1) | None | None | None |
| B27 | No | None | None | None | Wet Eye (+1) | Conj. (+2) | Wet Eye (+1) | None | None | None | None |
| B28 | No | None | None | None | Wet Eye (+1) | None | Wet Eye (+1) | None | None | None | None |
| B29 | No | None | None | None | Wet Eye (+1) | Conj. (+3) | Conj. (+3) | None | None | None | None |
| B30 | No | None | None | None | Wet Eye (+1) | None | None | None | None | None | Normal |
| Passage 2. Post Challenge Data | | | | | | | | | | | |
| G61 | Yes | None | None | None | None | Conj. (NS)[C] | Conj. (NS) | Conj. (NS) | None | None | None |
| G62 | Yes | None | None | None | Wet eye (+1), NE[A] | Conj. (NS) | Conj. (NS) | None | None | None | None |
| G63 | Yes | None | None | None | None | Conj. (NS) | Conj. (NS) | None | None | None | None |
| G64 | Yes | None | None | None | Conj. (+1)[B] | Conj. (NS) | Conj. (NS) | Conj. (NS) | None | None | None |
| G65 | Yes | None | None | None | Wet eye (+1) | Conj. (NS) | Conj. (NS) | None | None | None | None |
| G66 | Yes | None | None | None | Conj. (+1) | Conj. (NS) | Conj. (NS) | None | None | None | None |
| G67 | Yes | None | None | None | None | Conj. (NS) | Conj. (NS) | None | None | None | None |
| G68 | Yes | None | None | None | Conj. (+1) | Conj. (NS) | Conj. (NS) | None | None | None | None |
| G69 | Yes | None | None | None | Wet eye | Conj. (NS) | Conj. (NS) | None | None | None | None |
| G70 | Yes | None | None | None | Conj. (+2) | Conj. (NS) | Conj. (NS) | Conj. (NS) | None | None | None |
| P16 | No | None | None | None | Conj. (+1) | Conj. (NS) | Conj. (NS) | Conj. (NS) | Conj. (NS) | Wet eye (NS) | None |
| P17 | No | None | None | None | Wet eye (+1) | Conj. (NS) | Conj. (NS) | None | None | None | None |
| P18 | No | None | None | None | None | Conj. (NS) | Conj. (NS) | None | None | None | None |
| P19 | No | None | None | None | None | Conj. (NS) | Conj. (NS) | None | None | None | None |
| P20 | No | None | None | None | Conj. (+2) | Conj. (NS) | Conj. (NS) | Conj. (NS) | None | None | None |

[A]Observed clinical disease signs (severity of clinical disease sign: +1 = mild; +2 = moderate; +3 = severe).
[B]Conj. = Conjunctivitis
[C]NS = Not Scored In Passage 1, following challenge with the ILTV USDA challenge strain, all chickens vaccinated via the ocular route with ILTV Clone 5-7 were protected against clinical disease signs compared to chickens not receiving a vaccination. In Passage 2, there was no difference between birds vaccinated with the oral swab material collected in Passage 1 and the non-vaccinated birds. All birds in Passage 2 showed clinical disease signs compatible with ILTV induced disease. These results show that the ILTV Clone 5-7 is able to induce protective immunity (Passage 1) and does not spread to naïve susceptible chickens.

Thus, this disclosure describes an attenuated infectious laryngotracheitis virus (ILTV) that may be used as a component in a vaccine to immunize a subject against infection by a virulent infectious laryngotracheitis virus. Generally, the attenuated ILTV can be produced by serial passage at a temperature that is reduced from the temperature at which the ILTV is typically grown. Once the attenuated ILTV is so generated, however, one can generate the attenuated ILTV using conventional molecular biology techniques to produce a virus having the same nucleotide and/or functional features of the attenuated ILTV produced as described herein.

While described herein in the context of an exemplary embodiment in which the attenuated ILTV is produced by serial passaging an ILTV virus, the attenuated ILTV described herein—and variants thereof—can be produced by any suitable method. Also, while expressly exemplified herein in the context of an exemplary embodiment in which the attenuated ILTV possesses each of the genetic modifications listed in Table 11, an attenuated ILTV as described herein may contain fewer than all of the genetic mutations listed in Table 11 and still retain an attenuated character.

In some embodiments, the attenuated ILTV can be produced by serial passage of the virus at a minimum temperature of at least 25° C. such as, for example, at least 27° C., at least 28° C., at least 29° C., at least 30° C., at least 31° C., or at least 32° C. In some embodiments, the attenuated ILTV can be produced by serial passage of the virus at a maximum temperature of no more than 35° C. such as, for example, no more than 34° C., no more than 33° C., no more than 32° C., no more than 31° C., no more than 30° C., or no more than 29° C. In some embodiments, the attenuated ILTV can be produced by serial passage of the virus at a temperature within a range having endpoints defined by any minimum temperature listed above and any maximum temperature that is greater than the minimum temperature. For example, in one embodiment, the attenuated virus can be produced by serial passage of virus at a temperature of from 28° C. to 31° C. In one particular embodiment, the attenuated ILTV can be produced by serial passage of the virus at a temperature of 30° C.

The attenuated ILTV can be generated by any suitable number of serial passages. In some embodiments, the attenuated ILTV can be produced by a method that includes a minimum of at least two serial passages of the virus such as, for example, at least three serial passages, at least five serial passages, at least seven serial passages, at least 15 serial passages, at least 25 serial passages, at least 30 serial passages, at least 34 serial passages, at least 40 serial passages, or at least 45 serial passages. In some embodiments, the attenuated ILTV can be produced by a method that includes a maximum of no more than 50 serial passages such as, for example, no more than 44 serial passages, no more than 30 serial passages, no more than 20 serial passages, no more than 10 serial passages, no more than seven serial passages, no more than five serial passages, no more than four serial passages, or no more than three serial passages. In some embodiments, the attenuated ILTV can be produced by a method that includes a number of serial passages within a range having endpoints defined by any minimum number of passages listed above and any maximum number of serial passages that is greater than the minimum number of serial passages. In one particular embodiment, the attenuated ILTV may be generated using a method that includes seven serial passages of the virus. Thus, in some embodiments, the attenuated virus can be produced by a method that includes, for example, 30-50 serial passages such as, for example, 34-44 serial passages.

The serial passaging of the virus at a reduced temperature produces an attenuated virus that includes one or more genetic modifications compared to the ILTV that was the starting material. In the exemplary embodiment described above, the starting ILTV was a commercially available ILTV of tissue culture origin, LT-IVAX (Merck Animal Health, Summit, N.J.). Table 11 lists genetic modifications of the Clone 5-7 generated as described herein compared to the LT-IVAX. Some of the mutations are located in non-coding regions. Others, however, introduce frame shift mutations or amino acid substitutions As noted above, while exemplified herein in the context of an exemplary embodiment in which the attenuated ILTV possesses each of the genetic modifications listed in Table 11, the attenuated ILTV contemplated herein may contain fewer than all of the genetic mutations listed in Table 11 and still retain an attenuated character. Exemplary genetic modifications can produce, for example, a frame shift mutation in one or more coding regions of the viral genome. Exemplary coding regions that may be affected by a frame shift mutation include, for example, ORF B, ORF F, UL50, UL7, or UL9.

A frame shift mutation in ORF B may include, for example, a frame shift introduced at Phe54 such as may be produced by a deletion of a nucleotide or an addition of a nucleotide in the codon for Phe54 of ORF B. One exemplary mutation is a deletion of a thymine (e.g., the thymine at nucleotide position 23030 of the ILTV genome) from the codon, but a person of ordinary skill in the art can readily conceive of other mutations that could cause a frame shift at Phe54—or any other site—of ORF B.

A frame shift mutation in ORF F may include, for example, a frame shift introduced at Glu233 such as may be produced by a deletion of a nucleotide or an addition of a nucleotide in the codon for Glu233 of ORF F. One exemplary mutation is an addition (e.g., a guanine added between nucleotide position 5377 and 5378 of the ILTV genome) in the codon, but a person of ordinary skill in the art can readily conceive of other mutations that could cause a frame shift at Glu233—or any other site—of ORF F.

A frame shift mutation in UL50 may include, for example, a frame shift introduced at Asn10 such as may be produced by a deletion of a nucleotide or an addition of a nucleotide in the codon for Asn10 of UL50. One exemplary mutation is a deletion of a thymine (e.g., a deletion of the thymine at nucleotide position 15577 of the ILTV genome) from the codon, but a person of ordinary skill in the art can readily conceive of other mutations that could cause a frame shift at Asn10—or any other site—of UL50.

A frame shift mutation in UL7 may include, for example, a frame shift introduced at Phe104 such as may be produced by a deletion of a nucleotide or an addition of a nucleotide in the codon for Phe104 of UL7. One exemplary mutation is a deletion of a adenine (e.g., the adenine at nucleotide position 98125 of the ILTC genome) from the codon, but a person of ordinary skill in the art can readily conceive of other mutations that could cause a frame shift at Phe104—or any other site—of UL7.

A frame shift mutation in UL9 may include, for example, a frame shift introduced at PGlu771 such as may be produced by a deletion of a nucleotide or an addition of a nucleotide in the codon for Glu771 of UL9. One exemplary mutation is a deletion of a adenine (e.g., the adenine at nucleotide position 94565 of the ILTV genome) from the codon, but a person of ordinary skill in the art can readily conceive of other mutations that could cause a frame shift at Glu771—or any other site—of UL9.

In some embodiments, an attenuated ILTV can include a genetic modification to the UL50 coding region without necessarily possessing any of the other genetic modifications shown in Table 11. Moreover, in some embodiments, the genetic modification to UL50 may differ from the thymine deletion identified in Table 11, while still resulting in attenuation of the resulting genetically-modified ILTV.

The attenuated ILTV, when administered to a subject, can decrease the likelihood, extent, and/or severity of infection of the subject by a virulent ILTV compared to a comparable unvaccinated control subject. In some cases, administering the attenuated ILTV can result in increased weight gain and/or a decrease in the severity of one or more signs of infection by a virulent ILTV. Exemplary signs of infection by a virulent ILTV include, for example, conjunctival swelling and/or reddening, presence of an ocular and/or nasal (nares) exudate, nasal sinus swelling, labored breathing, coughing, and in severe cases, a bloody expectoration.

Thus, in another aspect, this disclosure describes a method that involves administering the attenuated infectious laryngotracheitis virus described herein to a subject having or at risk of having an ILTV infection.

Thus, treating a condition can be prophylactic or, alternatively, can be initiated after the subject exhibits one or more symptoms or clinical signs of the condition. As used herein, the term "sign" or "clinical sign" refers to an objective physical finding relating to a particular condition capable of being found by one other than the subject; the term "symptom" refers to any subjective evidence of disease or of a subject's condition. Treatment that is prophylactic—e.g., initiated before a subject manifests a symptom or clinical sign of the condition such as, for example, while an infection remains subclinical—is referred to herein as treatment of a subject that is "at risk" of having the condition. As used herein, the term "at risk" refers to a subject that may or may not actually possess the described risk. Thus, for example, a subject "at risk" of having an infectious condition is a subject present in an area where other individuals have been identified as having the infectious condition and/or is likely to be exposed to the infectious agent. A subject may be "at risk" even if the subject has not yet manifested any detectable indication of infection by a virulent ILTV and regardless of whether the animal may harbor a subclinical amount of a virulent ILTV.

Accordingly, the attenuated ILTV can be administered to a subject before, during, or after the subject first comes in contact with a virulent ILTV. Treatment initiated after the subject first exhibits comes in contact with a virulent ILTV may result in decreasing the severity of symptoms and/or clinical signs of the condition, completely resolving the condition, and/or decreasing the likelihood of experiencing clinical evidence of the condition compared to a subject to which the attenuated ILTV has not been administered.

The method includes administering an effective amount of the attenuated ILTV to a subject exposed to, or at risk of being exposed to ILTV. In this aspect of the invention, an "effective amount" is an amount effective to reduce, limit progression, ameliorate, or resolve, to any extent, the symptoms or clinical signs related to infectious laryngotracheitis.

The attenuated ILTV described herein may be formulated in a composition along with a "carrier." As used herein, "carrier" includes any solvent, stabilizer, dispersion medium, vehicle, coating, diluent, antibacterial, and/or antifungal agent, isotonic agent, absorption delaying agent, buffer, carrier solution, suspension, colloid, and the like. The use of such media and/or agents for pharmaceutical active substances is well known in the art. Except insofar as any conventional media or agent is incompatible with the attenuated ILTV described herein, its use in a therapeutic compositions is contemplated. Supplementary active ingredients also can be incorporated into the compositions.

By "pharmaceutically acceptable" is meant a material that is not biologically or otherwise undesirable, i.e., the material may be administered to an individual along with the attenuated ILTV without causing any undesirable biological effects or interacting in a deleterious manner with any of the other components of the pharmaceutical composition in which it is contained.

The attenuated ILTV may be administered to any suitable subject such as, for example, chickens, turkeys, ducks, pheasants, and peafowl.

In the preceding description, particular embodiments may be described in isolation for clarity. Unless otherwise expressly specified that the features of a particular embodiment are incompatible with the features of another embodiment, certain embodiments can include a combination of compatible features described herein in connection with one or more embodiments.

For any method disclosed herein that includes discrete steps, the steps may be conducted in any feasible order. And, as appropriate, any combination of two or more steps may be conducted simultaneously.

The present invention is illustrated by the following examples. It is to be understood that the particular examples, materials, amounts, and procedures are to be interpreted broadly in accordance with the scope and spirit of the invention as set forth herein.

EXAMPLES

Example 1

Generating P32 37C

The P32 37C virus was serially passaged 32 times in primary chicken embryo kidney cells (CEKC), incubated at 37° C.

Kidney cells were prepared from 17-20 day old embryos. The amounts indicated here are for preparing kidney cells from 10-15 embryos. Eggs were sprayed with a disinfectant (BIOGUARD, Bioguard Hygiene Solutions Ltd., Northampton, UK) and allowed to dry. Kidneys were dissected from the embryos, washed in Phosphate Buffered Saline (PBS) without calcium or magnesium (1.60 g $Na_2HPO_4$, 0.51 g $KH_2PO_4$, 7.30 g NaCl in 1 L $DDH_2O$). The kidneys were dissociated and treated with trypsin solution (0.25% trypsin in modified PBS+0.02% EDTA, pH 7.4-7.6) and stirred slowly for 15-20 minutes at 37° C. The supernatant was collected by pouring through a gauze-covered funnel into a graduated centrifuge tube with 5 ml of cold (ice bath-cooled) heat-inactivated calf serum. The remaining pellet was retrypsinized with fresh trypsin solution and the process repeated two more times. The collected supernatant was centrifuges at 1500 RPM for 10 minutes. The pelleted kidney cells were resuspended in 3-6 ml minimal essential medium (MEM), then added to MEM with 10% heat-inactivated fetal calf serum.

Cells were counted in a hemacytometer by resuspending in a known amount of media. 2 ml of cells ($2.5 \times 10^6$ cells/ml) were plated on a 35 $mm^2$ plate, which formed a monolayer in 1-2 days. When the monolayer formed, the cells were ready for inoculation.

1 mL of starting virus was used to infect one 25 mL flask with 80% confluent monolayer of CEKC's. The inoculated CEKC were incubated at 37° C. ILTV cytopathic effect (CPE) known as syncytia were observed in the CEKC at two days after inoculation. The cells and culture media were harvested and repassaged serially for 32 passages at an incubation temperature of 37° C. A seed stock of the virus was then prepared for further experimentation.

Generating P32 30C

The P32 30C virus was serially passaged 32 times in primary chicken embryo kidney cells (CEKC). Cells were prepared as described above for the preparation of the P32 37C virus, except that the inoculated CEKC were incubated at 30° C. ILTV cytopathic effect (CPE) known as syncytia were observed in the CEKC at 3-4 days after inoculation. The cells and culture media were harvested and repassaged serially for 32 passages at an incubation temperature of 30° C. A seed stock of the virus was then prepared for further experimentation.

Assessment of Vaccines

One-day-old, female commercial broiler chickens (Moyer's Chicks, Inc., Quakertown, Pa.) were assigned to one of five treatment groups shown in Table 9.

TABLE 9

| Group No. | Immunizing Virus | Vacc. Titer | No. of Birds (Oral/ED) |
|---|---|---|---|
| 1 | TCO Vaccine[A] | $10^{3.0}$ | 10/5 |
| 2 | CEO Vaccine[B] | $10^{4.0}$ | 10/5 |
| 3 | P32 30 C.[C] | $10^{3.0}$ | 10/5 |
| 4 | P32 37 C.[D] | $10^{3.0}$ | 10/5 |
| 5 | Negative Control | Sham | 10/5 |

[A]TCO = Tissue culture origin (LT-IVAX, Merck Animal Health, Summit, NJ).
[B]CEO = Chicken embryo origin (TRACHIVAX, Merck Animal Health, Summit, NJ).
[C]P32 30 C. = 32 tissue culture passages performed at 30° C.
[D]P32 37 C. = 32 tissue culture passages performed at 37° C.

The night prior to vaccination at 14 days of age, water was withheld from the birds. On the afternoon prior to vaccination, all birds were weighed. Birds in the oral vaccinated groups received 1.5 mL of water containing one drop of vaccine (0.03 ml) by hand using a blunt needle and syringe. Vaccination occurred slowly to ensure proper uptake by the bird. Each bird was held vertically, beak pointed slightly toward the ceiling to mimic drinking from a nipple. Each bird in the corresponding eye drop vaccine group was vaccinated by placing one drop (0.03 ml) of inoculum directly into the conjunctival sac.

Birds were observed daily for signs of vaccine reaction (conjunctivitis, nasal discharge). Six days post vaccination, all birds were weighed. Oropharyngeal swabs were collected from all birds to determine the level of ILTV present in the oral cavity by real-time PCR (Callison et al., 2007. J. Virol. Methods 139:31-38). Two birds from each water vaccinated group and the negative control group were euthanized. Trachea and eyelid were collected for evaluation of microscopic pathology.

Fourteen days post vaccination, all birds were weighed, serum samples were collected from all birds prior to challenge with the USDA challenge strain of ILTV ($10^{3.5}/0.1$ ml). ILTV serum antibody titers were evaluated using a commercial ELISA kit (Synbiotics Corp., Kansas City, Mo.). Five days post challenge birds were weighed and evaluated for signs of disease. Trachea and eyelid were collected after euthanizing via cervical dislocation.

Results are shown in Tables 1-3.

Example 2

Generating Clone 5-7 from P 32 30C Using the Limit Dilution Procedure

Serial 10-fold dilutions ($10^{-1}$-$10^{-6}$) of the P32 30C virus were prepared and inoculated onto CEKC. The inoculated cells were incubated at 30° C. The CEKC were observed microscopically daily for syncytia. Cells and media were harvested from the highest dilution showing syncytia. A culture plate at the $10^{-5}$ dilution, $7^{th}$ replicate plate met the criteria and the cells and media were harvested. A seed stock was prepared for further experimentation.

Assessment of Vaccines

Female broiler type chickens (Moyer's Chicks, Inc., Quakertown, Pa.). Chicks were placed in isolation in groups of 13 birds. At 20 days of age, birds were water deprived for at least two hours prior to inoculation. The following day, at 21 days of age, birds were randomly regrouped, assigned to treatment groups (Table 10) and necktagged for identification. All birds were weighed. Birds with bodyweights greater than or less than 2SD of the group mean weight were used in the swab control groups. The negative control birds were placed in isolation prior to handling any viruses. Birds in the negative control/oral group received 1 mL of water. No other sham inoculations were performed.

TABLE 10

| Cage No. | Treatment | Treatment | No. of Female Broilers |
| --- | --- | --- | --- |
| 1 | Negative Control | Challenge Controls | 5 |
|  |  | Oral | 5 |
|  |  | Ocular | 5 |
|  |  | Swab Controls | 2 |
| 2 | $10^{-1}$ | Oral | 5 |
|  |  | Ocular | 5 |
| 3 | $10^{-2}$ | Oral | 5 |
|  |  | Ocular | 5 |
|  |  | Swab Controls | 2 |
| 4 | $10^{-3}$ | Oral | 5 |
|  |  | Ocular | 5 |
|  |  | Swab Controls | 2 |
| 5 | $10^{-4}$ | Oral | 5 |
|  |  | Ocular | 5 |
|  |  | Swab Controls | 2 |
| 6 | $10^{-5}$ | Oral | 5 |
|  |  | Ocular | 5 |
|  |  | Swab Controls | 2 |
| 7 | $10^{-6}$ | Oral | 5 |
|  |  | Ocular | 5 |
|  |  | Swab Controls | 2 |

Inoculation:

Prior to inoculation with the Clone 5-7 dilutions, all birds were weighed and blood samples were collected from 10 birds. Six 8-ml tubes were filled with 4.5 ml of sterile water (pH 7.0—spring water). Tubes were used for to create the inoculum dilutions ($10^{-1}$ to $10^{-6}$). Six 10-fold dilutions of the Clone 5-7 ILTV were created by placing 0.5 ml of virus in 4.5 ml of sterile water (pH 7.0—spring water). 0.5 ml of the $10^{-1}$ dilution was then be placed into 4.5 ml of sterile water (pH 7.0—spring water) to create the $10^{-2}$ and repeated until the $10^{-6}$ dilution was created. 0.5 ml were removed from the $10^{-6}$ dilution and discarded. All dilution tubes contained 4.5 ml of the virus/water dilution.

Two separate tubes were marked as either for ocular or oral inoculation. The ocular tube contained at least 1 ml of the given dilution. The oral tube contained 0.7 ml of inoculum and 7 ml of water. These tubes were held on ice until used. Ocular treatment birds received 0.1 ml (100 μl) by eyedrop. The oral treatment birds received 1 ml of the water/virus preparation. Swab controls received 0.1 ml (100 μl) of a given vaccine treatment via eyedrop. These birds were used to assess viral load in the trachea by real-time PCR.

6 DPI Swab and Weigh:

Birds were swabbed at six day post-inoculation (dpi) to determine viral load by real time PCR in the oral cavity of the ocular and oral challenged groups. Tracheal and oral swabs were collected from the swab controls to evaluate viral load at both swabbing locations by real-time PCR (Callison et al., 2007. *J. Virol. Methods* 139:31-38). Body weights were also collected to determine the effect of infection on weight gain. Swabs were collected and placed in 2 ml of sterile Tryptose Phosphate Broth (Difco, BD Biosciences, San Jose, Calif.).

14 DPI-Challenge:

All birds were weighed and bled prior to challenge. The five "challenge controls" in cage 1 were used to verify infection of the broilers using challenge dose of $10^3$ per bird. After challenge, the challenge controls were relocated among the $10^{-5}$ and $10^{-6}$ treatment groups (cages 6 and 7). All birds in cages 2-7 received a challenge of $10^3$ EID$_{50}$ of the USDA ILTV challenge strain per 0.1 ml divided between the intraocular (one drop) and oral (remaining volume up to 0.1 ml) routes of inoculation using a 200 μl pipette.

Birds were evaluated daily for signs of clinical disease for a period of 10 days post challenge (DPC). At 6 DPC, birds were weighed to evaluate protection based upon suppression of daily weight gain compared to non-challenged controls. At 10 DPC, birds were weighed and evaluated for signs of clinical disease. All surviving birds were bled to evaluate ILTV antibody status following challenge. ELISA titers were evaluated to determine if they might be indicative of lack of protection or a booster response. The experiment was terminated after 10 DPC.

Results are shown in Tables 4-6.

Genetic Signature of Clone 5-7

Approximately 500 μL of the Clone 5-7 TCO supernatant was treated with DNase and the viral DNA was extracted using the DNeasy 96 Blood & Tissue Kit (Qiagen, Inc., Valencia, Calif.) according the recommended procedures. A DNA library was generated using the NuGen OVATION ultralow library system (NuGEN Technologies, Inc., San Carlos, Calif.). The libraries were sequenced on an Illumina Genome Analyzer IIx (Illumina, Inc., San Diego, Calif.) in a paired-end, 101 cycle run. Library reads were assembled to a reference ILTV genome using CLCWorkbench (CLC bio, Inc., Germantown, Md.). Variant detection within the Clone 5-7 assembled genome and the impact of the detected variation on amino acid sequence was performed within CLCWorkbench (CLC bio, Inc.,).

TABLE 11

ILTV Clone 5-7 Genetic Signature vs. Commercial TCO Vaccine

| Coding Region | Nt Position# | TCO Vaccine Nt | ILTV Clone 5-7 Nt | Non-synonymous or Synonymous | Amino Acid Change | Depth of Coverage at Position | Frequency of Mutation (%) |
|---|---|---|---|---|---|---|---|
| NC | 1160 | A | — | Not Applicable | Not Applicable | 2020 | 3.81 |
| NC | 104594 | A | — | Not Applicable | Not Applicable | 4493 | 93.08 |
| NC | 109606^109607 | — | G | Not Applicable | Not Applicable | 1981 | 72.19 |
| NC | 109614 | T | — | Not Applicable | Not Applicable | 980 | 6.22 |
| NC | 109616^109617 | — | G | Not Applicable | Not Applicable | 1689 | 3.02 |
| NC | 109622 | G | — | Not Applicable | Not Applicable | 1450 | 6.55 |
| ORF B | 23030 | T | — | Non-synonymous | Phe54fs* | 5030 | 6.92 |
| ORF F | 5377^5378 | — | G | Non-synonymous | Glu233fs | 5489 | 3.06 |
| UL36 | 53320 | A | G | Non-synonymous | Val2300Ala | 4082 | 16.39 |
| UL37 | 62826 | T | C | Synonymous | Not Applicable | 4129 | 3.44 |
| UL50 | 15577 | T | — | Non-synonymous | Asn10fs | 4582 | 92.45 |
| UL7 | 98125 | A | — | Non-synonymous | Phe104fs | 4737 | 5.3 |
| UL9 | 94565 | A | — | Non-synonymous | Glu771fs | 4339 | 5.49 |

*fs = frame shift
SEQ ID NO: 1, Genbank accession no. JN580312

Example 3

Female specific pathogen free (SPF) leghorn chickens were obtained at five weeks of age from Charles-River SPAFAS (Norwich, Conn.). Birds were periodically obtained in lots of 15 or 30.

Passage 1

For each passage, birds were assigned to one of two groups: Direct Inoculated (10 birds) or Challenge Controls (5 birds) (Table 7 and Table 8). Each bird was tagged according to treatment group. Clone 5-7 was diluted 1:100 and administered via eye-drop (0.1 mL/bird) to each of the 10 birds in Cage 1. On day 5 post challenge (PC), an oropharyngeal swabbing, culminating in the swabbing of the upper tracheal opening, were collected from each bird and placed into two swab tubes (5 swabs in each tube), each containing 2.5 mL of Tryptose Phosphate Broth (Difco, BD Biosciences, San Jose, Calif.) with antibiotics (penicillin (100 I.U.) and streptomycin (100 μg/ml), with fungizone (2.5 μg/ml)). Tubes were held at −80° C. until need for subsequent challenge.

Birds were observed and scored daily for disease signs (conjunctivitis, labored breathing/gasping, mortality) through day 10 post-direct inoculation. Birds were scored as 0=normal, 1=diseased (respiratory signs, swollen eye), or 2=dead. Swab tubes were screened for the presence of ILTV genome by real-time PCR (Callison et al., 2007. *J. Virol. Methods* 139:31-38).

Fourteen days post inoculation, the Direct Inoculates (10 birds) and the Challenge Controls (5 birds) were bled to determine ILTV serum antibody status by enzyme-linked immunosorbent assay (ELISA) (Synbiotics Corp., Kansas City, Mo.). All birds were moved to the Clone 5-7 Challenge Cage and challenged via eye-drop with the USDA ILTV Challenge Virus ($10^{3.5}$/bird). All birds were evaluated through 10 days PC for disease signs using the same scoring scale defined above.

Passage 2 to Passage 5

On the defined day of challenge, the two swab tubes collected five days post challenge with the previous passage were thawed at room temperature and centrifuged to pellet any debris. An aliquot of 0.5 ml from each tube was taken and pooled to create the inoculum for birds. The 10 birds in the direct inoculation group received 0.1 ml of the undiluted swab pool material via eye-drop. On day 5 post challenge, an oropharyngeal swabbing (culminating in the swabbing of the upper tracheal opening) was collected from each bird and placed into two swab tubes (5 swabs in each tube) each containing 2.5 ml of Tryptose Phosphate Broth (Difco, BD Biosciences, San Jose, Calif.) with antibiotics (penicillin (100 I.U.) and streptomycin (100 μg/ml) with fungizone (2.5 μg/ml)). Tubes were held at −80° C. until need for subsequent challenge.

Birds were observed and scored daily for disease signs (conjunctivitis, labored breathing/gasping, mortality) through day 10 post-direct inoculation. Birds were scored as described for Passage 1. Swab tubes were screened for the presence of ILTV genome by real-time PCR as described for Passage 1.

Fourteen days post inoculation, the Direct Inoculates (10 birds) and the Challenge Controls (5 birds) were bled to determine ILTV serum antibody status as described for Passage 1. All birds were challenged via eye-drop and evaluated through 10 days post challenge as described for Passage 1.

The inoculation procedure described above was repeated until ILTV was no longer detected by real-time PCR, the birds were susceptible to challenge, or a total of 5 bird passages had been completed.

Results are shown in Tables 7 and 8.

As used herein, the term "and/or" means one or all of the listed elements or a combination of any two or more of the listed elements; the terms "comprises" and variations thereof do not have a limiting meaning where these terms appear in the description and claims; unless otherwise specified, "a," "an," "the," and "at least one" are used interchangeably and mean one or more than one; and the recitations of numerical ranges by endpoints include all numbers subsumed within that range (e.g., 1 to 5 includes 1, 1.5, 2, 2.75, 3, 3.80, 4, 5, etc.).

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

```
<160> NUMBER OF SEQ ID NOS: 1

<210> SEQ ID NO 1
<211> LENGTH: 155465
<212> TYPE: DNA
<213> ORGANISM: Gallid herpesvirus 1
<220> FEATURE:
<221> NAME/KEY: exon
<222> LOCATION: (4680)..(6920)
<220> FEATURE:
<221> NAME/KEY: exon
<222> LOCATION: (14355)..(15605)
<220> FEATURE:
<221> NAME/KEY: exon
<222> LOCATION: (22871)..(23893)
<220> FEATURE:
<221> NAME/KEY: exon
<222> LOCATION: (51864)..(60218)
<220> FEATURE:
<221> NAME/KEY: exon
<222> LOCATION: (60357)..(63422)
<220> FEATURE:
<221> NAME/KEY: exon
<222> LOCATION: (92254)..(94932)
<220> FEATURE:
<221> NAME/KEY: exon
<222> LOCATION: (97360)..(98436)

<400> SEQUENCE: 1
attcgaaacc cctcgcggcc gcgaccgaac ggcgaaaaaa atttcacctc aatagaagcg      60
aacgggcgct ggcgagattc ggccaaaatc accggataaa tttccaccgc gaaatggcgc     120
gtttggcccc ctgccagcac gggccctgcg tacgtgcaca gcacccctgc cccgcggcaa     180 tcgctccect actttctgtt ttgcttcctt ggtatttctc cgcatcctgt tttcctgaaa     240
acttagacgc ggtgttgcta agcagctcct cggcatccgg tatatgcagg caagcaccca     300
gcgcgagcgc cattaaaagc gcggcagcgc acagcagcca cactccctac ctcgctccgc     360
ttcttccccg cctctctcca ctgtcctcta ctgctacccc ttcccattga ccctttctgc     420
tcctctacag ggacgtccac tcattggttc tttgttctct cttacagggt tcgcagtgcg     480
cttgtctctg acgggaccgc ccgccgttgg atttcgcgag gctccgcaga ggagactgat     540
tggggaatga ttggtaagct tgtgccaatt ccattcctct ttctgtctcc accgctgtgc     600
cattcgcctc tttccagtgg gtctcttcca ggtgctagga cgcgaccct gcctaagcga      660 ggctccgcac cggagactca ggaatggtca ttccattcct atctccctct ccgatgcggc     720
gcccgccgta ccctaccgtt ccgctttctg gttgcgcaaa ttgctctggc ggtgagcggc     780
ccaaatcctc ggctgaattg caggctgcaa tgacttcctg atttaattaa tttatccggt     840
gattttggcc gaatctcgcc agcgccgtt cgcttctatt gaggtgaaat ttttttcgcc      900
gttcggtcgc ggccgcgagg ggtttcgaat aggatcagag accgcctcca atccctctcg     960
```

```
ccccgcgct tggctctgtg ccgcacaccc caccctcctc gccgagcggc tgccaccatt    1020
ccctctctcc gatagatccg atgcctctgg gggtccgtgc caggccggtc tgatctgtgc    1080
tttaacgctg acagccgaga atgtgcacga agccgccggg ttggcatata cctccgcggt    1140
ccgctgcgcc ttcccccca ccccccttca gccgccacgc tatccaagct ctccgaggta    1200
tctgggtgcc gccagggttc ctccgcatgt actgagatcc ctgaggggcc tacccagatc    1260
ttcggagcct tggcttaccg acggcgcgcc ctgctctcca gcagcttta agcccctac    1320 ttgctgagag gtggcccgcg cttgctttcc gctcaactgc cttttagctc cacagctcta    1380
aaccccggtt ctacgatact agccgcggaa ggctgtgcga taggagccga gtacacttaa    1440
gtttatccgc tcctatgcag tagcctccgc aagctagcgt gtagatactc catcgatgcg    1500
ggacagcaaa ggtgcaggac ggcaggacgg caacatttga ctggcaggta gtaccgttgt    1560
ggaaaagccg tactgcccgc tcccgccgga gaccaagtta ctgcgtttag agctatcttg    1620
tctctgggtg ggttcggaga gtgcgggatt tcgggcatc tagtctctgg ccagtcgagg    1680
atggtccatc cagctgtcgt gtatgtatag cgagcaatga ccgtgtggtt ccctcatcac    1740
ggagtgctcg ttatgcatag atgcctgcgg gctaggtcac acttgctggg cagcggctaa    1800
actggctagc ctgcaaatag ccctccgacc tctcaggcga ccctcactta gggtcattgt    1860
cggagctttt cggcacaaag tacaagccca ttcactcgcc ctctgctaaa ctcaccagtt    1920
tgctagccag taacggttag tttaacagtg ggcgcatgaa agggctacac tgtaatccat    1980
acattccttt ttaggatttg catattcctt tgcctgtgat accgttaccg ccgaaggtag    2040
gtctagggtg tggatacttc ttgacctctc tttcggccgt cacagtatct tctggatatc    2100
ctcctcagcc atctcgacgg cgggcttccc agcggccggt attcctaacc atgctatctg    2160 taggagctttt gctccatagt tatgggtgcg gaatgtgtca gtatttagct attgttatat    2220
ttactgggca gggctcgttt atttgcccaa attgagcagc tcggactaca atacgaccta    2280
caaagagctg acacagcaca gtctctaaca gctgttcctg gagtcattta aacagaacga    2340
taaattcgaa ctaaatcggg acagtcccct cgcttgcacg gagtccaggt aacactgcgg    2400
atctgacaat aggattggtg agaacaagtg aagatgccag ctcccgacac gaactagtga    2460
cctagtccag acgaaaatgc ttaagcttgt ccttgattgg acaagcacga tgaaaacgaa    2520
accctgcata gatattggcg agctggctct ttacacactc tgcggatgta gcttagtggg    2580
cgggtatcgg gtttcgccgc actgccgaac gctgctttgc ttcttgctct atctatttta    2640
tagccgggcg ctttttaaaga atggacttcg agctttgcat gttcttaatt actttaattc    2700
tagcaattct tttatttta gctatattgt atctacagtg ggtccgtcat cgtagagaag    2760
ccgcagagag gctgctattt ctgcttttaa tacacaacat tcagaacgat gcgggcttaa    2820
gacggaaccg cgcggcacaa ggagcataac tgcggggtca gtgtttgttg ctgcgtggtt    2880
gtaattctct ttttggcact gcgaggctag gtttgttgcc gcgcgattgc agggtttttc    2940
tttgtgagac tggtgatggg gaaaagcttg attgtgcaat agtaaaagtg acttaggtac    3000
ttcatatact gggctgtggc atgtaggcac gtccaagctc ggctctgaat tctaagcttg    3060 cttttgtcgaa ccagttttgt tttcttttg ggggagggt agcacactct gcccgagtct    3120
cggcattgac ttaacagtga tgtgaaaccc ggaagatcga gcatgaacta atagcattaa    3180
agaattgtta tccgaggaat aatcgtggac gcgaatttac tcgaccgcta aaatctttct    3240
tctactgagc tggatacgtg aaatttggtg agtataacct ctcgggatac atagctttta    3300
```

```
aatacggggc gtgcaatatt aaattctgca ctcggggctg caatggagcg cggagcttta    3360
tttgacaaga ccgccaattg caaggactgg gtctcgatcg ggactactgt gtggggcgcg    3420
atcgatgcag atgacgggga cgacttagtc tgggattatg aaaatagccc atatccaagc    3480
atagtttcct cactattccc gggggaagaa acggactcgg caatttgtaa ctctgttgtt    3540
gccgcaaacc cctgtagcat acctcctggg cggcagcgtt tggcatggcc atgctgctgt    3600
tttcgtcggc cagacagctt ctccgtcccg cgcgtggaag ttaatgctcg ccttgttgcc    3660
gcggttgcac tgataatttt ctcattgctt gtagtgatct gtgttgcgtc atattggggg    3720
taacatgtct tcagaggaca catcgggatt cctaacgccc cccgcaagtg atgacgacac    3780
tgacccttcc gagccaccac caaatttatg ggatcctcac caggacgatt ttccgaggga    3840
cgctgattcc ccaaacccac ttttctaccc ctgggatgac tctgtgaata atactgggga    3900
tacgggcagt aacgaagatg actatgtaga tatggagggg gtaggtggat ccgaagacta    3960
tgaagacctc ggtacgggcg gggactctga ctatgacaat gtatctacag cgaccggcgg    4020
gacgtggttt ccttcccttg cttcttggtc atcagaggac cacggcccaa cttctccgga    4080
aaaccctatg caacaacttc aagtaacaat tcagcaggat tcagatccac agcaggaacc    4140
cgatccccag caagttcccg gtctccagca ggaacctgac cccagcaag atccacgaga    4200
gcctcgtgat cctcctccct atagtccgcc cccagaggac ccttttgggc tctcgccatt    4260
tactagtggg atgggcgggt ttgggccacc gccacggtgg cccagccac cctcgtatga    4320
tgaggcaatg ggggatggac ctttactac gactgggggt cggcgaccctt gctcacgcag    4380
gcgcggtcgt cgccggtctc gaggtcgatc tcggcgacgc aattggtgtg cagcaaagtt    4440
gtgctcagag gcatgtttgt ggcatctctt ttgggttgga gtggccttaa tgtgttggtg    4500
gctcttgtat cttattttgc gcattgtctg gggacagact ccgggataag gaaggttgta    4560
tccgcatcca gtactcctca ataaaagcgt ggtggtgcta cacgatgtct gttaattta    4620
caactccatt ttacaggtga tctagagaga cgctgagtgg cacttgtccc gacgggacc    4679
atg cag tcg aac agc agc gat gag gcc cag tgt gat gat gtc gag gag    4727
Met Gln Ser Asn Ser Ser Asp Glu Ala Gln Cys Asp Asp Val Glu Glu
1               5                  10                  15 gga tgg tcg tcc ata gct cca ggt gat gca ctg gat aca gat ttc att    4775
Gly Trp Ser Ser Ile Ala Pro Gly Asp Ala Leu Asp Thr Asp Phe Ile
            20                  25                  30 cca ggg cct tgt gcc acg tcc ata cat ggt ata tcc aag gca gtt tat    4823
Pro Gly Pro Cys Ala Thr Ser Ile His Gly Ile Ser Lys Ala Val Tyr
        35                  40                  45 ttt ttt ctg tgt gga gtt aat ctg gag gaa tgt agt aca ctc cca cag    4871
Phe Phe Leu Cys Gly Val Asn Leu Glu Glu Cys Ser Thr Leu Pro Gln
50                  55                  60 cat gtc caa tct cac cca tat gga cat cct gag ctg aaa tca ggc aaa    4919
His Val Gln Ser His Pro Tyr Gly His Pro Glu Leu Lys Ser Gly Lys
65                  70                  75                  80 tgg tac aag agg ttt tgc tcc ggg cta ggc gaa att gga gat aca agc    4967
Trp Tyr Lys Arg Phe Cys Ser Gly Leu Gly Glu Ile Gly Asp Thr Ser
                85                  90                  95 cag tgt cag ctg aca cga cta tgc tgc act tcc gga atg ccg gca cag    5015
Gln Cys Gln Leu Thr Arg Leu Cys Cys Thr Ser Gly Met Pro Ala Gln
            100                 105                 110 att ttt ggg cct tcg aga ttc agg tct ctg caa cag aag cca acc cat    5063
Ile Phe Gly Pro Ser Arg Phe Arg Ser Leu Gln Gln Lys Pro Thr His
        115                 120                 125 atg cgg gcc caa gat ttg ctc act agg cct tgc cat ata cta gag ttc    5111
```

```
Met Arg Ala Gln Asp Leu Leu Thr Arg Pro Cys His Ile Leu Glu Phe
    130                 135                 140 gat gtt ggc gct gac cta atc aat ctt ttc ttg tat atg gaa cca tgt    5159
Asp Val Gly Ala Asp Leu Ile Asn Leu Phe Leu Tyr Met Glu Pro Cys
145                 150                 155                 160 tca ggg aat cga tat tgc gta cat tta gga tac cat aaa act aat gcc    5207
Ser Gly Asn Arg Tyr Cys Val His Leu Gly Tyr His Lys Thr Asn Ala
                165                 170                 175 atg cgt gtt ttg agc ggt ggt ggg att cta tgg ggc aga ctt ccg tgg    5255
Met Arg Val Leu Ser Gly Gly Gly Ile Leu Trp Gly Arg Leu Pro Trp
            180                 185                 190 aag gac aac acc gag gag cac ggg tac tcg ttg cct atg cga gta ttt    5303
Lys Asp Asn Thr Glu Glu His Gly Tyr Ser Leu Pro Met Arg Val Phe
        195                 200                 205 ggg atc aaa ttg ccc cat aaa gtt tat gtg gca tgt cgc tgc cct gca    5351
Gly Ile Lys Leu Pro His Lys Val Tyr Val Ala Cys Arg Cys Pro Ala
    210                 215                 220 act cgg acg gaa cta tta ttt ggt gag ggg ggg gta gga ttc aac gcg    5399
Thr Arg Thr Glu Leu Leu Phe Gly Glu Gly Gly Val Gly Phe Asn Ala
225                 230                 235                 240 gaa aac ttt aaa cag tgc gga cgg ttg aaa aaa gag tgt gaa tgt ctg    5447
Glu Asn Phe Lys Gln Cys Gly Arg Leu Lys Lys Glu Cys Glu Cys Leu
                245                 250                 255 cag aag gct tgt ttt act gca caa acg gtg tta ggt gcg gca tat aag    5495
Gln Lys Ala Cys Phe Thr Ala Gln Thr Val Leu Gly Ala Ala Tyr Lys
            260                 265                 270 ttt act gta tac tcg agc aag gga cga ggt caa gaa att ctg cta tat    5543
Phe Thr Val Tyr Ser Ser Lys Gly Arg Gly Gln Glu Ile Leu Leu Tyr
        275                 280                 285 tca gga ccc atg aat gct aca acg gta atg cct gta gta ctg ggt atg    5591
Ser Gly Pro Met Asn Ala Thr Thr Val Met Pro Val Val Leu Gly Met
    290                 295                 300 tta agt aga gaa ccc cac agg tgt gca ggt aca ctc ata ctg tcc agg    5639
Leu Ser Arg Glu Pro His Arg Cys Ala Gly Thr Leu Ile Leu Ser Arg
305                 310                 315                 320 tcc tct gga aat tgc cgt gga ttt cat gag acc caa cac gat att ccc    5687
Ser Ser Gly Asn Cys Arg Gly Phe His Glu Thr Gln His Asp Ile Pro
                325                 330                 335 act aac ccg ggt ctg tat cct ctg tgt aat cat gag cac cct tac tat    5735
Thr Asn Pro Gly Leu Tyr Pro Leu Cys Asn His Glu His Pro Tyr Tyr
            340                 345                 350 gtg aca gtt aca gat gta tgc ggc aac tgt tgt tca tgg ctt gag cgg    5783
Val Thr Val Thr Asp Val Cys Gly Asn Cys Cys Ser Trp Leu Glu Arg
        355                 360                 365 gtt ttt ggg aga gta gct gcc cct gct ggt cta agc tcc gta tct gta    5831
Val Phe Gly Arg Val Ala Ala Pro Ala Gly Leu Ser Ser Val Ser Val
    370                 375                 380 tcc att aaa ggc tcc acc cac agc ggg act gac gtg aca gaa gaa cgt    5879
Ser Ile Lys Gly Ser Thr His Ser Gly Thr Asp Val Thr Glu Glu Arg
385                 390                 395                 400 gaa gag gac tca ggg aca cag caa acc tcc cac gac aaa ttg ccg gag    5927
Glu Glu Asp Ser Gly Thr Gln Gln Thr Ser His Asp Lys Leu Pro Glu
                405                 410                 415 cgc aac cgc atg gga gat caa aat tcg aat ttg cgg gga aga gat caa    5975
Arg Asn Arg Met Gly Asp Gln Asn Ser Asn Leu Arg Gly Arg Asp Gln
            420                 425                 430 tat tgg ccg cct gcc cca cac cgt agt cat tgt cac tcg gat ttt ata    6023
Tyr Trp Pro Pro Ala Pro His Arg Ser His Cys His Ser Asp Phe Ile
        435                 440                 445
```

```
ttc gat gaa cct gag cca gaa agt ggg gaa gac gtg cat aac atg cat      6071
Phe Asp Glu Pro Glu Pro Glu Ser Gly Glu Asp Val His Asn Met His
        450                 455                 460 cct cca cga ggt gca gat gag caa aca gcc gct tct gtg tca gcg cta      6119
Pro Pro Arg Gly Ala Asp Glu Gln Thr Ala Ala Ser Val Ser Ala Leu
465                 470                 475                 480 atg caa agt cta gca caa gca ttg gtg agt gca caa gct att agc agc      6167
Met Gln Ser Leu Ala Gln Ala Leu Val Ser Ala Gln Ala Ile Ser Ser
                485                 490                 495 atg gtc tct ggc tct gct tcc tca gtg ggc gta gaa gta gac tgt ggg      6215
Met Val Ser Gly Ser Ala Ser Ser Val Gly Val Glu Val Asp Cys Gly
                500                 505                 510 tac agt cag act cat att aca gag ggg ccg ggg agg gaa caa ttc ggt      6263
Tyr Ser Gln Thr His Ile Thr Glu Gly Pro Gly Arg Glu Gln Phe Gly
                515                 520                 525 aga gtc cca gaa aga ggg cca gag tat cct caa gat tac tgt gat ata      6311
Arg Val Pro Glu Arg Gly Pro Glu Tyr Pro Gln Asp Tyr Cys Asp Ile
        530                 535                 540 tat ggt cct gta agt aat ggg cct gct gga tac aga gca gga cca cca      6359
Tyr Gly Pro Val Ser Asn Gly Pro Ala Gly Tyr Arg Ala Gly Pro Pro
545                 550                 555                 560 gat gct cct agt ata caa gat agg acc ttc cca tgc ggc aga aga tgc      6407
Asp Ala Pro Ser Ile Gln Asp Arg Thr Phe Pro Cys Gly Arg Arg Cys
                565                 570                 575 gac gaa gca tgg ctt gcc tta gaa gta ggg aat atg cct tgg att tct      6455
Asp Glu Ala Trp Leu Ala Leu Glu Val Gly Asn Met Pro Trp Ile Ser
                580                 585                 590 tct ggt tca cat agt cca cct tct cag tat cat aac cct tat ggt tca      6503
Ser Gly Ser His Ser Pro Pro Ser Gln Tyr His Asn Pro Tyr Gly Ser
                595                 600                 605 cat agt cca cct tcc cag tct cat aac cct tat ggt aca tat agt ccg      6551
His Ser Pro Pro Ser Gln Ser His Asn Pro Tyr Gly Thr Tyr Ser Pro
        610                 615                 620 cct tct cag tct cat aac cct tat ggc tca tat agt ccg cct tcc cag      6599
Pro Ser Gln Ser His Asn Pro Tyr Gly Ser Tyr Ser Pro Pro Ser Gln
625                 630                 635                 640 tat cat aac cct tgt ggt aca tat agt ccg cct tct cag tct cgt aag      6647
Tyr His Asn Pro Cys Gly Thr Tyr Ser Pro Pro Ser Gln Ser Arg Lys
                645                 650                 655 cat gac tat tca cct cca tat ccg ata ctc aaa cca aag cct cga tta      6695
His Asp Tyr Ser Pro Pro Tyr Pro Ile Leu Lys Pro Lys Pro Arg Leu
                660                 665                 670 ccc cca ggc ttt gaa aat act gct ggg atg tgg cct cga tgt ccc cct      6743
Pro Pro Gly Phe Glu Asn Thr Ala Gly Met Trp Pro Arg Cys Pro Pro
                675                 680                 685 ggg ttt gag ggg cgt cca tac aaa tct ggg ggc atg ggt aac ttt cct      6791
Gly Phe Glu Gly Arg Pro Tyr Lys Ser Gly Gly Met Gly Asn Phe Pro
690                 695                 700 gga agt gca tgg acg gta ata gat agg ggg tct aac caa tgg cca gca      6839
Gly Ser Ala Trp Thr Val Ile Asp Arg Gly Ser Asn Gln Trp Pro Ala
705                 710                 715                 720 gac gtg cgg ggg cca ttc tca gat caa cga tgg gcc ccc aca gag cat      6887
Asp Val Arg Gly Pro Phe Ser Asp Gln Arg Trp Ala Pro Thr Glu His
                725                 730                 735 gaa acg cga cgt ttt tgc ggg tat tac agc tga gctctcatca tacccataac  6940
Glu Thr Arg Arg Phe Cys Gly Tyr Tyr Ser
                740                 745 tccactcata acccaaggcc cataaatcca taactcataa cataaattca tactttccgg     7000
tcgtccaggg caccacgtca tcaacaagga ttgcagataa ataaaaatgc tccacgttgt     7060
```

```
cggtgtccgt tgtattgtat tctttattat acctccgtaa ttttcgagag tcggggaaca   7120
ttctaaaaat tttaaccgtg caatactaca gtgtatttac aaggccggat tgcaacagtg   7180
aactcattac atcattgagc tcgcggcgcc atctgctgac cagtccacag agatggcaat   7240
cttcagaaac gtaggatggc accaattcca atacaatacc gccatctgtc gataggtgta   7300
tagaactgtc aaaacaagtc gcaagagaaa aatttcccta ctgtatactg gcggcttagc   7360
agctgcgcac aaaccactct gcattcctct ttgcggcaca catttgcgtg ctgcgccaga   7420
acgagtggga ttttttttaga acaggtccca ggatagtaca tgtcccacaa tgttctggcc   7480
gggtctattg ctttatgatt catgactatg gcctctggtc gcggatacac aattcttgag   7540
aaccggtcga agaaggtcag taataaagtt aaaggacatt ttgcgctact cagcgatagc   7600
tcctgagatc tagtggtatc tcttagttga ctgccaatgc tagagagata cacggcagg    7660 attggcccca gatgcatggc tagagattga catgcgcagt agatgttaga agagatagga   7720 tcgtggggggt aaatcctttc atcttcgaac tgatgccaaa gcatccatac aagtgtctca   7780
tcgcatgcaa aaagtagctc ttcaaatgag cagttcgcca aatatacagc tcgtgaaatt   7840
tttgccaacc tggctatatc cggacgcgat gtccagcggc cttttcagtga agctgcgcgc   7900 ccacaaaact gcttccacga agtgaatgca gcatctgctg caaggtcaga tgatcccgaa   7960
gacaaaaatg ctggaaagca gattcctcta tcacgatcga tatcatcaca atcatcatca   8020
tccactgccc ggtttaccat gtctaaaaga catttctgat tttctaatct taactcttca   8080
gtaatgcact ttccgagacc gccaaatgca gttgcggcct tttcaaaata ttgggccggt   8140
gttacgtttc gcaactcctt cgtttcggtc cgtgatgacg ttgggcatcg acaaagtct    8200 ctccaaatcg gtcttcgaag ttcatcccga tttctttccc aagacctgcg cgaatgcttc   8260
aacgaaacag taaagatagg cgccctatat cgcttttctg gtgtacctgc acggcgcctg   8320
ggtctagggg ggatgcctct tcggacttgg atatgcgcac ggcctctcat aaacttattt   8380
cgagggctac tgacccgcct tatggaagac cgtacgctca tacctgactg gttctcgtaa   8440
cgggaacgag gctcgccatt cgaatagcga cggcgccccc tgtcacgtga atcacggact   8500
cgtttccagc taccgcgccc agatgaccgg gatctggagc tactttctgt agaatgagat   8560
ctgcggcgaa tacaatgtgc ttcgtggcgg gattctgacc tcgagcgtga acggccatcc   8620
aggcgatctt ttgtcctttc cgttgctgat ctcgcttcgc tatgagtact tgtattggaa   8680
gatgatctgg aacgtgtctc acgcctatct ttatttattc cagatttctc cggtctcccc   8740
atcgcagtca gtgggttgat gtaccgcgtg cacgtcaaaa aaaatgaaac cgcacacaca   8800
acggttgaga cttctacgga ctcagaacag gtgtcaagct cggagcaggt gctgagaggt   8860
aagctgacag taatctggca cgctgtttgc gagctaatcc acttggcttt tgaatggtct   8920
gggccactcc cagtatacgt cataacacat acactggaac ccacaaacta caattgcggt   8980
ccagtagttg gtgcgaaata ttcacgcaga cataataatc tgcgagaact tctgcggatc   9040
cgacatgtaa cttaatcccg taatgtagtg cggcataccg tctaaaccgc aaacatccgc   9100
ttagtagaac acgccctaaa atcacccacg agtatacttt gtacattctg accgccagta   9160
gttactcctt tcaaacaatg atactcagcc gttagaacta gggctgtctt caaatggacc   9220
aaattcagac acaataccgc acaacgtgtt ttaacatttt attgccgttc aaggcccgaa   9280
caatttgttt tgtatcttct gttcgtattt aaatgcaatt attacaatgc tcgcaatcgc   9340
agccacgcac aatgcacgca agactaagct cgaagcaata ttggcaaggc atgaagtcaa   9400
```

-continued

| | | | | | |
|---|---|---|---|---|---|
| gatactggga | ggtttcgatg | cggagacttt | agtctttgcc | ggagtcgtgt | aagggatcag | 9460 |
| tgataagagt | tctagaaccg | ctgagacaat | tacatatacc | caagcactaa | tttttacgtg | 9520 |
| ttcatgtaaa | atatatgcac | acggatcata | gcaaatccgc | aatgtcatgg | tggacataat | 9580 |
| aagcgatgct | aaatataaac | cgatctcgag | tgttttcagt | agtaagaccc | ctggattaca | 9640 |
| gacgcaaaat | cctagagggt | ctgctacgta | gttcaagctt | ttgcaatctc | ggagatgttc | 9700 |
| aaattccctc | aaaaaccgtt | gcatctttgt | gtatggcacc | cgtaatatca | gcctcgaagt | 9760 |
| aaacgctgtc | cagtagttaa | gatgatatgc | atccatcgca | atgcgttctc | gcggcagaca | 9820 |
| tagcccgaac | attcgcctct | ggcgacgggt | cagcaagtaa | catatgtaca | ataccgtcga | 9880 |
| aatgaatgca | actctgatct | gggaaaacca | tatgtaaagc | agacagtctg | ccacttccat | 9940 |
| gacgaatact | gttctttggc | cggtgggatc | aagacgagaa | atgagtacag | tctcattttc | 10000 |
| aaaataagct | cctttaacac | atctcgtctg | gtggttctcg | tagttgttta | gacgctgtgt | 10060 |
| atattttgtg | aggacataaa | ctagtgaaga | attaaatgta | gcgggggggtt | ggtgaacagg | 10120 |
| attgaattct | tgctgtccgg | gcaggagcca | tttaatattt | gcgagtacgt | acaagcagtc | 10180 |
| gtcctttgag | tcagtggaaa | ttttagagca | tacataccat | accaagaaga | ctatatgtat | 10240 |
| cgttccggtt | aaaattactg | cccatttttag | acattctggt | cgcagcattc | tttggtcaga | 10300 |
| cgcactgtaa | actgagtttg | cagcgtgttg | cctccgcact | tagtcgcaaa | gcatttggtc | 10360 |
| tgaaatgccg | cgtagggatt | gccctgtgag | ttaattgcaa | ccgctacaga | agtaatgacg | 10420 |
| gtctgggcag | cggcacttcg | atgcgaatgt | ttaaggcagg | taaaagttgc | gcgccctccg | 10480 |
| caccctcgac | gatttcgtaa | tagtgatgcg | gtaatgcgcg | ttttgagcac | ccgcacgtct | 10540 |
| ccaaaactaa | tgtcgctgta | ttcgtgcgcc | aacgatggaa | aatgctcttt | tatgtaattt | 10600 |
| gttatgccg | gcagaacata | tgtcgtgagc | acaaagactc | catcgatcgt | atccaccccg | 10660 |
| gctcctgtcc | tgtcttcgca | cggtgctaaa | ttgacacgac | tgaatgcttc | cgcgaggcta | 10720 |
| agagacacag | ccgtttgggg | caagttgcta | gagggttttg | aaactccccc | tataacgtca | 10780 |
| ggaggacacg | cgattcgagt | gacgataata | tttggggtgg | gattgtctgg | acggaaagca | 10840 |
| tgaaaatgga | aattattagg | gtcttttgtgc | gctgccgcga | aagctacttt | atctgcacag | 10900 |
| tcagggggga | aaattataaa | cggcaggagt | ctcccagaca | tgaatccgga | ttcagaaacc | 10960 |
| ttggcaaaga | aaggtagccg | gagacttcgt | cctggcgagt | agattccagt | gtcaataaag | 11020 |
| tcatagtctc | tgataacatc | gtctaaacat | tcaatgattt | cttcctgcag | taaaattacg | 11080 |
| tgctgagcta | gcttcgcgat | agttttact | gtctctagac | caaacaaagc | atatggggat | 11140 |
| gggattggga | cgcagactct | gaacccgagc | ttttctttgc | atttgcataa | ggttgaattg | 11200 |
| gcacgatccc | gaaatacatt | taacgcatcc | tgtaagtctt | gaacagagac | tatggctcca | 11260 |
| tgttcactcg | catgctcatc | acaccatgac | atttcttcta | cccagccgct | atcgcagagg | 11320 |
| tacatgttct | cttcgtcttc | tatgtcatca | gaacatgtat | tctccaaaaa | atcaatatcc | 11380 |
| actgaggaat | attgtgcgtc | atggctctcc | ggggacgagc | agtgactttt | gtaaaagtac | 11440 |
| acgggatagg | tgtcatgact | gattgatgtc | tccggaaaca | ataaggctat | taattggatc | 11500 |
| aatgccacgc | gcacggcccg | catcgcttta | tgtaaggtca | acatcgttat | ggggccgtga | 11560 |
| tctagcttga | ggggtatgtc | gatatccagt | atcagggatt | gaattgctag | agattcgtta | 11620 |
| aggacttcat | tcctattcag | gtacatttgt | gacagaccgc | tgcaagatgc | ccgaatttta | 11680 |
| ttttcgaac | tagttcccca | tgcggtttcg | ttcattgcac | tagtccaagc | aaagtctatt | 11740 |
| actggcaaca | tggcctgatc | tgcgaggggg | gcatcactgc | gcattagtaa | gcaggagtcg | 11800 |

```
tgtatgctgg tgtcagatct tacatcagcg gttataatcg agtcccactc atcgctggca   11860
atggctgcaa aagcctgtcc gtgtccagcc aatgttactc tgtaaacggg acatggtccg   11920
ttcctagctg ttggtggagg aatgcttgtg ggtttcagag aatggaataa gagtgtcact   11980
ggtcgctttc cgcaaataac ttgatcagat gaaacgagag aaagtaacct acttaaggga   12040
gcaaaaatga tatctcctgt cttacagtat tgcccgtcgc gctctctttt ttgtgcaagg   12100
gcgtgtggag cggaagcatc atctccttcc tcttcttcct cttcttcctc ttcttcctgt   12160
tcattgctag atacagtgct cacatttctg accagcatgt cagccaagtg tgcccgtag    12220 cgacagagag tatcggaata tagacggtct atacgcgttg atacatcaaa tgcggaacga   12280
caaaaaccaa gaaaattgcg cccctgtatt tcaccgtaag atttttatagc tgcaaacttc   12340 cctgctacta cagccggcaa tttcatgact tgcatagtca catgctgtct gaagtacgaa   12400
gcaaaattac aacattccct taagctttta aaaaaatcac tttgagcacg agcagaactc   12460
ttaactggat tggtgagatt ttcagaaaga cattgcaagt gttctctaat cacgtttcgt   12520
ccatatcctt cactgtaagc taaatataca aatgagatga agtcacgagc tggaagccgc   12580
agggcatgtc tgtatttgca gataagtgct tccaattgtt ctgaatagcc cctgtcggcg   12640
ctagtacgta atctcaaatg atctctgaat agctttgcag attcgcgagt ggcatagtag   12700
ctgctgcacc agaatttaga aaacgcagag aaggacgtta ggcgcgctat agtcaggtta   12760
ctcctgttgt tgctattctc cgtttgaaat gtaatgcata gatcctttac tgcttgaagg   12820
tcaaacgtcc cagcaatacc atcgtcaggg gttgcttcta acaagtaata tctcatggct   12880
gcaacaaggg taatttctga cgggccgaat tttgatacga accaaaaggg gttcgaaaag   12940
ttcgagttgt aaagcctcct gtatgcggca atcacccttg actcatgctg aagcatcagg   13000
ccctccaggg caggtcttcc tctgggtaga gtcgcatgta tggcagaaaa aggaattttg   13060
ttggttgtat tttctgctcg gaaaattact ccgagtgcct caataatgtc cgtgtgcaat   13120
gcaaatgttt cctccaaatc catggtttcc agtaataact ttgcatcgat tggaaaccct   13180
tcggctaagg cttctctcat agttgcggcc ccttgaccga caaaacgaca cacaaacact   13240
ggtctagacc tctgcctgta cttctccgct ccggtattag caggaaggaa gaacgtgatt   13300
ttgagagggg aatctttgca aaaatcttgc gctagagcgt caacatgact aaaggccaga   13360
acataaattt caggctgcag ggcttggccg agtagaaggt gcaggagca tactactgga    13420 tacccatccg tagcatacaa cacgcgaatc tcttcgtacg aaacatcctc actaggggga   13480
gcgccgcagg gttcacaata tccagcttgg gaagtctctg tctcatttag catttcgacg   13540
agcatccagt catctgcctc atactcccat ttggcgtctg ggacacagtc gaagttcatg   13600
atagcaagga aatgtggcag ctactgaaga gcgtgttctg cggccggtct aactcagaga   13660
gtaaatacga agcccttcca actgggcggt gcctgcccgt agatgatcga aaagtacagt   13720
cggctgtgaa gcttattaaa atctttatcc ctaactgctt ggacgtcgaa gatgtcatcg   13780
gctcgaggga tgaacttaac aaactcgctc aagccaggca aattagccgc attctggcaa   13840
aatcggccgc ggctatgcag attgctaaga atatgagatg cccgcgagga gcagaggcgg   13900
ttttgcggca aacgattgtg gacaatggga cggtatttcg ttctctgtac tctgtactag   13960
cctacctata tctctcccct ggggcagaca cggatggact acttgcacaa gtaaccgctc   14020
aaaccgcaga caggacgatg atgctaggtg acatgaccgt gcttacacat gcaatgcacg   14080
tagacggaat ggatcgtgac catagctctt tggaactact gcgcatgggt ctggtaccaa   14140
```

-continued

```
attcagacct gaaagatcca atcgagctcg tgccggtaat tgataaactg cctgacaagg      14200
tactgttccc tgatcccgta ccgacactgc cagttgaaaa cccacccatg gagcgtacta      14260
gacctgcaaa gacacgtaaa gaactggttg ctgcgagtta agtgacttct cagcgcttta      14320
ataaagtatg tttaaatttt ccaatgtcag taca tta ttt gcc ggt aga tcc aaa      14375
                                 Leu Phe Ala Gly Arg Ser Lys
                                                         750 ccc ccc gtc acc ccg aac cga caa cgt att gcg ttc gtc tac tac tga        14423
Pro Pro Val Thr Pro Asn Arg Gln Arg Ile Ala Phe Val Tyr Tyr
        755                 760                 765 gtt tac tat ttt cca gcg aag ggc atc tgg ctc tcc gag aaa ggt gct        14471
Val Tyr Tyr Phe Pro Ala Lys Gly Ile Trp Leu Ser Glu Lys Gly Ala
770                 775                 780 tct ctt ctc agt aac tat tag ctg tgc cac tcg gtc acc tgc gtg aat        14519
Ser Leu Leu Ser Asn Tyr     Leu Cys His Ser Val Thr Cys Val Asn
785                 790                 795 act ggc cgc ttc atc tcg aat gtt agt tag cga aaa tga tat cca atc        14567
Thr Gly Arg Phe Ile Ser Asn Val Ser     Arg Lys     Tyr Pro Ile
800                 805                             810 att atc ctg cac atg tat cgg gtc gac taa cag tcc ttt cag att cat        14615
Ile Ile Leu His Met Tyr Arg Val Asp     Gln Ser Phe Gln Ile His
815                 820                 825 gga gga tct ccc tag tat gaa tgc gcg cca gaa agg tcc gca tgc tag        14663
Gly Gly Ser Pro     Tyr Glu Cys Ala Pro Glu Arg Ser Ala Cys
830                 835                 840 ttt ttg ggg aag ggt aat acg ggt aga cga ctt tgg aag aat tgt tac        14711
Phe Leu Gly Lys Gly Asn Thr Gly Arg Arg Leu Trp Lys Asn Cys Tyr
            845                 850                 855 atc ttt agt agc tct aat atc ata gcc tcc atc tcc tgg acg ttt ggg        14759
Ile Phe Ser Ser Ser Asn Ile Ile Ala Ser Ile Ser Trp Thr Phe Gly
860                 865                 870 ggc aaa gat ttc gtt aaa cgg aaa cag tgc ggc agg gca atc tgg atc        14807
Gly Lys Asp Phe Val Lys Arg Lys Gln Cys Gly Arg Ala Ile Trp Ile
875                 880                 885                 890 tga tcg cag ctc gac tgt ctg atc ttt aac gag cga tcg tgt agc tcc        14855
Ser Gln Leu Asp Cys Leu Ile Phe Asn Glu Arg Ser Cys Ser Ser
                895                 900                 905 gac gat gat atg gtg tcg cac ctg ggc tac aaa ctt gat gtt cga tgc        14903
Asp Asp Asp Met Val Ser His Leu Gly Tyr Lys Leu Asp Val Arg Cys
                910                 915                 920 gcc aca aaa acg att gat att ttc tgg cgt cgc tcc att cag tat aac        14951
Ala Thr Lys Thr Ile Asp Ile Phe Trp Arg Arg Ser Ile Gln Tyr Asn
            925                 930                 935 gat gcg ttc att gca ggc tgc atc ttg ctc ctg caa ttc ttc gaa tgt        14999
Asp Ala Phe Ile Ala Gly Cys Ile Leu Leu Leu Gln Phe Phe Glu Cys
            940                 945                 950 tct tct gta aaa cgt tgt aca tcc cat aca acc aat gtt gcc cgg aat        15047
Ser Ser Val Lys Arg Cys Thr Ser His Thr Thr Asn Val Ala Arg Asn
955                 960                 965 agt tat ttt cgc cct taa tat atc tgg agg tat act taa aag gga act        15095
Ser Tyr Phe Arg Pro     Tyr Ile Trp Arg Tyr Thr     Lys Gly Thr
970                 975                 980 tat aca ttt ctc gaa acc ttc acc caa ata atc atc ttc gcc ttg gaa        15143
Tyr Thr Phe Leu Glu Thr Phe Thr Gln Ile Ile Ile Phe Ala Leu Glu
            985                 990                 995 aga  atc tgc ggt ttc taa  gag  tag gcg cgc gta tcc cgt  ccc aca        15188
Arg  Ile Cys Gly Phe      Glu      Ala Arg Val Ser Arg  Pro Thr
1000                 1005                             1010 ctt gct aag  cat gga atc gtt agc  caa ctt tat aac att  tag ccg         15233
```

|  |  |  |  |  |  |  |  |  |  |  |  |  |
|---|---|---|---|---|---|---|---|---|---|---|---|---|
| Leu | Ala | Lys | His | Gly | Ile | Val | Ser | Gln | Leu | Tyr | Asn | Ile | | Pro |
| | | 1015 | | | | 1020 | | | | | 1025 | |

| agc | cct | tac | agt | gcc | tgg | tgg | aaa | tat | aac | att | tcc | gtc | tct | tgt | 15278 |
|---|---|---|---|---|---|---|---|---|---|---|---|---|---|---|---|
| Ser | Pro | Tyr | Ser | Ala | Trp | Trp | Lys | Tyr | Asn | Ile | Ser | Val | Ser | Cys | |
| | | | 1030 | | | | | 1035 | | | | | 1040 | | |

| ctc | tgt | gcc | agt | caa | aac | att | ccc | gcc | atc | gtt | tac | aag | tac | tac | 15323 |
|---|---|---|---|---|---|---|---|---|---|---|---|---|---|---|---|
| Leu | Cys | Ala | Ser | Gln | Asn | Ile | Pro | Ala | Ile | Val | Tyr | Lys | Tyr | Tyr | |
| | | | 1045 | | | | | 1050 | | | | | 1055 | | |

| cag | tat | tcc | caa | taa | tcc | tgt | ata | gtc | tgc | atc | tac | caa | tcc | tgg | 15368 |
|---|---|---|---|---|---|---|---|---|---|---|---|---|---|---|---|
| Gln | Tyr | Ser | Gln | | Ser | Cys | Ile | Val | Cys | Ile | Tyr | Gln | Ser | Trp | |
| | | | 1060 | | | | | 1065 | | | | | 1070 | | |

| aat | aat | ttg | ata | aca | tgc | agc | atg | gcc | ttc | cac | atc | act | gat | aac | 15413 |
|---|---|---|---|---|---|---|---|---|---|---|---|---|---|---|---|
| Asn | Asn | Leu | Ile | Thr | Cys | Ser | Met | Ala | Phe | His | Ile | Thr | Asp | Asn | |
| | | | | 1075 | | | | | 1080 | | | | | 1085 | |

| gat | tcc | ata | ccc | gac | tgg | caa | aga | agt | cct | aat | cgc | aga | atc | aat | 15458 |
|---|---|---|---|---|---|---|---|---|---|---|---|---|---|---|---|
| Asp | Ser | Ile | Pro | Asp | Trp | Gln | Arg | Ser | Pro | Asn | Arg | Arg | Ile | Asn | |
| | | | | 1090 | | | | | 1095 | | | | | 1100 | |

| tct | tag | gac | ggg | aga | gtc | ggt | gcg | tgt | ttt | cgc | tat | tgc | tgc | ttc | 15503 |
|---|---|---|---|---|---|---|---|---|---|---|---|---|---|---|---|
| Ser | | Asp | Gly | Arg | Val | Gly | Ala | Cys | Phe | Arg | Tyr | Cys | Cys | Phe | |
| | | | | 1105 | | | | | 1110 | | | | | | |

| aac | gtt | tgt | aat | gac | aca | ttg | caa | gga | atc | gag | | gcc | aaa | aat | gtc | 15548 |
|---|---|---|---|---|---|---|---|---|---|---|---|---|---|---|---|---|
| Asn | Val | Cys | Asn | Asp | Thr | Leu | Gln | Gly | Ile | Glu | | Ala | Lys | Asn | Val | |
| 1115 | | | | | 1120 | | | | | 1125 | | | | | | |

| cca | ccc | aga | tcc | aat | ctc | tat | taa | tgc | att | ttt | ttc | cgt | tgt | cat | 15593 |
|---|---|---|---|---|---|---|---|---|---|---|---|---|---|---|---|
| Pro | Pro | Arg | Ser | Asn | Leu | Tyr | | Cys | Ile | Phe | Phe | Arg | Cys | His | |
| 1130 | | | | | 1135 | | | | | 1140 | | | | | |

| ttc | cat | | ctc | cat | gcaagttgct | tagacgccaa | aataacaccg | accctttcag | 15645 |
|---|---|---|---|---|---|---|---|---|---|
| Phe | His | | Leu | His | | | | | |
| | | 1145 | | | | | | | |

| gaaatccgcg | tagttaaaat | cggcagtaga | ccggtaggat | acaaatagta | ccgcactgcg | 15705 |
|---|---|---|---|---|---|---|
| cgacttagag | gacccgtgaa | agagactgca | gggcgagctc | tcgcaaaaga | gcaatgaggc | 15765 |
| tgccgtggga | aaggagtttt | atgctgttgg | gagcagtggt | gtatttgctg | catttggcac | 15825 |
| tagtattcgc | gcaaccgggt | gtgacaccag | gacacggaat | ggagcatggg | tattatggtc | 15885 |
| ttggcgctgg | aaatatgctt | ggagcggaaa | attcgatgta | tagcgcgaac | atggaacact | 15945 |
| tttaccacag | tgcctgctcg | tcgcgcggat | tttccttagt | aaacggaaca | gctgcttccg | 16005 |
| tttttctttt | cattagcctg | gcagtggcgt | tgattggcct | gctggccgtg | ctatataacg | 16065 |
| gttgtttcaa | cagctttaaa | agcagtgtca | ttagttctcg | atggtagcgc | agtatctgct | 16125 |
| gtaaagacga | aaacatcggt | ggtgggacca | tattagctcg | aacactatgt | cttactacaa | 16185 |
| agatctctcg | gaggaggcga | agaagtatca | cgacgatact | cgacggaggc | gagataccac | 16245 |
| cacccgccgc | cccaaaccac | cccaattcga | acacccctgg | tctgggcgaa | gaacatctcc | 16305 |
| atatctagat | ttggatagag | gaagcgattc | tgattcttca | gaaggggatt | acggccatcc | 16365 |
| atcgcgcgct | cactattcga | gagatcatac | ggcaccgcct | caaggccgcc | gaagcccccc | 16425 |
| gatggaaagt | tttcgcaaag | aaaccactcc | aaaggaggag | cccccctcaaa | gtaaagggg | 16485 |
| ctggaatcct | gataatcatt | gcgctggcct | gatgcgacgt | ttaactatct | ctaagggatt | 16545 |
| tggtcctagt | gctacaccct | caggggatga | agacccatgg | catacttcta | ctattccagc | 16605 |
| aaatcgttcg | gccttcgtgc | aagccgtctc | tgtgacggca | atggcccagg | cagaattggc | 16665 |
| agcgagagag | gtgtgggacg | taacaaaacc | acgcacgaat | agggagttga | gggatatggt | 16725 |
| gagagagcta | gaaatcacta | taattatcaa | tccgggtgaa | tctttatggt | ctgttgccac | 16785 |
| ttcggtggca | agagcaatca | aagaaggaac | cccaataacc | cacgagctat | tgcagaaaag | 16845 |

-continued

| | |
|---|---|
| accatcaaag cctccaaccc gccgcaaaac tgaagatgga gccagaaaga gttcttcaag | 16905 |
| gccttctcaa cccaagcctg agcatttccc ccctccaaga agaaagacat ccgaacgaaa | 16965 |
| gtactagttt cgagagtctt tgcattactg tgttcctcgc catatttgta acaataaagt | 17025 |
| atacttatga ttggtaacat gcgtgtattg tcatgtgttc atagactata aaagcgccgt | 17085 |
| gatttacatt tctgcgcaca ctgcgcagaa ccatggaaga agaatcttcc actggagcct | 17145 |
| ttgcactgta tgaagtcgaa gacttcatcg aggaagtaga atctgggggct ggggggaggt | 17205 |
| gcagcgattt tgaggatgat gcgactgacc taattgaatt agaagatctc tattttgatt | 17265 |
| ggttacggaa tccaggtccc cccgcgctgg tcaatgcgcc aaagtacgtt aggccttcaa | 17325 |
| aatgttcagc atcgtttctc gcaaaaaacg cgctaacgga gctgcaattt gccgactggg | 17385 |
| acaaaataca gcacgtgttg aagacgataa acattgatat tttctcgtgt gtaccagtgg | 17445 |
| gagaaaatgg tctatgcaat atggattggt tttccctcga tacagaaaaa atatggacgt | 17505 |
| taatggattc aggaacacct aatgttagcc caaatttgct gataacacct ggcccgccac | 17565 |
| ccgaatgcat taaaactcca gaagaagctc cagcttattt tgaagcaatc tcgaattact | 17625 |
| ttgaatccgt gttagccgcc agagaagcca aatatgcaaa attactggcg gagtacgcga | 17685 |
| agtcgctcgc taaatacatc agacataaat cacaaaaagt agggcgcggt ctgcgagccc | 17745 |
| tcgaactgga cacagaggag gccaaaaaac gatttaccgt tctaatgaaa tccgaatact | 17805 |
| acaaagggat cgaaaaactt ctaattatat ttctggttca tttagtgctt aacgcgtgta | 17865 |
| gggatgttgc tcggataata tgggtccaac agagggactc ctcgtctgta ttgcagaagg | 17925 |
| taacgtatag gtgggaaagc caacagctac actgtatttt tcaaccatta cttgtttctc | 17985 |
| cgggtccagt ttttttggac aacgaccccct tgcctttaca gactttgcag catgtaaact | 18045 |
| acgtacgata tcttttagga gttccggtgc taagattctc catgatagaa gaatcccccca | 18105 |
| gtgcacaata tatcccttat gacaaaactg caccttctgc atatgatgtt ttagcgacta | 18165 |
| ttgcacgtac ttgcctaact tccagcggct gttcgcgtgc ttctcacgac catacctacg | 18225 |
| cacgcgataa cgaaaaacca aactactcct cctctcgaat cgtcttatta gctgattccg | 18285 |
| cccttgatac acctatgccc taaacatgac cgcccaggct ataaaacaga tggactggcc | 18345 |
| agacaacatc attgcagcga tggctgaagg cgatgggttt gaagagcgtc tccgcgctaa | 18405 |
| agcgcggtgc catcagatga agaggactcc gattggactc ctccaagtaa tccttgacgg | 18465 |
| ggcaaggaaa attgatccga aacggatttt agataattct tccccgagcg acttagctgt | 18525 |
| gttagctgag cgagagctac catcctcccct gctaggaccg gcgcgcgaag aatacttaaa | 18585 |
| atttggggat aaaaaactgc cagacaactt tatctcacgc actgtctcca atgacaccac | 18645 |
| ggatgagtat agaagaaatc ttgacgaagc gtttaaactc tttattgcac gcagaggggt | 18705 |
| cactgaaaaa tgcgttgccc gaatgctcag acatctctat gccaagcggt tgtccgtggt | 18765 |
| tttggatctc gatgtcccat ttggtgaaaa aataaacaaa gcgctttccg ccgatgatca | 18825 |
| agattttgta ctgaaactgt actactgggt tttccctggac aaggtctctg cgcctagact | 18885 |
| taaggaacca gaaatgcaag cttacctggc ttcagtaacc tatttgtcgt gcacctttaa | 18945 |
| gttcattgaa ggatacgctt attatatgcg ccccccctggg ccagaactcc attcaacaga | 19005 |
| aacgaccgct cgtctagcag ccctccttgt atatgtgaga agcatgtact gcaaactggc | 19065 |
| gtccttattt gacgcaatcg atgccgctgt gctgcgctct aaatttaata ggggagcttc | 19125 |
| ggctcaagct ctgactggaa tttatggata cacgcgaaac gggaagggaa ctataatgtc | 19185 |
| gcggtattct tcggaggcca tgagtgatga aatcatgtct gtgtgtcgca ctggttcgga | 19245 |

-continued

```
cactttgata gaatctttac gcaaagctct ggggagattg accgaccetta ttgctaggtg   19305 ggagctcatt tcggtagaga agaaaaggga cgcaaaagag gccgtgacgg cagcgttagc   19365
attaagtgga ctagttagcg gacatttggg atacttgcta aacctaatct caatggcata   19425
cgttttttgg ctccctgggc attatttaaa tatgcggtta atattggcgc tgagttccag   19485
ggaactccta agccatcttt tggctacaaa tccttcttca ttgagggaag tagccagctg   19545
cccgaaaata cttttctacc aatctgtaga agaatggaga ggacaggaaa gaggaacaca   19605
gatttggttg gattatgtta ctgtaagggc atggttggat tatatcgaca ctgggatccc   19665
tactattcgc tccgaggaaa caaatgcttc cataaatgaa atttccgagt atctggaaca   19725
gcgacgctcg gccagtccta ctgaatcctt tttatcttca gatggaccac caaactcaag   19785
cgcagcatcc ctgcccccta cacaaggctc aatgcaaaca caaaacagga gacgcgaacg   19845
acgcagtaac agtgtcgtta tccgaaagcc ctcccgctct gcgcattcaa agagtaatac   19905
cattcccgtg tttcaggaaa cgaccatttc ttattcggca ccgaattccc cggcggatca   19965
ttacgtagta atgaattaag cctgtataac tgtacagtaa atgcatcgcc aattttttata  20025 tttacgctct gaataaataa tgacattaca ttgacgtaag atgtacataa ttcgtattta   20085
tttactttcc tcgtagactc cgaaagacag ggcaactctc aatgccttaa tataccgcaa   20145
ggcaggcgaa atagcagggg acatgtagca tattactccg gcggttccag aacattgtag   20205
attctcgact agggccacgg acattttttg cgtgcttaga gatgcggtgg agtcatcatg   20265
tatagaattt atgaagtaaa cgttggcgca tttgccgcca tcatccgccc accatagtcc   20325
ttgaggtgaa gtgctcccgg accaataaaa taaccggtct aaaatagtga ggaagccgat   20385
tgcttttgaa gatgaggcaa ttttcccccc gagggcacgg caagaaagtt tagcattttc   20445
atacgtgtct tgaggcggac cacccccggc ccgataacat gaatccagat gttgaatcca   20505
gtcaggcgga cacaatccgc cttcccaggt gctgttcggc agtgcaaatg ccatgacagt   20565
gcttattaca aacataaaaa tcagtaatcc taggaaaatg ccaagcagga ttagaagaat   20625
cactttacac gccttccaat attgtccgcc tgtattttcg gggcgcattg aatgaagctc   20685
tccggaagga tgggggggaat aggtacttgt cgtagaggat gaagtagagg aacaaacgct   20745
tggctcatct tccaaaatag ccctgacttc gaagggaagt tctgccatca ttttttccaa   20805
atggcttcgt tgatcttcag atgggggtttg tgaaattata gggggggttca ggtagcttcg   20865 ctgatcttca gatgagggct gcaaaattac tggaagggac tggcctgctg ctatttcagg   20925
catatctaga aaatccactt gggccgctag acgaagcgag taacgagggc gctgcacgct   20985 cgaatttttaa aaagaacaaa tgtcatttct gcgtatagtt tcggccccgt tatggcgtta   21045
acgtcaatat ttcacgtatt atgttattga aagtggtgtc aaggtcatca catggtgacg   21105
ctattgctta attgcgcgaa aaatgtgcgg gcgcgagaaa ctggttcata gcactcggtg   21165
cgaacgttac gtatgcagtt accgcccata tcatgtaaat caggtcacgg gactggattc   21225
gtaacctatg attggtgcgg ggaggtctag aacaaacatt cgcacctcag tattaaaaat   21285
ataatataga tatactatat ttttaatact gaggtgcgaa tgtttgttct agacctcccc   21345
gcaccaatca taggttacga atccagtccc gtgacctgat ttacatgata tgggcggtaa   21405
ctgcatacgt aacgttcgca ccgcgatttc gagtaaccgg gagcataaat accgcgtgcg   21465
tttggcactc cgtgcgcaat atgcgcccgc cactgccgac gtcagatgct gttctgatcg   21525
aaaggttaca ggcgccggaa ttctgtacaa cctaacgtag ggcagggttc cggcgccata   21585
```

-continued

```
cgggtcgcaa gaaacaggta caatcccctt tccctaatt cattatgtca atatttttta    21645
ggttgtgggg cggcacatcc ggcaggatgt caatcgagat ttttgaatac aggtgatgga    21705
gggagtaacc gacacggtgc tggttttgac ggagcgcgac aggctcgccc tattcggacc    21765
cattctgttt cgaggagggg gacttacggc agcccgtgg gctgtttcag tagatgctgt     21825
tctaccgtgg accgaaaaaa ccatccccc gttaaaggg tccaagctca tcattgctgg      21885
ggaaccttac ttggggttaa catcatctga tgttctctcc aagtgtgaag gaaaaacatt    21945
ttttgtgctc atcgctgttc cagcagccct cggacgctgg atttgcgcgc cccgccacc    22005
gcttctagag tccgttgcag aaaatgtgcg ttgtaaaatt tcagcaaccc tatccaaaga    22065
gcatggagcg ccctttttgca ctgccgtata cattttgggg tcaactacac aggttccccc   22125
tggctctagc ttaggttggt cttgtgtcgg caacctgtc cttcgggccc ctttaaaaga     22185
agctaccaag cccgacgaat cgttacaatc tgcagagtgt gtatttaagt gtccgctttt   22245
tgcggatgag ttttcgggga ataacccgtt tgcaattggg tttttgtgcg cactggacaa    22305
gggagttttg aagcacgaat tgtttgcagc aattatgca gcaaaaagg caatttcgaa     22365
tgcatcctta gacgggacat tttgtgcttc gtttggagat aaagagatga aattagaaag    22425
tgtaagcacc cacttagggc ctgccgttgt ggtaacgcgt ggggcaatta cagacttccc    22485
tccaaagaac gaatttatgg atcggcttac atgcaagcga accttttttgc gtaaagatgg   22545
ggactttctc ctgggatctg cgttcttaat gtgtaagcca caaatagaa cgtcgccggt    22605
tttacgcagg tggaaaaggg cctggcttcg agataggcga aggaaacatt taatgcgcag    22665
ggcaagggtt tcggtaacag ctgagctggg ttgtcggatt ttatcgcatc caagcagaat    22725
agcatccttc gggctagaag ttacagaaag agatctgaat ttacagcgga ggctttcggc    22785
acatagaccg agggcccggg gggtggtata tgaagatttt gattagttac ctgaagagac    22845
acgccccaaa atcccaccca cgctg atg cat gcc ttg ggc ata aaa tac tct      22897
                             Met His Ala Leu Gly Ile Lys Tyr Ser
                             1150                1155
gcg atc ttc gca gtg gtc agg cat act tta tac gct cca act tca         22942
Ala Ile Phe Ala Val Val Arg His Thr Leu Tyr Ala Pro Thr Ser
    1160             1165                 1170
gtt gtc atg gaa cag cgg cga gac gaa aaa gaa gcg gag gaa cag         22987
Val Val Met Glu Gln Arg Arg Asp Glu Lys Glu Ala Glu Glu Gln
    1175             1180                 1185
aaa gta tct gca ata gcc agt gcc ttt ctc aat gtg gga caa ttt         23032
Lys Val Ser Ala Ile Ala Ser Ala Phe Leu Asn Val Gly Gln Phe
    1190             1195                 1200
ttt tct cgt ggg caa acg aac aag tct cga ccg tgg gtc aca tca         23077
Phe Ser Arg Gly Gln Thr Asn Lys Ser Arg Pro Trp Val Thr Ser
    1205             1210                 1215
tct gaa aca ata aaa gtt tct ata tat gca tgg act cgg tgc aga         23122
Ser Glu Thr Ile Lys Val Ser Ile Tyr Ala Trp Thr Arg Cys Arg
    1220             1225                 1230
gac tct cta cta ttt tca gat tac ttg ttt cgc cgc ggc acc atg         23167
Asp Ser Leu Leu Phe Ser Asp Tyr Leu Phe Arg Arg Gly Thr Met
    1235             1240                 1245
gat agt gcc cgg cag cag ttg cag gtt gga gtg cct aag aag ggc         23212
Asp Ser Ala Arg Gln Gln Leu Gln Val Gly Val Pro Lys Lys Gly
    1250             1255                 1260
ggg gtg tac aga cag cta tca cgt gat gat gga acg gtg ttc gag         23257
Gly Val Tyr Arg Gln Leu Ser Arg Asp Asp Gly Thr Val Phe Glu
    1265             1270                 1275
gtc agt ttg gat cct gca gtg tgc ttc gag ttc tca gtg acg tta         23302
```

```
                Val Ser Leu Asp Pro Ala Val Cys Phe Glu Phe Ser Val Thr Leu
                            1280            1285            1290 att tta ccg gga cat gat ctt ttc tgg ccg gta gtg ccg ccg ctg         23347
Ile Leu Pro Gly His Asp Leu Phe Trp Pro Val Val Pro Pro Leu
            1295            1300            1305 caa ttt ctc gag ctg ata agt cag cgc gcg gtt att ctg gca gac         23392
Gln Phe Leu Glu Leu Ile Ser Gln Arg Ala Val Ile Leu Ala Asp
            1310            1315            1320 cag ttt att tcg tcc tct atc atg aag cga gtg agc tta tct cca         23437
Gln Phe Ile Ser Ser Ser Ile Met Lys Arg Val Ser Leu Ser Pro
            1325            1330            1335 atc atg cta ttt ccg aag aat aca ttc atg ccc ggg tac tgg tcc         23482
Ile Met Leu Phe Pro Lys Asn Thr Phe Met Pro Gly Tyr Trp Ser
            1340            1345            1350 ccg gat ccc cag cct ggt cgg tac cga cca aaa ttt cag cct act         23527
Pro Asp Pro Gln Pro Gly Arg Tyr Arg Pro Lys Phe Gln Pro Thr
            1355            1360            1365 cga tca gaa caa cat ttc atg acc gtc ggc aag ctg gtg cca ccg         23572
Arg Ser Glu Gln His Phe Met Thr Val Gly Lys Leu Val Pro Pro
            1370            1375            1380 ttt caa att gac ttg cat ggg aaa aag aat aat ttc atg gct gga         23617
Phe Gln Ile Asp Leu His Gly Lys Lys Asn Asn Phe Met Ala Gly
            1385            1390            1395 att gcc gtg ggt ttt cac ggc ccg ccg acc ttg acg ggc act att         23662
Ile Ala Val Gly Phe His Gly Pro Pro Thr Leu Thr Gly Thr Ile
            1400            1405            1410 cgc gcc ctg act gaa caa gca att cac aac gct gtg gcc gag gtg         23707
Arg Ala Leu Thr Glu Gln Ala Ile His Asn Ala Val Ala Glu Val
            1415            1420            1425 gtt cga acg ctt gaa ccg atg act gtg gtt ccg atc act ctg aaa         23752
Val Arg Thr Leu Glu Pro Met Thr Val Val Pro Ile Thr Leu Lys
            1430            1435            1440 aat gga act gga gct ctg atg gga ttg act tca gac aac aag ggt         23797
Asn Gly Thr Gly Ala Leu Met Gly Leu Thr Ser Asp Asn Lys Gly
            1445            1450            1455 ctt cgg ata ttg ata aaa ccg gca cta gga gaa ttg gcc agg tct         23842
Leu Arg Ile Leu Ile Lys Pro Ala Leu Gly Glu Leu Ala Arg Ser
            1460            1465            1470 cca cga aga cgg cgt tcc gaa tcg cgc gga aga gag tct gtt tta         23887
Pro Arg Arg Arg Arg Ser Glu Ser Arg Gly Arg Glu Ser Val Leu
            1475            1480            1485 tta taa attgaataaa cgcagacttt ttattactgt caataattta tttattggtc     23943
Leu tttattacac ggctccttcg ggtaacatta tacgcgactc gattgcctct ctggcaacca   24003
ctaccgcgtt ctgcatagta gggatacaca gttcttgtta ttgcggcaaa acgaccaaaa   24063
tgcctggcaa aaaactgcaa aacctgtacg gggaatctat tacttgcgcc ccggccgttg   24123
taaaatctgg cgttggtcca ctttctgaca acatggcggc ggcgtaaaaa ctcacgtttc   24183
caagaatcga ataggacctg tcccatctca agtttgcgta ggttgctgcg gagagcgcat   24243
cggggagaga cagggattcc gcacgcgtga aggttttagg ccataatctc agatatggga   24303
cgaagtattg ctctccgaga aactcttctg ggaaggcgat tggggcgtca atattccaa    24363 tgcgtactct tcgcgttaga catgttccgg aaaaatatat cggaatgtca agagatattg   24423
gggaagatgc tcccttgcag cgcttttcgt ataaaaagcg cgggcccaat atttccacta   24483
atattgcctg tagtgctggt gcaaataaag ggtcgcctgt gtgatcaaaa gccgattgaa   24543 tccctgtat ctcatcactg gtcttgccaa agagttccgg tagatgctca ggcagtatgc     24603
```

```
tgatgtgatg ataagatctg ttagaaaata tccaacaagg gccctgagca ctaggagtag    24663
gcctttgctg tcgtatagag tttccgtgtc gttccttgtc taccatactg tcgagaagct    24723
ggttcgttat ttcagcattt tcttgtggtt catcatcttt tttacgccgg agtgtttggc    24783
gtatccagcc actccgaccg gagtgggagt tcttaactga aggtaatgat ggcgcgggtt    24843
tcagcggagg ggaaatcggc ccagatattt ccagtcggtg tagctgaggt tccgatcgag    24903
agaagcgctt gcggcgtcca aacggcatga atttgctcag ccagcccatg gtgtctcgcc    24963
tagagagttc tgagtttcag agcaggctct cgcctagaga gttctgagat tcagagcaga    25023
ccctcgaacg cgttcgaggg cttttaggtg cttgttgcat ggggcgtgta ctgggcgtgg    25083
atataagaca tgtgcctcga cgcccgccac gcacgatttc cgcagacatg agttccatgg    25143
cctgctctcg ttttcagaaa ccaaaagcga agaatgatag ttcgcccgaa aaatgtgaac    25203
gcactgccaa gcaaattgtc gcagcaagtg attattgcaa tgattcggaa aaattagagg    25263
aagagatggt cttcgtcgga gctggaaaga tttcatattc ttcgtggatg tacgaggcaa    25323
ttttttcctg tgattgtatt cccgacggat cagcgtttgc agttgctaag catgcagtga    25383
tcctaaatcg cgtaaacgga ggcttgccat cttgtcttgg gagtgcacat gggttgacca    25443
tttaccctgc caggacaagc cagcgtggaa ggttcagccg tttagcatac agaaatgata    25503
tgtccccagc tccacaatca gaaaatactg tcgatgtgga tggagagctt ggagcgtgcg    25563
ccatcggcgt gttggagatg ggcgaagaag tgtgggcaca tgaagaaatg tttttttttac   25623 cggtggttcc taagttagat cgcatgtggc cgtgtgttcc caatcctgct ctgtttggg    25683 gcctggcgcg cgcgcttaac aatcttcccc ccaagatact cgtttcagga aaacttgcca    25743
aagggttcat ttgccctcta tactatctta gcgtaccaac ttttggagaa gagagcaaag    25803
aaactttcct tcgcacgaga cagaagcagc gaagtctata tgacccttgg tttgacccgt    25863
cttcattact tgttcagcca caattttttg gatgtgatgg tattaaggat tctaataact    25923
ttcaagctgg gcttggcata gttttccagc ctcaggatgg atggacggca aaaacaaagc    25983
tgctcgagtt ggacagagtt cggtcggaac ttgtcacact atttgcacgc caggagcagt    26043
caaggcctat taccgtgata attactaggg gggcagtcag acgccggctt gtgttttcta    26103
ctgttggagg gtttaggttt tcatcctcgt tcgaaccctc tgggacaccc cttaaaaccc    26163
actcggtgac tttacatatt taatggaaca cacatacgaa ataaaagttt gtcagaaatg    26223
tatttgcgtt tattgatgtt tatgtttcgg gtaattatcc aaacagatca ggccgcgtcg    26283
caattcccat gttcttccat gcttcggaca ctgctgtgca agcagccgtc ttaaaatcgc    26343
ctatctcatc gggggtccaa tgagagtgca ataaaatgcc gagtctaggt ggatcgtacg    26403
cgtggcaaat tgctgcgcac agaaacttgc cgcacatggg agtttcttct aaaagagcgc    26463
gccagaaggt aaagcctcgc ccagtaagcc agctagtagc tcttgatgcc catgtatcta    26523
ccgctagata tgacgcttcg tccgatgcca atacccccga aactgggaaa aacgcgcaaa    26583
gaatgtgagt tccttcgga atcgaggctg tctgctgtgc gcgcggtgga tgtatttggc    26643
tgtcgccaat cgcaacacaa aacgggatac ggaaagccca ttcttcgcgg caagtaatta    26703
tcggcgaagc tatctgtgat cgatacgcgc gtaacccagt aaatatcgcc gcttgtagta    26763
gtccgacggg cgagtgatgc gggctgtctc cgtgctttaa atcaaggatt tctccgctta    26823
gagtaagtga tggaggactt tgaaagaaca aggcccgct gaatgcgcgt acagcagcaa    26883
caaccggaga aagttccaaa tccgagataa gtcctaacat tagaaatccg actccatctt    26943
```

-continued

```
tccacttgtc tgcagacaac agtttaaaag gcaaatactt ggctccaaaa gtcatcgggt    27003
tttttgaatg cacgctatca gctacggctt gccatctttg gaatttttt aaggaagctc    27063 ttttcatggc aagaaggagc tgctcgacgc caatctctaa attagaatta gttgtgtagg    27123
gagttctagt catgataatt gcagtagaag gaattccagt gtcgttggaa agggattctt    27183
gcggatcctc aaataatggt gctgctacga atcggatttg agagttatcg ggctgttttg    27243
agtcatggtc ttgaaacaca tgaatagtca aatccttgtt gcaatccaga aaaaacgatg    27303
ctgtgccgtg cagtacagct aggccatatt ctaccttttc tgtccatagt tttccacgat    27363
gtgttcctaa ttcatgtga gacgagtcta caaagtttgc gaggcagtga gttactgcaa    27423
aacgacattc gcgattgctg gtagacagtg ctttggaagc ctgagactgc ttctttgacg    27483
gagccatagc cagttattcg tgctgccgca agtgcagttg aaaagggttt gtaaggaaca    27543
aggattaaag ttcgctctcc tcgtcagacg gtagccgtac acgtctaaat tgcgttgccg    27603
agctgaggca gaatttatat atagccctga tggcactcca tagagcaacc aatccaacaa    27663 gtgccctac cacaataccg ataatgtatg ccttgtcaaa aactattatg cttctgtcaa    27723
gtcctaaaat tcggacagca gttccgtgtg gtcctagaag cgcgtagtta tagaactcgg    27783
ggttcataga cttaaaaaat gcaatagatg agttggcacc ggctaacagt tctgattgaa    27843
catatgcact gtctataaag aaagcatcct ggaaccccg tagaccgtat tgaactatca    27903
ggtggttgca atatatgcaa gttttcgctc gtccattcaa atgaccatcc tccattttg    27963 ctgttcgcgc gatttgcggt agggagttgc aacttgaatt cacaaacgtt acaaacaaag    28023
gggcagctgt tgaggtatcc ggaagtctgt aggtcattcc agtgctcggc gggctacttg    28083
tcatcaccca actagaatgc gcggtaacag ggaggaaaaa tacgatgtgg tgttccaggt    28143
cccagtttaa acatttcttt acctctggaa aaaacgcagt tgccaggatc tgaggggtca    28203
acagagcttg tggcggtatc ggtgcactat atgatggcaa ttcaccttca gatgataaat    28263
atattttggt gtaaaaaaat cgaaatggag cagatgctgt cagaattatt ttccatggtg    28323
cacttctgga aatatcaaac cttgtcgcaa ttgcacaagg agaaaaccac tcttcaattt    28383
tcgatgcctg tccttttctgg aagctcccgt ctggttggga gtgaatctcg ttgatatcgg    28443
ctagccggtc gacagagcat aaaattgtca tgcgcctgag gaagttcctt ccatgttgta    28503
tagaaagttg aggagcccgc aaaataatgt acgtagaaac tgccaataac tttctgtacg    28563 cggggggtcat tacctttgt gtaatgattt ctctgtaact gttatctatt atttcaagag    28623
ccagttggct gggggtcact ccatcgatgc tcgccaggaa tgcattttgg ggatcttgtt    28683
ctgcagtgat aagcaccgca ttcatgatag taagaagcag gttatgattt tttatcatgg    28743
gttcccatgg cctgtcgtgc ataattttaa gaatactgga tgggatagaa gtaagagcac    28803
caccgacatt ctgaataaag cgaatattcg ttgtatagtt tactgaattc gccccccaa    28863 aacacactgc gacttggtct gcccatgttt gcgtttctgc aataaactcg acgatctccg    28923
aatcagttac gtatgcatcg atcgtaaact ttagaaatcg aaaccacgcg gccataaacc    28983
gtgctgcgaa tcttacaaaa aaagactcgt ctatggtatt cgggcaacct gcgattgcga    29043
ccttctgcaa agttaaaaag tgtcccgcgc atatttgttc gtcgaagctg gccagctcta    29103
agaaatcttg agcagcggtc gttactgctg taaacaaatt tggccgataa tttggtccag    29163
ctgcgacgtt gatgcgcaca gttaaccct gatcttcagc cttcagcata tagggccatg    29223
acttcaggga cgtttcttta accttcgcgc tggttggtgt aattatcatc tctatttgag    29283
gagaatgctg ggtcgcgatt ataagggtcg ccacattcag tccgatgtta atcttaagat    29343
```

```
ctatgtcact agtaactgcg aggctaatat atcgtgtaaa cacaaatgga aaaacagttt    29403
gtaaaggatc actgtaaatt acacgaatcg gagcgatgat gctctcgccc ctatgaactg    29463
agttatttgg tggaaagttg acgagtttcg cagatgtaag tgcattcccc ttgtatccta    29523
ccaaaagtcg atgctcaagc tttgatcgt tgctgaattt tcgtggttgg atggtagcct    29583
cgctagcaga accccatctc gagtaagtat aggctacgta cagttgtcca agcaaatcta    29643
gagcgatcga taaattcctg ttagcgcttc caggaggccc aaagattaag tttcgatcga    29703
caaggcatag ttgtgtgatg tggccgtttt cgactgctgt cgctatcgca atgaattctt    29763 tcggagggc caaattttca ctggtggggg gcacgaagac aattttttgcc tttgccttgt    29823 catccccttt agctctaagt aatatcgcca gaatgaggaa aaatatttct ctcgcgtgtc    29883
ccatcggcgc gggttgctgg tgaagccacg ctctctcgag taagaatgag tacaaagcaa    29943
ggaaatgagt aaaggacata ctcttattgt gaaggattat ggatgcggaa cattacgaac    30003
ccatatcagc attgtagcgc tctactgcgt caattaagct cgcgatcgcc gctcgtttgg    30063
ttgtaagaga acttgccgtc tcggcaaact ctaaacattt cagtgcacat gcctccgggg    30123
tgaggccatg tgctggtaag taaaaaatgc acaagttttt caataccgtc gcgagttttt    30183
gaaccacaaa tgaaagtaca gttttttaatc tttccccgtg aacattttgc tgatcaaaag    30243
ctaatattgc aaatagcgtc tggtcgattg aaggattgat ttctggaaca gtagcagttt    30303
ctaagcactc tctcttgaat tttaagagcg tggcacttgt taaggcttct tgctccttca    30363
acaatgctgg ataagatgta cgttggaggt aggtggtagt attcatgagg cagatgtacg    30423
agttacgtaa tgcacacaaa tacgtccagt cgaccgtttc ccctgggcgc ccccttgta    30483 ttatacgccg tgcctgttcg caaatatcca aatccattaa aacaatgttg gagtgtgttg    30543
gaatgtcagg aattcctgac aataaagtta ttaaatctcc aaattcgagc gctccgctta    30603
gatattgtgc aacagggaaa cacaaacatg ccgcgagtgg gtgcctatct acgaggaata    30663
agacatcatc tggtccggat gcagctgcgc tgtagcagcg ttcagatccc aaataattat    30723
aaatgacgtg gttcattatt cttagtgggg cagcaatagt catctgaact tccgctacgc    30783
gacgagacgc ctcccgacat tcaagttttc cggaagcctt tagggtttgt atttcattaa    30843
tttctttgat catatccgct ccgccaaacc attggcgcca tgcttgcata ggttccgcta    30903
agtatagacg gcaacctctc caatttggca tttgcatcaa cgtctttgca gtgactgttt    30963
taccgactcc gaatggcccg tcgacgtaaa gaagtacaac gcggcgaaag tcggagtcat    31023
cgttctcgaa ctcggagcaa aactgcacac caccggaagt tttcacgcg ccagctacg    31083 ccatctctgc gggctagact aaatgccgga atccgttgcc ataatcgctt ttaccgagct    31143
ctcgtcagat cactggagga agtctttgaa ggggtggag acgaaggct ggcctatacg    31203 ataattcccc aatgcaaacc tgccggggc aaaattgtag tcatgtttga agtgaaccta    31263
gggttgcgga aacctgattg catttgtttg ctggagacac aacatgaaat gaatgtatt    31323 gtgattgaac tgaaaacatg tcgttttttcc aaatctttga tgactgaaag taaattaaga    31383
caaggatata ctggcactct ccaacttcgc gattctgcac gattgttgga gaatctggct    31443
gttcctggca ctgagaaagt aaagattctt tctctactgg tatttgttgc tcaacggggg    31503
atgaacatct tggcggtaaa acggttggg gaaacggtta taaatgtatc gtctgagctt    31563
ttctttgtca ctctagctac cagaagccag tatttaaaga cttctgcgc gaaattagag    31623 ccacgcgtgt cgcatgcgcg cagtaagtat caacaagaaa gtgcaaagaa tgcggatcta    31683
```

-continued

```
gcgtctcccg ccccttcagc cttacaaacc gtagctgcat tgttttcgtc gcgcgtggga   31743
aaagagtccg caaccaaacc cgcgagctat tccacttcta cggaggagtc caaaaacttg   31803
tccgaaccat gtttcgaccc agattcgaac ctatgaattt accaaaggac agcaacaagc   31863
cgtctacctt gatggtttta gccgatcgtt taaactttat ctcctgcgcg gaaggctcga   31923
gtaaatatgc atctaagctt ttcgaaggaa ctctaataga cgcagaaatc atgaccaatc   31983
gtgcaaggat tgaagatctg gaaaggcgga acagggctgc caaggcagct ttagagcaac   32043
tggaaaatat gagcgctact gttcccgtac atgtctcatc ggcattgcaa actattgaat   32103
atcccctaga gactgtaatt gatgtcttgg atgatttagc ccagcgggcc gtgcaggaga   32163
aggacattgt tgggtcttat aaaacactag acatccgtgc gcctggcgag gatgtccctg   32223
cgaacgtaat ttggatagtt aagaatggag aaccattaac ttttaataca gattttcaag   32283
tagattttct gacaacttcg tttgctattg ctggcaatgg ccggctggga ttcgggtctt   32343
ggtttcgcgc gctacagact cagctcctag ataacaataa agctatcgct agggttttga   32403
atgtaatggg agacacgcgc atctcggggc ggtttatgaa aacggctatt cgagcgctgc   32463
gatcggcgat ggaaatttat gctgggactc gacaatatag cggattcgag gctactgttt   32523
tatgcttact gcactactcg cggtctagac aatctgcttc aaacattaga catggtcttg   32583
atgtttctat atttgaagat gcattaagac atgttccaac gtatttaaat tatatgctgg   32643
aagatattcg ggccgagtgg ggctcagtta cattttcatt tgaccggtca aaactccccg   32703 taaactttt ttccccaatt gacggcagaa atattcgaa tggagtgttc gatcctcaca   32763
tagtgtatca attgctaaag cgtactggga ccctttccac cacagtacga gatataacga   32823
aagaaactct gcttccaata gatccagatt ttgttcgttt tgatgacccc attgctgctc   32883
tctccatttc atttttccct tcgagacgaa cgccgttaat tcttcatgaa gatgatccgc   32943
ttgtgcgaac ggttatagac tcgatatctc tgctcctagt cttgcaaaag ctaatgttta   33003
atagtaatgt ctatacgagc acacatctca atcgatttca gccatctgcg ttctttgaat   33063
tgccacttgg aacccaatcg gaacaggagg cagctaaatg gcccgtcgcc cctgggtcaa   33123
gacctcaagc caccgcaagc acatttgatg acaatggaca agatatggcc agtcgcgaca   33183
acaacttgtt cttttttattc gagaaatatg ttgtacctat gtatagatat gacaacagat   33243
gtgaagttac tggtttcttt cctggtttag ctgcactctg cataacgggg cgcgttaaag   33303
gaataccgac agcggtacgg ttgggggagt actattcctc cctctgtaat ctaattgagc   33363
ttgatctcag aaaaacgtca catgtgggta gcggggcagc tgctgttttg gcggtacacg   33423
attcattgac aggtgacgtt gaagagggag tgtccaggtt acttgaggta tttgatgcaa   33483
aaaagcattt gaaaggaata ttgaggacat tcaacgtgga gtctgattct gacctgatct   33543
attttatgtg tcttggatgc ttgccacatc acgtgacata tggataatgc ttagtatttt   33603
cgcgatcgcg tctctgttta gacaataaaa gggttatatc tttctgatca gtccgtctgt   33663
tttgtcagtg tgttgatact ttgcgggtcg agtcggtctc gctatgtcgg agaacgtcga   33723
catcaaatat atcttcgttg ccggctattt ggtagtatat gaccaccaag aaagtgccgg   33783 gcgagaaatat gagcttactc gcgagcaaag caaatcggct ttaccagttt tgcctggaac   33843
aattccgata acattgacc acgagtcatc ctgcgtggta ggtacagtgc tgacgatctt   33903
agacctgccg agaggactgt tttgtttggg tgtcgtgtca actgctcttg cacctatttt   33963
tttaagctac gtgcaagatg atgctctttt tgcgaatgcc gaagaggggga tggttttgac   34023 ggagacagag aaatttctct atcttctcag caacattcta ccttctctat cgctctcttc   34083
```

```
aaggcggctt gaaaagaacg aagtgcccgg aaaagatttt tttgcacacg tggcgctctg    34143
tgagttgggt agacgtgaag gcacggtagc aatttacggg gccaccgctt cggaagctat    34203
tggagcattt gatgatttga gcgcaccaat aaagaacag ctgtatgaaa tagctacacg     34263
tgagaaatgt gcagaagtcc ctagagagtt gtcgcgacca gaaattacgc gagtcctgat    34323
gaagaaattt attcacgggg cgttttgat ggatagggt acctgtttga aaacgcgacg      34383
cgagatggca gctgtttaca acccgaaata tttacaagcg aatgaggtaa taaccatagg    34443
gattaaggaa cactccgaag agactcctga gaatgctatt aaagaccgtt cagtttctac    34503
gcaaacggcc ccaagcttcg atataagcga gagtcagcaa ccgtccggc aaacacacgt     34563 tccagccatg gagtcggcga catgctccgg ccagttcttg caaacaaaaa acggagcttc    34623
accgtccgca tctcgtgaag atatggtcta tgtcccattc gagaagtatg cgagtcttct    34683
tgcggcatca gcccgcagag ataacgaccg gagacccgtg tcgccatcac gagagttttc    34743
ccgtaggtcg cgggactcta ctcacgaatg ttcaccagga cgtgatattt ggccgcgtgg    34803
attcgaacga caccctcgcc tagaatcttt tatgggtccg gggatgaacc acacttacag    34863
accggctctt tacgaagacc caaatttctg cgggcgtttc ccatatattc cttatcaaag    34923
ccccgcatct acttaccccg tgcatccaaa ttattatagt tcgaacttcg gccagtttcc    34983
tggggctgga acgtatccta tacagtatcc atcattacat gagcagactg ttgtttcacg    35043
cttagatgcc ttgatttcgg ctcttgagaa aaataataaa cgggatagcg aatactcgga    35103
gaataaccct cggaagagat ccgctaggac catttctgag aatgaccgt acttccctgg     35163 ggaaatggtt ccagcaaaaa agataactac ggagcagcag ctatgtgaaa aaaggaacc    35223 cgttggtagc ggaattaatg atatttaca aggaattctg acccttcaaa aagaggttgc     35283
cggtcttaaa tcagcttcca atgccgattc gtcttcagag agaaagagg aactagaaaa     35343 tagtaatcaa gagtctgctc gggagacagt cgatgcttct atgccaaaac gactgaaaga    35403
tgctcagaca aaattgaaaa gaaagaaaga agcagccgca tttgcgcaaa tgatggcaga    35463
ctgagtcatg tgaatagtaa tgtcatttta ttaaataaac tgcatttaaa cttattcgtc    35523
ttcgctttct tctgcccacg aagggtattc gagcaggggg tagtcatctt ccttggttcg    35583
gggttttctg cgaaataggt ttctcatatt tttagcaaaa gcagaaaacc gcgctttctg    35643
tcttcgagct ttctgttcat ccttgtgtag aagctcaagg cctttcagaa ctctggtggc    35703
aagtatcctg tcgtcctcat cactatcctc ctcaacctcc tcctcatcct tgtagtaacg    35763
tctagagggt cgtggaggag ttccggccgg gggaactgcg cctgggaaca gaacctgaac    35823
tgggtttgat ttcaggttca ttacatattt gaacgccagc agtcctaaaa taatgctcac    35883
caccaccgct atcccaattc cgagtgcggc gaacgggtta gaaagaaatg aggcgatgcc    35943
agatactgta gaaattactg ctgccgcggc tgtcatcact acagttccca atgccttttcc   36003 tacttctcca agagtgttgc caaaaaaatc tgctattgct ctaaagattg catctcccct    36063
atctccacgt attacagtgt caatgtctct gaaccttttg ttataaatat tttgatatct    36123
gaccacatca tcatagtttta aagtcccagt atctctgagt tcctcgcgag tgtatacttc    36183
gacgggcaca aagtccaaat cttctagtat agtggcgttc aagttgatga atatgctcac    36243
ttcttcgatc tcggaagcat ttacttgtct aacaaatgta tagtcttcgt aaagaaggta    36303
gttttctccc aacagaaagt accgtctgtg attgatcatg catggttcta tcaaattccg    36363
cccttgtaaa atttcattat gttctccgag ttggcctaat atgtcaagat tgtggttttc    36423
```

```
tgttgagttc gcagaaaact gtgactcagg ggaggacgaa tacctgaaaa taagtactgg    36483
tctggtatag cacatggttg ggtcccctgg catgcgcatg gaatcctgca tcctaatatt    36543
ttcgattgga atttctatac attttgatac cgctacgatg tctcccaata gcctggcgct    36603
tacaggttgt ccgaacaaag atgtcatcag tgagttcggg tttagtttct tcatctcatg    36663
ccatacaatc agttggcggt tctgaagctc acaccacgct tccaacaaat ttccgataag    36723
ctcgttaaca tgggcttgga ttttgtcgta tgcaaattgt aacatggcaa atgttgcaga    36783
actgtgggta gtaattctat caccctgagg tccagactgc agcgacgccg tgcggcgacc    36843
tgcggcttgg cgacgctctc tccctctcgg gagatgattt tgtctttgtg cctcttctag    36903
gtacatttca gccaagccat ggctcatgag tttctgaaat gcgatcagaa atccgccact    36963
accgagatag tattcgatgt ccccagaacg gacatgagtc gaactatact ttctggcaaa    37023
gatgccatct atggcctccg aggctatggt aggaacgcat tcagccaaat gaagcctgct    37083
gatgttaaaa ggttgttttc cggacgagaa cgtcatagtc gtatctttaa gtgaaaagtg    37143
gtaactgttt ttgtacgaaa cacgaactgc ttccgggact tcaatccatt tactgagagt    37203
acatacagat tccttttctt ccattgcatc ccagcctata gtgaattgtt catctgttag    37263
aaagtttctt tttttagggg gtcttatttg tccggtttcc aaatccctga cttgataatt    37323
tgcgatttcg agaaatctat agtctctgta gacactgtga cgccttggtc cggtcgtgtt    37383
tttggtataa aaaggagaaa tttctactgt atcacctgtc gccattccaa agtaatcata    37443
cgggtataca gatctagcct gtagatattc cacaacacag tcgaccgatg tagacgttcg    37503
gtatcccagg gtttgatgtc gcttagtaaa gttagttgta tgaaacgcct tggagacagt    37563
tgatcttaac agtgatggaa ccaggggcaa ttttttttct gcttcatcat tgtcgtaagc    37623
ttcaaaaaac atgaaatttt tatgatacgt tgctttggat gagcattctc ccgatcgatc    37683
aatcctgaca atttcatgat agtctattgg aaccctggtc acgtactcat ttgttatttg    37743
gggtcttgag aataatgccc acgtagtaac tgtggttata tgtttatagt atagagtcac    37803
attaaagacg tacggggcaa tgttttgctt gaagactacg gcaattcctt cagtcatgtt    37863
agtcgaatcg gcatgtcggt gacaatgtcg tggctgggca agcctcgcaa cactggcgcc    37923
agttggagat gagcacgcaa aaattctgtt tctaatctgg ggttctttcg gtgcccccga    37983
cccaatggct tcgagaaaag agattttttcc aacatccatg ctggctgtat cacgagggtc    38043
tattattcca gcaattccgt gtgaatcttg agatagggta gatgggatca ggattgccac    38103
gcacacgcag atcagcattt tcaagctagc catgtcaatg ttcacggcga tgtaggattg    38163
catacaggac cgcgtataaa tctttctcta ctatgatagt agacgctgga cccagtttcc    38223
cgcggtcatc gacgcccac actgcaacta atggatgttc ctcttcaaat gttaaatata    38283
gcccgttttc caaaatcggg ccgtcgaggt cgaattcgac acaatctgct cgcagtaact    38343
tagtgttacc gctgtggaaa attttctcga aagccgttgt agcaaagagt gcctctctga    38403
tatatccgca cgcggctctc tgaatagcag ttgaattaga aatgcccgcg aagttataga    38463
atcggcgaaa ctcacttgtc atccaatcac atgatctgtg acgttttgta aagttggcca    38523
actcttcttt caaatgagga agaagtccta cgttctctac agaaaagtat atagacgtgt    38583
ttgggggttg gggaaatctc tccttgtgat gtttgaaaag ggggccgctt aaaatttcaa    38643
aaaaccgatt ggtgaggcgc ggtaacatgg tttggtcgat ttggtatctg gtgatggaag    38703
agcgtatgta ttgatgccaa tcataagcac gcccatcatt ttgatcgatg cgtagaattt    38763
tcgaatgtag agactcttca gcgcaaacaa tatccagaaa tgcgcgtctt gctagaaacg    38823
```

```
cattctttag cgttacgtac attaccggaa gagtttctcc gtaaatattc acacgcatta    38883 attttctag ctcggctcgc tgaattttaa tgcatcgatc caagtttgaa aatgatcgtg     38943
cagaaagctt ttcgacgtag ttcttttgtc tgacatcaag atctcgctct gcctttttta   39003
gaagaacttc tatcgaatcc tcgtcccttt caatagttcc tctgaggtta gcagtcaggt   39063
cgcttgtact agttccttct gtgacaggtt gtgtctcctt gtctgagcca cgcagttttt   39123
ccactaattc ctccagtgca tctgtatcta ctttctctgg gtttcttaat ctgcgaaaca   39183
atgggaggga tagatggtgg tcatagcagg ctttgatcaa ggcagctatt tcggtatccg   39243
gtgaagtggc cagtactcct gtgatcagcg tatccactaa agaatgttgt ggggatatta   39303
actcagctcg cgcgaccctg tgaaaatgtg catgcacctt ttcaaacagt gttctttcta   39363
gacggatgca ttcctgttca aagtcttcag ctcttttgaa cagttcgctc agatctttgt   39423
ctaactgctt taacacagat tgtgaagtag tagtttgtga ctctactccg ctgggggtcc   39483
ttttacccga cgctagccag tattgtaatt cacttagttg atagacgggc cccggtggtt   39543
ccgtaaacac atcatatttg tttaagattt tggaagcttc tgactctcca ggggaacttg   39603
ataaggtgcg tcctgcttcg acgtggtttt cagcttcgat gcgagtctcg tttgaaagca   39663 catttttaa tttttcggga tccacatccc ttaaaaatgg aagatggcgt ttaaggtcat     39723
ccgtagatac attgaccgga aactgtcttg tcaagtgatc acaaattttg tatccaaggc   39783
gtcgataaat tgtttctccc tgattagcgg ttacactaag ctcttctaaa cacacataac   39843
acggctgacc atgatcgtaa gtatccggtg ctgctacgag acttccccc gagctgagaa    39903 ccaaaaactc atctattgta tttagagctt caattgcgtt tttacaagat acaacgcagt   39963
gacagtagtt tagttgcttc ataaagtttt ctacatcgtt gatcagaacg agttcctttg   40023
aaataattga actcattcca tataattgta gctggacctc cgcatgcaaa ggacagatga   40083
atcctttccc gtacccaagc gtagcttcaa aaaacatttt tctatccttt aggacagaat   40143
acttgtctat ctcattacac aaagctgcta tttcggagca cgctcttcga agccagagcc   40203
acacgcaata tgtctgaagg gttaacctat aatttacttg catagagagc tcattagaaa   40263
ggagcgaatg aatgtacaat gccattagcg cgttgtgttt gattctcgac cgcagtcgct   40323
tctgcaacaa tatctctgga tcgcagcgct tcaaatatc tatttgaaat aacagcgtct    40383
gtagctgacc tgccagagcc ataaggcgta actgtgtttc ttcagccata ttccccagta   40443
agaatgaaac aaaatacgta caaggacttt cttatattta tttgtttatt ctgagcatgc   40503
gcagttactg ttaacagaac agaatatcag ccgatagcga aggttttttt gcacttggcg   40563
cgccaagttc aatatcttcg ctgatgtcgc cagtgtttgt atcttcatcc tcgtctgccc   40623
agaccaacat ctctcctgca ttttccgggc atgtatcttt ccctctagc tcactgagca    40683 tactttgtgc ggtagccacg gaccacccat tctgacttcc agaaatgtcc tcatggagct   40743
ctactaatat atctaccaga tacttgtcgt cagtaattgc catccatgtt tcggcagtaa   40803
tgtctttcat tccttctccc agaactctca gaacggctgt gtagatggaa gtgggactac   40863
ctcctgcatc aattaggctt ctcacttgag aggcaatggt gttttcttga aaccctgatg   40923
ccacttgccc agatgacaga atagttccta cccttttaca agcaagtgca aactttctga   40983
cgggatcatt cgtcagcgcg gaattaaccg attgggaccc tgaattgcct ataaggctac   41043
cccaattgcc ggactgaaag acggtggtcg agttttgttg tcctacatat ttgctgatca   41103
taatccctaa cattactata ggtttagaac tcaataccac gcggcacgag tttgacgtac   41163
```

```
tggatccgct tatgcagtag tcagagactt cttcgtgcct ttcctctgac tggtgtgcac   41223
ctgtgtctcc gagttgtgcg cgcgcgaaac tctctttgcc ctcacttgtt ggctttatgg   41283
aggtcgtaat gatcatcgat ggagtactta tataatattg tgctctgtcg gccatctctc   41343
cgtggtcgca gaactccaac accttgttgg cgagcataaa atttgctagt tcaagcaggg   41403
tagttgggga gcacttaata aagtttccct ccccatagac ctttgaagtt tttcttataa   41463
attccaaata ggtaatgtgc tctggagaaa ggcgtcgttt gggcatattc ccagtcaaga   41523
tcaaattcca gaatcgaaat gcgttcatgt ctttgccgaa aagatttgca tggtcacgct   41583
tgagtataaa tcccaatggt ccacccaaaa tattgattgt tttggtgccc ggtttcaaaa   41643
aggcatcagc cattccttgc aatctgcctc tgttgctacc cgactcgctg gatccgttga   41703
acacgacgcg gttcttcacc ttaaactctt tcagtttcag gacttgtccc ctagaaagag   41763
aatactcata ttgtgcgatt gcctgttctg tgtttgggcg cattgtatcc ggagcgttaa   41823
cacacggaac tgatattgaa aatggctcat atttttccaga aaggaatcct ttgtccagca   41883
tcccgttaaa ggctgatctt agggccggca tggcagaaga acggaacatt tttgactctg   41943
gttgccgcgt atcaaatgtt ccatggattt gactgagaat caaatcttgg aaaagtattg   42003
agcgagtctg ggcgcacaat aagctaagta ctggacagta cgcagaagaa tacgggttca   42063
gggtgattcc aaatgtatgt acgattgagg ataagtgctc tttgtaatga tatgctctca   42123
ctcctgagag ggcagaaatg aacttagagc attctgatcc aacgaagttc tgaattttt   42183 caaatacagt ttttaattct gctaggcttg aaatattatg cgtgtcttcg cccgtgtctt   42243
tgtttatcaa ccttctgat actagatatt gaaagactcg ccagcctatg ccctgtatg   42303 tgtcattcat aactgctttg gctggttcac cgtcacctgc cctctttaac tgggaatacg   42363
gggcaaaatt ccccaaaatg tcgcagtccg tgtagtctcc atcaactgct cctatcactg   42423
cgatagggct tcttctcatg gttcgtggaa taggaaaacg ggttctcagt cgctgcatag   42483
tgtaacggat gcaatgattc ctagactcgt cattgcacca ccggcattct ggtacggctc   42543
cagtacaagg cgcttttcca ctgttagaaa tcgaaatcag attcatgttt ggccgagtgc   42603
tgagttgctt ggaacatttt tccaaataaa atatgatacg ggacaggagt cggggctaa   42663 aaccacaggc atatgcgagg tgctcaggat catattcgaa tgtgttctga ggtgtgagtg   42723
gagatggaca tgtgccttcc caaactctct tccctgagta gtccacctgg gggcatccca   42783
ataaatgcaa tccacatgtc agataaaaac gggttagtcc gctcgaggcg cgctcgccgg   42843
gctccggcgc accccatcg actacctcac ttgcataaag gggggagtta tttgaaaaaa   42903
ttgctgctcc tacaatgccg gccaattctg ctgagaaccg atcgagagct tgaacgcgct   42963
ccatttgagt tttgcaatcg cagaacaacg gccactcttc atacggcaga ccgcagccat   43023
tatcaaaggg atatggagcg caggagacag agagtctagt tgccagcgca agttcagcag   43083
ccaagctaca ggcggcgcgc cgttctactt ctacatttg tttagggggt cctgtttgtt   43143
gtatgttctg agccagctcg gtaaaggtct tgtccgaggt taatacacag ccttcgaagc   43203
ttccatcgaa cgcgagcatt gccgctccgc gcgccacggc ttctaggtct ctggttctca   43263
gactttgtcc ctgtgttccg agtgttgtcc catgaatgag tctgttcaaa gctttgttga   43323
ataatggggt agggtaaatg cagccttcac cgatgttacg gctgtttgaa tcaaatgggt   43383
tacggcaaag ccgcagcgcg atgtctggca tgtacatttg cacagggtag attggtatgc   43443
gcgtaacaag cttagaattg atgtaaagcg tctcgactga tccatagtga atgtatgtgt   43503
tgcatacata caccgcctca caaaacggtt cggcaactac gagatagagc atcgttttgt   43563
```

```
cagggtccat attcagggat ttgcagatct cttctcctgt agtttcgatg gcatttggaa   43623
ccggtccatt tggggtagt gaactgaacc cgaacctttc ccttgcgtcc tcgcatattt   43683
ttgtgaggtt tggagtgaat gatgtaggcg ggatgcactc tcctccatga aagatatata   43743
ccgttgttga aaaatggcag ggagataaaa tagccgtaca attacctcca acgactcctg   43803
atgacttagt tccgatgact gctgcgacgt ttggcttgaa atcagactct acagtaagcc   43863
cccgtatgag aggagcgatg gcgcaggagg gctggtcttg acttttggcg cacagtatct   43923
tccattcctt tccatcaatc tcttcgcggg gtcttgcata tacgtagcca attggcccaa   43983
tacaccatgg tccgccatcc gactttccgc ccttagttgt gccagatgaa ctcttttcca   44043
tttgcgcgag ttatctcaga cagtatgatc tcagatcaga gttccgcgta gtagagtagt   44103
ctccgtcact gagcgcggac ttaagtaccg cggaaaggac acacctatgt atactttaga   44163
gagttcataa atatcgatga ttgcagtagc tgggcaccga gtttgtcact ctgcactatg   44223 gacactttt cctccgccgg tactggagct gctcgtgtag ccccgataat tggcctcggg   44283
ccgcactctg gcgcgtctta ttatacttct gtgagagaat tcccgtatgt atgtccaacg   44343
tgcattaatg ggggcggaag gataggaacg cagattggaa gggctacaag caaaccaacc   44403
ttttaccaca acgagcgaca attagacatc ttgacaagca cacatggagc gtggcccgtc   44463
aggatgaaat attggaatgc tggtcctgga atgactcacc acaacaaggg agatgtaaag   44523
ttttatgaat ttcacgttta tgaccttttt gaaaacactg agatcgctca gtcatgtgta   44583
cgatggatgc attccagatt tcttgataca ctgaaaccga ccggtactgt aataacctta   44643
gttggaaatt ctgcatgcgg aaagcgcgtc gccgttcatg tgtatggatc tttgccatac   44703
ttttttgtta aaaagcgaga aattgaccaa gccgcgaaag tcacgaactc ggaagagttg   44763
gcgcatgctc tagcattagc gacgcgtaag acatctttaa aaaattcacc ttttctagct   44823
gtttcagcgg aaagtttttg cattgatgtt gttcggcgca gagacattta ttatttgaa   44883 tctgaggagg aggacttcta ccgtgtaaaa gtgtgtaatg gcaaagtgat gaaatttata   44943
tgtgataatt ttttcccgag cgtacctaaa tatgaaagca atgttgacgc tattaccagg   45003
ttcatcctcg acaataatct gacttctttt gggtggtatc gctttagagc tcaaggtggc   45063
gcactccaaa ttcgagaccc aggacaacat gctacatcag ctgatgtcga aattaactgc   45123
acagcaagta atttggaact cggaaacaat gtctcgtggc cagactacaa attactgtgc   45183
tttgatatag aatgtaaagc cggaggggca aatgagtttg catttccttc tgctgagaag   45243
gtagaagatc ttgttatcca gatttcggca gttacatatt ctttgttaac taaggaaaaa   45303
gagcaggaaa tcattttttc cctagggacc tgtgaacttt ccgaagattg tagtgatggg   45363
ataactgtat gcgaatgtgg ctctgagttc gagcttcttc tgtgctttat gacttttttc   45423
aagcaatatt cacccgaatt tgtgagcgga tacaatattc tagggttcga ttgggcctat   45483
ctttctaaca agctgagcaa ggtgtatggc atgcgtctcg atggatatgg gaaagcaaac   45543
tcgtggggga cattcaaact tcaagatccg tctgcgcgcg gacttggaag attcaaaaaa   45603
gtcaaaatca atggcgtcgt caacattgat atgtttacca ttagttatga aaagctaaag   45663
ttaccatctt ataagttaaa tgcagtagca gagtgcgttc ttggagaaca aaaaattgat   45723
ctggcttaca aagatatccc agtcatgttt gctgcaggcc ctaaagaaag ggggaaaata   45783
ggggagtatt gtttgcagga ttctagactg tcagggagtt tgttttttcaa attctcccct   45843 catttagaaa tgtccgctgt cgctaaattg gcctgtatac ccttgacaag agcaataggc   45903
```

```
gatggacagc agctgcgcgt ttatacatgc ttgctccaac gctctacggc gtccgggttt    45963
gtgttgccgg acaaaaagag tgcgttttcc ttcggttcta ctcttgcttc agacgcgtct    46023
gatgcacctg ctacaagaaa tgtaggctac cagggagcca aggtactaga tccagaaata    46083
ggattccatg taactcctgt ggttgtattc gattttgcca gtttgtatcc gagtattatt    46143
cagagtaaca atctatgtta cagtacgtta acgcacgacc ccgccgcact ggcaggtcta    46203
cagccagaaa aagatttctt ccagattgat gttcagggtc ggaaatttta ttttgtcagg    46263
gagcatattc gcaaaagttt gctgtcagac ttgctaggtg attggttatc tatgaggaaa    46323
gccgtgcgcg caaaaatcaa dacagccgag actgaagaag agcgaatctt attagacaaa    46383
cagcaagctg ccattaaagt tgtctgtaac tctgtatatg ggtttactgg ggtgatgcat    46443
ggaatgcttc cttgtttaga agttgcttca acagttacag ctataggaag ggacatgctt    46503
ttgcgtacaa aggcgcacat cgagaaggag tggagaagtg gaaatcagtt tgccgaaaaa    46563
tttttgcccg gtccgaacg  tattcagcta aaccaatact ctgtccgggt catttatgga    46623
gatactgatt ctgtatttgt gaagtttacc ggagttgaca ttgaaacttt aactcaagtt    46683
ggtggctgca tggccgatga gattacacaa gcgcttttta gagctccggt aaaacttgag    46743
tgcgaaaaga ttttcgtgcg cctgttactc attgctaaga aaaaatacat tggggtgatg    46803
catgagggta aaatgttgat gaagggcgta gatctagtca ggaaaacaaa ctgtaaattt    46863
gtcaatacca cagcctcccg attagtgaat ctacttttcg aagacgacga aatagcgatg    46923
gctgcagata cagcaagagc cggatttgag gattttgact gtcttccgag cggacttact    46983
aagcttggcc ggttgattgc agaggcaagg ctagctatta ccggcaacgg actaaacatt    47043
agggacttca taatgaccgc ggaattaagt cgtgcggtgg ataactatgc cagtttgaaa    47103
ttgcctcatc tcacggttta tcaaaagaaa gctgctcggc gcgaagaatt acctcaaatt    47163
aaagaaagaa tcgaatatgt catcatagaa ccgggacaat ctgtcccgaa tgatccagca    47223
actgagtctt ttcctgaact aaaagaaact tctttgattt ctagcctggc agaagatcca    47283
gaatgggtcg tatcaaatgg tctaaaattg aatgtagaat actactttga ttcgcttatt    47343
agaacattaa gtgtaacatt taacgcaatt ttcggtgatg caaaaacagc agaggatgtt    47403
ttaagaagct ttattccaga gaaaatacag ttttctgaga agttgcaga  ggctcttgca    47463
cgaaacaccg cgacatttgt atccatcaag aagtaatcgg agggctgtaa gttgcaaatg    47523
ttgaataaag tttagtgtat cgtgaatttt tttcgtctgt tactaggata tcgcagtatc    47583
gtcgatacac tgactccggg ttcagcttaa cgcgctgatg ctcagagtaa cccggtccat    47643
cttctttgga aacgatcaat aagaacgtac cagcgaatac gtccacgtgc caagtgtatc    47703
ctgggcaatt aaatattaat tgtttcagaa gctttgcccc tagatgaagt ggcgtgctct    47763
gtttaaatac aaaatacata aggtatcccg atggaaactt cttagatctt ggatcgttca    47823
ccaagagaac ggtaaaatct tgagagagtc cgcccttac  tgtatagtat gcataaaaca    47883
aagtcgcctg ggccagtaga tttttgatag tgtcaagtag gaattcgttt tcatatgctc    47943
cagatccaac taccgattca cctgaaaata cccgcaggga cgccactaac tctttgaatt    48003
cgaccacaga gctcaggtga tggagaaagg ccaattccaa cgcaggcaag ctaacggtg    48063
gggcatttga ccatccatat gagcaaagtg agcagcatcc accaggtcca acggtgtagc    48123
ccatctcgga aagagagata cagtcgccag gggcaaaact tgcattcaca ttgtaaggaa    48183
gggagatatt ttcttggcgt atgacaggaa tcgtcattgt tctaagaagg gagatagtat    48243
cttccggaga tgaagccgtt agcttgaaaa aagcatcgaa gaaagttctc cgtgtgtcta    48303
```

```
gattagccct tgacctagac gatcgcctct tcgatctgag gtatgagatg tagcgatggc    48363
gttcgatggc ccccgtaata cttttcttc ggatgcgcag agcagcggcg cgagaacgga    48423
agtcagacat atcgagtcag tgcgtgttct aaagcaatgc agctgattcc gtgcctcttt    48483
aaataggtct cagcgccgcg aatgaaagaa tttaaagcgg tagggcgagg aggagaaagc    48543
tggtaagctt taaatgtgaa ggctagaatc cacagcccgc ggcaaacccg ttcttgaaat    48603
atgttagccg tggcgatttc ggctttataa agctgcagca gttctgggtc cttgggttgg    48663
ccttcccaca aaacttttgg atttacgcga agcgtattaa ctgcacacaa tggatcgcaa    48723
aaaaagtgtt tgtaaattgc gtttgccccg gccatcctca ataaggttaa cattcgcccc    48783
ccatcgttta acgcagtata gtcttcgaac gtttctaatg ctggttcaat cccatcgaac    48843
aagctgctat ttacgttact gcagccgact actttacttt tcagctttcg aagagcatgc    48903
cagtgttccc gagtaagcat gagattgcac aacacgcatt cccctccagt atctcctcgg    48963
ctagtcgggt gaggcaaaat agacgccaaa attgggccaa tggcaagtga tggtttggta    49023
ttgtcgcaaa tgtactgctt cgctgtcttg gggagcctag tattttgac ctgttggatt     49083 agcgttgcgt gaaagtttc cactacggta tttcttgtcc gaattatagg ggcaacgaaa      49143 tttctccat tatcatttgt atcatcatac tcaggctcgt cgctgcagct ggcatcgagt      49203
tcccgatttg gcataccggc tgttccagca attaataatg ccgtcaggtc ggtaaatccc    49263
catttacttg ggggttgtcag ggtttcgctt ggtccccctt ccacatattt tgactccgtg   49323
ctaatatctt ctaaagcagc tttttgcgca caggttcgaa aagcgaagga ggcagtctct    49383 gtattttcc tctttaacat acactgcgcg gagcaaaaac actcgagtgg tctggcatac     49443
tcacgccatt ttaacaaagc cacggccatt ccgctacttt tttggaagtt gaaatctgca   49503
gacgcgccag agaccggggc aattttttgcc ctaagtgctt cttgatatct agtagatagt   49563
aacgcatagc gtgctaccga ctgcactagg aacgaataat tatttagatc tattttagag    49623
tccagtcccc cttccaccgc tttgaaacag ccgttaaaaa agaagtgctt ctgaatatcc    49683
ccgagggaaa attcccgacg gcttatagcg ccaactaaag aggtgctgtg ggaatgcaag    49743
tagtgtttgt ccatgatgaa gatgaactca aaagcagtta tgaaggtaga tgtagcacac    49803
agggggatgc tttgagattt gaagcacaat aaagagtagt ccaccatcca ttcgggagtc    49863
acggggaatt ttttttgata tttggtaata atcttgcaga cggcgcatga tttatctagg    49923
gtgtataagt cagccatggt ttctacgaaa gaatcaatgt ccggaattct gttttgttct    49983
tcagcttgtt ctgtactttc ttcatgatat atttcaatta ggtgagctcc atacaatagt    50043
tcgtccgaca acttgtcatt aaacgtcaga atcgccgggt cgtagccagt atatagtttt    50103
gagagcactc cagctttcca tcccttggaa agttcagtgc gagtttctgc agttgatcgt    50163
ttggatgtca tggcatccac agttccgagg cgtcttagtg aattggtaga tgaagaggag    50223
ttagcggaaa ggccactctc agaactgttc agaaagtata ttggatctgc aggtagtccg    50283
gtatatgaaa tatggtttta tgacctatcg cctccggaaa ttgaagtagc tctgcctact    50343
accgatgcta aactaaacta ccttgcgcac acagccaatg tcgcggccga acttcggtac    50403
cgcaatttag atgggaaaag gatgtgcgca cacgcagaac ttattgctcg ccgtcgtgaa    50463
cggttcgcgc aaattctaag taagttttg gatcttcacc aaatttagg ggcgctagaa      50523 ccttgttagt ctggtagtat tataaataag agggcgagtg tgtatggtat taagacggat    50583
ccagaagacc atgaagaaag caatgaaacc ccaaggcgcc agaaatcaag gagacaaata    50643
```

```
ctgtcaattg gtgcgcgtcg tgaatgctgg attaagcctt gccggaacga cagcgagtct    50703
ggtgtatacc agagataatg cacgtctcgc acccactgga gatattttta cgcttcttgc    50763
taaacttgac ggtcccccaa ttccagcgga atatatccta gaggcaatga atagcttcct    50823
taatattgga gagtcgtggc tgcgtattca aaatacgggc caggctgtca ttgttgccgg    50883
atgctctacc aagaccgcta attgcaaaga ccaaatatgg cctgcttcta gtcctaccat    50943
atctttagcg gctgcaaaat ctctgtgggt aagttcctca tcggtgaagg aaatgaaaag    51003
acttcaaaag ttaaaaaacg ccccgctcgc aacaatgatg tacattagtt tttacagggg    51063
gtcgagaact gatattacca tcagattcgc attttaccgc tcagactcgg aacccaattt    51123
gattaaaatt actcgcagag tgcaagaggc tatagactcc gcggagcaag aagattcata    51183
taaaacggcg gcccttctta aaaaaacgtt gatggaaact acaagcgaga tgcccacaag    51243
tcactcggtt gctgagtcga agccatcacg ttctattttc gagcgcgtca ccacatattt    51303
tcgaatacat ctaaaatgtt taaacccgag gtccttctct ttacagccac tgatgtgggt    51363
gcttatgggt gtggcatggc ctgcttttt gacactactg atcttctatt taatccgagt     51423
acaggcgacg agctgaaatc ataccacacc tggaggcaga tatgagcagg caatctaact    51483
ctcattccac gccccaacca caggacagag tcaatgcggc cgcagaaatg ttgaaagctt    51543
ttttattgac ccctccgaga gatcgagctc cggactacat gcaaaccta aacggaatta     51603 ccttggatca actcacggaa gtagctcgag ccttgaaaaa tgaaatcccg agagaagata    51663
cagttcggca aaatattctt agaaataata tcacactcgc gctaatggct ttaaaccgag    51723
ctccaatgct tcgagatcgg ttaaatataa ggcccgtatt tgctcgcctt tcaggccctc    51783
aaggattgtg gacgtttgga gtgagacaac gcaccaggcc aagaccgaga cgctaagcaa    51843
aacgcaataa atataccaat tta acc cag tat tat ttt tat ttt gtg tgt         51893
                          Leu Thr Gln Tyr Tyr Phe Tyr Phe Val Cys
                                       1490                1495 ttc atc cgc tat gcg ggc ctg ctg atc taa agc gta atc tct cgc            51938
Phe Ile Arg Tyr Ala Gly Leu Leu Ile     Ser Val Ile Ser Arg
        1500                1505                    1510 gtg ttt tat tcc ttt aag cac cat gcg gca ggt gac tga cag cga            51983
Val Phe Tyr Ser Phe Lys His His Ala Ala Gly Asp     Gln Arg
        1515                1520                    1525 tgc ata aat atc act gcg cgc ggt ggg tgg caa ggg act aag aat           52028
Cys Ile Asn Ile Thr Ala Arg Gly Gly Trp Gln Gly Thr Lys Asn
        1530                1535                    1540 ttc tct ttc acc cgc ttt aga ctc ttc cgc atc gct tgc aag gtc           52073
Phe Ser Phe Thr Arg Phe Arg Leu Phe Arg Ile Ala Cys Lys Val
        1545                1550                    1555 ttc tga tgg ggc ttt gtc att tat tga ggt tcc gga aga tat ctc att      52121
Phe     Trp Gly Phe Val Ile Tyr     Gly Ser Gly Arg Tyr Leu Ile
            1560                                1565 tac agc atc atc ctc ttc cga act aga atc agg tgg agt ctg aat          52166
Tyr Ser Ile Ile Leu Phe Arg Thr Arg Ile Arg Trp Ser Leu Asn
1570                1575                    1580 gga ttt cag ata ggg tgt gat cgt tcc atc ccg caa tgc gtt gtc           52211
Gly Phe Gln Ile Gly Cys Asp Arg Ser Ile Pro Gln Cys Val Val
1585                1590                    1595 caa ttt tct caa ata agt atc taa agc ttg agt atc cct tac taa           52256
Gln Phe Ser Gln Ile Ser Ile     Ser Leu Ser Ile Pro Tyr
1600                1605                    1610 cct ttc tcc ctc ttc aat gcg ccc ttt ctt atg ttc atc ggc tct           52301
Pro Phe Ser Leu Phe Asn Ala Pro Phe Leu Met Phe Ile Gly Ser
        1615                1620                    1625
```

| | |
|---|---|
| gcg aga aga ttc ctc gtg aag ttt gtg cga ccc ttt gac ata tgc<br>Ala Arg Arg Phe Leu Val Lys Phe Val Arg Pro Phe Asp Ile Cys<br>1630                    1635                    1640 | 52346 |
| cgg tgt aaa atc ctc gtc aga act ttc tcc ttc cgg ggg atc gac<br>Arg Cys Lys Ile Leu Val Arg Thr Phe Ser Phe Arg Gly Ile Asp<br>     1645                    1650                    1655 | 52391 |
| ttc ctt gtc cca cgt gta act gta tgt tgg gaa gtg agc tat atc<br>Phe Leu Val Pro Arg Val Thr Val Cys Trp Glu Val Ser Tyr Ile<br>        1660                    1665                  1670 | 52436 |
| ctc att atc tga gca atg tgt ctg ttt ggc ttc cgc ggt gtc atg<br>Leu Ile Ile     Ala Met Cys Leu Phe Gly Phe Arg Gly Val Met<br>        1675                    1680                  1685 | 52481 |
| ttt atc tct gtg gct tgt tat gct ttc tgg cgg gcc ctc gtg ttc<br>Phe Ile Ser Val Ala Cys Tyr Ala Phe Trp Arg Ala Leu Val Phe<br>     1690                    1695                    1700 | 52526 |
| gct agt ttt acg tgt tgt tgc cag gtg gct tcg atc ttc tgg ttc<br>Ala Ser Phe Thr Cys Cys Cys Gln Val Ala Ser Ile Phe Trp Phe<br>        1705                    1710                  1715 | 52571 |
| cgg gtc tgt ggg atg ctc aag gtt agt ctc gtc tgt aat aac tgc<br>Arg Val Cys Gly Met Leu Lys Val Ser Leu Val Cys Asn Asn Cys<br>     1720                    1725                    1730 | 52616 |
| gaa att atc aga cgg gtc aga agt tat tga cgg act ctg aat ttt<br>Glu Ile Ile Arg Arg Val Arg Ser Tyr     Arg Thr Leu Asn Phe<br>        1735                    1740                  1745 | 52661 |
| cca atc aca agt ttc tga gag tac ttg ttc gaa ttc cga taa ttc tga<br>Pro Ile Thr Ser Phe     Glu Tyr Leu Phe Glu Phe Arg     Phe<br>              1750                        1755 | 52709 |
| ttc tgt tcc gct ctg cac tgg act agc aac aga gta tag act ggt<br>Phe Cys Ser Ala Leu His Trp Thr Ser Asn Arg Val     Thr Gly<br>     1760                    1765                    1770 | 52754 |
| atc ata att tgg atc cca cag ttc ggt atc ggt gtc tgt ttc cgg<br>Ile Ile Ile Trp Ile Pro Gln Phe Gly Ile Gly Val Cys Phe Arg<br>        1775                    1780                  1785 | 52799 |
| act cga ttc tgt gcc aga ttg agt tgg gga ttc act atc aat agt<br>Thr Arg Phe Cys Ala Arg Leu Ser Trp Gly Phe Thr Ile Asn Ser<br>     1790                    1795                    1800 | 52844 |
| gcg caa gtt gtc tgt agg tgt gct aat ggg cga gct ttc atg ttg<br>Ala Gln Val Val Cys Arg Cys Ala Asn Gly Arg Ala Phe Met Leu<br>     1805                    1810                    1815 | 52889 |
| atc tgt ctt cgc aca tac cgt gct atg aat tgg gcg cgg gcg cgt<br>Ile Cys Leu Arg Thr Tyr Arg Ala Met Asn Trp Ala Arg Ala Arg<br>        1820                    1825                  1830 | 52934 |
| aca ttc acc att ctc aaa act act ttt ttc aga agc agt att<br>Thr Phe Thr Ile Leu Lys Thr Thr Phe Phe Phe Arg Ser Ser Ile<br>     1835                    1840                    1845 | 52979 |
| gtg ctc ttt ctc act ttc gga tga atc gct agg aag agg aat ttt<br>Val Leu Phe Leu Thr Phe Gly     Ile Ala Arg Lys Arg Asn Phe<br>     1850                    1855                    1860 | 53024 |
| gga agc atc tgg ata cct tac agg aga ttt aga aat ctc ggt agt<br>Gly Ser Ile Trp Ile Pro Tyr Arg Arg Phe Arg Asn Leu Gly Ser<br>        1865                    1870                  1875 | 53069 |
| tat gac atg ttc atc aga tga gga aga tag caa gcg tga cgg tgt ttt<br>Tyr Asp Met Phe Ile Arg     Gly Arg     Gln Ala     Arg Cys Phe<br>              1880                        1885 | 53117 |
| aca cga ttc tga agc ttt gaa ata gcg aga ttt gct act cct gcg<br>Thr Arg Phe     Ser Phe Glu Ile Ala Arg Phe Ala Thr Pro Ala<br>1890                    1895                  1900 | 53162 |
| ttt gct cga gtg ctt tgg atg ttg gga tga ggc ctt ggt gtt gcc<br>Phe Ala Arg Val Leu Trp Met Leu Gly     Gly Leu Gly Val Ala | 53207 |

-continued

```
       1905                1910                1915
agg ctc cgg ttt ctt aaa ggt tat ccg agg ggg aag ttc cac gtg    53252
Arg Leu Arg Phe Leu Lys Gly Tyr Pro Arg Gly Lys Phe His Val
            1920                1925                1930 ttc ttt tag ctt ttc tcc ata ttc cgg tct acg ggt aca aat gtc    53297
Phe Phe     Leu Phe Ser Ile Phe Arg Ser Thr Gly Thr Asn Val
                1935                1940                1945 ctc tgg atc ttc gaa tat tgg gac atc tcc ccc tac tac atc gct    53342
Leu Trp Ile Phe Glu Tyr Trp Asp Ile Ser Pro Tyr Tyr Ile Ala
            1950                1955                1960 ata aaa tat atc ccc agg atc ccc gag att aga cga gaa cgt ccc    53387
Ile Lys Tyr Ile Pro Arg Ile Pro Glu Ile Arg Arg Glu Arg Pro
            1965                1970                1975 cgt gtc tga aaa ttt tac tgg gag gtc ctc ata ttt ggg gtc tcc    53432
Arg Val     Lys Phe Tyr Trp Glu Val Leu Ile Phe Gly Val Ser
                1980                1985                1990 atg gag cct taa aac gaa tgg cga tgg agc tgt ttc gag aga aac taa 53480
Met Glu Pro     Asn Glu Trp Arg Trp Ser Cys Phe Glu Arg Asn
                    1995                2000 tat ctg tgt tat ttt gtt tcc cct gtc gat ggc aaa aag taa cga    53525
Tyr Leu Cys Tyr Phe Val Ser Pro Val Asp Gly Lys Lys     Arg
2005                2010                2015 cgg agc atg ctt gag ggg ttt gct gga cag tac ggt tga taa ctc    53570
Arg Ser Met Leu Glu Gly Phe Ala Gly Gln Tyr Gly         Leu
        2020                2025                2030 tgc tat ctg gga ggc cag aca ggc gtt ctc tat ggg gtt ggc atc    53615
Cys Tyr Leu Gly Gly Gln Thr Gly Val Leu Tyr Gly Val Gly Ile
            2035                2040                2045 acc ggc aat aat gtc tcc caa ttg aat tgc cgt ctt ggc agt agt    53660
Thr Gly Asn Asn Val Ser Gln Leu Asn Cys Arg Leu Gly Ser Ser
            2050                2055                2060 aga gga cag cgc act ttc taa tgg att tgt ttt ccg tcc atc gaa    53705
Arg Gly Gln Arg Thr Phe     Trp Ile Cys Phe Pro Ser Ile Glu
            2065                2070                2075 aat agt aga aaa caa aac caa acc gtt att tga gct tag ttc ccc tgc 53753
Asn Ser Arg Lys Gln Asn Gln Thr Val Ile     Ala     Phe Pro Cys
            2080                2085 ttc ata tgc gat gac gac agg tgc tcc aaa aag aag tga aat aat    53798
Phe Ile Cys Asp Asp Asp Arg Cys Ser Lys Lys Lys     Asn Asn
2090                2095                2100 tgc gat atc aaa agc ggt taa gtc cca tat gga ttt atg ggg ctc    53843
Cys Asp Ile Lys Ser Gly     Val Pro Tyr Gly Phe Met Gly Leu
        2105                2110                2115 ctc ccg aag gga ata tat ccc agc acg atc tac ggt ccc gaa caa    53888
Leu Pro Lys Gly Ile Tyr Pro Ser Thr Ile Tyr Gly Pro Glu Gln
        2120                2125                2130 ttt gtc atc agg ggc ctc gaa gac tcg gct gag atc act gtt tgg    53933
Phe Val Ile Arg Gly Leu Glu Asp Ser Ala Glu Ile Thr Val Trp
        2135                2140                2145 gga aaa gtc ata atc gca gct tgg cga tga gcg gga aac cat ata    53978
Gly Lys Val Ile Ile Ala Ala Trp Arg     Ala Gly Asn His Ile
        2150                2155                2160 atg aat cat ggt atc gat ggg ctc tcc atc aat atc gtc atg ggg    54023
Met Asn His Gly Ile Asp Gly Leu Ser Ile Asn Ile Val Met Gly
        2165                2170                2175 tcc cat gga aac cca tag tgc ctc cag gat att cct cgg gat gca    54068
Ser His Gly Asn Pro     Cys Leu Gln Asp Ile Pro Arg Asp Ala
        2180                2185                2190 ttt gag ggc aag aat cat tag aaa ggc act tgt ctc ata ttc ttc    54113
```

```
Phe Glu Gly Lys Asn His     Lys Gly Thr Cys Leu Ile Phe Phe
            2195                    2200 tcc gga aca aaa ttt ttc aag cat gca tat ccc tga cct gac aga      54158
Ser Gly Thr Lys Phe Phe Lys His Ala Tyr Pro     Pro Asp Arg
2205            2210                2215 ggg aaa tct ttt cca ggg gtc taa aaa tct caa aat aga gga ggg      54203
Gly Lys Ser Phe Pro Gly Val     Lys Ser Gln Asn Arg Gly Gly
2220            2225                2230 cgg agg ttg gga aag cca gtc ttt agg gtc tat cac aaa aca tgc      54248
Arg Arg Leu Gly Lys Pro Val Phe Arg Val Tyr His Lys Thr Cys
        2235            2240                2245 ccc agc tga agg atc gaa atg ctg cct acc ttt tga tag agg gaa      54293
Pro Ser     Arg Ile Glu Met Leu Pro Thr Phe     Arg Glu
        2250                2255 aga gag tgc ttt ttt att ctg agt ttt tct ttg gta agg atc aag      54338
Arg Glu Cys Phe Phe Ile Leu Ser Phe Ser Leu Val Arg Ile Lys
2260            2265                2270 aga tgt tat tcc tac ctt ctc gcg cac tgc cct aga taa aac aac      54383
Arg Cys Tyr Ser Tyr Leu Leu Ala His Cys Pro Arg     Asn Asn
2275            2280                2285 atc tag ggt att tac tat gta ttc agt ttg ctt taa ata att aag      54428
Ile     Gly Ile Tyr Tyr Val Phe Ser Leu Leu     Ile Ile Lys
        2290            2295                2300 cct gcc aaa gta aac tag gtg tgc agg ttc gca tgc agt taa aag      54473
Pro Ala Lys Val Asn     Val Cys Arg Phe Ala Cys Ser     Lys
        2305                2310 gat taa aat atc aat agc ggt tat tga gta aat gcg aac tgc ttt      54518
Asp     Asn Ile Asn Ser Gly Tyr     Val Asn Ala Asn Cys Phe
2315            2320                2325 gtc gaa ttg att ttt ctg att gat ctt atc cag gtc tgt gtg ggg      54563
Val Glu Leu Ile Phe Leu Ile Asp Leu Ile Gln Val Cys Val Gly
        2330            2335                2340 tat aaa gtt gcc cat ctc atc tat tat tac atc ccg cgc tga ccc      54608
Tyr Lys Val Ala His Leu Ile Tyr Tyr Tyr Ile Pro Arg     Pro
        2345            2350                2355 taa agt ttt tga cag agt cag ata agt cag ggc act gta aat tgt      54653
Ser Phe     Gln Ser Gln Ile Ser Gln Gly Thr Val Asn Cys
        2360                2365 aca tgc ggc gac cat cgg agt atc tgt ttg ttt gtt cga gct tgg      54698
Thr Cys Gly Asp His Arg Ser Ile Cys Leu Phe Val Arg Ala Trp
2370            2375                2380 cca ggt tcg ggt gga aca gaa aat ggt gta aga atg gaa gcc cgc      54743
Pro Gly Ser Gly Gly Thr Glu Asn Gly Val Arg Met Glu Ala Arg
2385            2390                2395 ttc tat atc gct agt cct ggc tct cat cca tag agt tgc cgc gac      54788
Phe Tyr Ile Ala Ser Pro Gly Ser His Pro     Ser Cys Arg Asp
2400            2405                2410 caa tga gag ggc tgc att ttg tct gac gga taa ttt ttt tac taa      54833
Gln     Glu Gly Cys Ile Leu Ser Asp Gly     Phe Phe Tyr
        2415            2420                2425 ctc gtt gtc ttt tgg att ctc aag ttc caa gga gag agg ctc act      54878
Leu Val Val Phe Trp Ile Leu Lys Phe Gln Gly Glu Arg Leu Thr
        2430            2435                2440 ttg gtc cga aga tgt gca taa cgc agc tga cca caa ggc ggc agc ttt  54926
Leu Val Arg Arg Cys Ala     Arg Ser     Pro Gln Gly Gly Ser Phe
        2445                2450 tgc agt ggc cgt tcg ata aca aag agt gta ttc cag ggg cat tcc      54971
Cys Ser Gly Arg Ser Ile Thr Lys Ser Val Phe Gln Gly His Ser
2455            2460                2465
```

-continued

| | | |
|---|---|---|
| gtt atc tgt gac cat gac cga gcc tat tgt tcc gag gtg gtg aaa<br>Val Ile Cys Asp His Asp Arg Ala Tyr Cys Ser Glu Val Val Lys<br>2470                       2475                       2480 | 55016 |
| cgt aac cgt cat aac cgc ttt ttt att ctg tct cat ata gct gga<br>Arg Asn Arg His Asn Arg Phe Phe Ile Leu Ser His Ile Ala Gly<br>2485                       2490                       2495 | 55061 |
| agc cct ggc gag ttc ccg gac tct gga aga aaa ggg agt ctc cgc<br>Ser Pro Gly Glu Phe Pro Asp Ser Gly Arg Lys Gly Ser Leu Arg<br>2500                       2505                       2510 | 55106 |
| aga aga tag tct cgg gat gat gtc gtc tga aaa agc tat acc caa<br>Arg Arg     Ser Arg Asp Asp Val Val     Lys Ser Tyr Thr Gln<br>2515                       2520                       2525 | 55151 |
| ggc ctt gta agc aag gta aag ttc aag tct tag cag tat taa ctt<br>Gly Leu Val Ser Lys Val Lys Phe Lys Ser     Gln Tyr     Leu<br>2530                       2535                       2540 | 55196 |
| ttt aat atc ttc ata ctt tgc tcg gta cca ctt tgg aac aga ctc<br>Phe Asn Ile Phe Ile Leu Cys Ser Val Pro Leu Trp Asn Arg Leu<br>                   2545                       2550                       2555 | 55241 |
| aaa aat tgc agt taa ttc taa atg gag aga ttt caa agc ttt gaa atg<br>Lys Asn Cys Ser     Phe     Met Glu Arg Phe Gln Ser Phe Glu Met<br>                   2560                            2565 | 55289 |
| cat ctc tgt ctt tgc ttt aaa gat tac ttc gtc gaa tgt tcg cat<br>His Leu Cys Leu Cys Phe Lys Asp Tyr Phe Val Glu Cys Ser His<br>2570                       2575                       2580 | 55334 |
| ggc att agt cag tgt gat gat gtt ttc ttc tgc ctt ttg taa tat<br>Gly Ile Ser Gln Cys Asp Asp Val Phe Phe Cys Leu Leu     Tyr<br>2585                       2590                       2595 | 55379 |
| ggg agt ata ttc tga aat gtc ttt ttg ata ctt ctt tat ttc cgg<br>Gly Ser Ile Phe     Asn Val Phe Leu Ile Leu Leu Tyr Phe Arg<br>2600                       2605                       2610 | 55424 |
| agt tga tgt aac ttg agc ctc tac cat ttg caa ccg gct ggc taa<br>Ser     Cys Asn Leu Ser Leu Tyr His Leu Gln Pro Ala Gly<br>                   2615                       2620                       2625 | 55469 |
| gcg ttc tcg tga ttc ctt tag att gtg aac tgc att gac gta tgc acc<br>Ala Phe Ser     Phe Leu     Ile Val Asn Cys Ile Asp Val Cys Thr<br>                           2630                            2635 | 55517 |
| cca tga ctc ttc gct ggt gtc ttt ttc ttt tcc gga ggt ttc ctt<br>Pro     Leu Phe Ala Gly Val Phe Phe Phe Ser Gly Gly Phe Leu<br>2640                       2645                       2650 | 55562 |
| aaa gga agt ggc agc tga taa aaa ata ctt ata gta agc ttc gag<br>Lys Gly Ser Gly Ser          Lys Ile Leu Ile Val Ser Phe Glu<br>2655                       2660                       2665 | 55607 |
| atc ttt cag acc cgc gtc agc ctc ttc ata cag tcg ttt aag ttc<br>Ile Phe Gln Thr Arg Val Ser Leu Phe Ile Gln Ser Phe Lys Phe<br>                   2670                       2675                       2680 | 55652 |
| atc caa tcg ctt ttt aaa atc ttc taa tgg tcc gcg ttc atc gat<br>Ile Gln Ser Leu Phe Lys Ile Phe     Trp Ser Ala Phe Ile Asp<br>                   2685                       2690                       2695 | 55697 |
| aga gtt tac tag ttc aca tgt atc gag aat gtg agc cga aga aaa<br>Arg Val Tyr     Phe Thr Cys Ile Glu Asn Val     Ser Arg Arg Lys<br>                   2700                       2705 | 55742 |
| cat cca ttc caa tga ttt ggg gtc cac gga agt tat acc ggt gga<br>His Pro Phe Gln     Phe Gly Val His Gly Ser Tyr Thr Gly Gly<br>2710                       2715                       2720 | 55787 |
| att gct ttt ctc ttc cac ttc gcg aaa gag att aag gaa aag gat<br>Ile Ala Phe Leu Phe His Phe Ala Lys Glu Ile Lys Glu Lys Asp<br>2725                       2730                       2735 | 55832 |
| aat tat atc ttc aag tga ttc tgc cct ttc gat gcc cgg ggc aac<br>Asn Tyr Ile Phe Lys     Phe Cys Pro Phe Asp Ala Arg Gly Asn<br>2740                       2745                       2750 | 55877 |

```
ttc ctt ggg cac gcg acc caa tag taa ccc ttt cag ctt ttt taa     55922
Phe Leu Gly His Ala Thr Gln         Pro Phe Gln Leu Phe
            2755                2760 gcc ctt ctg cat acg caa gac ttc ctc ttc tct tac act cca taa     55967
Ala Leu Leu His Thr Gln Asp Phe Leu Phe Ser Tyr Thr Pro
2765                2770                2775 ttg ctc cag cat gtt ttt aat ttt gcc gtc tgt gtt ctt ttt ttg     56012
Leu Leu Gln His Val Phe Asn Phe Ala Val Cys Val Leu Phe Leu
        2780                2785                2790 ttg ttc cgc ctt gtt aat ttc tgc gga taa aaa taa ttt aac atc     56057
Leu Phe Arg Leu Val Asn Phe Cys Gly     Lys     Phe Asn Ile
    2795                2800                        2805 tcg caa cgc cct gtg aga agc atc ttg ata ggc ggt atg gtc aaa     56102
Ser Gln Arg Pro Val Arg Ser Ile Leu Ile Gly Gly Met Val Lys
                2810                2815                2820 cac agt gac atc atc gga gtg tag act gtc tgg cag ctc ctt gag     56147
His Ser Asp Ile Ile Gly Val     Thr Val Trp Gln Leu Leu Glu
            2825         Val        2830                2835 tgc gat gag ggc cgt ggg tat cac ttc gcc gcg gtc taa ccg ctt     56192
Cys Asp Glu Gly Arg Gly Tyr His Phe Ala Ala Val     Pro Leu
                2840                2845 ttt ggc att ttc tgg act tct ctc tat ctg tgc act ctc ttc agc     56237
Phe Gly Ile Phe Trp Thr Ser Leu Tyr Leu Cys Thr Leu Phe Ser
2850                2855                2860 taa ttg aag ctc ctt ctt taa ctc atc ttg caa cag gat tgc ttt     56282
Leu Lys Leu Leu Leu     Leu Ile Leu Gln Gln Asp Cys Phe
2865                2870                2875 ttc ttt aat agt ttg aat ctt tga tga aaa ttc gat gaa ttg ttc     56327
Phe Phe Asn Ser Leu Asn Leu         Lys Phe Asp Glu Leu Phe
        2880                2885                    2890 atg cgc ttg caa gta aaa gtc aac aaa ttc tga taa ttc agg aat gcg 56375
Met Arg Leu Gln Val Lys Val Asn Lys Phe         Phe Arg Asn Ala
            2895                2900 cat caa ttg ctc gga cag tcg gaa aac tac gcc cct ggt atc aat     56420
His Gln Leu Leu Gly Gln Ser Glu Asn Tyr Ala Pro Gly Ile Asn
2905                2910                2915 ttg aga ccc ttc tac ggt aac ttc tgc cgt ttc caa aat atc ctt     56465
Leu Arg Pro Phe Tyr Gly Asn Phe Cys Arg Phe Gln Asn Ile Leu
2920                2925                2930 tgc aat tgc aca aac ggt cgt cag gcc ttc tac ctt tgc tcc aaa     56510
Cys Asn Cys Thr Asn Gly Arg Gln Ala Phe Tyr Leu Cys Ser Lys
2935                2940                2945 taa agt ttc ata gta ttt act gac caa cgg gaa tga atg tac cca     56555
    Ser Phe Ile Val Phe Thr Asp Gln Arg Glu     Met Tyr Pro
2950                2955                2960 cgt aga agc ggc tat agg agc tac ggc tat ttt gtt tcc ctg ccc     56600
Arg Arg Ser Gly Tyr Arg Ser Tyr Gly Tyr Phe Val Ser Leu Pro
        2965                2970                2975 tgc ttc tgc att acc aga ata tgg gtt gaa gga gaa aaa cga tcg     56645
Cys Phe Cys Ile Thr Arg Ile Trp Val Glu Gly Glu Lys Arg Ser
                2980                2985                2990 aag aag ttt tgt gcc ggt tgc gag cca gtc att tac aac gtt ttg     56690
Lys Lys Phe Cys Ala Gly Cys Glu Pro Val Ile Tyr Asn Val Leu
        2995                3000                3005 agc tag atg ttt tag ttc tgt gtg ggc ttt atg tgt act att aac     56735
Ser     Met Phe     Phe Cys Val Gly Phe Met Cys Thr Ile Asn
            3010                3015                3020 atg tgg tcg gag atc ata tat cgt ttc cca atc gtc tgc cga aaa     56780
Met Trp Ser Glu Ile Ile Tyr Arg Phe Pro Ile Val Cys Arg Lys
```

-continued

```
                    3025                3030                3035
ctt  agc  act  gct  acg  atc  ttg  gag  gag  tgc  agc  ctt  cgt  tgc  ttc        56825
Leu  Ser  Thr  Ala  Thr  Ile  Leu  Glu  Glu  Cys  Ser  Leu  Arg  Cys  Phe
               3040                3045                3050 cag  cca  ctc  gat  ttc  ctc  tat  ggc  aag  tat  ggc  att  atg  cgc  agc        56870
Gln  Pro  Leu  Asp  Phe  Leu  Tyr  Gly  Lys  Tyr  Gly  Ile  Met  Arg  Ser
               3055                3060                3065 ctc  gga  aag  gtt  gct  aca  tgc  ttt  ttc  tag  aga  taa  taa  ttc  cgg  gga   56918
Leu  Gly  Lys  Val  Ala  Thr  Cys  Phe  Phe       Arg            Phe  Arg  Gly
               3070                     3075 aaa  tct  ttc  ctc  att  ggt  aag  atc  taa  ctg  tgc  cac  ctc  ttt  ctt        56963
Lys  Ser  Phe  Leu  Ile  Gly  Lys  Ile       Leu  Cys  His  Leu  Phe  Leu
               3080                3085                3090 aac  cct  ttc  cac  cag  cac  tgt  agc  cga  gtc  tgc  tat  ttg  tcg  atc        57008
Asn  Pro  Phe  His  Gln  His  Cys  Ser  Arg  Val  Cys  Tyr  Leu  Ser  Ile
               3095                3100                3105 acg  taa  ttc  tgg  gac  att  cag  ttt  ttc  cgt  ggc  gtt  caa  aat  gtc        57053
Thr       Phe  Trp  Asp  Ile  Gln  Phe  Phe  Arg  Gly  Val  Gln  Asn  Val
               3110                3115                3120 ttt  agt  cag  tct  ttc  aat  aac  atc  cga  tag  ctg  ttt  tct  cct  tgc        57098
Phe  Ser  Gln  Ser  Phe  Asn  Asn  Ile  Arg       Leu  Phe  Ser  Pro  Cys
               3125                3130                3135 ccg  ttg  ata  agc  ttc  aga  ctc  cag  ctc  gta  gag  att  atc  acg  gat        57143
Pro  Leu  Ile  Ser  Phe  Arg  Leu  Gln  Leu  Val  Glu  Ile  Ile  Thr  Asp
               3140                3145                3150 gct  aaa  tag  aaa  ctg  agg  tat  ttg  cga  agc  ccc  tct  gtt  att  ttg        57188
Ala  Lys       Lys  Leu  Arg  Tyr  Leu  Arg  Ser  Pro  Ser  Val  Ile  Leu
                    3155                3160 cac  atc  atg  aat  aac  tgc  ctc  cac  ctc  ttg  tct  ggc  gcg  aga  gaa        57233
His  Ile  Met  Asn  Asn  Cys  Leu  His  Leu  Leu  Ser  Gly  Ala  Arg  Glu
3165           3170                3175 ccc  atc  cgc  atc  tcc  att  tgc  ttt  cgc  cgt  ctc  tat  gac  gaa  cag        57278
Pro  Ile  Arg  Ile  Ser  Ile  Cys  Phe  Arg  Arg  Leu  Tyr  Asp  Glu  Gln
3180           3185                3190 aag  ccg  ttc  tgc  atg  atc  gag  aaa  gac  ttc  aaa  cgc  tct  gtt  cag        57323
Lys  Pro  Phe  Cys  Met  Ile  Glu  Lys  Asp  Phe  Lys  Arg  Ser  Val  Gln
3195           3200                3205 tgc  atg  ttt  gtt  ttt  tcc  tcc  gga  aag  aag  cgt  tgc  tgt  aaa  acg        57368
Cys  Met  Phe  Val  Phe  Ser  Ser  Gly  Lys  Lys  Arg  Cys  Cys  Lys  Thr
3210           3215                3220 gat  agc  gtc  gac  aag  atc  atg  caa  atc  tgt  ggt  att  tag  gga  tcc        57413
Asp  Ser  Val  Asp  Lys  Ile  Met  Gln  Ile  Cys  Gly  Ile       Gly  Ser
3225           3230                3235 aaa  tgc  acg  tcc  ata  ctc  ttc  cag  caa  gtt  ttc  gaa  atc  gtc  ccg        57458
Lys  Cys  Thr  Ser  Ile  Leu  Phe  Gln  Gln  Val  Phe  Glu  Ile  Val  Pro
     3240           3245                3250 tac  atg  ctt  tcc  aat  aaa  atc  atc  att  tct  agc  aag  gtt  tat  aac        57503
Tyr  Met  Leu  Ser  Asn  Lys  Ile  Ile  Ile  Ser  Ser  Lys  Val  Tyr  Asn
     3255           3260                3265 ttc  ctc  ttg  ggg  aat  gtt  tct  tgt  ctg  gag  cgc  gct  ttt  tat  att        57548
Phe  Leu  Leu  Gly  Asn  Val  Ser  Cys  Leu  Glu  Arg  Ala  Phe  Tyr  Ile
     3270           3275                3280 tct  tag  tcc  ttc  gaa  ttt  ttt  taa  cgg  gcg  caa  tat  ctg  cgt  cac        57593
Ser       Ser  Phe  Glu  Phe  Phe       Arg  Ala  Gln  Tyr  Leu  Arg  His
          3285                3290                3295 ggt  acg  ttt  cgt  ttc  ttc  gtg  cgc  agt  ttc  ttc  ctt  tct  aat  ctc        57638
Gly  Thr  Phe  Arg  Phe  Phe  Val  Arg  Ser  Phe  Phe  Leu  Ser  Asn  Leu
          3300                3305                3310 ttt  gga  gaa  ttg  atc  tat  caa  acg  tga  agc  gcg  gtc  ttc  tag  cgc        57683
```

-continued

```
                Phe Gly Glu Leu Ile Tyr Gln Thr     Ser Ala Val Phe     Arg
                        3315                3320 gtc aag gcg acg gct ttg ttc cac ggt agt tct cgc ggc ttt ggc           57728
Val Lys Ala Thr Ala Leu Phe His Gly Ser Ser Arg Gly Phe Gly
3325            3330                3335 tac ttt gat tga ttc ctg tgt gtg aag gac ata ttg cag gcg tac           57773
Tyr Phe Asp     Phe Leu Cys Val Lys Asp Ile Leu Gln Ala Tyr
3340                3345                3350 ttg ggg ggg cgc tgt aat agc ttc cac tcc ctc gag ctc gtt ttc           57818
Leu Gly Gly Arg Cys Asn Ser Phe His Ser Leu Glu Leu Val Phe
        3355                3360                3365 taa ttc agc cag cat att ttc agt tag ccc aaa act ctg agc aat           57863
    Phe Ser Gln His Ile Phe Ser     Pro Lys Thr Leu Ser Asn
        3370                3375                3380 agc gtt gat gtc atg aat agc gga gat cca ttt tgt agg tga tgg           57908
Ser Val Asp Val Met Asn Ser Gly Asp Pro Phe Cys Arg     Trp
            3385                3390                3395 gac aag tcc ctc tgc atg agc ttc gaa tag atg tag gga cca tct ctt       57956
Asp Lys Ser Leu Cys Met Ser Phe Glu     Met     Gly Pro Ser Leu
                3400                3405 gag ttt ttc atc ggt ggt aag gtc ttt ccc atc gat tac cag atc           58001
Glu Phe Phe Ile Gly Gly Lys Val Phe Pro Ile Asp Tyr Gln Ile
3410            3415                3420 tct gaa aat tct caa tgg ctt tct tgt gaa cag tac ttg taa gtt           58046
Ser Glu Asn Ser Gln Trp Leu Ser Cys Glu Gln Tyr Leu     Val
3425            3430                3435 ctt cga tgg gtt tcc tgc aag ttg cct aat caa ctg aaa ccg cct           58091
Leu Arg Trp Val Ser Cys Lys Leu Pro Asn Gln Leu Lys Pro Pro
        3440                3445                3450 ttc aat ctc ctc tat gtt ttt tag cca att gac agc att ctc tac           58136
Phe Asn Leu Leu Tyr Val Phe     Pro Ile Asp Ser Ile Leu Tyr
        3455                3460                3465 aaa tag agt agg gat gct aaa cct tcc caa tac tcc acc gac ccc           58181
Lys     Ser Arg Asp Ala Lys Pro Ser Gln Tyr Ser Thr Asp Pro
            3470                3475                3480 aga tga taa tgc cga tat gct ata gtc aat ggc gcc cgc ata ttt           58226
Arg         Cys Arg Tyr Ala Ile Val Asn Gly Ala Arg Ile Phe
                    3485                3490 ctt tag gaa ttt gac cgc agc atc ctc aat tct gat aat tgc gtc           58271
Leu     Glu Phe Asp Arg Ser Ile Leu Asn Ser Asp Asn Cys Val
3495                3500                3505 gtc gag ctt tcg att aat atc ctg aac gtc gag tcc tgt aaa ttt           58316
Val Glu Leu Ser Ile Asn Ile Leu Asn Val Glu Ser Cys Lys Phe
        3510                3515                3520 cct caa acc ctg tat aat tgc ttg tgg tat gtc cgg agt ttg ggt           58361
Pro Gln Thr Leu Tyr Asn Cys Leu Trp Tyr Val Arg Ser Leu Gly
3525                3530                3535 tgc ttg gat att gat cac atc tac tcc tat gtt aca aat ttc atc           58406
Cys Leu Asp Ile Asp His Ile Tyr Ser Tyr Val Thr Asn Phe Ile
3540                3545                3550 aat gac tgt cca cgt att ggc gag aag tga tag tac tgc aat ttt           58451
Asn Asp Cys Pro Arg Ile Gly Glu Lys         Tyr Cys Asn Phe
3555                3560                    3565 ggc atc agc gaa gcg tgc ttc act ttc tat cac aga ttt cgc agc           58496
Gly Ile Ser Glu Ala Cys Phe Thr Phe Tyr His Arg Phe Arg Ser
        3570                3575                3580 acg ctc tac tac atc agt aat ttt gtg tcc gtg tga att aac atc          58541
Thr Leu Tyr Tyr Ile Ser Asn Phe Val Ser Val     Ile Asn Ile
        3585                3590                3595
```

-continued

```
ttc tat tag aat act cgt ttt att tga aca ttc cag cag ttc ttc gga    58589
Phe Tyr     Asn Thr Arg Phe Ile     Thr Phe Gln Gln Phe Phe Gly
            3600                3605 taa ctg ttc gta cgc agt tgg aag ttg atc acg ctc ggc act gtc        58634
    Leu Phe Val Arg Ser Trp Lys Leu Ile Thr Leu Gly Thr Val
3610                3615                3620 tgc gat ttg att caa ttt agc aat taa cat ttc tgt ctg cgt taa        58679
Cys Asp Leu Ile Gln Phe Ser Asn     His Phe Cys Leu Arg
    3625                3630                    3635 cag gga taa act gac ctg ctg cgt ttt tct taa aag aac act gcc        58724
Gln Gly     Thr Asp Leu Leu Arg Phe Ser     Lys Asn Thr Ala
        3640                3645 ccc ttc act gtt aga gtg gca tag ctc cag gag caa gtg ttt ctt        58769
Pro Phe Thr Val Arg Val Ala     Leu Gln Glu Gln Val Phe Leu
3650                3655                3660 ttc gat aag atc ctg ata acg cag tct tgt agt ggt caa tat att        58814
Phe Asp Lys Ile Leu Ile Thr Gln Ser Cys Ser Gly Gln Tyr Ile
    3665                3670                3675 gct gat att ttt ctc tcc gat gcg agc caa tag cgt tgc caa tgg        58859
Ala Asp Ile Phe Leu Ser Asp Ala Ser Gln     Arg Cys Gln Trp
3680                3685                    3690 gtc tat tag aag gtc cac cgt gct ttc caa gtt ttt tgt gga gac        58904
Val Tyr     Lys Val His Arg Ala Phe Gln Val Phe Cys Gly Asp
        3695                3700                3705 ccc gtt ctc tat aat aaa aaa taa tat gcg att gca ggt aat tct        58949
Pro Val Leu Tyr Asn Lys Lys     Tyr Ala Ile Ala Gly Asn Ser
            3710                3715                3720 cac ctt ttc ccg taa aat ccc aga tcg caa aaa tct cgt cag tgc        58994
His Leu Phe Pro     Asn Pro Arg Ser Gln Lys Ser Arg Gln Cys
                3725                3730 cgg ttc gaa tgt ctc ctg tgg ggc cgg taa cca ctt aag agg atc        59039
Arg Phe Glu Cys Leu Leu Trp Gly Arg     Pro Leu Lys Arg Ile
3735                3740                3745 ttc caa ggc att ttt tat tgg tgt tat gga tcc taa ttc aat tgt        59084
Phe Gln Gly Ile Phe Tyr Trp Cys Tyr Gly Ser     Phe Asn Cys
    3750                3755                3760 tgc tga tgg gtt tgt gtc ttc tgc cgt aag taa att cca aga tag        59129
Cys     Trp Val Cys Val Phe Cys Arg Lys     Ile Pro Arg
        3765                3770 ctt cct cct ggc gct atg cgg ctt agt att gct ttg agc ttc tgg        59174
Leu Pro Pro Gly Ala Met Arg Leu Ser Ile Ala Leu Ser Phe Trp
3775                3780                3785 gtc tga acg tac gga gtg ttt tct ttg ttt tcg tgg tgt gag gtt        59219
Val     Thr Tyr Gly Val Phe Ser Leu Phe Ser Trp Cys Glu Val
3790                3795                3800 tgt cag ttt ttc tga gct tcc gat ttg atc agg att ctt tgg ctg        59264
Cys Gln Phe Phe     Ala Ser Asp Leu Ile Arg Ile Leu Trp Leu
    3805                3810                3815 tgg ctt ctg tct ctt ttt tga tct tgg tct tac cgg aac gct cca        59309
Trp Leu Leu Ser Leu Phe     Ser Trp Ser Tyr Arg Asn Ala Pro
            3820                3825                3830 tgg agc aat agc ctt tct acg gtc cgc gag ttc aaa aag gtt ctt        59354
Trp Ser Asn Ser Leu Ser Thr Val Arg Glu Phe Lys Lys Val Leu
        3835                3840                3845 ctg aga aaa ctc tgg gtt tag tcc gag agc ata gac atg cgc cgg        59399
Leu Arg Lys Leu Trp Val     Ser Glu Ser Ile Asp Met Arg Arg
            3850                3855                3860 aaa tgg atg aat tat ttg tgt gct taa cgt aac act gct taa ttc agc    59447
Lys Trp Met Asn Tyr Leu Cys Ala     Arg Asn Thr Ala     Phe Ser
            3865                3870
```

```
atc tga tgc gcc ata tga tgc cat tac tga tgc cgc aat gat ttc       59492
Ile     Cys Ala Ile     Cys His Tyr     Cys Arg Asn Asp Phe
3875                3880                    3885 ctg gag cgt ttt ctc cga tac ctt ttc ttc gtc cca ccc atc cgc       59537
Leu Glu Arg Phe Leu Arg Tyr Leu Phe Phe Val Pro Pro Ile Arg
        3890                3895                3900 att gaa cca gta gag aaa att cat atc tat tcc aac tcc aga cat       59582
Ile Glu Pro Val Glu Lys Ile His Ile Tyr Ser Asn Ser Arg His
            3905                3910                3915 att ctt tac ata tgc ccg aac aaa ttc tgg gag gtc atc aat tct       59627
Ile Leu Tyr Ile Cys Pro Asn Lys Phe Trp Glu Val Ile Asn Ser
                3920                3925                3930 cct tag ctt gca tac ata agc act tga cat ttc cca tcc atg tga atc   59675
Pro     Leu Ala Tyr Ile Ser Thr     His Phe Pro Ser Met     Ile
                    3935                3940 aaa aat gta cac agg atc gtc ctt tcc ccc aga aca cac ggc tgc       59720
Lys Asn Val His Arg Ile Val Leu Ser Pro Arg Thr His Gly Cys
3945                3950                3955 aac tcc cct gtc acc gat gat cat tat gaa tcc caa tcc ttt cct       59765
Asn Ser Pro Val Thr Asp Asp His Tyr Glu Ser Gln Ser Phe Pro
3960                3965                3970 aat ttt ctt ggc aat gat ttt ggt aat gcc gtg tat att cat gga       59810
Asn Phe Leu Gly Asn Asp Phe Gly Asn Ala Val Tyr Ile His Gly
3975                3980                3985 aga tgg gaa acc ttc gat tgt gac ttc cat gtc ata acc cac att       59855
Arg Trp Glu Thr Phe Asp Cys Asp Phe His Val Ile Thr His Ile
3990                3995                4000 ccc gta tgt tat aga agg tat cat gag cat gtc agg ttc atc cca       59900
Pro Val Cys Tyr Arg Arg Tyr His Glu His Val Arg Phe Ile Pro
4005                4010                4015 tga tga tct cca gag tct ggg aag ttc gtg aca atc aat cat tcg       59945
Ser     Pro Glu Ser Gly Lys Phe Val Thr Ile Asn His Ser
4020                4025                4030 aaa cga aca ttt ttt tga ctt gtc ctc cac ctt ggc ctt ccc tgt       59990
Lys Arg Thr Phe Phe     Leu Val Leu His Leu Gly Leu Pro Cys
        4035                4040                4045 tct cgt aat ctc cgc ccc ctg gtc taa aat cgc atc caa act gtc       60035
Ser Arg Asn Leu Arg Pro Leu Val     Asn Arg Ile Gln Thr Val
            4050                4055                4060 cgc aga gag cat cga atc gat ccc gta gca ttc gca ccc ccg cag       60080
Arg Arg Glu His Arg Ile Asp Pro Val Ala Phe Ala Pro Pro Gln
                4065                4070                4075 gaa ggc ggc gga cgt ctc cat aca cat ata gta tct aac agg ttc       60125
Glu Gly Gly Gly Arg Leu His Thr His Ile Val Ser Asn Arg Phe
                    4080                4085                4090 ata ttt tcg agc aaa ttg gct ggt cga cgc ggc tac aat aaa ttc       60170
Ile Phe Ser Ser Lys Leu Ala Gly Arg Arg Gly Tyr Asn Lys Phe
                4095                4100                4105 tcc gaa tgc cgg tgg taa tct tgt cgg agg atg gaa atc ctg agc       60215
Ser Glu Cys Arg Trp     Ser Cys Arg Arg Met Glu Ile Leu Ser
                4110                    4115 cat gttcgtgacc tgctagaact gtacatcagt ctgcttctgg ggccttttat       60268
His
4120 ttgtttggga agagtttcgt aaatgtctag ccaaccgcac acaagaacgc gataaataca   60328 caccactcaa ttactcatta gtctttcct tta ttc aaa cat ttt tac att tgc  60380
                                   Leu Phe Lys His Phe Tyr Ile Cys
                                   4125
```

```
act ttc caa aac tcg atc gga aac tgt cag aag agt ctc tga tga    60425
Thr Phe Gln Asn Ser Ile Gly Asn Cys Gln Lys Ser Leu
        4130                    4135                4140 gat tag ttt gtc tgg aag tgt gtc tac aca ccc att gtc tat ccc    60470
Asp     Phe Val Trp Lys Cys Val Tyr Thr Pro Ile Val Tyr Pro
                4145                4150                4155 ttc ttt tgt cga gtg tcg aac ata gag cgg ggc ttt gtt ggt ttt    60515
Phe Phe Cys Arg Val Ser Asn Ile Glu Arg Gly Phe Val Gly Phe
        4160                    4165                4170 atc cca cga agt aat gtc tga cgc ctc ggt aat aaa ttg att tga tga 60563
Ile Pro Arg Ser Asn Val     Arg Leu Gly Asn Lys Leu Ile
        4175                    4180 tgt atc ttg ata tcc cct ggc atc agg cgg ccc taa aag agt aag    60608
Cys Ile Leu Ile Ser Pro Gly Ile Arg Arg Pro     Lys Ser Lys
        4185                4190                    4195 agc tga cgc tgt atc ttc ttt aga agg ggc aga aat ttc aat ttc    60653
Ser     Arg Cys Ile Phe Phe Arg Arg Gly Arg Asn Phe Asn Phe
            4200                4205                4210 ttc caa ttt tcc ttc aag ggt cgt ggt ccc tcc ctc tat atc        60698
Phe Gln Phe Ser Phe Lys Gly Arg Gly Pro Ser Leu Leu Tyr Ile
        4215                4220                    4225 tag cag agc tga tgc cgc gcc aat aac ttt aac tac atc ttc agg    60743
Gln Ser     Cys Arg Ala Asn Asn Phe Asn Tyr Ile Phe Arg
                4230                4235 ttt tgg att aga tgt ctc gag agc agc ttc att atc tga aaa agt    60788
Phe Trp Ile Arg Cys Leu Glu Ser Ser Phe Ile Ile     Lys Ser
4240                4245                4250 ttt cca ggc ttt tac cac atc gcg ggc cct ttt tac ccc gac gcc    60833
Phe Pro Gly Phe Tyr His Ile Ala Gly Pro Phe Tyr Pro Asp Ala
        4255                4260                4265 tgc gag tga acg aca taa tgt cca cga acg ctg gac gac agt att    60878
Cys Glu     Thr Thr     Cys Pro Arg Thr Leu Asp Asp Ser Ile
        4270                    4275                    4280 cct cgc gtc cgc tat gcc aga taa ttc ttc agc tac ttt cct aca    60923
Pro Arg Val Arg Tyr Ala Arg     Phe Phe Ser Tyr Phe Pro Thr
        4285                    4290                4295 aat gtg aga gcg tgt ttg agc att acc cgc aag ctg cca gta tgt    60968
Asn Val Arg Ala Cys Leu Ser Ile Thr Arg Lys Leu Pro Val Cys
        4300                4305                    4310 ggt ctc aag tgc atg cgt ttt aac ctt tgt gga atc taa tgc ccg    61013
Gly Leu Lys Cys Met Arg Phe Asn Leu Cys Gly Ile     Cys Pro
            4315                4320 aat agc ttt ttc tgt gtg ccg gat tgc agt ttc tgc aaa att gac    61058
Asn Ser Phe Phe Cys Val Pro Asp Cys Ser Phe Cys Lys Ile Asp
4325            4330                4335 ggc ttt cca tat ggc ctg cat tac agt atc gtc ctt cca gtg tcc    61103
Gly Phe Pro Tyr Gly Leu His Tyr Ser Ile Val Leu Pro Val Ser
4340            4345                4350 tag ttc ttt ttt gtc acg gca act tga gaa aga aac att gcc caa    61148
    Phe Phe Phe Val Thr Ala Thr     Glu Arg Asn Ile Ala Gln
4355                4360                    4365 aaa atc cgc att tgc tga ctg tga aag cag tgt tct tat ggt agc    61193
Lys Ile Arg Ile Cys     Leu     Lys Gln Cys Ser Tyr Gly Ser
            4370                    4375                4380 agt ctt aga aag tag tat ttg cac tgc agt aga tat ctg cat aga    61238
Ser Leu Arg Lys     Tyr Leu His Cys Ser Arg Tyr Leu His Arg
                4385                4390 tgc gtt att tag agt ctt gga aac ctc ctc aag gtc tct cgt tgc    61283
Cys Val Ile     Ser Leu Gly Asn Leu Leu Lys Val Ser Arg Cys
4395                4400                    4405
```

```
agc ttg ctc gaa tgc ctg gga aat gaa ctt tga tct cat ggt atc        61328
Ser Leu Leu Glu Cys Leu Gly Asn Glu Leu     Ser His Gly Ile
    4410                4415                    4420 gac ggc agg gac agg ctg gac tgt ttt ctt aaa tgt ttc tgg aag        61373
Asp Gly Arg Asp Arg Leu Asp Cys Phe Leu Lys Cys Phe Trp Lys
    4425                4430                    4435 agt gtc gag gct cct gtc gca tgc gtc aga aat ttt aag caa tgc        61418
Ser Val Glu Ala Pro Val Ala Cys Val Arg Asn Phe Lys Gln Cys
    4440                4445                    4450 ttt ttc tat cgc gct tgc act ttc gat gga tat ctt ttc tgt cgg        61463
Phe Phe Tyr Arg Ala Cys Thr Phe Asp Gly Tyr Leu Phe Cys Arg
    4455                4460                    4465 att ggt ctt tgt aat aaa tgg gga gac cgc taa ctg aaa ttc caa        61508
Ile Gly Leu Cys Asn Lys Trp Gly Asp Arg     Leu Lys Phe Gln
    4470                4475                    4480 aat tgc tcg cct gta ctt ctg agt atc aga cag gtt ttc tga gag        61553
Asn Cys Ser Pro Val Leu Leu Ser Ile Arg Gln Val Phe     Glu
    4485                4490                    4495 ccc aaa atc tct agc cca cga taa aag ctt tac cgc gtg ttg tac        61598
Pro Lys Ile Ser Ser Pro Arg     Lys Leu Tyr Arg Val Leu Tyr
        4500                        4505 cgc gtc aac ggt gaa tgg ata agt tga tac tgc gta aac aat gtc        61643
Arg Val Asn Gly Glu Trp Ile Ser     Tyr Cys Val Asn Asn Val
4510            4515                        4520 tct caa tac ggt cgc tac aaa aag att gga aaa gag ttg cat atc        61688
Ser Gln Tyr Gly Arg Tyr Lys Lys Ile Gly Lys Glu Leu His Ile
    4525                4530                    4535 gat ttt cgg gtc cgt tcc att gcg cga aca tat ctc ttc agg ctc        61733
Asp Phe Arg Val Arg Ser Ile Ala Arg Thr Tyr Leu Phe Arg Leu
    4540                4545                    4550 cgc gcc ccc aac ttc aat ggc ctg gac taa ttc tac ggt ttg ctc        61778
Arg Ala Pro Asn Phe Asn Gly Leu Asp     Phe Tyr Gly Leu Leu
    4555                4560                    4565 aaa tcc ata agt gta gga ttg ttc gtc ggc act cgc ata ccc ctt        61823
Lys Ser Ile Ser Val Gly Leu Phe Val Gly Thr Arg Ile Pro Leu
    4570                4575                    4580 atc tct ggc ctt ttc cct gcg ttc gag cca atc caa att ttc ctg        61868
Ile Ser Gly Leu Phe Pro Ala Phe Glu Pro Ile Gln Ile Phe Leu
    4585                4590                    4595 cgt ctt tcc tcc taa gtc aga tat gag gcg ttg tac aaa atc gaa        61913
Arg Leu Ser Ser     Val Arg Tyr Glu Ala Leu Tyr Lys Ile Glu
    4600                4605                    4610 cac cac caa atc tcc aag cgc ctc ggc tcc tcc atc gct ccc atc        61958
His His Gln Ile Ser Lys Arg Leu Gly Ser Ser Ile Ala Pro Ile
    4615                4620                    4625 tat aac tga ggc cag agt gtc cct aat gat gtt tag agc atc ttc tga   62006
Tyr Asn     Gly Gln Ser Val Pro Asn Asp Val     Ser Ile Phe
        4630                4635 tgg ggc tgg ggc aaa tga tcg tag tgg tag tag ttc gct ttc aga        62051
Trp Gly Trp Gly Lys     Ser     Trp         Phe Ala Phe Arg
4640            4645                                    4650 cac ccc tac ccg ccg gag aag atg cga ata tgg gtc tac aaa atc        62096
His Pro Tyr Pro Pro Glu Lys Met Arg Ile Trp Val Tyr Lys Ile
    4655                4660                    4665 aga tat aag ccc agc gta atg ccc tga ata ctg tag cgt ccg cgg att   62144
Arg Tyr Lys Pro Ser Val Met Pro     Ile Leu     Arg Pro Arg Ile
        4670            4675 ata tgt ata cat tga gtg cgc agc gag tcc tat aag tga tgt ata        62189
Ile Cys Ile His     Val Arg Ser Glu Ser Tyr Lys     Cys Ile
```

```
                  4680                  4685                  4690
   tac  aac  ggc  tcc  tag  gaa  atc  tcc  aat  gat  tgt  tcc  gtc  agt  atc       62234
   Tyr  Asn  Gly  Ser       Glu  Ile  Ser  Asn  Asp  Cys  Ser  Val  Ser  Ile
                  4695                  4700                  4705 ttc  acc  cca  aag  cgc  ctc  agc  ctt  ttg  gat  ata  cag  ttc  gca  gtt       62279
   Phe  Thr  Pro  Lys  Arg  Leu  Ser  Leu  Leu  Asp  Ile  Gln  Phe  Ala  Val
                  4710                  4715                  4720 gct  ctt  ggt  aaa  ccc  cct  aag  cac  taa  agt  acg  aat  tac  ttc  ctc       62324
   Ala  Leu  Gly  Lys  Pro  Pro  Lys  His       Ser  Thr  Asn  Tyr  Phe  Leu
                  4725                  4730                  4735 tgg  gcc  acc  ggt  agc  ggc  caa  gtc  cgg  caa  acg  cgc  cat  cat  atc       62369
   Trp  Ala  Thr  Gly  Ser  Gly  Gln  Val  Arg  Gln  Thr  Arg  His  His  Ile
                  4740                  4745                  4750 ggc  ggt  act  tgt  tgt  ata  agc  agt  tag  ggt  ctc  ctt  ttg  ttc  ctc       62414
   Gly  Gly  Thr  Cys  Cys  Ile  Ser  Ser       Gly  Leu  Leu  Leu  Phe  Leu
                  4755                  4760 tgt  caa  gtt  att  agg  cgc  gtc  ctc  gaa  aag  ctg  tac  gat  ggt  tgg       62459
   Cys  Gln  Val  Ile  Arg  Arg  Val  Leu  Glu  Lys  Leu  Tyr  Asp  Gly  Trp
   4765                  4770                  4775 gac  atc  tag  ggc  gag  gcg  ttt  aat  ggg  aat  agt  taa  tag  act  atc       62504
   Asp  Ile       Gly  Glu  Ala  Phe  Asn  Gly  Asn  Ser            Thr  Ile
        4780                  4785                           4790 taa  gtc  gtg  ccg  cca  gca  aac  tac  atg  tcc  agg  aac  atg  cgt  ctt       62549
        Val  Val  Pro  Pro  Ala  Asn  Tyr  Met  Ser  Arg  Asn  Met  Arg  Leu
             4795                  4800                  4805 cgg  agg  atc  tcc  taa  cac  gag  tag  tgg  gtc  tcg  act  gta  tgc  agc  att  62597
   Arg  Arg  Ile  Ser       His  Glu       Trp  Val  Ser  Thr  Val  Cys  Ser  Ile
                       4810                  4815 ggc  gta  cag  ttg  cga  gat  aga  aaa  gta  tct  tga  gtc  caa  atc  ttt       62642
   Gly  Val  Gln  Leu  Arg  Asp  Arg  Lys  Val  Ser       Val  Gln  Ile  Phe
   4820                  4825                  4830 agc  gat  cca  tga  ctt  ggc  cga  atc  tgt  gtc  cag  atc  aaa  ggc  agc       62687
   Ser  Asp  Pro       Leu  Gly  Arg  Ile  Cys  Val  Gln  Ile  Lys  Gly  Ser
                  4835                  4840                  4845 tag  cgc  cgt  ctg  tgg  aaa  ctt  ccg  ata  agg  ggg  ttt  tac  tgt  agg       62732
        Arg  Arg  Leu  Trp  Lys  Leu  Pro  Ile  Arg  Gly  Phe  Tyr  Cys  Arg
                  4850                  4855                  4860 ttc  aaa  ata  ctc  tct  gac  cat  aga  gag  ggt  cat  cag  cgc  ttt  agt       62777
   Phe  Lys  Ile  Leu  Ser  Asp  His  Arg  Glu  Gly  His  Gln  Arg  Phe  Ser
                  4865                  4870                  4875 ttt  ggg  tag  ccc  ggt  tga  agc  cgt  gat  ata  att  taa  cat  tgc  atg  gta  62825
   Phe  Gly       Pro  Gly       Ser  Arg  Asp  Ile  Ile       His  Cys  Met  Val
                  4880                  4885 tcc  cac  taa  gcc  ttg  tag  ctt  tgt  tcc  aag  ata  ctg  tat  ccc  gtc       62870
   Ser  His       Ala  Leu       Leu  Cys  Ser  Lys  Ile  Leu  Tyr  Pro  Val
   4890                  4895                  4900 ttg  aac  cat  ttg  gtg  gtc  gta  taa  aag  tgg  ata  att  ttc  aat  taa       62915
   Leu  Asn  His  Leu  Val  Val  Val       Lys  Trp  Ile  Ile  Phe  Asn
                  4905                  4910                  4915 agg  aga  tag  gag  ttt  ggt  tgg  ctc  gag  tcg  gtc  tcc  gga  tgt  ctc       62960
   Arg  Arg       Glu  Phe  Gly  Trp  Leu  Glu  Ser  Val  Ser  Gly  Cys  Leu
                       4920                  4925 gaa  caa  ttg  tcg  ctc  gtc  aac  tac  caa  tct  tgc  caa  act  ccc  aaa       63005
   Glu  Gln  Leu  Ser  Leu  Val  Asn  Tyr  Gln  Ser  Cys  Gln  Thr  Pro  Lys
   4930                  4935                  4940 ttc  cgt  taa  cca  gcc  act  aat  tag  act  cca  ata  ttc  tac  att  tgg       63050
   Phe  Arg       Pro  Ala  Thr  Asn       Thr  Pro  Ile  Phe  Tyr  Ile  Trp
   4945                  4950                  4955 atc  att  taa  ccc  agg  aaa  ttc  ttt  acg  tac  agc  tgt  ttc  tag  gtc       63095
```

|  |  |  |  |  |  |  |  |  |  |
|--|--|--|--|--|--|--|--|--|--|
| Ile | Ile |  | Pro | Arg | Lys | Phe | Phe | Thr | Tyr | Ser | Cys | Phe |  | Val |
|  | 4960 |  |  |  |  |  | 4965 |  |  |  |  |  | 4970 |

```
atg ttg cag tcc agt aaa tgc ttc tct caa ata ttg aat tat tct         63140
Met Leu Gln Ser Ser Lys Cys Phe Ser Gln Ile Leu Asn Tyr Ser
            4975             4980                 4985 gaa atc ttc tcc aga gtt cca tgg aac aga tat gcg gct aat aag         63185
Glu Ile Phe Ser Arg Val Pro Trp Asn Arg Tyr Ala Ala Asn Lys
            4990             4995                 5000 aga gcg tgc aaa taa ttt caa tgt aac gtc cgc tac tgc cgg agg         63230
Arg Ala Cys Lys     Phe Gln Cys Asn Val Arg Tyr Cys Arg Arg
                5005             5010 cgc cat tgt gca tgc gag cat tat agt ttc aac cat gtt ttt cct         63275
Arg His Cys Ala Cys Glu His Tyr Ser Phe Asn His Val Phe Pro
5015            5020             5025 agc ttc tac ttt ctc caa atc ttc aag tgg aat tct gtt tct gga         63320
Ser Phe Tyr Phe Leu Gln Ile Phe Lys Trp Asn Ser Val Ser Gly
5030            5035             5040 gat tag aat tcc ggt gag ggc tga agt aac acc cgg aac ttt act         63365
Asp     Asn Ser Gly Glu Gly     Ser Asn Thr Arg Asn Phe Thr
5045            5050                 5055 gca gtc ggt gtg tac agc ttc aag gca agc ctt gag gct atc cgt         63410
Ala Val Gly Val Tyr Ser Phe Lys Ala Ser Leu Glu Ala Ile Arg
        5060             5065             5070 gat ggc ctg cat ggtttcaata gtcgcgtcaa ctcacggaac cagctggtag         63462
Asp Gly Leu His
            5075
```

```
ctttataggc acgcttctga atgctttcac agcacagttt ttttcagaag tgtgattaga   63522
gccagtgttc tccagcttat aataagcgtc agaacttcct ttccgcgctg ttacatcgta   63582
agcatgtccg gattacttgc tcgcaatgga tcgaacgata aaattcgagc gccagaaaga   63642
gggctgagtg gattcgcaaa cactcgcact catccttatt tacaaagtgt acttcctcga   63702
agaactcacc agcataatct gttatcagcc gcgctggggc gcctaacaac tggccggaat   63762
ttttctcatg gtcttggaac gaggccaggg aaattcttta ttggctcggg gccacgtaac   63822
cccgaagaaa caaataatgc aacgcttgga aaggaagata caagggccat cgcatctaaa   63882
attcttctcg atgttgaatc tacgaggaca aatgatgtaa tttctttaac ccaaataact   63942
gtcatagacc tctgccagcc aggggtcgaa gagtctgggt ctctaatgct cttttgaaa    64002
ggggttaaag acttactcaa gattttggga tcacgacccg cccgcgagca aattgtgaga   64062
gatttagaga ctgcatttat caatttgaac cgcgcctgcg gcttatcggt tactggggag   64122
agtgctgtca aatccttcga gctttcagcg gtgtctttga gttttgtagc tgcggccggc   64182
gcggctcact accgaaataa ttgcggagta gaggcactac gcgcgttcgt aatcgcgaat   64242
tataaggatt ccgccattac cgaaaagctt gccaattttg atgcattgct tctggcaaca   64302
attgaggcac gagcgtaccc ccattttttta ctatctttag gtgggggctt gataaaagct   64362
accgaaagtg aaacagtaac gtgcatgcga ctcttggtca gagggactca cgaagcagca   64422
gctgccggag atctttctga gaaaaaatgt gccgtactcc acttccctgc atgtctgtta   64482
cttgacctcg atgaaggttt tgcccacca aggacaaaga tcaatgcaga aggcggtgtt    64542
tactttctac atttattatt cctgtactct accgatatgg gacacccgag ctacgaacta   64602
tatgtggcaa aaacatctct ccccgaaagt tgcatgagag acattttaaa tgaaagattt   64662
acacgacgca gaataaataa cactatagct tccttaacac acatgcaagc tcaagaacgc   64722
caagcctttc cccctttaa tattgcagaa gctgcggttg ccgcgcgaat ggatctggga   64782
```

```
cgagaaagat caagacatcc actggatcca gttcaaggtc gtgatcaacg tcttagggat    64842
atgcagataa cgtccactgg aataccagac cattcggctc tagtattcgc cgcatactgc    64902
atgctaggga cggcgggcag tattggcggg gagccttctt tttctactat ccagaaaaac    64962
gggactagtc taaagtatgt tcacattcgc gattttaact ttagggggcgg cccatggaat    65022
gtttgtatgt aacacaccca cttctaaata aatacaagtc tgttcacccc atgtgtctat    65082
tcagttctca ttcgaggcaa gggagcaagg atccctctca ggacaattat aggattatct    65142
cctgagcagc ccggagccat gctttcgttt ttcgatgaac tcgaaagcat tgcccatcta    65202
gaagagtgtc tgcgggacat cgaaacgcgt atgcgaacgt ctgggtttga tcctaaatcc    65262
atcattagag acgattttga cataagggct gggcgcgagg gcctcgccaa ccggatctcg    65322
atgcttgtgg acgggtttaa agtttccgtg ctatttaacg tagaactata ccgactcctc    65382
gcggaactcg ttcatttaag aattcgcaca aaagcagtct cattttcgga gtggctagat    65442
actaggggc tatctgcgga ctgtaaacaa tttattttgg aaaatgcaga acatatttct    65502
gcggtcgtca aagacttcta caacggaaca taccatcagc ttgcaagagt cggtcttcag    65562
tcagctcaaa aatatgaatc gctgtatttg ggaaaacttg gcaatggaaa gctggagagt    65622
atgggtcaat tttttactag actctctgct gaggctgcca gaggagcttt taatattccc    65682
caatttgcac aggcattgga agttgatggc caggttacac cggcagacgt ctttactagg    65742
ttttttacgt gtttgagtag ccaactgatc gtacctccta ccccagtaat gcttttcggg    65802
ggtacgtctc tggctgctta tgccagttgt ttttgatag attcatctgg cagaaataca    65862
agagaggcgt tcaatgtcgt tgccgaagaa gtaattccga tcatgaataa tcgcggagga    65922
attggaatat cactgccgtg ccttggcgct ccccaaaatg agtcggggtg cctgggattt    65982
cttaaggctc tcgattcgct agtagccgcg agcaacggcg ccgcaaagcg gccaacaggg    66042
ctttgtgttt atttcgagcc atggcattgc gacacattaa agattctgaa aattcgtggc    66102
agctcggccg ggaatgaaga gttcagatgc gataacattt ttactgccat ttggatgcct    66162
gatcttttta tgaaaagact gcagcagcca ggaagtaaat gggcactgtt cgaccatagg    66222
ggggagcatc tgtctaactt gtttggagag gagtttgaga aggagtatga acgtcttgaa    66282
agggaaaatg ttggagtggc cactatccct atcaccgaga ttatgtttca gataatcaaa    66342
agtgcagttt ccaccggcac tccatttgtc gtctttaaag acgccttcaa ccgtcactat    66402
ttttacaata tgcaacaccg agcactgaag tgttctaacc tctgtacaga aattgcccac    66462
atggcagact ccgatactgt tggagtatgc aacttgatta gcatcaattt ggcggcaatg    66522
gtcaaaaatg ctcgcgcagg acttgctggg aaacccggca gcttcttcga ctatgaactc    66582
ttaagggaaa cggcaagaac tgcaacaatt ttcgccaatg tcatgatatc acttggaaac    66642
atgccaagcc aacgggcaca gagcgggaac cacaggttac gatccctcgg tgttggagtc    66702
cagggactgc acacagcctg cttaatgcaa ggttttggga tgactagcgt tgagggcttt    66762
gaatttaatg acactgtgtt tgagctactt gccttggaaa caactggaat cagctgtaga    66822
ttgtgtgagc tggggttgcc tccgtttgat aaatatagag aaagctatta tgccttagga    66882
tggctgcata ttgatgggtg gcccaatacg aagctgagat acaaaaatga gtgggatagt    66942
ctaagacata gaatagatca atctggtttg tacaactgcc aaacagttgc tttgatgcca    67002
accgccagtt cttcccaaat tacagaagtc agcgaggggt tccagcccgt attcgggaac    67062
atgtttagta agatctctac tacaggagag gaagtgcgac cccatttggc gctaatggat    67122
gccatcgacg agctgtattc tgaccaggga gaaaaacaag catttctagc aaacctaaaa    67182
```

```
aaacatcagt ggtctgtgcg cgctgctctg ggaagtgctt ggtcagagtc tcacgtcctc   67242
gcgaaatttc aaaccgcatt tgaactcgat caggaaaagt tactatactt aagcgcacgc   67302
cgcgctccat tcattgatca ctctcaatca aacactctct acatcaccga agacgtggac   67362
ggtactttaa gtgcgtcacg tgtatcccgc ctactgcaag ttgcctttaa atacgggctc   67422
aagactgcca tgtactactg caaggtgcgc aagatcacaa acaacggagt gtttgtcggg   67482
tcttgcggag acagcctcat ttgctctgcg tgtcaataat cttgctaaca tggcagaata   67542
tcagtccaca gactattatt acttgcccca gtgtgatgac attcgcgagc tccgagacct   67602
gagcatagca aataactgga acgaatttga actatgctac agtcgcgatg agaaagatgt   67662
tgatctacta actccggaag aactagattt ttacaaattc gtgtttgcat ttctggcagc   67722
cgcagacgat ttgataaatt tggatatcgg gaatctcatg actttgttcc ctcacaagga   67782
cattcaacac tattatgctg agcaaataag aatagagacg gtccactcta gaacctacag   67842
cttggtgcaa atgatccttt tcaagggaga ccttcatgcg cgagacagat atgtgacaga   67902
agctattaaa gatcccgcca taaagaagaa gatagactgg ctcaaccgtg tccaagtaga   67962
aacggatctg acacttcctg aaaaatacat tctaatgatt ctccttgagg ggatttttttt   68022 cgtggcgtcc tttgccgcga ttgcgttttct taggaggcgg aatattttttg tggtgatgtg   68082 ccagtcgaac gacctcatca gtcgcgatga agcggtgcat acaacagcat catgccgcat   68142
ttacaacaac tggctcgggg atcacaagaa accatcggct aaacgaattc accaacttttt   68202 caaagaggcc attgaaattg agtgtaactt tttagcatct agagcgcctc aagcttcgag   68262
actcatagat ctagaagcca tacagagttt cgtgagatat agcggagatc gacttttgac   68322
cgccatcggg gttcccacta tttttgatga accgccccct gatccgtcgt ttcccccttac   68382 cctgatgtcg atcgacaaaa atgtcaattt ttttttgagcac cggagcaccg cgtataatgg   68442
caacgttatc aatgacttgt aaaagaaagt tcaaacagtc aagcattata taaataaaaa   68502
ctactcagac agatattaac atttttatact tgttcttgtt catttttttcc acaaataact   68562 tctcgtaatg acggcagagg ctttagatgc cccttcttaa taagctcaga aaaatatttc   68622
ggggcatcat tagaaaagta tttacacaat acttcatata cagcgatcat gtcgagctgt   68682
tcctgaacca cgggcacgcg cttaagtagt ttgtgtctgc catttatttc tcgtgggccg   68742
atgacactca aaacgtagga cagaaactcg tcattttttt catttctggc gccattattt   68802
accgaaggat cctgagggcg gtaatcaatg tccgagttac catcgtcggg aggttcttga   68862
ggaaactgag tcagtacata tacatagcgt ccaggcaaag gttcacgcac atctgttttt   68922
attccaaaaa catcactatc cgcaggcaag accccgcgct gctcaacaca cttttttggta   68982 tcgttgttttt catttttttttc gtggtcacgc cattccgcca acctggcaga aaatgagtat   69042
attgaatcgg tagaatggat gttagtatga cagtccacac atgcattggc aaactcttcc   69102
ccggacatgc ccaaatattc aataatactt ttataaaaga tagcgactgg aaatgctggg   69162
gtcagatccg taatcacatc acaacccatg aatactaagt cactatcgct agacaggacg   69222
tacgccaccg tgcgggtatg gaatagattg gcacatgcat agtcggcttc cattccttgc   69282
acatagaccg tagcaaatcc tgcggtagtt attaagtccc aacataactt gtagtgcgga   69342 ggacgtatttt ttcgacgtgt cttgtaaata caatccttgg gctccttaat atcgctgcat   69402
cttcgcgcgg caggtgcagt cggaacagat tcttcctggc taaggtgttt aggttccttg   69462
tattcgcgcc gacgcccacc atcaaaaaca aatacaggat agcacgattt ccgactgagt   69522
```

```
aatgaaaata agaacaccaa actttaaaaa gttctctcca tgcatcccat atttccgtcc   69582
gggtcaattc ttcgcaaaat tagaaaaaga acattccatg tgtcgactgc cagtggaaga   69642
taaaatccct tctcaatttt taacgataaa tgaacactga gtccatggtt tcgaataaag   69702
cgacacattc ccaagattcc catatcggta tatttcgagg agagcaaatg aaaagacaga   69762
agcccgcaag tctcgtatca gcaaactaat atttagggcg ctttgaaagg cggtatttgt   69822
atgtacaggg gttgggcaat ccacaccctc gtaatcgcat tacacataag gtgtgacatg   69882
gtggtagccc caaaatttta tgcacaggct acagttgtat ataaaccgcg cggatgttta   69942
ggagatgttc agagacaccg gggaagggaa cgaacgtaca cacgaattac gttcgttgga   70002
agatggattt ggatactgcg acaagaagta aatgtttgct ccgactaact ttaggaaagc   70062
atgggatttc ggtggtttcc cccattgcca aaaacatgcg tgggattctg caacactctg   70122
tgctggcttt tatgaatgac tgcatagtaa tttcctgttc cgctccgttt gggatggctt   70182
tcttaaaaat caagtggcaa ttgttcgact catttgaata tttatcagac gatgagagta   70242
tactacctat catgttcaat aatactatac accagcgccc tggagacctc ttggattttc   70302
tgtgggactc taagaaaaaa actgtcggaa taccaacttt agccacattt actatatcag   70362
aaagtttcaa atccgatgaa actagggctg tactcagact gaaagtctgt cgcgagatag   70422
aagagagcgc gtcgtgcccc caaaatacgg aaataagcac gaaattcaag tactcttcat   70482 cggatgacc tcctatatac ctgcctcgtt ccgataaggc atgtcgggcc tcgctggaac   70542
agtattcgtt caatgaaatt acaaagtggc tttcgaagat ccctaaagat aactcaatta   70602
cagtcacact cacaagagag tatgtcacgt tctcgtccgc agaagacgag caacgcctaa   70662
cctttaacgc gaaatggttc ggcgaccaga caagtattgt atcgtctgcg tcaattttgt   70722
ctcagctatg tggccatgaa cctgcgccta aaaaaagaga gctctcaagc cgagccatcg   70782
gtaagaaact aaaagaagcc cgcattatcg ctgttcatgg ggacaaagat gcctgcccca   70842
ttgtagtatc actctccaga cccggatctc tgaaacagtc actagggtgg ctgaaaagcg   70902
gtccttgggg accaccgtgt cttacatttt acaaagactc tgtgaatagt cttggagtag   70962
aactctctga agaggagga gaagaattag ctgctgggat ttttttcctt tccgcgtttt   71022
ctgcagatgg agcaatctct gagcaatgcc atgatgactc agacacagcc atgcacgaat   71082
ttttggcgga ggaggagcgc ctcatacaac agaccacgct atcccattcc aactcaagta   71142
agaagaggtc gctcgaaaat tacgaggaca ccgatattag cccatcccac cacccacaaa   71202
agcgggggaa attaaagaac ggctcacttg cacggaagaa ctaaaatcgt ctcctcgcgt   71262
ctaccgggga gcttagttta ctgccagcgt ttgtgaccca agtgtgcacc gtgatttcaa   71322
ctctaccgca actatgacgg gggctaccat aattgatcca ttcgcaccgc ccaagggtaa   71382
atggtggccg ttcaatttga acgggatagt ttttccttg atgatgttta ttatattttt   71442
agcctggata ctgtgcattg actatggact cgcgttagct tacattacct gggcaaagct   71502
ttctacgaaa gaggcaagat tcggatggat gatcggacta ttggtggcta cgattactgc   71562
cagttttctg gatattcaat actcggctca caaacagtc gaatttatt ttctggtgat   71622 gctttctatg gcgagcgcag taataattat atttctcatc cattccaaca gcccaatgc   71682 cgcgatagtt atggggctat tctccgtttt ttcggaagtt tgcttgatac tgattttggg   71742
atttcaactc cgaccggcca ttttctgcag cataaacatg acctggctct ttcttgaagc   71802
catgctccta aatttgaccg tactttcttg gaacttgatg caccttcgag taaaccctag   71862
atacttggaa ccgttggccc tttttactat taacattttg gcatacaatc cctctcgttt   71922
```

```
tttgctcaag agtgattttt ttaagaccag catgataact ctgacgggca gtatagaacc   71982
attttccgaa gataacacga tttatacacc cccaagacaa cataaagata ctcgcccttc   72042
actgaatgac ggaccaactc ggtggtgcgg ttactgtatt ctcgtatcta caacattggt   72102
tactgccgct ttcgcctgca cattatcatt accgttcctg ggcaaagatt taggtactgt   72162
acgcatcggc atgcaaacga atttttaaaat cctcatggta gcgtgcggtt cggttttggc  72222
atttggatct acttgcattg gaaaactatg caaaatccat atcgttgtat ggttcgtgat   72282
aagcatacta ttaaccttcg tgtctctgct atcactgatt aagttgattg aggacccagc   72342
tggcattcca tttggtgtca ttcttgcatc ggtttcttgt ctgtttcaag ttggagccct   72402
cttttttccga gaattaaaaa cggccaccca tacacaagga tggatttcat gcgcccttct  72462
tttctgctcc cttttcattc caattgccgc gccgcttgtg tgtgagtaca agctctgaat   72522
tcttgtctaa gggagacgtg ccaattctga caacgcccta agccaacaca aatgccttcc   72582
tcaatttacg cgctagcttg aacattccaa caagatgaat gcatcgctaa catggcttgc   72642
tttaactttt aaagttacct tgagtttcag cctgctctga atgttttcct ccaaacctaa   72702
gatgttctta gttgtacgat ttttgtattg cgaataccac atcatccagt accaaagtac   72762
taatggtcgg caatcgaata gaaatcaaac atggcacgca ggagactgtc gcctcgaaac   72822
tgccttcgcc gagctgcaga aattcggaac gaggacatta gaaacagatc tacattccac   72882
cgagcaaccg tttactggag aaaatgctag agaataacct aacaggcggc cttcaacttt   72942
cactacttaa caactggaac tatattgtcg aggattgtca tagtcacgaa catgatgcag   73002
tattgcttcg gatgcaatct atattttgac attgttaata aagcacatgt actatgcaaa   73062
gtttgcattc gtgtaattcg tcgagagaga aagttacaag ttcgattctc tcgcgctagg   73122
agtgtttcca cgtgcgaaaa cgcaaaaatt ttcatattat tcgggcggac tgtgtccata   73182
gtagctaaat taccgcgatc tggagactag ggcattcacg actcaacatg cagcatcaga   73242
gtactgcgct agtttcgagt atacttttgc tcttgagcct gcaaagcctt gcgtttgaat   73302
ttttctgtga tccgccacac gttttttcgag ggcagctcgg tgaccccatt ctattgcaat  73362
gcttcagcga cagacctcta acccacgaag aatctgtaaa agtagaagta attcgacacc   73422
cagccagctt agttgaaact gcgctaagcg cctacgggat ccccccttcg ctagatccat   73482
ggagagctac tccaagaact ctctacacat atgatgccgc tactgattca atcaaggacc   73542
taggatacat tggtgaagat ggaattaacc caccatattt ggacgactgt cgttcaggtt   73602
ttttcaatgt ctctatcaag tctagcatga gatctcacat ggcgcgttat cagtggaccg   73662
caagtcgagg gtctacaaaa ctaaatagct cttttatcga cgtcttttg gcaagaccac    73722
ctacaactgt ccgcatcaaa tcagaagaac tgtacgaaga ctcagataag gcttcgcact   73782
taagtgttga agcgcttggc gcttatcctc catctgctgc gctgggtaca tggatgatac   73842
ataatgcatc tcttgctgaa aaatacagtt tagaaagaag agttctttat gcatcaggag   73902
agaatggatc ggtggatcag acatgggaac tggaaatacg tggagaagcc agccagcccc   73962
tcccttccaa aattcaattt gtatatcgat ggacccctcc tgaggacttt gaaatgctac   74022
gacctgaaac tcgcttgtta aggttgactc ccagctggat tagcaagccc cgcatcacgg   74082
tacaattcgt ccctcctgcc tatgccctgt gtagagcagc taatattata gacggccgag   74142
gatttattga atggatcgta gataatagaa tttcgacgag cccacaccag accttttgttt  74202
tggatgagcc cgaggggaaa aatatcgtta cactaatgga cgtcataaaa ctaccaccgg   74262
```

```
aggatacatt tcaatctgcc tctaattacg tgtgcgtcat aagaggctat gaacatgcat    74322
acagatatct caacgcctcc ttaatgatag ataatctgcc aatgcggcaa ggattccccg    74382
cagtcgctgc gattttatt ataattagta tcgcttttgt gggtgggtta ctagttgctt    74442
gcttgggcgc atggtgctgg aagacaacat aaacgctcat ttaataaatg acattacaaa    74502
cgtgcactac tgtctgtcca atttatttca tcggaaacct tgcactggca ggtagtctca    74562
agcaagccta aacgatatta tagatttcaa tatttctacc agatccgtcc gatattccca    74622
aatgattgga gaaatttctt ccttagtcat cttccacaga tcttcgattt tgcgcccaag    74682
ctcaaaattt ccagtaattt cagaaacctc actggccgcg tatgcctcct cgtacaagta    74742
aatgcagacg agagccgcgg cggttcgctt tgcagtgttg accaaaattt cttgtggaat    74802
tttagttcga aggcacgctg cggtacttac atctttcatt aaacgggttt ttgccgcatc    74862
gaggagtacc gctgtttctg ggattaacgg gatactctct ggtggatacg aacatctcgg    74922
tttgggttgc actttgggat tcaaacaaca gctgactagt gcatcttgca aaacatagtg    74982
cgtggccagc aaagttttca atatattgag aacaacttcc gacaattctt gtaattgtag    75042
agtttcgggg ctctggattt ttttgagccc gctttttca atatatcttt cacagacaac    75102
tgtaatttcg tcaaagtgac aaggatagtg cccgagcata agtaaataat taaacagagt    75162
ataaggaatc actgagcttc gcccgaatga tgctttgctg aggcatcgtt ggccagggta    75222
tggcagcgtg accagaatgt cagcctcgtc gcgcaatgta cttttcagtt ttgctccatc    75282
agtctcccat gaaagtccga tagttgcgag aagtccatgt cgtgaaatcg tggccgcatc    75342
cacgatcatt aacatcttcc agagtcgctt taatactttc caacattccc agaaattttc    75402
tacatcttcg tcgaacattt ggtcggggta aatgtgtttc acctgcacat gatctgagag    75462
gatagttttt ttcttacacc cacgcagggc tttttctca tttcctactg cgaccgtact    75522
aatgatttta cctcccgtaa taataatagg agtaaaaatc tgtgattgtt catgaatcgg    75582
ttctcttgtt agggagttca agaataaatc ttctaaatct tcttctatga acttcggcag    75642
agtagtaata tgtgcctgcg ttagcaccag cgcactacta tctacttgat acctaaatcc    75702
tgtcgtcgta ttgattagat ccggggttct aaataacctc agtactttat tcctcagaga    75762
gacttcccca actcgtattt ctagcgtttc ggaaacctgc aggccgacaa atattttgca    75822
caagatcggt cgtctgatct ccacggtaaa attatcaatc aattcatcat gtggagattc    75882
tgaaatttca ccaagatgag aagtaaaaat gtattcttcc tcctggcggt caaaaggcat    75942
cccattcaaa cgattcagtt cagtgttaat aatcgcacac atggtagggt gtttgatcct    76002
aaaaccgaat ttggtaatat tttttatcgg cccgcgagta gagatcgagt agatgcatcc    76062
tccatagata atgtagagtc gtccgctgtg gtgatctatg tagcgtgcag gagactttga    76122
tccgcgcttg gagacttctt gaaaagccac ttccatttca gtccttctcc aaagagcttg    76182
cgcgtcaagt gacggtaccg ctattggtgc tttaaaagta tccgcccttt atactgctcc    76242
aattctatcg tagcataaag ttttgacgat catacagcgc ctgcgtcttg gcaccaccta    76302
caaccaaacc tgagctctcc ttcaacatga caactggaaa cgaagccaat tcaatccgcc    76362
tctcttcagt acaagtaccg ggaaattgtg agattgacaa gctgttggct ggatttgact    76422
acgaaaaaga acgtgatggt gactattcga cactgaacga aggatccata tttctaaacg    76482
atcgccttat agcttcggga agtgaagata catctgatct acaatatacg cgaatgagga    76542
aacaaacttt ttatcctagt ttagcccttc tttttaaaaat actctgttgt ctgcctttct    76602
tttggtacgg gaattgcacg cgagagaaat atttatttgt aaacgctctt attatcactg    76662
```

```
ccctctcctg tctagaagga ctattgattt ccttttttgt gtaccgaaac gtgaaggctg   76722
atcgtcttcc tttaaaaggt cctgaaaaac tcattcaaat ggtgttatgt atgataacgg   76782
ctatatatgg ggcgattatc ttttcaaggc acctttttgc ggacgatgac cttgctattt   76842
caatatttgc gaaaaactgg acagacacac aggaagcctt gagaattggt cattgttatc   76902
tctctccgta tttttcgatg tgggctgcct gtctgtactt tataattctt ctatacgacg   76962
ttattgacgt gacacttcct cttttgtggg cctggacaat attaaggaca gcaataagct   77022
tctaaatcgt tttactgcta cacgaaatcg caaagttagg tggaaggatc gcgttactgg   77082
cctcataaac cccgccttga agcctcaccc ccggtaaaga cacgataaag gcagagactg   77142
cagtattata acgggctgac ttcgtaggat aaaggcaacc tacaactctg tgtgctcaat   77202
atttagccat gaatcctgac aacgggatcc cgcataacag tcatcatgat cgcgcagcat   77262
tcccaagatc tgctgcccct ttcgtagcat ctggggaact gttaggaatt cttcgagaaa   77322
attgccatgc gcatctatat gaatggataa gccgcgaagg ggattgttgc tacagacaca   77382
gctttgatat tctgctggga tcttatttca atacactaac gctcaccaac tttctagaaa   77442
ccggactttc agttgcatgt atttgcgtga aatttccaga gttacgctat gcagaccgag   77502
gaataatcca gtttgtagtg gctaatccca tgattgcaag aagtgattgt gaagtacctt   77562
ctcggccatc atttacctac atcagtaaga gatggtctag gacgacatta tcctcatccc   77622
ttgtgatttg tgcaccagct ctgggcttgc taagtggcga gtcacttgac gggaccgaaa   77682
tatctgagtt ttctagatta caggcgttaa accaacttgc acgaaacctc aaactaactc   77742
tagactcatt tgaaagagga acaataaatc atgtgctgag aattctaatc cgaaaagctc   77802
caccacttcc tcttctacga cccatgatgg cggcgttgga atgtgaacga gaaatgtcta   77862
cggttgccag agcaaatatt atctccagta tgaaggcagc cctatgtgaa gatttgtttt   77922
tcatagataa ggagagggg cacgagactc cggatttcgc ccgaaagcta ttagccttaa   77982
ttaattgcac gcttcctagt gtaaccgatg ctcgtgttac acacataggt ccggatggtc   78042
gacttataga agggtgatt gttacaaccg aagccgtaaa aggcctcatc gcggcccgcc   78102
ttggcatcga aactgcccgt gccaacgtcc cggcaatgta cagtgagatg gtattatctg   78162
gaaatagcct tgtaacggcc ttactgctgg ggaaaaccat tcgtaacttt gatgaagccg   78222
ccgcaaattt gttaagcttt ttggacggtg aaaaaaatct cgccgatttt ccagaaatac   78282
cgtctaataa cgcagaccaa gttccaacaa tgtccgtcaa aatgtccctg ctcaacgtgg   78342
gggaccatct tgtcagcata gaagcactag agcgtgttta cacgcgcact ggagttccct   78402
acccactctg tgaaaatgtg gatctgacat tcttttttccc acttgggttg ttcaaacctg   78462
caatagatcg ttattccaca tctgagattg ctcctgcgt cggagccccg gattatcgcc   78522
agtttccccc tacagaaatg tactttttca ataaggacgg catgatggtt aaactcacgt   78582
ttgaagactc attgccaacc gtcgcacatc ccatagcaca tggaatgctg gaagctttgg   78642
cagaactttg tcaagaacca tgggtttcaa atcgcagacc tgctccgatg gggttcacaa   78702
ttcaacgtat cggactaaac ccacctcgcc tgttaatgat cgaattcttg gaagcggtag   78762
cacgtactgc ccctgcacca tacccagacg caactttaat caatcggaaa atccagatc   78822 aattctctag ccataccaac ccgttccttc cattagaggt tcacccgttc tatgatgtgt   78882
acagagttgc gcaggatcta actattccct gtgatgaacc attgttttcc ccagccgaac   78942
caataacact ggccgcctct aggcgactct gcaacgggga tattccgttg ccgctgtctt   79002
```

```
cagtcgattt tagacttgcc aggggggtact gtatcgctgc aggaagacac agactgcacc    79062
cttcaacgga cgcagccata gaaacaacac tatctgatgt gaattaccca ctggctttct    79122
atgtaattga agcttgcatc catggcgatg aattgatttt catggaatcg cagaggctag    79182
tagcgcagtg catcaatagc tattggcata catcaagggg actagctttt ataaacagtt    79242
atccaatggt aacgtacatt tatcacaaca tgactggaat gatcgatcga gattgccact    79302
ccagatatgc ggatgtaatg ggcctgcttc acgcactgag ggaaacaatc agaaattata    79362
ctctccctgc ggaaccaatt ctcctgcgtt ctcatgagga attaaacaat ctcatgacgg    79422
acccggcact ttttccgccc atgatttatg actgtgattc catcctaagg gcacgcactg    79482
catgcgcgac tagaggggtt acgatctcca ccttcggaga gagagcacct accgtttctg    79542
tcagggaata tccagcccaa gtggatttca ccgttcttag taacactcta aatcacggcc    79602
cagcatatac tgctggcgga agacatgaag gaggaaccca tcatgactcc gaatggacag    79662
tactcagcaa attgttttac tatgtttttc tacctgctgt ctctagaggg aggtgttgca    79722
gtgcaggagt cgagtttgaa atgatctacg atctcattaa cactaccaga cttccagata    79782
cagttgatga aatggacaat caggcaggtg ccgtcgacag aggtccttttg gcggatgaaa    79842 atcttgcccc cgaatccttt aacactttgt tggcaaatgg atccataaat ctggtggata    79902
atgaagctct ggtagcattt atcgctgccg cacggcgccg tcaggcagta cacacgatac    79962
ctctgagagt taactattta cctgacccgg gcttcgaaac tatagacagc ccgaggaatt    80022
ttttggtaga cggagtctta tacaatggaa taatcatgat gaactatgct caatatgacg    80082
cgacagctat tccatctcgc tatttctatg cattgcctgt gaatggattc tttatgaacc    80142
gtactatcat agaagcatct cacagggcta acgtcaacct tactaatgta cctgaggact    80202
tgccactagt tcctacattt ttggggagcg aagtgtatcg ctccataaga gcaccgtcgt    80262
acctatttgc ttcgagagct tcaaactatg cctcaaactc ggtcgcggca tacagcttgc    80322
tggcaggata cttcaagacg tctcccgtcg cacttgtcca tcagttgaaa ttaaatcttc    80382
atccagggtt tgctctcact gtcgcccgcc aagacagatt tgcggcggat caaattttat    80442
ttgcccgaag agcatcggaa tcttactatc taggatctcc agttgtaacc aaccgcccag    80502
agaatgattc tctcgtaatt gagataagtc agccaagggg gcacatagat atgggtctgg    80562
gatttacagc gagtcgtgtt cctgcaaaaa ttaatacagt ggttacagac atgggcaatc    80622
attgccaaaa tctcttcaat gcccgctacc ctggtcagtt tcgccatgcg gaagttgcgg    80682
attttattgc ctctgaaata acagacaatg actctacagc cttgcctaga gcgcagcctc    80742
ccattctgct gtcttacgaa aaggcaccca tcccccttg catagagcgg ggacagcttg    80802
ctacatgtga gttctttta actccagtga ctgccgatct tgcatatttt tatacatcag    80862
caaatccccg agggcgcagc agctgtatcg cgtgcaccaa ctgcgaggat ccatgcgcga    80922
gtgaaactga aaaggctatg tatgaccatt ctaccccaga tgcagcacac ccgtctaggg    80982
ctacgaataa tgcttgggca tcgcaaaagt attcagtggg agacaaaatg tataatgcgc    81042
ggcggggttt tattacggcc agtgattttt acagtcctct gagcaagttt atgacgccat    81102
ctagagctga agataagagt cggtgcctgg ctcgtttgat gagagattcc tctgcggcaa    81162
ttagttcagt tacgggtgac actgagtatc aatttgtcgc cccgcccggt gccaacgaat    81222
tagtaactga tccgtgcgca atgtttcaag aagcgttccc accccttgt agcagtgaca    81282 aggtcctctt cgcaacctac gaaggcccta atagagcatc tggatctggt gcaagagaaa    81342
accactttgc gcagtatttg attcacgata agtctccaat cgccaatgcg ttaaaaaccc    81402
```

```
catgcaacac gcgtcgctaa gacggaattc gcaaacgatt tctacccgtg aaatcacgtc  81462
accgcctggt ctgtttgggc ggagcccttt caaaacttct tcataagtgt ttcctgtgca  81522
gatgatttgc ccacggaggg atatatagcg catacctaac taaatttcag aggacagaag  81582
tacagatcgt atcagccaga acgatgacaa gcggacagta cgagatccgc gttgttctgc  81642
caaatggact gacacgagat gaagaagatc gtctcagaag cttgcgtggg actattttaa  81702
tggcgccaat tttgcgaagg tgtgtttttc tgcacgaaat cgatcaaaaa tcatttttcg  81762
cccatggaaa agaaccagac tatgcaactc tgctcacagc ctacaggaga cgctttccca  81822
tattaatagt ttgtgtcgaa aaccgagaat tgagcgccat cgcgctatcc ataggatacc  81882
cgcgcggaat cagcgtgcgc aacactggtc catttagttt gaacaacggt gatctcgtgt  81942
ctttactgcc acccattacg aatacgcgtt ttcgcgtcga cttgccatcc tgcggctctg  82002
taatcgagcc agccatgaca attcctttcg agatcggaac agaactgatg ggaaagattt  82062
ttgcagggat ggcctatgac ttctgcgtta gaaatcaaat agcgacaacc cgtcctcgtg  82122
atatttatgt tgtaacatat aagaacaaga cactcgatct atctacattg cccccgtctg  82182
atgcggctgc acttcaagat acaatgaaaa gcctattttc atcggttcta ttttcgatac  82242
acgagggggt catgtccgtt ttgtcactaa tgcctgcttt attggcagga ggggcgaacg  82302
atccatttct caatgccatt ctacaaatgc aaagcatgac cagactttcc gtgcagcttt  82362
ttaatccacc cgcgctagaa ttaccggaac ctgctggcag ctctgggcga tatcatgtat  82422
ttgatgcttt tgccgcgtgg ctttcaatgt ctcaccgact tggtgattta ttcaatttga  82482
aaccggtcct caaagtagta atgttttact cggatgattc taccgcagac gagggagacc  82542
tcctcaacgc cattgtacct taacccgtct gtgcatctct atgaaatgac gagacatcat  82602
atctctttga tttgtgaata aagtatttat tatcgaaatt gaatttatgc tggtctctgt  82662
cttctaccga tcggtgcgat ggggtgatat ccggcagtcg gggaaccttc tagtgctaag  82722
tatgtagaca ttacagcggc cactaacatg tcatcgggta cgcggccctg cttaccgcta  82782
aaagttcgaa aggaatcggg cccttggcca tgagtaacag taatgttcct tatttggtct  82842
acgagatact cgcatggatc tttactgagt acaagggtgt tcgagacaag ttcctgggaa  82902
gccataaagc gcccagagtt aaataggctg acaaacaagt caaatgctct gctcttttgt  82962
ttgtttagaa gataaaaagg gtgagccatt gcagttccag gctgccgact gtgggcaaaa  83022
gtcagagaaa agcctaacct cctacgcaaa gaatccaaaa gctctgtcaa gttgccggct  83082
atggcagcag cagaatcctg actcgaattc ccctccaccg ctatacgaat ttctcgaaat  83142
gcgccagcgt gaataagaca acagtatgct atacacaaat acacgcactg ggcaatttcc  83202
agcgccgcct ctccggtcag tgcatccaag taaaaatgtt cagctcccat gagaaccata  83262
gagtctcgca gcgcagtcac taatgctatg ccagtaccag atgcgcttct gtttgtggta  83322
aatgcaggat ctacatacac agtgagaatt ttcccgagcc cagagatgtt gggtttactt  83382
gaggtagatg gtctgtaaat caaaaactga tccaaagctc gcacaggaac aagtgtacga  83442
tcggagtcat attttccagc acgtccaccg gcaatctcat gcataaacga atcttttacg  83502
aacaaatctg cggtatttcg aacctcgctg tccatactaa caaagactgg tttgtgcaaa  83562
acataacaag aacaggtagt cacgtctgtt cttttctgga tttcaggcat gtgttcgtcg  83622
catatatagg taacaacatt aagcagagag tttgtctttc ccttaagatt gtacagtaga  83682
ctcgtgttac tatggcaagt gttggtagaa gatacgaaga aaagtttgca gttagtctga  83742
```

| | |
|---|---|
| ttcaaaaacc ccatcaccgt gtggagagca gccggtttta taaaatttgc ttcatcgacg | 83802 |
| aacaggaaat tgaagtcctg cccccctgaga ccctgcaaaa acagaccagc aataaaagat | 83862 |
| cacactcaac ggacatgatt cattcaccag cgcgtcgcaa tggaagtaca tgtcttagca | 83922 |
| gcgacatcga agctattatc ttgcggtgaa caggagggag gtcctgcgcc gatactaagt | 83982 |
| cacctagtcc tgtccacgca gtgcttagaa ggatttgaag ttccggttca ccttcttagt | 84042 |
| gacaataagt tttatacaga aattcaaatt cgacaccacg gatgttttga ctgcacagag | 84102 |
| tggaaacaag ttttctcaac ttttgtcgga caccgggcac tcgacaaaat tctattacct | 84162 |
| gagttgggga attgtcaaga gcgccccttt cgaattacgt atgatggtgg gaatgactgg | 84222 |
| ggaggactgt tcatcactat cccggtatat tgcgacgcag aaaagatgac atatgatgat | 84282 |
| tttactgcgg tggctatacg aatagctata ggagctgcgt tggaagaata ttatgaactt | 84342 |
| ctattcacgt atggagagct ggtaaactct tctactcgct acaatgtaga cagtgccaga | 84402 |
| ttagaggcgc tttcgtgcca gctattagag tactctccat cacatttaaa tgaagctcaa | 84462 |
| accaagtatt ttcgcgatat taaaaaacgg ctctccgaat tactcggcaa aaaccggcaa | 84522 |
| tatgtaataa gcgcagctga atatctctca aacaatctac aacgatttga tgcgccaccg | 84582 |
| gacacgtcag ccaaacaggc tactataaaa gaaaggatag acgagtctac acatctcttg | 84642 |
| aaacaggtgg caggcgcttc catgctgccc atgaagaagt acaccccgt tccccaagga | 84702 |
| agtgaaaatt tgagggcggt ggcccaaggg ttgagcgctc tcgtaaaaac gctagggacc | 84762 |
| cgaggcactg aaaagatagc agatgctcgg ttttcatcaa atactgcaac atctgaatta | 84822 |
| gagccaccag gttgcagcag aggtttcgaa aaggcggcac caccaatgcc tgatataaga | 84882 |
| aatgttatca tgacagacag gcaaaaaacc acaatgtcta ttacatcaag atcggtaact | 84942 |
| tattatacta tgtatgattg tctggcagca gcctgtgaaa tcatggaggc agaaaataat | 85002 |
| tctaccagaa gatcatggtc actcggaaaa atctcaattg tgttgatgtc gtgctataac | 85062 |
| tctggagctc caatcatggt tgtaaattat cccaagact cgttaaagtt atgctatcca | 85122 |
| aaggttagat ctggagcttc aatactagct acaataatga daccgctggg agaaacctca | 85182 |
| gtacaaaatt taaccgaagc agctcagcaa gaaatagtga agaatgcccc atgttttcaa | 85242 |
| tgtcctttga aagctttgaa agatccagat tctctaacta aattgtttgc agtggactgt | 85302 |
| gaacagttgc tccttatag tttccaagcg cgcgtggctg cagcattcac cgcagcggtg | 85362 |
| tccgaggcca ttgtacgagc aactcacaca gagagcaata ctactcggct cggacagcta | 85422 |
| ataaactacg acatcccttt ataccagcca tttgacagct tggaagcaaa ctggccaaca | 85482 |
| caaatagcac gtatggcttc agacctaatg gcagttctct gtataactct tcaaagtgaa | 85542 |
| cgcttgtccg tctttatgaa aagtggaata tggcgcgcca tcttggcaat gttaattcga | 85602 |
| aaggaaaatc accgaagacc atacctggcc cctgttcatg tggaggatga cgtgtaccta | 85662 |
| ttcgattatt tcagattcgg atcgagtaat attgtaagaa ttaccacaga gcctgttgtg | 85722 |
| ttaaaggctc gcaaacccaa aatagacggc ctctacgaac ttgatttcat cgctagtccc | 85782 |
| ccctctggcc tccacccgtg gactaaacaa aaattccgcc caggagaatt tcactcctat | 85842 |
| atatgcgttg gtttcaattc ggccctgaat gctcttctca tctttcctgg agggtttgga | 85902 |
| ttagaatttg attttggcga agcactaaaa gaagtctggg aggatcacct ggatcactta | 85962 |
| gtattgaaac gctttagtag gcgtgcacca tactaccctg aatcttatct cccgagctgc | 86022 |
| gaattcatgc aaaaagataa acacagctggg tagctagaaa ttgcgccatt ggcacgtctg | 86082 |
| caggcattct tgcttaaatg taatagcgta ggacatagaa agcagttaat accgagtaat | 86142 |

```
taacaattag tggtcaaatg gattactgtt aggactaggt aaatgtacag aatacttaca   86202
ttcgtatttt gactggaggc gaagacaatc gcacttttgt ttccattgcg aaatgtaaat   86262
gtgatcgttt cccccttgac ctgttctacc tgttttgcgc caaaccattt gtacaggcga   86322
gtaaaatttt caataaaaac gggctctgtt gcttttctta agtgggcagt gtatccaatg   86382
cgtattcctt caaagatgaa accagtagg gaaatgagcg gaactaaaaa ccacgttttc   86442
ccgtgcctcc ttggaactaa aaatacagta gttctttgtc taaaatgttg aatgatattc   86502
tctgaaaata atgaggtatt aaaaacggta gacaagtatc tattacttcg ttccgtggat   86562
ccttccccca agcaaatact tgacgcaaag tatgtagcat gcattaagat catttttgaa   86622
aataattcca gtgttccgtc tctctgttcg ctagttgttt tttccaactt tgcccgtttg   86682
tagtcatttg aagcttgacc agaaaatgac ttttttaaca gtgtgtgaaa tctgtaaata   86742
aagttgttca gttgggaaaa ttcatcagac ttgacaaacc cccggtagcc attcattatt   86802
ccgtcgaatc ctttgtcatg tattagggag tcgcttggag caaacctggc aaaatttaag   86862
tttgcgagtt tctgtcttag tgccggaagg atactgtcct cggctgcacc tgtgaaaagt   86922
tgccgtttag gggatacctg taaatcgttt agtgcggcat cggtatctgt gtacttggta   86982
gaataggagg ccagattttc gtaaatgatt tctgacgcca tatatgaaaa cgcacgcgaa   87042
atagcacagc aattatgaaa agatcctata ggggcaatgc acgcttgatg gcgctgtgga   87102
acatcaatcg caaattgaaa tctgctcgcc ggtgaattca tggtatccct cgctgaatca   87162
ttcctatcac atatacttgc agtagttata aaattggagt cactcatttc ttgcccatcc   87222
acgtcgtctg gtcctcgttc cattgttcgc ttacgcaaag catcgcggta tcttttgaca   87282
atttcgaccg attcctttcc aagcatgtct tctgcgagag actaccgaaa cagggctcgg   87342
gccgaagtta tgaactacat taaagggcaa gcctataaag ctgcggtcat cgagatgatg   87402
tctctcaaag ttcctcgaat gcacccagct ctgcgctatt tcttgcatc agctaggag   87462 caggaagctg tttcagagat aaacgtgcgc tcaaataagc gcctcagctc tgtcaggtgt   87522
catgttgctc ggataaaagc agctacagag agtcagagag cattaagact ggagttggat   87582
ggctacagaa gatatctaag gaacgacttt ttagaaacat tcgctcaaga gtcagaagcc   87642
attgcagatg cggagctaga cttgcagcgg gcagaagaag aaattgctct gtatatttca   87702
ggtgaccctg atcgcagaga cagcttagat tgtgaggaag acgacttttt attaaaatgg   87762
caactagaaa acgtaaatcc tccgacgcta ctgccatcac cacatgcacc aagtcccgtc   87822
agtcgcggga actcgccaag aactccaccg actcccagtc caacttttca agaagacgaa   87882
tgcccagtag aagaatacta agcaacgatg atggaatcga ccttgagcat atagccccgg   87942
tctcagaaga tttgacaaaa gaatcgagac agcttgcgat ctacataatg ccgaaaccta   88002
acaaaatatg tctcaaggtc aatccaaaaa tgagctaccg atggtttaac ctagaagggt   88062
caacggtaat tggaaatggt ggatatggat cagtgcagta tgccccaaag taccacatgg   88122
cagtaaaaat atttgaatcg gatggtcatt ttcgatggga actagcaatg tccttgattc   88182
tttccaatgc ggcaagaaga ccagaacttt ccgacatcgc caaacatttc ttacagatct   88242
atgccttttc aaaaatcgag agagcttttg taatggaacc gttgagccat gacctaaaaa   88302
cgtacgccaa aagatacaaa gacaatttta caatggaaac attgaatacc ctgacatctg   88362
agttcaaagg acttgcgaag gccttggcat ttctgaacat tgattgcgga ttggtacaca   88422
tggacgtcaa gagtaacaac atactggtca aatgtgatgc gaatggaaaa cttagtcgac   88482
```

```
ttgtattggc agactttagt ttgacaggcc ctaatactaa ttctattctc aaccagagca    88542
tgatggtgtg tccttcaaga ggagtagtgg aagggctaaa aattatagat tcaacgactg    88602
taaagaatca cattccatct gactctttta tcatatataa cggccactgc cgagctccag    88662
aagtgataat aaattattgt aatgggaaaa ggtatcgcga ccagccaatg gacgccctgg    88722
aaacacttgg attggatcta ttttcccttg ggcaagtagt gcaggaaatc ttatttgagg    88782
gaattctgtg cagatcgcgc gagttttcgt ttaaaccaaa accaaacact attcatgaaa    88842
aattaagtca cgattacatg atgagggttt tggcatatcg aattgtgctt tccgacaatc    88902
taatctctag aggctgtgat ctaagtttca ccggtccact aagtggaaca gtagaatcag    88962
tgaacgcatc cctatttcga gaattagaca gaatccttt ccagagtcac gtcgaaatgt    89022
atgagcgcat cgatctacga gaaaaactgc tgaacgtcat cattcctccg gaaaccagag    89082
gactttgtac cctggcggga ctgctatgtc actgggatgc ggatttgcgc cgctctgcag    89142
tgaccttctt ttagagattg tgatcgttac ttataccaat aaacttttc agagctttgt    89202 attacgtcgt ttttttgtga ccggggactc tatcaagggg cgtggttgcg cgataatggg    89262
gtatattttg gcctaatggg taacaggcag caaggtgttc cgttcactag tcttcatctc    89322
gcagaggaga aacatgacaa gtgttcaaga ccagtctcct ctgaacgaaa acatgcaatg    89382
ccagaagact ttagaattgt cggttggaat gcagattccg aaagaactac caggagtggc    89442
aatgtttaca ttctacgatt acttagccga cctggcacgc ggaggacacg cgcaaagtga    89502
cattcttcaa caggaaccac tacatcaccg cctggcttac atcagccacc tgttttcgtg    89562
gctcgaaaaa gaaggtttcg cgtatggcat tttgaacaaa tttttggtt ctgagcgcgc    89622 tctgagcgca tcagaaatta gtagtaattt atcgcaacaa cagatcaatg aaatcttatt    89682
tttcatagaa tctgaaacga aacaacaagc gtcgtgtgac ctgtggaaag ttttaagaca    89742 attttattg acggcttcaa ctttgaagtg gatgaaaaat aaaccgtgct caaagccgga    89802
atggtttaag gtacaggaat tcaaaggcgg acaccttggc tatgccacac agtccatgcc    89862
tttgattttt ggcaatacta acgaaagctg cgcccgatcc cttcttttgg gatatgtaac    89922
tggagaggca tggaaaactt cagaagatcg agaagagttt tacaaatttg acgacggcca    89982
tccaccagaa gaagcattta catgtggact tcttttagat aaacggagtg gaatgttggg    90042
agcatcaatg gatatggcga tagtaaagcg caggaaacag tgcgctagaa aagtggagat    90102
atacgaaatt aagtgcagag caaagtatgt gttctcggtc gagaaccaga cgcatccact    90162
ttctcaactg tacgataaaa tgttgcaaca cccatgtgaa aattctattc gcgatttctt    90222
gctgggaatt tcctcaccgg gggtagaatt tgttgaagag agcggaatcc ctacagcatc    90282
agaagctcta ctaacctgcg acaaaacttg gaaaactgac aggtggaaga aaaatttacg    90342
agaacgtgct tgcctaatgg aaaagcgtca cttgtccctg aatagaacca caactcatc    90402 tgtgttttg tttgaaagcc cctgtctgga aacaaacacg atcagacctg tccagtggcc    90462
ggacggtgaa aacaatatcg agttaccaat cttcattaac ccaaaacatc agaatttcaa    90522
acagattttt gtacagacat acgtcttggc cgaatatttt gaaacaattc ctatatctcc    90582 attttagtt acatttatag gtcgcaacag aaagacggta gagcgggac gtgtatttaa    90642 gctcgaacac acattagacg gtatagaaga accggtggaa ttgaactgca agcacgcgat    90702
accggtacta ctaataataa ccccacacaa catcgacaga aatcatttca gtgatttgga    90762
ctcgcttggc agagaagcgt tcgagttttc tgtgaaggaa acatgggcca aggtctctgt    90822
ggacacctcg gagaatgttg ctgcccctgc tgttcaaagt cctgcggggg tgacacaaga    90882
```

```
                                                         -continued tcccgaaaat ctggagagcg cttgtccta ttagacgaca gctttgacga attcaccata    90942
accgaagaca tgcctatgat tcaaggagga aaaagaaag agaagcgtag caaaaaagaa    91002
gccgaaccaa ttgtagttga gccagtggct gctagaaggc attgaaacat gttatttcaa   91062
ataaacagaa ctacaaccaa atacatgcgt caacctttat ttgcgttatg cgtaatctaa   91122
attacagttc gtcgtcatag ggtacagttt cataaacgtg cttgtctctt cggcttttgt   91182
attttccgcg gcgcgttttg cgtttcacgg ttttatctaa agcttctgtg caacggtcg    91242 ttaccttgcg gatgaaatcc gtctgtctgt actggtgata tctgtatgcc cgtacgactc   91302
gcagaatagc caaaactaaa acaaggaggg caaatactcc tagaattcct gccgcagccg   91362
gcttccagtt gggatgagtt ccgctatcca acgtattagc atagtgcagg gatgccgtcc   91422
caagcattcc aagagcaatg atgagtccga atgcggacc aataagtaca tgcacatact    91482
tcgctaaaac cagctcggtc acaatcaagt atatgatacc tatgataaga aatgcaatca   91542
ttgccccaag tgtagaagca gggacactga ctccaaaatt cacggtcatg acgagtgctc   91602
cggacaaggc cattataagc ccccaaactc ccatgataga ggcgtagacg tttaatacca   91662
ctgccttaaa cggtgataca acacaatgaa cttcagggca tgcacttttg agctgtgagt   91722
taaaaactga gtactggtca ggtgtctttc cggaagacgc gaacgtaccc aaaaatacga   91782
tgccggatac aaaaataatg caaaatgtga cagctgatag cgtaagctgt ctgtacgaaa   91842
ggagtagtac aaacaactgc cacgcccata ctgtgataat aatagacatt aaggcaggtg   91902
tgctgatcac ggccgaagtc aattcggacg ctccgtatga acgatcgtga ttacaagtct   91962
tggctctaac tgcgccaaga gtaacgtata tcgccaagag tatccacacc gccatagtcg   92022
cgtaaacggt aaatatcatt cctggcgacg aaataaaaaa aagtccatct tcgttcgccc   92082
ttagcagtcc aggttgattg atcaaaggcg ttgctggctt aaggtgtcca ccggcgacgt   92142
tgccgaaaaa acagggaaac cctgcttgcg gactaagggc ggagaaagct gaggccagtg   92202
atatcaacac cagaaccaca aaagagatta cttcaatcag ccacatgcgc c atg caa    92259
                                                          Met Gln tcc tct cta aac gcg att cct gtc cac tat agt agt agc cgc tca         92304
Ser Ser Leu Asn Ala Ile Pro Val His Tyr Ser Ser Ser Arg Ser
    5080            5085                5090 ttt tct gcg cta tgt gaa tta gcg cct acg tcg ctc agc ggg agg         92349
Phe Ser Ala Leu Cys Glu Leu Ala Pro Thr Ser Leu Ser Gly Arg
    5095            5100                5105 aac gat atg tcg cca aat aat ttt gct cct gga gaa caa ctg tgg         92394
Asn Asp Met Ser Pro Asn Asn Phe Ala Pro Gly Glu Gln Leu Trp
    5110            5115                5120 ttg tcg ccc agc gtc gga ctc gca cga aga ctg tac gga tgc gat         92439
Leu Ser Pro Ser Val Gly Leu Ala Arg Arg Leu Tyr Gly Cys Asp
    5125            5130                5135 ctc agc gat cgc cta tta tcc aat ccg aca atg agt agg ctg agc         92484
Leu Ser Asp Arg Leu Leu Ser Asn Pro Thr Met Ser Arg Leu Ser
    5140            5145                5150 cta gat cag cag cat ggc cat ccg gtt acg ttc cca ccc ccc tca         92529
Leu Asp Gln Gln His Gly His Pro Val Thr Phe Pro Pro Pro Ser
    5155            5160                5165 cgc tcg cga ccg gtg ttg att gcg cgc gct ccg atg gga tcc ggg         92574
Arg Ser Arg Pro Val Leu Ile Ala Arg Ala Pro Met Gly Ser Gly
    5170            5175                5180 aaa act acg gca ctg att gaa tgg ttg gct gga ttt cta gac cac         92619
Lys Thr Thr Ala Leu Ile Glu Trp Leu Ala Gly Phe Leu Asp His
    5185            5190                5195
```

```
cag gat aga agc gct ata gtc gtg tca tgc aga aaa agc ttt act    92664
Gln Asp Arg Ser Ala Ile Val Val Ser Cys Arg Lys Ser Phe Thr
    5200            5205                5210 aac agt ctt tgt cga cga ttc caa cgg gat ggt ttg gtg ggt ttt    92709
Asn Ser Leu Cys Arg Arg Phe Gln Arg Asp Gly Leu Val Gly Phe
    5215            5220                5225 gct acg tat cta gac tgc gaa aaa tac ata ata gat gag att tca    92754
Ala Thr Tyr Leu Asp Cys Glu Lys Tyr Ile Ile Asp Glu Ile Ser
    5230            5235                5240 cac cga cgg cta ttg gta caa ctg gaa agt ctg cca cgc gtc tct    92799
His Arg Arg Leu Leu Val Gln Leu Glu Ser Leu Pro Arg Val Ser
    5245            5250                5255 agt gta cta ttg gat cac tat gat gtt cta gta gtt gat gaa gta    92844
Ser Val Leu Leu Asp His Tyr Asp Val Leu Val Val Asp Glu Val
    5260            5265                5270 atg tct ttg atg aat caa ttc ttt tcg cct aca gtt aga aaa cta    92889
Met Ser Leu Met Asn Gln Phe Phe Ser Pro Thr Val Arg Lys Leu
    5275            5280                5285 cgt gaa acg gaa gct ttg ttt tca tta ttg tta tct aaa tgt cag    92934
Arg Glu Thr Glu Ala Leu Phe Ser Leu Leu Leu Ser Lys Cys Gln
    5290            5295                5300 tat atc gta gcg atg gac gca acg ata aat gca act ctt gtt gaa    92979
Tyr Ile Val Ala Met Asp Ala Thr Ile Asn Ala Thr Leu Val Glu
    5305            5310                5315 atg ctc gca gat ttg aga ggg gca gaa aat ata cac gtg ata gtg    93024
Met Leu Ala Asp Leu Arg Gly Ala Glu Asn Ile His Val Ile Val
    5320            5325                5330 aat gat ttc gta tcg agc ggg ttt gcc aat cgt caa tgc aca atg    93069
Asn Asp Phe Val Ser Ser Gly Phe Ala Asn Arg Gln Cys Thr Met
    5335            5340                5345 ctt aac gcg ctt ggc gcg gca ata cct gcc agt ttg tta aag ccc    93114
Leu Asn Ala Leu Gly Ala Ala Ile Pro Ala Ser Leu Leu Lys Pro
    5350            5355                5360 tca gaa gga aat gag gac aaa gga ctc gag gat aac aaa agt act    93159
Ser Glu Gly Asn Glu Asp Lys Gly Leu Glu Asp Asn Lys Ser Thr
    5365            5370                5375 gca cag gtg gat cca tct cta ctt gaa ggg tcc ttt ttt cat gaa    93204
Ala Gln Val Asp Pro Ser Leu Leu Glu Gly Ser Phe Phe His Glu
    5380            5385                5390 atg cag gcg cgc tta ttg cgt gga gaa aat att tgt gtc ttt tcc    93249
Met Gln Ala Arg Leu Leu Arg Gly Glu Asn Ile Cys Val Phe Ser
    5395            5400                5405 tct acg cta tca ttt tca aac gtc gtt gcg ttc ttt tgt tca gaa    93294
Ser Thr Leu Ser Phe Ser Asn Val Val Ala Phe Phe Cys Ser Glu
    5410            5415                5420 att cta agt cct ggg aca gtt ctc tta ctg aac tcc aac tct ccc    93339
Ile Leu Ser Pro Gly Thr Val Leu Leu Leu Asn Ser Asn Ser Pro
    5425            5430                5435 cac gta gat acg act aac tgg ggg cga ttt cga gca gtc atc tat    93384
His Val Asp Thr Thr Asn Trp Gly Arg Phe Arg Ala Val Ile Tyr
    5440            5445                5450 act aca gtg gtg aca gtt gga ttg agt ttt gac tct tgc cac ttc    93429
Thr Thr Val Val Thr Val Gly Leu Ser Phe Asp Ser Cys His Phe
    5455            5460                5465 cac tca atg ttt gcg ttc gta aag ccc aca atc cat gga cct gac    93474
His Ser Met Phe Ala Phe Val Lys Pro Thr Ile His Gly Pro Asp
    5470            5475                5480 atg atg gct gtc tat caa gcg atg ggt cgg gta aga cgt cta cta    93519
Met Met Ala Val Tyr Gln Ala Met Gly Arg Val Arg Arg Leu Leu
```

-continued

| | | | |
|---|---|---|---|
| cat gat aag ctt ttt ata tat tta gat gtt tct ggg gca tgg ggc<br>His Asp Lys Leu Phe Ile Tyr Leu Asp Val Ser Gly Ala Trp Gly<br>5500                                             5505                                    5510 | 93564 |

```
                5485                    5490                    5495 cat gat aag ctt ttt ata tat  tta gat gtt tct ggg  gca tgg ggc      93564
His Asp Lys Leu Phe Ile Tyr  Leu Asp Val Ser Gly  Ala Trp Gly
        5500                     5505                 5510 gca cca att ttc act ccc atg  att tta aac tcg gag  ttt agc act      93609
Ala Pro Ile Phe Thr Pro Met  Ile Leu Asn Ser Glu  Phe Ser Thr
        5515                     5520                 5525 acc cca tgg cca gta gac att  aca gtt cca gca gac  gcc atg tgt      93654
Thr Pro Trp Pro Val Asp Ile  Thr Val Pro Ala Asp  Ala Met Cys
        5530                     5535                 5540 gta aaa ttt aaa aac cgt tgc  aga cag atc aac aat  cat cga gac      93699
Val Lys Phe Lys Asn Arg Cys  Arg Gln Ile Asn Asn  His Arg Asp
        5545                     5550                 5555 ggg gta ttt acc cgg ttc aaa  aat aag cat tat gta  gaa aga tgt      93744
Gly Val Phe Thr Arg Phe Lys  Asn Lys His Tyr Val  Glu Arg Cys
        5560                     5565                 5570 aca cta acc agt gct aat gac  agt ttt agt ctc cta  cat act ctt      93789
Thr Leu Thr Ser Ala Asn Asp  Ser Phe Ser Leu Leu  His Thr Leu
        5575                     5580                 5585 cta gtc aat aac aaa ata aat  gtg gag ata atg agc  gtt gac tcc      93834
Leu Val Asn Asn Lys Ile Asn  Val Glu Ile Met Ser  Val Asp Ser
        5590                     5595                 5600 tcc gat ccg aaa ctg gaa aat  ttg ggt caa ttc ata  tct ggt ctg      93879
Ser Asp Pro Lys Leu Glu Asn  Leu Gly Gln Phe Ile  Ser Gly Leu
        5605                     5610                 5615 cgt gca gat agt tat cgg aat  agg gct cca ctt aag  cat ctg tac      93924
Arg Ala Asp Ser Tyr Arg Asn  Arg Ala Pro Leu Lys  His Leu Tyr
        5620                     5625                 5630 tcc gcg ttg gaa aag tat gaa  aag agt caa gat ata  ttt tgc ctt      93969
Ser Ala Leu Glu Lys Tyr Glu  Lys Ser Gln Asp Ile  Phe Cys Leu
        5635                     5640                 5645 cca tca aac cca act cct gag  gaa aca gct ttg atg  ctc atg gag      94014
Pro Ser Asn Pro Thr Pro Glu  Glu Thr Ala Leu Met  Leu Met Glu
        5650                     5655                 5660 agt gaa aat gta aac cag ttc  att gct cgt ttt ttt  gaa ctt gac      94059
Ser Glu Asn Val Asn Gln Phe  Ile Ala Arg Phe Phe  Glu Leu Asp
        5665                     5670                 5675 cga tcg cta gaa aat ttc ggg  gaa gac ttg caa gcc  ttt ctg caa      94104
Arg Ser Leu Glu Asn Phe Gly  Glu Asp Leu Gln Ala  Phe Leu Gln
        5680                     5685                 5690 cag ctt ggt gac aaa agc aaa  act ata gat gca cta  att aat gcg      94149
Gln Leu Gly Asp Lys Ser Lys  Thr Ile Asp Ala Leu  Ile Asn Ala
        5695                     5700                 5705 gct gtt gtg gaa aca gga tgc  acc tgc gat gaa gat  gaa tgg ttt      94194
Ala Val Val Glu Thr Gly Cys  Thr Cys Asp Glu Asp  Glu Trp Phe
        5710                     5715                 5720 cag atc aat aca gag gca ttg  tcc aaa gat cga gac  agt aaa ctc      94239
Gln Ile Asn Thr Glu Ala Leu  Ser Lys Asp Arg Asp  Ser Lys Leu
        5725                     5730                 5735 gac tct tgg ata tca tat tat  ctc gat ggt cca ttt  gtg tgt cta      94284
Asp Ser Trp Ile Ser Tyr Tyr  Leu Asp Gly Pro Phe  Val Cys Leu
        5740                     5745                 5750 agc aac gga cgt ccg gcc gtg  att gag gtt tgt aat  gaa acc gaa      94329
Ser Asn Gly Arg Pro Ala Val  Ile Glu Val Cys Asn  Glu Thr Glu
        5755                     5760                 5765 gtt aag aat cgt cga aac cta  tta aga cta tgc ata  aac att gcc      94374
Val Lys Asn Arg Arg Asn Leu  Leu Arg Leu Cys Ile  Asn Ile Ala
        5770                     5775                 5780 agg acg ata ggc tgg aaa cct  tca gcc gat cca aac  gag act gaa      94419
```

| | | | | | | | | | | | | | |
|---|---|---|---|---|---|---|---|---|---|---|---|---|---|
|Arg|Thr|Ile|Gly|Trp|Lys|Pro|Ser|Ala|Asp|Pro|Asn|Glu|Thr|Glu|
| |5785| | | |5790| | | |5795| | | | |

| | | | | | | | | | | | | |
|---|---|---|---|---|---|---|---|---|---|---|---|---|
|att|gaa|ctt|gat|gtt|atc|gtg|aag|gca|gta|aat|gac|gca ttg aac|94464|
|Ile|Glu|Leu|Asp|Val|Ile|Val|Lys|Ala|Val|Asn|Asp|Ala Leu Asn|
| |5800| | | |5805| | | |5810| | | |

| | | | | | | | | | | | | |
|---|---|---|---|---|---|---|---|---|---|---|---|---|
|gca|ggg|atg|ggg|aat|tgt|atg|cta|gaa|tat|ctt|cgg|tta aac ata|94509|
|Ala|Gly|Met|Gly|Asn|Cys|Met|Leu|Glu|Tyr|Leu|Arg|Leu Asn Ile|
| |5815| | | |5820| | | |5825| | | |

| | | | | | | | | | | | | |
|---|---|---|---|---|---|---|---|---|---|---|---|---|
|aca|gaa|ccc|tca|tgg|tta|act|gga|cct|ata|agg|aac|ctc cag tgt|94554|
|Thr|Glu|Pro|Ser|Trp|Leu|Thr|Gly|Pro|Ile|Arg|Asn|Leu Gln Cys|
| |5830| | | |5835| | | |5840| | | |

| | | | | | | | | | | | | |
|---|---|---|---|---|---|---|---|---|---|---|---|---|
|tat|ctt|gga|gaa|aaa|aaa|atg|tct|cgc|cgc|gaa|cgg|aag act tct|94599|
|Tyr|Leu|Gly|Glu|Lys|Lys|Met|Ser|Arg|Arg|Glu|Arg|Lys Thr Ser|
| |5845| | | |5850| | | |5855| | | |

| | | | | | | | | | | | | |
|---|---|---|---|---|---|---|---|---|---|---|---|---|
|gac|cca|cta|gag|atg|gca|gct|gta|aag|atc|ttg|cgc|act cta tgg|94644|
|Asp|Pro|Leu|Glu|Met|Ala|Ala|Val|Lys|Ile|Leu|Arg|Thr Leu Trp|
| |5860| | | |5865| | | |5870| | | |

| | | | | | | | | | | | | |
|---|---|---|---|---|---|---|---|---|---|---|---|---|
|gcg|gag|tta|ttt|gat|gta|cgg|gta|ttt|aaa|agc|caa|aag aca ttt|94689|
|Ala|Glu|Leu|Phe|Asp|Val|Arg|Val|Phe|Lys|Ser|Gln|Lys Thr Phe|
| |5875| | | |5880| | | |5885| | | |

| | | | | | | | | | | | | |
|---|---|---|---|---|---|---|---|---|---|---|---|---|
|cct|ggt|acg|gca|agg|gtc|aag|aac|ttg|cga|aag|gag|gag ctc tgt|94734|
|Pro|Gly|Thr|Ala|Arg|Val|Lys|Asn|Leu|Arg|Lys|Glu|Glu Leu Cys|
| |5890| | | |5895| | | |5900| | | |

| | | | | | | | | | | | | |
|---|---|---|---|---|---|---|---|---|---|---|---|---|
|gct|ttg|cta|gac|cgc|att|cac|gtt|ccc|tac|gat|cgc|aag gaa acg|94779|
|Ala|Leu|Leu|Asp|Arg|Ile|His|Val|Pro|Tyr|Asp|Arg|Lys Glu Thr|
| |5905| | | |5910| | | |5915| | | |

| | | | | | | | | | | | | |
|---|---|---|---|---|---|---|---|---|---|---|---|---|
|cac|aag|caa|cta|tat|gct|aaa|ctt|atg|tgt|cat|aga|gaa cag ttc|94824|
|His|Lys|Gln|Leu|Tyr|Ala|Lys|Leu|Met|Cys|His|Arg|Glu Gln Phe|
| |5920| | | |5925| | | |5930| | | |

| | | | | | | | | | | | | |
|---|---|---|---|---|---|---|---|---|---|---|---|---|
|aag|ggt|tct|cga|cta|agt|ttc|cgg|act|gct|gcg|tgg|acc cgt ttt|94869|
|Lys|Gly|Ser|Arg|Leu|Ser|Phe|Arg|Thr|Ala|Ala|Trp|Thr Arg Phe|
| |5935| | | |5940| | | |5945| | | |

| | | | | | | | | | | | | |
|---|---|---|---|---|---|---|---|---|---|---|---|---|
|tta|aaa|gga|cgg|tgc|ctg|gag|gac|ttc|cat|ttg|atg|act cca atc|94914|
|Leu|Lys|Gly|Arg|Cys|Leu|Glu|Asp|Phe|His|Leu|Met|Thr Pro Ile|
| |5950| | | |5955| | | |5960| | | |

| | | | | |
|---|---|---|---|---|
|tct|tcc|cat|cat|gta tga tgaaagcata ctttatggct acttatgggg|94962|
|Ser|Ser|His|His|Val|
| |5965| | | |

```
catctcgata tatacgattg agactaaaca aaatgcgtca ggaaatatta cagacatgtg   95022
ggtattgtat gaattagctg tccatgattc tactaagggt gcccatgaag tactttatgc   95082
atccttacag tttgaagaaa gcgacctcag tgtggcctcg tggcctcatc cagctctgaa   95142
tgccagatta ctgacggact tcgttggggc tgtaaagaat ttccatcaga gggtgtacaa   95202
gctgaatgca aaaacaatta acttcggatg gattctctca tgttctactt ctagccagat   95262
tgctctccgc ctggtgacag gaagactact tcatgaaatc aggcgcgcct tgactctgcc   95322
agaattttat tctccttcta tttttttatgt ttgcaaagac agtggattga tcactaaggt   95382
ctgcgaggat aaatccaagc cacgtatggc aactgcatct tacgcagcat gaatgcttc   95442
gtctaacttc caagcaaatt acattgaacg caatctgcaa gccggacatt gttgtgaact   95502
gagaaatttt ggatgggctc gcatacaggc aatctcatct ggaaaaatta atccaagaag   95562
catgaccgcg gaatgggtgt gggctggtgg aaagtggatt gatggaagag gaaatgaagc   95622
attttctgaa acagggactg atcccacttc cgacgatggc cttgctgtcc cctttgcctt   95682
aacacccgcg aaaacaattt atggaccgac gtggtttgtt cccagacgca tgcttgtagc   95742
gtcattggtg cccaaggagt tcgaatatgc catctatctc aaggatggaa gtacgataat   95802
```

-continued

```
ctctttagtg tgcgcaataa taaatctgta ttgcagattt taccaaggaa acattgttgc    95862
acaatctaca tttctcaaac ctattatcct ttttctattt ccgacaagtt cttcccgaat    95922
ggacggctca gagaaggttt catctataaa agactcctac atgtatacac ctggattccc    95982
gagtataaat tttgttccca ttacgacgca gaacatgtca aagatgggag ccttgaatgc    96042
atgcagaata gtctctcttg tggaggggtt atggccagcc tataatatca gagcattact    96102
catgctggat cgcggagatc gagcgaaaca tgggtctcag atcacaacac tacccagaga    96162
cctcgagagc actttagaag tgtacccagc cggtaaaata tccaccatag ccgatctccc    96222
gactgttatc agtggcagga ttttaaaaat ggacttttct gctttctttc catgtttgta    96282
catggcatgt ggcggaggca gccaagcgct atgccgcatt atcgaggcaa gattaaacag    96342
ggagccgcag tcagagaagc ttaaagctgc cttggtagct ctggtgggtg gctaaaata    96402 tacagatcca tcgaaatata aattagtaat agcgctctgc aacagcattg cattggctgt    96462
cgaaaatgct gccaatagcc tccagtttgg aatagctatt tatatgaagg atggattcat    96522
aggagctttt gataaacatt cctctacaag cgcagaggaa ctgagaagca aatgcgaatg    96582
ggccgccatt gaagaattgc agaagattct tctagaatgc ggccaagcaa ttacaggaat    96642
gccgactctg aaactaaggc tagagggaga atttacagag ggcctgcttc ttaattgcaa    96702
caagtattgg ctccacaaca ggaataccgg aaagagtttc atatgtggga tacctgggct    96762
tcgagaagag aatgggctga gtgtgttaac agaacgtaca gcttgtgaac tgctcgctgg    96822
catttacact gccaacaccg taagcaccgc taccgaaaca ctcacgcgaa ttctagatgg    96882
atatgccttc tctgccttcg aagctagagg tgacataaac ttctggcaag agacgctaaa    96942
aagtagcttt acccccatgca tttcagattc cgcagccatc agatctgcca gtttcatgac    97002
acgcccagat gagctggaag gagagactca ctttgtttac cttactccga caaatttgtc    97062
ctcccatggc tccgccaacg ctggcggtaa agttatctac ccaagttctc tcgcagaaga    97122
gaatttctgc attaaaatat gttattcggc tcacctaatc cccaaaatgt cagcaatggt    97182
ggagcttgta cagaatatgg tgtggttaaa attttatcat aattctgtgg acaatgatga    97242
ggagacacgg ggtaagttat tgaaaacgtg tgactacgat tacagagaa catcttttt    97302 attctcataa ttaaacagaa catttccaaa gaccatgata cttggtactt cgtcatt      97359
```

| | | | | | | | | | | | | | |
|---|---|---|---|---|---|---|---|---|---|---|---|---|---|
| tca | aaa | ata | ggt | atc | ata | taa | ctt | ata | tgc | act | gcg | atg | aag ctt | 97404 |
| Ser | Lys | Ile | Gly | Ile | Ile | | Leu | Ile | Cys | Thr | Ala | Met | Lys Leu | |
| | 5970 | | | | 5975 | | | | | 5980 | | | | |

| | | | | | | | | | | | | |
|---|---|---|---|---|---|---|---|---|---|---|---|---|
| gcg | gtc | att | cca | cca | caa | tct | taa | tac | gcg | agt | aaa | aaa gtt | tcc | 97449 |
| Ala | Val | Ile | Pro | Pro | Gln | Ser | | Tyr | Ala | Ser | Lys | Lys Val | Ser | |
| | | 5985 | | | | 5990 | | | | | 5995 | | | |

| | | | | | | | | | | | | |
|---|---|---|---|---|---|---|---|---|---|---|---|---|
| gtt | gcc | ata | tac | ccg | att | caa | agt | tga | att | cct | tga | ctc | taa gat gat | 97497 |
| Val | Ala | Ile | Tyr | Pro | Ile | Gln | Ser | | Ile | Pro | | Leu | Asp Asp | |
| | | | 6000 | | | | 6005 | | | | | | | |

| | | | | | | | | | | | | |
|---|---|---|---|---|---|---|---|---|---|---|---|---|
| ggc | tcg | ttc | att | ttc | att | gga | agg | cag | gtt | cat | gat cat | aag tgc | 97542 |
| Gly | Ser | Phe | Ile | Phe | Ile | Gly | Arg | Gln | Val | His | Asp His | Lys Cys | |
| 6010 | | | | | 6015 | | | | | 6020 | | | | |

| | | | | | | | | | | | | |
|---|---|---|---|---|---|---|---|---|---|---|---|---|
| gtg | ggt | aga | ata | aag | aga | aga | tat | tag | ctc | ttc | tcc | aat tgg agc | 97587 |
| Val | Gly | Arg | Ile | Lys | Arg | Arg | Tyr | | Leu | Phe | Ser | Asn Trp Ser | |
| 6025 | | | | | 6030 | | | | | 6035 | | | | |

| | | | | | | | | | | | | |
|---|---|---|---|---|---|---|---|---|---|---|---|---|
| ggt | aat | ttg | cat | gag | ggg | ctg | cgc | cac | tcg | ata | atg | agg caa tac | 97632 |
| Gly | Asn | Leu | His | Glu | Gly | Leu | Arg | His | Ser | Ile | Met | Arg Gln Tyr | |
| | | 6040 | | | | 6045 | | | | | 6050 | | | |

| | | | | | | | | | | | |
|---|---|---|---|---|---|---|---|---|---|---|---|
| caa | ccc | ggg | atc | aaa | ggg | agg | aag | atc | atg | cat taa | tag caa | tgt | 97677 |
| Gln | Pro | Gly | Ile | Lys | Gly | Arg | Lys | Ile | Met | His | | Gln | Cys | |
| 6055 | | | | | 6060 | | | | | 6065 | | | | |

```
att taa gag cca ctc ccc tcc att cac caa tag ctc gcg cac ctt    97722
Ile     Glu Pro Leu Pro Ser Ile His Gln     Leu Ala His Leu
            6070                6075 atc att gat tga aat agt tcg cgc gaa acg ggc aat tgc gct tcg    97767
Ile Ile Asp     Asn Ser Ser Arg Glu Thr Gly Asn Cys Ala Ser
6080            6085                6090 taa ctt ata gca gtg ttc ttg agt aac ctt aat ggg gtc aat gtt    97812
    Leu Ile Ala Val Phe Leu Ser Asn Leu Asn Gly Val Asn Val
        6095                6100                6105 ttc caa ata cat gca aat caa aca gag cgc aaa gtc ttc aaa ttt    97857
Phe Gln Ile His Ala Asn Gln Thr Glu Arg Lys Val Phe Lys Phe
        6110                6115                6120 ttg ggg cat aat tct gtg aat cct gtt taa aaa atc agg cca tgt    97902
Leu Gly His Asn Ser Val Asn Pro Val     Lys Ile Arg Pro Cys
        6125                6130                6135 aac atg cac agt ggc aac gcg gtc ctc tga ggc tgt gat tac tga    97947
Asn Met His Ser Gly Asn Ala Val Leu     Gly Cys Asp Tyr
        6140                6145 aaa tat aaa gcc agc atg atc atc tag gcg cac aca cgc gca aaa    97992
Lys Tyr Lys Ala Ser Met Ile Ile     Ala His Thr Arg Ala Lys
6150            6155                6160 gta ctc ttc aat atc cac tac tgc tcc aga aat cag ctc tag gat    98037
Val Leu Phe Asn Ile His Tyr Cys Ser Arg Asn Gln Leu     Asp
        6165                6170                6175 aat ttt ttc ccc atc cat ctg gat gtc cat ata tgt tat gga atc    98082
Asn Phe Phe Pro Ile His Leu Asp Val His Ile Cys Tyr Gly Ile
        6180                6185                6190 aga cgc aaa caa tgc tgg cgc ccc tgg cgt gga tcg tac ttc aaa    98127
Arg Arg Lys Gln Cys Trp Arg Pro Trp Arg Gly Ser Tyr Phe Lys
        6195                6200                6205 aaa aaa tct cgg gat agc ctg ccg cga tat ttc ctt aat taa ctg    98172
Lys Lys Ser Arg Asp Ser Leu Pro Arg Tyr Phe Leu Asn     Leu
        6210                6215                6220 tga tgt cga ttc tcc aga gga ggc cag acg ttc aag ttc ctc aag    98217
    Cys Arg Phe Ser Arg Gly Gly Gln Thr Phe Lys Phe Leu Lys
        6225                6230                6235 ggt agg gcc gtg ttc ggg ttc ttc tgc gat gtc ttc caa tcg tat    98262
Gly Arg Ala Val Phe Gly Phe Phe Cys Asp Val Phe Gln Ser Tyr
        6240                6245                6250 agg tcc tac ttt ttt ctg atg ccg gca tat cgc gtt gaa tgc ttc    98307
Arg Ser Tyr Phe Phe Leu Met Pro Ala Tyr Arg Val Glu Cys Phe
        6255                6260                6265 ttc ggc cca tga tac taa ctt tcg agt cgg ccg att ctc tgt cgc tgc   98355
Phe Gly Pro     Tyr     Leu Ser Ser Arg Pro Ile Leu Cys Arg Cys
        6270                6275 ctc tag aat agg ctc tcc tgt ctc ttt cag ctc ttc cat ccc atc    98400
Leu     Asn Arg Leu Ser Cys Leu Phe Gln Leu Phe His Pro Ile
6280            6285                6290 gtt cat ctt gcc gat tgg cgc acg aac gtc tga cat ttgctatgta    98446
Val His Leu Ala Asp Trp Arg Thr Asn Val     His
        6295                6300 acgtacgttc agatctttca aatacgaacc tacccgcgag ctggcaaata atgtttgaca    98506
caactcctcc tctgacttat atgtagtctg gctcgataca aggaatccta gacgtgacgc    98566
cttcagaact ttgtgaaaaa atggaccgac aataagcgtg attgcgctag tactgtacga    98626
caaagatact tcctcgcctt gattattcat atttctttga attttaaaca cgcgcagtaa    98686
ttcttgttcc cagagcgccg acaatcgagt ctcctcctcc agataaggag gaatgtaccg    98746
```

```
cgccagaaaa ctattagcaa tatactgttg gtcattcatg tccttactta catcaacgag   98806
gttatatgat aaattctcag ggagcttcga tagcgactct agagtttctt tgcactccca   98866
agcctcttcg atacctccaa gggtctccca tgctgggcaa cggtcatagt ttgcttgggt   98926
gcgctcagtc cgcctggcag attccattct agcctcaacc aattcttttt tcattttccc   98986
attactatag accaagtttt tattgctttc cttgagatca gagacagtct tgaacaaagt   99046
atttactacc tttccaacac ttgtattaac ggcagctcgc acagcattcc ccatgcgatc   99106
ttctgcatta tcaatgggcc gctgccctg cgctgccgct cttccgccac acccaacacg   99166
ggtagggtca agcacgagtt gtctctcgat gttagaaaca ttttcacgca agtaagagtc   99226
cactacgtct gccacatcac caactttgcg catattttga atatcaataa tgaacttgat   99286
cagcctagct gctgcagatg taccggcctc ttccacacct tctcccagag ccttatccac   99346
cacttttgtt acatgatctg gatcctgtgc attctcagtt cgtagaccaa gcaaaacctt   99406
gatcggagcg gtatttacta attgacacaa ttttgcatgc tcgcgcatag cctgagcttt   99466
gagaacagga ccgtgcaatc gttgcatagg agaatcaaat aatactcccc tgtcagttac   99526
caatggttcc caaacaacca tacattcccc aagctcccca gtatttccat cataggcgcg   99586
gatttcactg gttttaacgt tcattattat tagtgttcgc tcatactcta aaatatgtac   99646
tgcccctaat acagcacgga gatacttcag catttcgaac cctctggcaa aaagtgaagg   99706
cgcgacatgt aggtggtggt gtatttcagt cgttgtactt tccaggtctt catttccgag   99766
atcactgcca gtggggcgct tttcttgagg ttttcttcct cgtaccaaag gaaccatacc   99826
cagacatgtt atccaatcta taacgtac gtaggaagga gccttcccag cttcgcttaa   99886
cccgcgcaag cttaactcag acacgccccg tacaaaatca gtaacactg tctgcaataa   99946 aaaggaccac aactcgaacg cctgctctgc aactcgaatt ccatcttccg aattgtgaca  100006
gtaacgtgct gccagttcat ccggtgtcaa ccctcttgtt ctgatgtgag tgtcccaatc  100066
gcgctccaca tcctcaaatc gacagccatc caatatattg cggagaaccg ccacttgaat  100126
ttgtctaaca acagattctg ttgctcggac cgagttatac acgccttgtc cagaagtgta  100186
cgtcgatgcg cccaggagaa tttccctgaa tcccatcgtg cgctttgttg gatggattat  100246
tatccagtca tcaggctcgc ctgttagaat cggctccaag accgcgataa ggttgtcgat  100306
atcaaaggca caaggtacct gacgcaattg ggaaaatggc atgtccattt tcggggaaga  100366
gcaggcggga aatagaaatc accactcctg tttacttaaa ttttttcggca atgcagagca  100426 ttcaggcgat tttatcggac attacaatcc tatcagaaca agctgttcat gaagactcca  100486
agccgcaact gtcttggttt gagactgtgg cacgtttaga tgaaccgacc actttgcctc  100546
tggcggaatt accatttaat gtttatctaa tcaccggtaa cgccggctca ggaaaaagta  100606
cttgcattca aactcttaat gaaacattga attgcatcgt tactggctca acgcgcatag  100666
ctgctcttaa tatcttcaat aagctatctg cctcttacac ctcttgtccc attcatacta  100726
tttttcaaaa ctttggcttc aaaggaaaca acgtacaggc tgtgctagga cgattcaagt  100786
ttgaaaaacc tcacgaacaa cgttcgttgg cagaacatca aatggccgac atttattatt  100846
attgggacgt gataaaggac attactgcac gcgccataga cacggcatct ccggtagctt  100906
tgtctgtcct tcaaacactc cagcagaaaa cttcacgcaa atttgtaaac cttgcacctt  100966
tcctaatttc ctctatgcct ccatttgtca aaagcaacat tatccttgtt gatgaggctg  101026
gagttttagg gaaacatata ttgactgcaa tagtatattc gtggtggctc atgaatgcat  101086
tgtggaaaac gcctatgtat caggacggga agaagccagt gatcgtgtgc attggctccc  101146
```

```
ctacacagac agacgcaatg gaaagcagct tcgagcacag aaatcaacga caccttatat  101206
ccagcagcat aaacatttta agtaatctta tttgtactcc tacactgttt tcagtcctga  101266
atatcaagaa gcagtgggcc atctttatta ataataaacg atgctcggag cctgctttcg  101326
gagaagtatt aaaggcattt gaatttgggt tacctttgac agaacgccat gccagattct  101386
tagatcagtt cattgtatca gaatcattca tcaaagatcc atcaaagctt cctggatgga  101446
ctaggctttt ctcgtcccac gaagaagtta agaatacgt ttctaaattg cacgcaaagc  101506
ttcgtgcaca gaaatctgaa aaatataggg tatttctcct gccgatgtat acaatagtag  101566
atatggcggc atttgaaaag tataaatccc tgacgggtca agagacacta aatattgatc  101626
gctggctgca aaacaattcc tctcgccttg gaaactattc acagagcagg gatctagatg  101686
tgaccgcgcc cagatttgaa taccatcgag atgagagtaa tgaatataca ctagtaacga  101746
ctgatgcctc gcacgtactc aatagccaga tcacggtaac aaaaaaggta aaaaaattga  101806
tcttcggttt tgagggaaca tttgaaaaat tcgcacatgt attatccgaa gatagctttc  101866
tcaagacgta tggagaagac aaagtagaat ttgcctatca ctttctgtcg accttgctat  101926
actatgggat gattaaattt tacgaatttc tccgaacaga gggcctcccc gaagataaat  101986
taacaatggc gtatgacagg ttgtactccc tagcaatgcc ggagccagaa actcagaact  102046
ttgcatgggg aaatggtgaa aaattttgtt ttaacgaaga tgaatgtccg aatgccgatg  102106
tgaatgacaa agatgattta ttcgatattt ttgataagtc gttagatcaa ttctatctaa  102166
attatgagat ttgcgggagc gatgtccacg gtcaagaaat atttagttat ttcgagcaga  102226
tgaaaagaat ttatacttta cgttacgcgg tgctgtgtga gctctttggg agtgtattta  102286
ctgccgcccc ctttagctca ttcgtcggaa cggcttcttt ctcaagtcaa gaaatttcta  102346
tctccagttt caagggagca gtatgtgcat ttgctgctca aaccgacaca tataccttac  102406
gcgggattac gcgagcaaga tttccgggat atgctgagga caacctcaaaa gcccacgaat  102466
gggccgagcc aattttacaa atgctagact tgccaagact tgtcgtaagg gatcaaatgg  102526
ggttcgtttc agtcctgtgc cataacaaag caacttttgt cgataatata ggtggacagg  102586
aattaaggat ggccataaca attgaccacg gaataagttc gagccttgca atgacgatca  102646
cacgatctca agggttaagt ttagacaggg tagcaatatg ttttctcac ggaacaatga  102706
aattaaatac tgcatacgta gcaatgtcta gagtaacgag tagcgaatat ttgcgcatga  102766
acttaaaccc cctgcgaacg aaatacgaag atactcgaca agtaagccaa cacattcttc  102826
gcgcgctcag atgcaaagaa acgcgactag tatactaatc ctcaaaagta gccacacgca  102886
tggctttaaa atcagtttcc caccgtcgtt tggagtgttg catacctcc tcgtcccgag  102946
aacatgattt tcataagcta cgtaatggta ggagtccaag gcttggggca tggctcggcc  103006
accgaatacg aacaagtagt atactcatgc gatggaggaa tgcggtttat ttgcatcgga  103066
aataaaatgt atcgccacca attaccaccc gggaaagtaa tagtaattca caatcccgtc  103126
gcaacaatga tcgctgtaga ctgtgaagaa gaattttgcg catactgttt ggagcgcaat  103186
ggttctcacc gaggaccctc aggagaaaca ttagcttttc agttctcggc atgttggttt  103246
ctagggcgcg gaggaacgcg agaacggtgg agcagcggca acatcaccat gatgaattt  103306
ttgggcgtcg ctcacttaac tgtaaccata tacgaaaccc cggaagatct agcatctagc  103366
gcgcacacca ccccacatg ttcccaatcc tctccagaat cgctgagtg tccagaggaa  103426
agcgttcctc gagatcttgt agagtttgcg gcaaggcatg ccggactgtt agaggaataa  103486
```

-continued

```
ataaaagtaa taaacaccaa attatgaaat acgagcattt aattattgcg tcgcattgcg  103546
gaaatgagtt gaccttcata gttgctgtca cttagctgca gctggaggta gtagtgagga  103606
aaatcgggtc tcgaaatgtc tagagggtag ctcaggcaac ttttccgact tcggtagaaa  103666
gcaatatcca ttaccctgta acgcagccgt ccgtgccgaa gagcacctgg agttcttccg  103726
tggaggctgg cgagacatgc gggcaaagtc catatcagtt gcaatagcag cctgaccgta  103786
cttcatagtc caggaagtgc aatattcgcg ttctgagtaa ctttcgcaat ggggcaggta  103846
taaatgttct agcgctgggt tccacccaga ggcgcaccca cgtaagtcaa cacgccattc  103906
ctccagtcat atgcctggcc aatctgcgac aggcatgggc aagattgtcg cgtggaataa  103966
ataccggggc atgggctaca aactcgtgaa agaaaactgg cacaccgggg tgagtttctc  104026
catcctcgga ctgcgtaaaa tattttcttg actttcttga cgaaataatg tcttttaggc  104086
gagcccttat ttgcgggggca tgtcttctct tgcaaaagag aaacatctgc aaacttttct  104146
gatgtctatt tgcacctgca aatgcggacg tcttagtaca tgccatcgga actctgtcta  104206
gggaagtaca aatgtctttt cgaatgttat cggtaagctg tcttctcccg agttcccga   104266
atgaaaatat catgaaaaca ctgtcaaagc cacacgagtc caaagattct acatcttcgg  104326
tgttattcgt tttgacatgc ccttggacgg ctacgtcttt tgcgtggtcc ggagtaacat  104386
gagaatgcgt atcatgacat tcgtacgatc cggaaacaca gtcaatagac gaggctccat  104446
atagaacttc tgtcacagag gggatctcgg tacccatatc agagaccaca cgccaccaca  104506
gagaaaggtc ttcaatttat tgtttatctc gcaattttac atatatttta acagcaacaa  104566
gctccgcccc aaaataaaca ccggcggaaa aaacatacta atctaaattc cagtcaatcg  104626
gtgacaggcc cttagattcg aagtattgat ttgcttcctc gaaatggcga cagttgaacg  104686
gacgtcgcgt gcaggtagaa ggatggatga actccaactt taaatgattt ttaggcacgc  104746
ggggaataaa tcgtctagct tcttggcccc aaagcatcaa caccgtagat gacaactttt  104806
ctagtagcga tgagatcact ccctttgtaa atttgtccca gccgatggtt gagtgcgatc  104866
taggaaaacc ttgttccacc gtcaagtatt tgttcaaaag caatactccc ttcctggccc  104926
aagattctag acacccgtga gtttcctttg gaatagatgg gtaacagtcg cgtagagctt  104986
ccaaaatgcg gcgcaagctg ggcggtatac ggcaccccct agggacactg aaagctaagc  105046
catgcgcgtg tccttccgtg ggatacgggt cttgcccaac gataataaca cgcacatctt  105106
gcggattgca gtatcttgtc catgcaaaaa tatctccttt aggaggaaag attttgcgga  105166
atctagaaca gtaggagtac tgtaacagcg tctcaccgaa atcttcattt tcaattagag  105226
gtttcagaat tgactcccat gatgatggta ttgaaaactc tatgccacg tcggtccact   105286
ccggtacgag cttcctcgcg gatggtataa ccaattggac ggaagtcatg ctcggagggg  105346
ggagagtacg gcgttttta gcagcgttgg ggtcggtatc tctttggttg ctttcagtag   105406
gagagctaat gtccagcgga cgcttgaagg gactttttat gggctgctcg catagtccgg  105466
gtgatagtgg ttgatgttcg tttccggcca tctgaaattt atggtggtcc ttttatacaa  105526
cgaatcaaca agtccacgag ccaagacgtt agcagccgca agcccggtag cttccagccg  105586
gtcttgaaga agtctaatcc ccaagtacgg attcactttt gcagcgtacc cattcttata  105646
gtagaaaaca acttccgtgt ttacgcacag aggtctgtaa ataatcacag tcaaattttc  105706
aaagtagtct cccgatggca acggcccgaa aattcgcgca ccgttatctc gcgaattact  105766
atcacatggt gcggccgcgg cagaaacagg atcacgaaaa atgccaggta tatcgacact  105826
tgaacatagc ataagagatg ctattagaaa aaaacaagtc aacattttaa aaatcattat  105886
```

```
catatggaga cctaggtctc cgttcacgat ccgtgttacg tcgacgagca gatggaactc 105946
tttgcgcccg acttctaaat ggatcgtcgt cagaatctga gtcgtccgaa tacaaatgta 106006
gtggtctaca ggaaccagta ggtactcttt gtggcggact tttgaatgga tcgtcgtccg 106066
aatcagagtc gtcccaatat aaatatgacg gcctagatgg agtacttcgg ctctgtagtc 106126
ctgaaggacc ttcacctgcg tcatcgtttc gcatgcggag gctccgattc tgcatggaat 106186
cgaggtctaa aatacctctg tctgcggcga cgggggattc gggttcattc tttatccccc 106246
catgacgagt ctgtgtacca gtcgtatttt gccctgcgcc atcataatta gacgaggggt 106306
ggtggggcga aagctgtgga ggggagcgtc tagatggcga ggggagggat gataacctga 106366
ggtctagggc cgtaggagat ggcgcagaaa ataaaggggg tatagaggac ggacgtgcgg 106426
gcggtggact atgagcgggg ctattttcta tttcatgccg cacgacccgt cgcacccacg 106486
acatctcata tacatctcgc acttctgctc tactcgcaag gccatagttg ccttcccect 106546
cttctgtctc cggtaacata aacgtatcgg atacggtggt cggccgcttt ttaaccattg 106606
gatgtgcgag cccaactggc ttgacgtccg tgctgtcatg agactcgcct tgacaggaa 106666
ggcggatcga caccatcccg gcggaatttt taaaatattt caaatccacc gtgagtggtc 106726
tggtcagcat gtcgggctgt atcgtctcag gaatggccat tcctaccctg tactctagac 106786
ccgatgcact ctgtaccgtc ggggtttgtt cgtacgccaa aaagctatca tatccgctag 106846
ggtgattcgt cgtaaactca cgtatccatc cattgatcct ggttagaaac gagtaaaata 106906
cttcaagcat ctgttcttca tcctggaatg gcaattccac tgcgcgtagt gcggaatttg 106966
ctccgcgcgt caccagatga cgcgcgtttg agatttctgg agctgaggcg attgccatac 107026
tataaacgac acttttagcc ctcagtagag tagaatacag cgcctcaaaa tttctccacg 107086
ttagttgacg agttacaaac gtttcaagca ttatcgccct caaaacgact acaacgtcat 107146
ctatggggga tagccttccg gtatggtgtc ttcgagttac tggtctttcc tgttccaaaa 107206
tagtctggat ggcttggcgt tctccatcgg taataggggt accggcctgc cgcctggttt 107266
gaagtaatct cctaacgctt tcaactgttg tcggaaaata agctacaaca gaaaccaaac 107326
cattaatcct cgtacctcaa aaaatcttac acgcgtcatc ccaccccaca aaccacttac 107386
gcctcatcaa gacccagaaa tccatatagt gcgcttcatc gatgtccgcc acgaatgcta 107446
tattgaaatc tccgttcatt gtcattcttg cgcgcgattc tttactctct ccagatcact 107506
aacgcgctcg ccgttgcact ggaaagaata tccgtgcagc tccgacgcac gtccttatta 107566
gccccgcgc ggatacacat gcgcgacgta acggtatatc cgagttttcg gattagttcg 107626
gtagcggcac actcacccac ttactaatca aataaacaca ccgtacgcgc caaaataata 107686
aacattcgtt tattgatact ttgtcagtct ataaatcagg tccgtcgatg gatctggatc 107746
ggttcctaga cctggacctt aactggtatc tatccctgcc cctgtgaggc ccaattcttc 107806
tatcgtccaa acctacattg cgtaatattt cacgcgccct gcggacacga attaaaaata 107866
cgcgcgggtc cgtcgggcgt tgcatggggt tgttgttttc tccttcatcc gcgctcaaat 107926
cagattctga gctcaatacg atagtctcta ttggttcctc cctccgttgg gggtcgcggg 107986
gttcaacctc acgcacatca gccagcggct gcgggctctc ggcctcccg ccctgtcccc 108046
ctccatgcca accctccacc atttccggcg gtgggtcgta ctcagagtaa ttgccgtctg 108106
aatcatttga ttcggaacta agctgctcat cttcggctcc aaatgggca tcgtctgcgt 108166
cttccatcag cgcttcttgt actgcagcgt cgttcattga gtcatcgcta tcgttttcac 108226
```

```
ttgtggacag tcgggcatcc tcactggagg aggagtgccg gtagtggacc acaaattcat   108286
tatctacagg tgctcggaga cgccagctct ctgactgtgg tatagccaca ctcacgttga   108346
cgggacgtac agagcttacc aggggggtccc cagcatctcg gacaggcagc ttaattgtca   108406
cctctcccac agagttctta aatgcggctt ccctgcgcga cttatagcgc tccggagctg   108466
caggtcgcac cctcacaagc gtgtcttttt tgggcatctt tctagggttg acgtaatacc   108526
tcatctcatt ttcctggata tttgtgcgat gctccaaata gcctatgtca gctttgtgac   108586
cgcgtcgatt agttctactc ttgaacttac gacaccacct aatggagtgt cgcaggaatt   108646
gtaggaaatc ctctgccatc gactctgggt cacgtactgg gagaggaaat cgtaggaaaa   108706
tttcgtatgc gcccccgtac acctttccg  ttaggagctc gggctgattt gtacgtgtca   108766
tgatatcata tactacctcc ttaagtcgta caaaagcctt tagtatgtac agaatgtgct   108826
ttatcgtcaa tttgtgcagc aatagcatct ccatcgtggc ggctttcact accatcaggt   108886
attcgtctac aggagacatg cgacccgact ggtgtcgtct gatgacggtg cgttcgttgt   108946
ccagcacatg ctgaattgca ctgtggtcgg atgcagagat cttacgcccc tcttccggat   109006
tttcatgtct cgctcggacc tcccctagct tccccaactg ttttacgtca tgcattctgg   109066
taggaaagag cgctagcaaa aagaaacaca aaaacaatag tatggtggtg tctcacattt   109126
gcccatgtcc actcaggcac ccactaccca tccacatcac tcgcccaagt ttcccttccc   109186
gccccggctct tacgttcttc tatctccagt atgcgttccg ttaactgggg cgtcaactgg   109246
agttctaccg tcaaatcttt ctgcacgcga ctaagatttt cctcgtcacc cattcgcgcg   109306
aaatttatcg ccatgcccg  ccgggccgct gccatttcaa cgaacgggcc cgatggcgct   109366
gtgggaagag caactcccga cgcgtcgcag cgatctaccg tctattgcaa cgaggtgctc   109426
gatgcgctgc ttcttaatga cttgcccatc gccgctgccc gctctgtact acctttcttt   109486
cattttttcc gccacgcgaa agtgaccatt gatgtactgc attgcgtcgc ggaagcgcat   109546
gcagtgccgc gcgcgagggg tttcgaatag ctccacagcc ccgtcgtcgg caataaaccc   109606
gggggggtgt tttgcggggg ggggctatat atgagcagcc aaggatgcag ggtgtgtgca   109666
ctggtggtcc gcggttttct ccgacccgtc ccctcccagt ccctgagtg  ctcccgccc   109726
ttccaatccc ttgtggtttc atgtccgacc cctactatta gatgctggac aggttctggg   109786
gttgcgagat acttgacggc ccgacatcaa acgccagcgt ccgccaaccc ccccccccaa   109846
gttcttccac ccgtggagag caaacggtca gcgcgggcag ccgtgaaact agttctacta   109906
gattttccag tttagccttt tccggagctg aaaaggttca ggtgggcacc ggtgggctcc   109966
gactggacct cgaagcgcga tcacagaatc gtcacgcagt tcgccccgtt tgtaagtttc   110026
gcggcagcgc gaggtgcttt gctcagtagt catacaggtc acgcccgtgg ttcttgcaca   110086
ataagcgcca cactggaatt ttcgatttcc agcaacgctc actggcaaga acggacacga   110146
acgtgaaggc cccggggggg ggggtcttat tccgtataac cgcctcacta tgtggccacg   110206
gccggttacc gcgagttata atagtcaagg attgaaagaa gacagagcgg ttgggtagct   110266
gacagttgtc aggccgaagg taatacgcgc tatcgatgtg aaagctatcc gggtaacgac   110326
accttggcct aaggccgcaa ttaggtgcta ctcaggttaa gcacttagct aagcgcagta   110386
gcacctaact gtgcccgcac ttatctttgt agagtgtcgc ggaagcaccg tgctcccagt   110446
ttctggtatt cgtaagcacg tgctgtgagt ctcagaggtt tcaaaaattc tcgttctggt   110506
aagttgttca cgcgcaaccc acggcgggaa aattttctgc tcttgcaagg gctctagtgt   110566
agccgcttcc gggtatagtg ggggctaggg cttttcccgcc acgtaaagct atataaatgg   110626
```

```
tggcagtgta tccttaggga agaacccaga gggagaacta ggggagaagt ttcgcggcgg  110686
cggttgcgcg cggtgggaat gcctggcaag tcgaagcctc cattgtccgc cgcactggcg  110746
ttactggtgt tactacttgg agtcggggat gctcgcagta tacgcgcggc acccttgaag  110806
ttactggcgg agagcatcag aatactgcac cgtgtgcaga aggacgtaag gcaactcatt  110866
ctcgttggac catgctgaca tgcctgcacg gtctttgtaa ctatgtacgg ctattcagtc  110926
tatgttcacg ttcataactg taggctctct cgtttcctta taagggttcc tgcgacggta  110986
gaagagttcc gaacatcttt acgtccgaca cggtgagtaa aagccagctc atttgtcaca  111046
tgttctcaac ggcaatgccc tggaggccgg ccgcgcgcta gccccagatt aaaaatgtag  111106 atttttttgct taggtctacc ctgcccaata atctgctcgg cggtttatta acgaatcttg  111166
cttttcctgc agcgtctaaa cgaaactgaa gagttgtgcc aatccctttc ggtcattttg  111226
aaacaccaac agtgtcacaa aaaactgcag gggctctacg tcaatttgta ttacgtgctg  111286
aattctgtca gtaatggcgg tagctctcgc aaggtaagat aatggcagca tcgcgcattc  111346
tgtactttga agagactatc taacgcgcag cacagtatct ccgagacatc ttttgtctcc  111406
gtgctcacgc ggtccttatt ggtcgcatga cgagtctaac attgtatctc ctatttatta  111466
caggcaccgt gccctataac agtggaggat tcgtatttga tgaagtcgtt cctgaatgac  111526
ctggcgaacg ccctacagag acgttacgtc cgtcagagca ggcaatacta gacaatctag  111586
tattttgatt gcgatttta tatcggcgct tgcaatagta ataatgctgc cggccagcat  111646
tacaagcttc cgtggatctt atgtatcaaa atgaacgaat taaatattca agtgcattac  111706
ttaacacctc gttccgcctc ctcccgatat tcgtacttgc ccccattctc gtccctttc  111766 taatatcact ccatggccgc acgggtagaa tgttcagcaa agctaaagtc aacggggcta  111826
gatcatttcc ccggtctttt tctacaagtc gtcggtggct gacaagctcc gactagcaaa  111886
agaatgagca cgcaaccaga agtaaattgt acaaaaagtt ttaataagtt aagttaataa  111946
cggaaaccac ggttaccacc aagggtcagt gacagtggga tgcggtagag ggtagttagt  112006
catgcgtcta tggcgttgac gcgaccgcct atcctctgaa gagtctaatc tgggtacaag  112066
ggttctagtt tccccctcc ctgaggagac ggttagcctt gggcgcctgg tgcgcgtgtg  112126
tccggtgcat ctgggtgact ctggcgttgc tccccgcgga gcactccagc aacaacacat  112186
tggggaccga ttgcggggag tgtgataatg ggaatagtcg tcaccaagta gcaatgcgag  112246
aggggcggga tttctggcac gcataagcgc tagtccttcc acgtgaagcg ggttccgacg  112306
cgcccgcgcc cctggcgcat ccgggtaata atcggagatg atgcggagaa cttcctgtgg  112366
aattttgctg ggatcggacc aggacgctgc gagagggagg gcgggaatta ccgtgtcccc  112426
cccccacgca gcgacggccc taaaggaagc agaagtgcct cccacaatat cagcacaggg  112486
agtgcgcacg cggtagtccc ggccacggta cacgcggtcc cgaatcggga ggcgctggcg  112546
gccgcgccgc tttccacctc cggcgcgctc acgatcttct ttctcgttct tctcgtcccc  112606
gtcttcttca gatgagctgg agtctgaaga agacgacgac gaggagcatg aggaagagga  112666
agacgacgaa gaagaatgca tagtggaact ggactcggaa aggtccggac atggcggcat  112726
cgccccggcg cccacatggg gctgggccat gtacggatac aagacggctg aagcttttcc  112786
gatttcggag tggctccacc cggcatccat ggcacgagca acgtcgcgta atctcctgag  112846
agttacgtga gtgaggaagg ggtgcttaac gggaggacac ttctctctgt ctcctgtacc  112906
ctcatcgtcg ttgtcggtct tcccaacgct gaggggccat gagacagtga gtcgcctgtc  112966
```

```
cattactacg tgacctacat tgagcccacc ccgttccaac cgttcggccg ccggaccggt    113026
aaacagtttt acaaggtaag cgtgcgacgg ggggctagtc cgggcataga caacacccct    113086
ccgcccggta ggtatgcgcg gacccgagcg ggaatcctcg tccccgggat ccctagcatc    113146
tacgaccacg catgcgcgcc cagatgtact gagagcgcgc tcaagcatcc attctaccgc    113206
cccggcgtat ccaaggtctg tcgtacagag aatggccacg ctgcggcccg ggtctttctc    113266
gtcgggaggg atatagggat actccccgcg tgtccacgat tctggccaac aggcaccgcc    113326
cggcatgcag gcacgtccgc agagggccgc gtaggcgtac gcgcgttcta aaaattcgcc    113386
cggggcacgt tctgagacaa gaatgatgag gtcatagatt ttgtcagccg gatgtcgcaa    113446
cgtccaggaa agccgctcct ctaagacgca gcgccccct ctgttcacgg gtgaaatcct     113506
cttgcaaaac tcccccaggg ctactgggtc cctcgcaaaa gcaggtagcc aatctgcggg    113566
tccggtcgcg gaatagcttc ccgccggacc gctgctcaac ccgcgcaaat agttcgcgag    113626
ccgctccaaa gcaggacgcg cgcgatgggc gggcacgtat ggctcccctg cggagagcgc    113686
aacgcccaag ttttttgccat ggggacggta aacatcccct tggttcggga tgaaaccctc    113746
cggtgcgaac aggatggtag ggctgattgg ggtagaatga aacagggcct cacctatctc    113806
ggaaatgtga aaggacgggg attgtggttc ttgcggttct tctcggggcg gacatggtgg    113866
accctcggga gttatgggc atggcgaaag gaggaggttg tctctatctg tttctggaac     113926
cgctggaggt aatgaatctg gtaagccctg gaggccacat gttttttag tcgcgttgcc     113986 ttctgggatc gggtccgcgt gatcttcaga tgactttctt ttcagacctt tacgggtctc    114046
aaagtcatca tctggagggc ggtcgggttc gggcccgtac ggtgacacag ataatggctc    114106
ctgttcatcg cacggtggag ctctgggcca ggggttggcg ggagattctt gggcagccga    114166
aggctctgct ccgttgccgc cgccaggact cccgtagagt aggaggtggg ccgcgcgatc    114226
gggagtgcca ggaggtaggt cgtaccggca agtgctccgc cggccgcctc gtcttttgcg    114286
cctgtcatgt tggtgggtgt catcatctgc gggacaatcg tccgtgacgt gctcgctgcc    114346
gggcgcggaa tcatctccta gcatggtagc gatcatcctc caaccagagg ccgcgtaggc    114406
aattgaaggc cgcacgtcac cctcgtcgga gcagccaagc acgcccacgg cagcttccat    114466
ggcttctaca agaagagtga catcatcggt agatggcagc ggcagggacc ctatgacgag    114526
gcgactccat agcgaagccg cgcagtagcg catggcgcgc tcccacgtaa agactgtttt    114586
gggcgccctc gagagtgctt gatacagatc cgggcgacgc ttggcggggt ttattgtaac    114646
tggtgggcag tctatagcag taagcgccgc catgagatct gcggcagcaa caatgcaagt    114706
tctagtatgg cgcaatagcg ccgaagagga aagttttttcc ggggttgccg caggtggctc   114766
tttcgctgcg gcttccagct ccctcgtggc acgcgctatt cgcctggcgc caacgagtac    114826
agggtggtcc ccagaagcag acgccgccgt aggatccacg gccgctcctg gaaatacaaa    114886
cgggacaaac gctctcctaa gagccgccaa caggtaagtt ttctgcggat ggtcatagcg    114946
gcggcacacg cgtacgagct cggtaaggtg cggcagagct aatgacacac ggccatcacg    115006
catggcgtgc gctacgtgcg ggaggcacgt cggcaccgca gaacgagaca atcctccctc    115066
ggaagaaccc ggaccgcgga gagcgcacag ttcgcagagc cgtttgtcac gtgggctcag    115126
cttggggccg ccatacccat acgaaacgcg cgacaggggc tggaccatga actcctccac    115186
aaggcgctct aactgttcca ctggcatccc gtactcttcg agatacacgg aagctgattt    115246
cggattggca tggaattcgg ccgcggcctc ccgaacctgc gggtcatcga ccaaagactg    115306
tctatagcca cttccatgat atacttgtcc tctactgggt ggggacggga taatagcttc    115366
```

```
tggaacaaaa acgcgagcct cggaactatg gaggtcgacg gccaacgctc gtgagagtac   115426
attcagggta atgccgcggc ctaggtctgg gagctccgta ggcgcggtta ctgactgaac   115486
cgacccgtct gtaccgtccg tttcgaccca ctccctcaaa actcgccaga gtggctctag   115546
cgcgacatcg ggacattctc caggtagcac taattgggca gagtcccggt cggggctttc   115606
ggcggatttt tcacttcccg cgctttccag ccttcgggcg agacgtcccc tcctccctga   115666
cagcgagaat gaggaagagg aggaagagga ggaagaggta aggtggctcg ggcccatctt   115726
cttcgaaaat tccctcttcc ctcgcttggg gagacggtct ttgctggtcc tctgcggcga   115786
agggacgggg cgccggttgc tcaaagatcg cgccacggcg cgtcgcgaac gagatctggc   115846
cactctctct gacttcctca ccacttcttg acgcctcaca gcggttgttt tctctactgc   115906
aggtaatgga cacgggcatt caacgtgctg ctgctccatg ggagtttcgc agggatgtgc   115966
gagcgagtcg atgaccgtat aaactccggg ctgatcggta tccacgttaa tatctagtgc   116026
cacgacatca ctggtagcgt tcggacacgg ttctatagag tttatgtttt cgggatccat   116086
gtcgtttaac atcgctataa ggtcgcggag agacatttct cgcccgtcca cgtcttgggc   116146
cgcgtcttgg gccgcattct cagcgatgac agagtgaaag agctcgtcct cgctggaaaa   116206
aagaggtggc gtgctgtacg aaaagctatc agtagtggtc tcacaggtag gtgcgtttgg   116266
agggttcggg atgggagaac ccaaagaatc gtagcgccca ctcttatcgg cgcgcaaaaa   116326
ggtaaataga tctgagggcg ggccagttga gaatcccgac tcatcaacaa ttggagcggc   116386
caaattactc ggcgtcgagg aatcagagga catgatagaa tgctagtgga aggactagcg   116446
atttccagaa tcctgcagaa caagacccga gtgacaaggt tacgtaagtt ttgtgcagaa   116506
gttggaagaa acgtgaagct ttctggtggg gagtagtaac agaaaaaata aagatgcgcg   116566
actctcgaaa cctcccgttt ctcgcgttgg cctgtttatt tccgtccccg caatgcagag   116626
cacaataaag ctccgcaacc ataggcacaa ttttggaaca gcaatacatg ctaaagaagt   116686
ggattatcgt tttgtgcgct tcatgttcat ccataacagc agcccatact cttgactgta   116746
tgggggaatt attcgaagcc cacagtcata ttttttgcacg ataccccatg caaaaggata   116806
tttcgtggtc ccctcaaata atgacagccc acctaatccc accccaaaat ttataacaga   116866
atattggttt catgacttac gttttgcgaa gaggtccttt ccacgctggg taggtttcag   116926
caaaggtgtt gtgaagaaag aactttggag agtcaacccc tcggtcttgt gcagttggtt   116986
tgggtatggc atttgtattg aggcatgata taattcagaa ccaatggcgc ccatgcggcc   117046
tgcatatcgt tagcgagcgt atttccagtt ccggtgtgcc atagccaatg catgccatgc   117106
gcccagcata ccattaccgt accaggaact tccggcattt tttatgagcc aacataataa   117166
acaaacctga gcctactgta gaacagatga cgaagataac aaaacaatac attgcttgtg   117226
tccacaggtg cgtgcaattc ggtgccgggg tgtgtgccta ctctagaaag gtcacgcgtg   117286
ttttgttggc attgatatta cccgagaaac acgctcgctt gcacgttatt ggccacaccg   117346
ggaagcagtg aagtttattt tgaatgccaa ggaaagcaca tgggtcacgc ttcctgggag   117406
tgccaaggaa gttgtgacag aaaaaagatc cccatatggg agagttgaca tgtgtaaata   117466
tcaccgtgag cacttgtgtt acttgtgtgt tctaatctct agcaatttc cacgaaagat   117526 tattatcttc tagccacccc tctaacccag cctaaataaa aaattcagac aacgcaaaag   117586
cttggttcca tgttccacgc gagtagttcg cgggaacaca taattacttt attgagacat   117646
ttgccgctcg ggatgcacga atcgcaaatt ttgaatctcg ggatgcgttc tgtatttgca   117706
```

```
gggcactttt cttcttttga gagatatggc gagaaggtcc atgctcggga atatagttcg 117766 caatctggtt tgcgatttac aaacggtgaa gaaagaactt tggagagtca acccctcggt 117826 cttgtgcagt tggtttgggt atggcatttg tattgaggca tgatataatt cagatccaat 117886 ggcgcccatg cggcctgcat atcgttagcg agcgtatttc cagttccggt gtgccatagc 117946 caatgcatgc catgcgccca gcataccatt accgtaccag gaacttccgg catttttttat 118006 gagccaacat aataaacaaa cctgagccta ctgtagaaca gatgacgaag ataacaaaac 118066 aatacattgc ttgtgtccac aggtgcgtgc aattcggtgc cggggtgtgt gcctactcta 118126 gaaaggtcac gcgtgttttg ttggcattga tattacccga gaaacacgct cgcttgcacg 118186 ttattggcca caccgggaag cagtgaagtt tattttgaat gccaaggaaa gcacatgggt 118246 cacgcttcct gggagtgcca aggaagttgt gacagaaaaa agatccccat atgggagagt 118306 tgacatgtgt aaatatcacc gtgagcactt gtgttacttg tgtgttctaa tctctagcaa 118366 ttttccacga aagattatta tcttctagcc acccctctaa cccagcctaa ataaaaaatt 118426 cagacaacgc aaaagcttgg ttccatgttc cacgcgagta gttcgcggga acacataatt 118486 actttattga gacatttgcc gctcgggatg cacgaatcgc aaattttgaa tctcgggatg 118546 cgttctgtat ttgcagggca ctttttcttct tttgagagat atggcgagaa ggtccatgct 118606 cgggaatata gttcgcaatc tggtttgcga tttacaaacg gtgaagaaag aactttggag 118666 agtcaacccc tcggtcttgt gcagttggtt tgggtatggc atttgtattg aggcatgata 118726 taattcagaa ccaatggcgc ccatgcggcc tgcatatcgt tagcgagcgt atttccagtt 118786 ccggtgtgcc atagccaatg catgccatgc gcccagcata ccattaccgt accaggaact 118846 tccggcattt tttatgagcc aacataataa acaaacctga gcctactgta gaacagatga 118906 cgaagataac aaaacaatac attgcttgtg tccacaggtg cgtgcaattc ggtgccgggg 118966 tgtgtgccta ctctagaaag gtcacgcgtg ttttgttggc attgatatta cccgagaaac 119026 acgctcgctt gcacgttatt ggccacaccg ggaagcagtg aagtttattt tgaatgccaa 119086 ggaaagcaca tgggtcacgc ttcctgggag tgccaaggaa gttgtgacag aaaaaagatc 119146 cccatatggg agagttgaca tgtgtaaata tcaccgtgag cacttgtgtt acttgtgtgt 119206 tctaatctct agcaattttc cacgaaagat tattatcttc tagccacccc tctaacccag 119266 cctaaataaa aaattcagac aacgcaaaag cttggttcca tgttccacgc gagtagttcg 119326 cgggaacaca taattacttt attgagacat ttgccgctcg gatgcacga atcgcaaatt 119386 ttgaatctcg gatgcgttc tgtatttgca gggcactttt cttcttttga gagatatggc 119446 gagaaggtcc atgctcggga atatagttcg caatctggtt tgcgatttac aaacggtgaa 119506 gaaagaactt tggagagtca acccctcggt cttgtgcagt tggtttgggt atggcatttg 119566 tattgaggca tgatataatt cagatccaat ggcgcccatg cggcctgcat atcgttagcg 119626 agcgtatttc cagttccggt gtgccatagc caatgcatgc catgcgccca gcataccatt 119686 accgtaccag gaacttccgg catttttttat gagccaacat aataaacaaa cctgagccta 119746 ctgtagaaca gatgacgaag ataacaaaac aatacattgc ttgtgtccac aggtgcgtgc 119806 aattcggtgc cggggtgtgt gcctactcta gaaaggtcac gcgtgttttg ttggcattga 119866 tattacccga gaaacacgct cgcttgcacg ttattggcca caccgggaag cagtgaagtt 119926 tattttgaat gccaaggaaa gcacatgggt cacgcttcct gggagtgcca aggaagttgt 119986 gacagaaaaa agatccccat atgggagagt tgacatgtgt aaatatcacc gtgagcactt 120046 gtgttacttg tgtgttctaa tctctagcaa ttttccacga aagattatta tcttctagcc 120106
```

```
acccctctaa cccagcctaa ataaaaaatt cagacaacgc aaaagcttgg ttccatgttc   120166
cacgcgagta gttcgcggga acacataatt actttattga gacatttgcc gctcgggatg   120226
cacgaatcgc aaattttgaa tctcgggatg cgttctgtat ttgcagggca cttttcttct   120286
tttgagagat atgcgagaa ggtccatgct cgggaatata gttcgcaatc tggtttgcga   120346
tttacaaacg ttcctgtaat tttcttacgc ggatctggaa gtaatcgcag gagcctctcc   120406
gcaggagact tgccgattcg ccggtgaatc gcaaatacac ttccagatat atatgtcggg   120466
gggtcaaggc actgtctcta caggtttctt ttaggaaacg cacctatgtc ggattgcccg   120526
tgggactaaa accagttatc tgcgcgtgga agcagccgca ggcttagcag atgcgctcga   120586
aacaaagcac gagttgcaat agccggtata atatcaaggt acgggctata tacatgcgcg   120646
taatacatcc atactggatc tacccagtaa tcgtgttaac tgacggtgtt acaacgcagt   120706
cgtagcagta atatgaaagt atgcaatatg tatgcaataa gcaagggcaa cgaagccgat   120766
aacctgcacg tcggtgggcc caaacaactc agcggcccta ttaaagagca aataaagtag   120826
tgagcccggc acatgccgaa cggctcaagt aaaaacaaaa attcataaag tgcaaacccg   120886
cctatggcgg ttcagtgtta actagctctt cacgacaatc gactttgttg ggtccttatt   120946
ttctgggtca ggtaaactcg aacatgagct ttcgtagagt attttttaacc cgcgatgtct   121006 tggagagtat cggtcacgca gcctccggat gagttcatcc cgccgaatat cacttcccga   121066
tcacattcag ggtcgggggt cgagggggt gctcgacccg ggtcgtgtgt atcgtgagga   121126
caagcctctc cgatcggcga cccatcccca tctgggacag tgcatggctt taaacgagc   121186 ctgcgtcggc gtggtctgga ggcatcggcg gggggatttt cgggttgctc atgtgagaag   121246
acaatgaccc atcccattgt gcccccagta tgaaatcttc tcccctcttc ctggggtaat   121306
ccgagcagga cccgatggtc ccgctatatg cggggacagc gacctggatc gttcttttat   121366
gcagtgcccg aagatgcaag tcacagctca ttggctggaa gggggatgca ggaccctcgg   121426
tgcgaacgtg acgtaggtgg gtgccaccca catcatgtaa attaggtcac ggggtaggat   121486
tccggctccg cgattggtta tgaggcccct aaagcaaaca ttcgcactcc agtatttaat   121546
atattaggtt ttccctaata tattaaatac tggagtgcga atgtttgctt tagggggcctc   121606 ataaccaatc gcggagccgg aatcctaccc cgtgacctaa tttacatgat gtgggtggca   121666
cccacctacg tcacgttcgc accgagggtc caacattttc ctaaaatggc aaagcgggac   121726
tggggtccgt gggtaaattt tctaattttt tcccacggtc tgtcgcaaga gcgtattctc   121786
caagatagaa tgctgttaga ttttcccgaa ttttgtcgag gtcacgcgtt ttgtaatgga   121846
atatggcgcg agaatattga gtttaaattt tgtccgcgcg ccaaacttga agtgatatta   121906
ggacatagtc aaccaaccga catacgttga accatttgcg ggcagcgctg agggaagacg   121966
agatgtatgg acaacacaac gaccggagaa gagggcgtaa agaacatcac ggtcttgctc   122026
tacggtgggg ggtaacaaca atttaataaa taaaagtttt ctttaatata agagcggtat   122086
agcagattta ataaaacacc ttttttgaaa aaatattgac ctgtctcgtt gtagattctt   122146
cgcatccgcg ttccgtcatt attccaagat tttgcgtttc attccaattc aatcaatcct   122206
agaaggcaaa agaaaacata acacgcaaat ataaggatcg gtattttgac attttaaatg   122266
tgtttttaag gaaaagggta gaactttggg gaggagttgg tacgtggtag tcacaatttg   122326
acagacaggt agacagacaa cgaattacaa gcggcctagg gtaatagcgc tgagcccatg   122386
atgtgtccgt gcatatgaga cgactaataa ggtagtcacg taaaccccg tcaatcacac   122446
```

```
gcgaaagaaa gaaagaaagg aaaaggcctc aaagcaaatt ttgtagctta aaaagagggg   122506
ggccctaaag aagaagcaac atcgtctcgg gctgtgtttc cgacgttggg gtgcattatg   122566
cgattttact accagtgttt ggtgtggtgt ggtaagggga aatgagacga gaattttcg    122626 cgtgcgctcg aggacagagc tacgcccaac cgtgagcaaa ttgcgcggcg cttccttgtt   122686
agcgtggcgt cacgtataaa tgcacagaag cttcgtcagt aacgaagcgc ctctgccaga   122746
gttattaaca ttaggactcg agagagtctc gagaagagac ttctcaaaga gagtgccgct   122806
ttgatctcca gatcacttca cagcccatta agactttcc tttttgacac acgagtaggg    122866
cgatattttg tgcttatccg agaacggccg caaaccacgg cctactcgaa ccgcgcattc   122926
cctgcggaaa gacaacacga gtaaataaga cccagtgcgc aagatatgag ccacagtcct   122986
ttgtcgagtg atccctctcc cttgccagaa gagacctatc cgtcgccccg cggaaagtca   123046
ccagagcagc ttccctggga tcccgaagag ctctcccaga agttttctt ttcggacgta    123106 tcggaggacg aagaaccggc acgcgggagg agctggagcg acccggagtc ggaggaagag   123166
cagcctgggt gccggggagt ggacttgggc gaggaggaca cgggacacag ctccaccgag   123226
tcagagccca cgcaatctga cttagactt attgacgaca gctctccggc gccgccgcca    123286
tttgctatcc cccgcgtccg tgcgttattg cggtgcgcgg caccccgcaa agacccacgg   123346
aaggcttcgg ccgccagggc gggtaggcgc actcttaaaa gacggaggtt gtcattttct   123406
tcttcctctg acgaggaatc cgaggagaga agtaaaaaag aagaagcggc ctcgacccct   123466
gcacggcgac gcaaggccga ggcctcgacg agcagataga ggagacgcgg ggcagaacct   123526 cccctccct cccaccccc tactctggac atttattgcc cgctcgatcc attctcatcc     123586
agaacttctt tcccgctcag ccttcacgca gaagcggacg cgcgccctt tgcgaccgcc    123646 ggacatcccg ccgccccccc cccttcacg cccggcgcaa tccgtagccg tccaactcgg    123706
cccagcacaa ccgcagtaga ccgcccggac cgctctcctc tagacacatc cctaaatgga   123766
aaacatgctc gacgggtgct acccgctggc gctgatggac agcgatcaca ttactgcgca   123826
cgcggtacct cgtggcgagc gcaggcggca aggtgccgct gtcgcctcgt cggagtcggc   123886
cgactcggta gacccgtgca ttcggatcgc ctcgcggctc tggcgcgagt tagtcgagat   123946
atcgtccgaa ctcaaggacg gttacggaga gttcacgtca gcgagagacc gccgcaacgc   124006
gctgattgct gccaacgaac ggctacgttc ggcttttctg ggggccagcc gggcgacgcg   124066
cggcctaggt ttgaggccgc ggtgggcgtc gacggagagc gtcgccaact cccccactga   124126
cccgaataac ggcaacgggt tgggagaatt agaggaggca atggaaggga tcgagggcga   124186
tttctggctc gactctctgg acggtgaccg cttcgaggac gagagccgta ccatgcagag   124246
cgagaatatg cgtttcgtga tcgagaaaga actgttatcc tggctgtccc gacacctgcc   124306
ggccgacctc gcgtccgccg agcgagagac ctcccggtct ctcctggcgg ccgggcactg   124366
gtgctgcttg tggcaccctc ggccgtgccg gaagcgtgt ttgtacgact cgatttacgt     124426
gcagagtctt ttctgcgtcg ggacggggag agtcccgcaa tcggagatgc gccgtcgcga   124486 ataccctggcc gccttgcgcg ccggcgcggc tgccgccaac tctcccgaag tgagcgcctc   124546
gatctttgcg agggacgctg gaatcgcgct ggcgctggcg cggcgccgtt gacgggagaa   124606
tgacgccctc tagcggcttc cttacctccg cgtccctgac aacctcgcgg gttttacac    124666 tgtcctccgt ccactctccc ccctcaccca ctccgcggca gcgaaacaca acccccccc    124726 tccccagaaa cgagcgacac gcgagcgctg cgaaataaat aaagtaatat tattgtgtgt   124786
ttttcacgtt gttgcaatcg agaggccgtt tgtctgtctg tgtctgtgcg gagctaggct   124846
```

```
ttcccgggcg gccccgttcc accgttcggt taggccggtg gcgacgggac atagagaaag 124906 atagagcgcg cgccctggcg gcgagagggt gttgcggggg taaatgggac cctgagctca 124966 ccattttggc gggggattgc acgggtaaca aaaagctctc tcgcacataa tgatttccct 125026 taaacagtgg ctgtaaaagc tttcttcgac tgggacgcgc acgtccggag acatgatctt 125086 atcggtagct acacagttca tgaggtgggc cacgaacgcg cggatcgagt tttgggaacc 125146 ttcggggagg tcttccggga gggtgaagtt tgacagaggc agcgctatca ccaggaggct 125206 ccgcaccatc tccatgccta tccttatcgc cgcgagtccg gcggccggcg cgctgctctg 125266 gttattccag tgcgcggacc gcgagtgcgc ccctccccgg gctctgatat agagcaccgg 125326 cagctcgacg gcggcggaga aaaagaaag aatgtccggc ccaatgactg gaactttggg 125386 cacgtctctt atttcccacg cggcggcccg gggaatctgc ttgccccaga ccttgctttc 125446 caactccccg ttcggccccc caactaactc cgacagcgcg gtccacagtc ctaccgccgc 125506 tgcgacggcg cgcttagccg cgggcgctat tcgcgggtcg tgcgccgtga tatcttcggc 125566 gacctgcaga ctgcccagcc tttccttccc ttcaaaatac gcgcgggcgg cctgtacgat 125626 caccgcggcc agatcgggcc aaaagaaaat atcgcaactc tgcgacgccc gccagaatct 125686 ccctccgggc aggtccgtgc ccctaaaggc cgccgagaaa gctaagtcca aatgtgacgt 125746 cggaggtctc gacatggtcg ccaaccctcc aaatgctacc cgccggccca cgcaacgcgg 125806 gcttttataa agatggcgcg cgagacaata acacttactc atccgcgtac gcgtttatta 125866 ttgtcaatat ttgtgtggtt attattactg ctaccgccct tgtttctgca aggccctcgc 125926 cgcggcccag gccactattc cggcagcggc cgccgacgcg cgagcgtcg ccgctaacgt 125986 cggcgccgcg gggagcgggg tttcttcgac ttaaatagac tcccgagaaa aaattttggc 126046 tgccgttcgc catcatccga gtcggaaaca cagtatgcgg ccgagttagg ttttactttt 126106 aaaaacttta ccgtgctgta cggccagggc gttctcaggc tcgaagggc aagagttgtc 126166 cagactgatg ggtgactcag agacagcgtt gtcttgtctc cgtttaccaa aaatatttcc 126226 actcctctct caaaattttt acctccggtt tcggtaatta ggaaagtttt tggcgcaggg 126286 aggtttaaag ctgccatgca tatgtcagcg gtacccagca cccacaaatg gaactctttt 126346 gcggcatacg cgccagatga caaatggtaa accctgcgt ccaagccgct ccactcggga 126406 cttactccag gcgggtcgcc ccctcaccg aaccgaatca cgggtctgca catcctggga 126466 agggaaaaca gctccccgga aacttcgtac agagatgccg ggcgcacgat taccgataat 126526 gtactcggac gatcgtaact cgccatagtt ttcactgcgt gaaccaattc tttccatcca 126586 gaatccgaga gctcaaatct agaattaggt agtttgtagt gcgaatcgac cgcagaaact 126646 atagtcactt ttacaggcgc catcgccgct cagactccac cccgctatga tgtcagaaat 126706 ataacgctct tattctagca gagtcaggcc aatatataca gcttagagaa gatgcggttt 126766 cggcgcatct gttcacgctc tagggcagaa aaacgaagaa gaacaaccga gaatccgctt 126826 acctcaaaac gcgtttgcgt attggatagt ttctcacgga caatgtcatt gcgccctat 126886 gcagaaattt tgccgaccgc ggaaggcgtc gagcgcctcg ccgaacttgt tagcgtgaca 126946 atgacagaac gcgcggaacc tgtgacagag aatacagctg taaacagtat ccccccggct 127006 aacgagaacg ggcagaactt cgcatatgca ggcgatgggc cctcgactac tgaaaaagtt 127066 gacggctcgc atacagactt cgatgaagca tcgagcgact acgccggccc tgtcccgctc 127126 gcgcaaacta gattgaagca ttcggatgaa tttcttcagc acttccgagt tttagacgat 127186
```

-continued

```
ttggtggagg gggcttacgg gtttatctgc gacgtccgtc gctacaccga ggaagagcaa 127246
cgtcgaagag gggttaacag tactaaccag gggaaatcaa aatgtaagcg cctgatagct 127306
aaatatgtga aaaatggaac aagggcggcc tctcagctgg aaaatgaaat tttggttctc 127366
gggcgcctaa atcacgagaa tgttctcaag atccaggaaa tccttcggta cccggataat 127426
acgtacatgt taacgcagag gtatcagttc gacttgtaca gctacatgta cgatgaagcg 127486
ttcgactgga aagacagtcc aatgcttaaa cagactagac gcatcatgaa gcagctcatg 127546
tcagcggtct cgtatatcca ttcaaagaaa ctgattcaca gggacatcaa actcgaaaat 127606
attttcttaa actgcgacgg caagacagtg ctgggcgact ttggaactgt cacgcctttt 127666
gaaaatgagc gggagcccct cgaatatgga tgggtgggga ccgtggctac taactctccc 127726
gagatactcg ccagggattc gtactgtgaa attacagaca tttggagctg cggagtagta 127786
ttgctggaaa tggtaagcca tgaattttgc ccgatcggcg atggcggggg aaatccgcac 127846
cagcaattgc tgaaagttat cgactctctc tcagtttgtg atgaagagtt cccagacccc 127906
ccgtgtaatc tgtacaatta tttgcattat gcgagcatcg atcgcgccgg acatacggtc 127966
ccgtcgctca tacggaacct ccaccttccg gcggatgtgg aataccctct agttaaaatg 128026
cttacttttg actggcgttt gagacccagc gcggccgaag tattggcaat gccactgttt 128086
tcggctgaag aggaacggac cataacaatt attcatggaa aacataaacc catccgaccc 128146
gaaatccgtg cgcgggtgcc acggtccatg agtgaaggtt aataataaag gacgagata 128206
gagaactgaa gcgtcagatt tttttaaaaa aataaatgat cgagaactta tgatttgtct 128266
ttcttgaatg accttgcccc atcgattaac gaaaagacct ttcgcgcgtc gattctgctc 128326
ggtctttgtg atacattata gtgagactaa actcgaccga tataacaaga caatgttact 128386
ctatagaccg gactcaacca tgcggcatag cggaggcgac gcaaatcaca gagggataag 128446
gccgaggcgg aaatctattg gagcgtttag cgcgcgcgaa aagactggaa aacgaaatgc 128506
gctgacggaa agcagctcct cctccgacat gctagatccg ttttccacgg ataaggaatt 128566
tggcggtaag tggacggtag acggacctgc cgacattact gccgaggtcc tttctcaggc 128626
atgggacgtt ctccaattag tgaagcatga agatgcggag gaggagagag tgacttatga 128686
gtccaaaccg acccgatac agccgttcaa tgcctggccg gacgggccga gttggaacgc 128746
gcaggatttt actcgagcgc caatagttta tccctctgcg gaggtattgg acgcagaggc 128806
gttgaaagta ggggcattcg ttagccgagt tttacaatgt gtaccgttca cgcgatcaaa 128866
gaaaagcgtt acggtgcggg atgcgcagtc gtttttgggg gactcgttct ggagaataat 128926
gcagaacgtt tacacggttg tcttacgaca gcacataact cgactcaggc acccttccag 128986
caaaagcatt gttaactgca acgaccctct atggtacgcc tacgcgaatc aatttcactg 129046
gagaggaatg cgcgtgccgt cgcttaaatt agcctctccc ccggaggaga atattcaaca 129106
cgacccaatg gccgccgttt ttagaaacgc ggggctggt ctgttcctgt ggcctgccat 129166
gcgcgcagcc tttgaagagc gcgacaagcg actgttaaga gcatgcctgt cttcactcga 129226
tatcatggac gcagccgtcc tcgcgtcgtt tccattttac tggcgcggcg tccaagacac 129286
ctcgcgcttc gagcctgcgc tgggctgttt gtcagagtac tttgcactag tggtgttact 129346
ggccgagacg gtcttagcga ccatgttcga ccacgcactg gtattcatga gggcgctggc 129406
agacggcaat ttcgatgact atgacgaaac tagatatata gaccccgtta aaaacgagta 129466
cctgaacgga gccgagggta ctctgttacg gggcatagtg gcctccaaca ccgctctggc 129526
ggtggtttgc gcaaacacct attcgacgat aagaaaactc ccgtccgtgg caactagcgc 129586
```

```
gtgcaatgtt gcctacagga ccgaaacgct gaaagcgagg cgccctggca tgagcgacat   129646
ataccggata ttacaaaaag agttttttctt ttacattgcg tggctccaga gggttgcaac   129706
acacgcaaat ttctgtttaa acattctgaa gagaagcgtg gatacggggg ccccgccatt   129766
tttgttcagg gccagctcgg agaagcggct gcagcagtta aataaaatgc tctgccccct   129826
tctcgtgccg attcaatatg aagacttttc gaaggccatg gggtctgagc tcaagaggga   129886
aaagttagag acattcgtta aagctatttc cagcgacagg gacccgaggg ggtccttaag   129946
atttctcatt tcggaccatg caagggaaat tattgcagac ggagtacggt ttaagccggt   130006
gatagacgag ccggttcggg cttcagttgc gctgagtacc gctgccgctg ggaaagtgaa   130066
agcgcgacgc ttaacctcag ttcgcgcgcc cgtaccgggc gcaggcgccg tttccgcgcg   130126
ccggaaatcg gaaatatgat aaaaatgctt ggcatttgcg ggcgaagagg cgtgatctga   130186
agggctccac aatgacgtaa ctgagctacg catccctata aagtgtaccc gctgaccgct   130246
agcccataca gtgttacagg aggggagaga acaacttca gctcgaagtc tgaagagaca   130306
tcatgagcgg cttcagtaac ataggatcga ttgccaccgt ttccctagta tgctcgcttt   130366
tgtgcgcatc tgtattaggg gcgccggtac tggacgggct cgagtcgagc cctttcccgt   130426
tcgggggcaa aattatagcc caggcgtgca accgcaccac gattgaggtg acggtcccgt   130486
ggagcgacta ctctggtcgc accgaaggag tgtcagtcga ggtgaaatgg ttctacggga   130546
atagtaatcc cgaaagcttc gtgttcgggg tggatagcga aacgggcagt ggacacgagg   130606
acctgtctac gtgctgggct ctaatccata atctgaacgc gtctgtgtgc agggcgtctg   130666
acgccgggat acctgatttc gacaagcagt gcgaaaaagt gcagagaaga ctgcgctccg   130726
gggtggaact tggtagttac gtgtctggca atggatccct ggtgctgtac ccagggatgt   130786
acgatgccgg catctacgcc taccagctct cagtgggtgg aagggatat accgggtctg   130846 tttatctaga cgtcggacca aaccccggat gccacgacca gtatgggtac acctattaca   130906
gcctggccga cgaggcgtca gacttatcat cttatgacgt agcctcgccc gaactcgacg   130966
gtcctatgga ggaagattat tccaattgtc tagacatgcc cccgctacgc ccatggacaa   131026
ccgtttgttc gcatgacgtc gaggagcagg aaaacgccac ggacgagctt tacctatggg   131086
acgaggaatg cgccggtccg ctggacgagt acgtcgacga aaggtcagag acgatgccca   131146
ggatggttgt cttttcaccg ccctctacgc tccagcagta gccacccgag agtgtttttt   131206
gtgagcgccc acgcaacata cctaactgct tcatttctga tcaattattg cgtattgaat   131266
aaataaacag tacaaaagca tcaggtgtgg tttgcgtgtc tgtgctaaac catggcgtgt   131326
gcgggtgaaa ccgtaaatta cgtgataata aatagcatag gagttggcgt gcagcgtatt   131386
tcgccgagag atggggacaa tgttagtgtt gcgccttttc ctacttgcag tagcggacgc   131446
ggcgttgccg accggcagat tctgccgagt ttggaaggtg cctccgggag gaaccatcca   131506
agagaacctg gcggtgctcg cggaatcgcc ggtcacggga cacgcgacat atccgccgcc   131566
tgaaggcgcc gtcagctttc agattttttgc ggacacccct actttgcgca ttcgctacgg   131626
cgctacggag gacgaacttg cactggagcg cgggacgtcc gcctcagacg cggacaacgt   131686 gacatttttcg ctgtcatatc gcccgcgccc agaaattcac ggagcatact tcaccatagg   131746
ggtattcgct actggccaga gcacggaaag cagctattcg gtcatcagtc gggtcttagt   131806
taacgcctct ctgaacggt ccgtgcgcct ggaaacgccg tgcgatgaaa attttttgca   131866
gaacgagcct acatggggct cgaagcgttg gttaggcccc ccgtcgcctt atgtgcgaga   131926
```

```
taacgatgtc gccgtgttga caaaagcgca gtacattggg gagtgctact ccaactcggc    131986
ggcccagacg gggctcacgt ctctcaacat gacctttttc tattcgccta aaagaatagt    132046
aaacgtcacg tggacaaccg gcggcccctc cccctcgcgc ataacggtat actcgtcgcg    132106
ggagaacggg cagcccgtgt tgaggaacgt ttctgacggg ttcttggtta agtacactcc    132166
cgacattgac ggccgggcca tgataaacgt tattgccaat tattcgccgg cggactccgg    132226
cagcgtcctc gcgtttacgg cctttaggga aggaaaactc ccatccgcga ttcaactgca    132286
ccggatagat atgtccggga ctgagccgcc ggggactgaa acgaccttcg actgtcaaaa    132346
aatgatagaa accccgtacc gagcgctcgg gagcaatgtt cccagggacg actctatccg    132406
tccgggggcc actctgcctc cgttcgatac cgcagcacct gatttcgata caggtacttc    132466
cccgaccccc actaccgtgc cagagccagc cattactaca ctcataccgc gcagcactag    132526
cgatatggga ttcttctcca cggcacgtgc taccggatca gaaactcttt cggtacccgt    132586
ccaggaaacg gatagaactc tttcgacaac tcctcttacc cttccactga ctcccggtga    132646
gtcagaaaat acactgtttc ctacgaccgc gccgggattt ctaccgagaa ccccgagcgc    132706
ggcacatgaa actacacaga cccagagtgc agaaacggtg gtctttactc agagtccgag    132766
taccgagtcg gaaaccgcgc ggtcccagag tcaggaaccg tggtatttta ctcagactcc    132826
gagtactgaa caggcggctc ttactcagac gcagatcgca gaaacggagg cgttgtttac    132886
tcagactccg agtgctgaac agatgacttt tactcagact ccgggtgcag aaaccgaggc    132946
acctgcccag accccgagca cgatacccga gatatttact cagtctcgta gcacgccccc    133006
cgaaaccgct cgcgctccga gcgcggcgcc ggaggttttt acacagagtt cgagtacggt    133066
aacggaggtg tttactcaga ccccgagcac ggtaccgaaa actactctga gttcgagtac    133126
tgaaccggca attttttactc ggactcagag cgcgggaact gaggccttta ctcagacttc    133186
gagtgccgag ccggacacta tgcgaactca gagtactgaa acacacttttt tcactcaggc    133246 cccgagtacg gtaccgaaag ctactcagac tccgagtaca gagccggagg tgttgactca    133306
gagtccgagt accgaacctg tgcctttcac ccggactctg ggcgcagagc cggaaattac    133366
tcagaccccg agcgcggcac cggaggttta tactcggagt tcgagtacga tgccagaaac    133426
tgcacagagc acacccctgg cctcgcaaaa ccctaccagt tcgggaaccg ggacgcataa    133486
tactgaaccg aggacttatc cagtgcaaac gacaccacat acccagaaac tctacacaga    133546
aaataagact ttatcgtttc ctactgttgt ttcagaattc catgagatgt cgacggcaga    133606
gtcgcagacg cccctattgg acgtcaaaat tgtagaggtg aagttttcaa acgatggcga    133666
agtaacggcg acttgcgttt ccaccgtcaa atctccctat agggtagaaa ctaattggaa    133726
agtagacctc gtagatgtaa tggatgaaat ttctgggaac agtccgccg gggtttttaa     133786 cagtaatgag aaatggcaga acagctgta ctacagagta accgatggaa gaacatcggt     133846
ccagctaatg tgcctgtcgt gcacgagcca ttctccggaa ccttactgtc ttttcgacac    133906
gtctcttata gcgagggaaa aagatatcgc gccagagtta tactttacct ctgatccgca    133966
aacggcatac tgcacaataa ctctgccgtc cggcgttgtt ccgagattcg aatggagcct    134026
taataatgtt tcactgccgg aatatttgac ggccacgacc gttgtttcgc ataccgctgg    134086
ccaaagtaca gtgtggaaga gcagcgcgag agcaggcgag gcgtggattt ctggccgggg    134146
aggcaatata tacgaatgca ccgtcctcat ctcagacggc actcgcgtta ctacgcgaaa    134206
ggagaggtgc ttaacaaaca catggattgc ggtggaaaac ggtgctgctc aggcgcagct    134266
gtattcactc ttttctggac ttgtgtcagg attatgcggg agcatatctg ctttgtacgc    134326
```

```
aacgctatgg accgccattt atttttgagg aatgctttt  ggactatcgt actgctttct  134386
tccttcgcta gccagagcac cgccgccgtc acgtacgact acatttagg  ccgtcgcgcg  134446
ctcgacgcgc taaccatacc ggcggttggc ccgtataaca gatacctcac tagggtatca  134506
agaggctgcg acgttgtcga gctcaacccg atttctaacg tggacgacat gatatcggcg  134566
gccaaagaaa aagagaaggg gggccctttc gaggcctccg tcgtctggtt ctacgtgatt  134626
aagggcgacg acggcgagga caagtactgt ccaatctata gaaagagta  cagggaatgt  134686
ggcgacgtac aactgctatc tgaatgcgcc gttcaatctg cacagatgtg ggcagtggac  134746
tatgttccta gcacccttgt atcgcgaaat ggcgcgggac tgactatatt ctcccccact  134806
gctgcgctct ctggccaata cttgctgacc ctgaaaatcg ggagatttgc gcaaacagct  134866
ctcgtaactc tagaagttaa cgatcgctgt ttaaagatcg ggtcgcagct taactttta   134926
ccgtcgaaat gctggacaac agaacagtat cagactggat ttcaaggcga acaccttat   134986
ccgatcgcag acaccaatac acgacacgcg gacgacgtat atcggggata cgaagatatt  135046
ctgcagcgct ggaataattt gctgaggaaa aagaatccta gcgcgccaga ccctcgtcca  135106
gatagcgtcc cgcaagaaat tcccgctgta accaagaaag cggaagggcg cacccc      135166
gcagaaagca gcgaaaagaa ggcccctcca gaagactcgg aggacgacat gcaggcagag  135226
gcttctggag aaaatcctgc cgccctcccc gaagacgacg aagtccccga ggacaccgag  135286
cacgatgatc caaactcgga tcctgactat tacaatgaca tgcccgccgt gatcccggtg  135346
gaggagacta ctaaaagttc taatgccgtc tccatgccca tattcgcggc gttcgtagcc  135406
tgcgcggtcg cgctcgtggg gctactggtt tggagcatcg taaaatgcgc gcgtagctaa  135466
tcgagcctag aataggtggt ttcttcctac atgccacgcc tcacgctcat aatataaatc  135526
acatggaata gcataccaat gcctattcat tgggacgttc gaaaagcatg gcatcgctac  135586
ttggaactct ggctctcctt gccgcgacgc tcgcacccctt cggcgcgatg ggaatcgtga  135646
tcactggaaa tcacgtctcc gccaggattg acgacgatca catcgtgatc gtcgcgcctc  135706
gccccgaagc tacaattcaa ctgcagctat ttttcatgcc tggccagaga ccccacaaac  135766
cctactcagg aaccgtccgc gtcgcgtttc ggtctgatat aacaaaccag tgctaccagg  135826
aacttagcga ggagcgcttt gaaaattgca ctcatcgatc gtcttctgtt tttgtcggct  135886
gtaaagtgac cgagtacacg ttctccgcct cgaacagact aaccggacct ccacaccgt   135946
ttaagctcac tatacgaaat cctcgtccga acgacagcgg gatgttctac gtaattgttc  136006
ggctagcga  caccaaagaa cccattgacg tcttcgcgat ccaactatcg gtgtatcaat  136066
tcgcgaacac cgccgcgact cgcggactct attccaaggc ttcgtgtcgc accttcggat  136126
tacctaccgt ccaacttgag gcctatctca ggaccgagga aagttggcgc aactggcaag  136186
cgtacgttgc cacggaggcc acgacgacca gcgccgaggc gacaaccccg acgcccgtca  136246
ctgcaaccag cgcctccgaa cttgaagcgg aacactttac ctttccctgg ctagaaaatg  136306
gcgtggatca ttacgaaccg acacccgcaa acgaaaattc aaacgttact gtccgtctcg  136366
ggacaatgag ccctacgcta attggggtaa ccgtggctgc cgtcgtgagc gcaacgatcg  136426
gcctcgtcat tgtaatttcc atcgtcacca gaaacatgtg caccccgcac cgaaaattag  136486
acacggtctc gcaagacgac gaagaacgtt cccaaactag aagggaatcg cgaaatttg   136546
gacccatggt tgcgtgcgaa ataaacaagg gggctgacca ggatagtgaa cttgtggaac  136606
tggttgcgat tgttaacccg tctgcgctaa gctcgcccga ctcaataaaa atgtgattaa  136666
```

```
gtctgaatgt ggctctccaa tcatttcgat tctctaatct cccaatcctc tcaaaggggg   136726
cagtatcgga cacggactgg gaggggcgta cacgatagtt atatggtaca gcagaggcct   136786
ctgaacactt aggaggagaa ttcagccggg gagagcccct gttgagtagg cttgggagca   136846
tattgcagga tgaacatgtt agtgatagtt ctcgcctctt gtcttgcgcg cctaactttt   136906
gcgacgcgac acgtcctctt tttggaaggc actcaggctg tcctcgggga agatgatccc   136966
agaaacgttc cggaagggac tgtaatcaaa tggacaaaag tcctgcggaa cgcgtgcaag   137026
atgaaggcgg ccgatgtctg ctcttcgcct aactattgct ttcatgattt aatttacgac   137086
ggaggaaaga aagactgccc gcccgcggga cccctgtctg caaacctggt aattttacta   137146
aagcgcggcg aaagcttcgt cgtgctgggt tctgggctac acaacagcaa tataactaat   137206
atcatgtgga cagagtacgg aggcctgctc tttgatcctg taactcgttc ggacgaggga   137266
atctattttc gacggatctc tcagccagat ctggccatgg aaactacatc gtacaacgtc   137326
agcgttcttt cgcacgtaga cgagaaggct ccagcaccgc acgaggtgga gatagacacc   137386
atcaagccgt cagaggccca cgcgcacgtg gaattacaaa tgctgccgtt tcatgaactc   137446
aacgacaaca gccccaccta tgtgacccct gttcttagag tcttcccacc gaccgagcac   137506
gtaaaattta acgttacgta ttcgtggtat gggtttgatg tcaaagagga gtgcgaagaa   137566
gtgaaactgt tcgagccgtg cgtataccat cctacagacg gcaaatgtca gtttcccgca   137626
accaaccaga gatgcctcat aggatctgtc ttgatggcgg aattcttggg gcgggcctct   137686
ttgctggatt gttcccgcga tactctagaa gactgccacg aaaatcgcgt gccgaaccta   137746
cggttcgatt cgcgactctc cgagtcacgc gcaggcctgg tgatcagtcc tcttatagcc   137806
atccccaaag ttttgattat agtcgtttcc gacggagaca ttttgggatg gagctacacg   137866
gtgctcggga aacgtaacag tccgcgcgta gtagtcgaaa cgcacatgcc ctcgaaggtc   137926
ccgatgaaca aagtagtaat tggcagtccc ggaccaatgg acgaaacggg taactataaa   137986
atgtacttcg tcgtcgcggg ggtggccgcg acgtgcgtaa ttcttacatg cgctctgctt   138046
gtggggaaaa agaagtgccc cgcgcaccaa atgggtactt tttccaagac cgaaccattg   138106
tacgcgccgc tccccaaaaa cgagtttgag gccggcgggc ttacggacga tgaggaagtg   138166
atttatgacg aagtatacga acccctattt cgcggctact gtaagcagga attccgcgaa   138226
gatgtgaata cctttttcgg tgcggtcgtg gaggagaaa gggccttaaa ctttaaatcc   138286
gccatcgcat caatggcaga tcgcatcctg gcaaataaaa gcggcagaag gaatatggat   138346
agctattagt tggtcatgcc ttttaagacc agaggggccg aagacgcggc cgcgggcaag   138406
aacaggttta agaaatcgag aaatcgggaa atcttaccga ccagactgcg tggcaccggt   138466
aagaaaactg ccggattgtc caattatacc cagcctattc cctggaaccc taaattctgc   138526
agcgcgcgcg gggaatctga caaccacgcg tgtaaagaca cttttttatcg caggacgtgc   138586 tgcgcatcgc gctctaccgt ttccagtcaa cccgattccc cccacacacc catgcctact   138646
gagtatgggc gcgtgccctc cgcaaagcgc aaaaaactat catcttcaga ctgcgagggc   138706
gcgcaccaac ccctagtatc ctgtaaactt ccggattctc aagcagcacc ggcgcgaacc   138766
tatagttctg cgcaaagata tactgttgac gaggtttcgt cgccaactcc gccaggcgtc   138826
gacgctgttg cggacttaga aacgcgcgcg gaacttcctg gcgctacgac ggaacaaacg   138886
gaaagtaaaa ataagctccc caaccaacaa tcgcgcctga agccgaaacc cacaaacgag   138946
cacgtcggag gggagcggtg cccctccgaa ggcacggtcg aggcgccatc gctcggcatc   139006
ctctcgcgcg tcggggcagc gatagcaaac gagctggctc gtatgcggag ggcgtgtctt   139066
```

```
ccgctcgccg cgtcggcggc cgctgccgga atagtggcct gggccgcggc gagggccttg    139126
cagaaacaag ggcggtagca gtaataataa ccacacaaat attgacaata ataaacgcgt    139186
acgcggatga gtaagtgtta ttgtctcgcg cgccatcttt ataaaagccc gcgttgcgtg    139246
ggccggcggg tagcatttgg agggttggcg accatgtcga gacctccgac gtcacatttg    139306
gacttagctt tctcggcggc ctttaggggc acggacctgc ccggagggag attctggcgg    139366
gcgtcgcaga gttgcgatat tttcttttgg cccgatctgg ccgcggtgat cgtacaggcc    139426
gcccgcgcgt attttgaagg gaaggaaagg ctgggcagtc tgcaggtcgc cgaagatatc    139486
acggcgcacc acccgcgaat agcgcccgcg gctaagcgcg ccgtcgcagc ggcggtagga    139546
ctgtggaccg cgctgtcgga gttagttggg gggccgaacg gggagttgga aagcaaggtc    139606
tggggcaagc agattccccg ggccgccgcg tgggaaataa gagacgtgcc caaagttcca    139666
gtcattgggc cggacattct ttctttttc ccgccgccg tcgagctgcc ggtgctctat    139726
atcagagccc ggggagggc gcactcgcgg tccgcgcact ggaataacca gagcagcgcg    139786
ccggccgccg gactcgcggc gataaggata ggcatggaga tggtgcggag cctcctggtg    139846
atagcgctgc tctgtgtcaaa cttcaccctc ccggaagacc tccccgaagg ttcccaaaac    139906
tcgatccgcg cgttcgtggc ccacctcatg aactgtgtag ctaccgataa gatcatgtct    139966
ccggacgtgc gcgtcccagt cgaagaaagc ttttacagcc actgtttaag ggaaatcatt    140026
atgtgcgaga gagcttttg ttacccgtgc aatccccgc caaaatggtg agctcagggt    140086
cccatttacc cccgcaacac cctctcgccg ccagggcgcg cgctctatct ttctctatgt    140146
cccgtcgcca ccggcctaac cgaacggtgg aacggggccg cccgggaaag cctagctccg    140206
cacagacaca gacagacaaa cggcctctcg attgcaacaa cgtgaaaaac acacaataat    140266
attactttat ttatttcgca gcgctcgcgt gtcgctcgtt tctggggagg ggggggttg    140326 tgtttcgctg ccgcggagtg ggtgaggggg gagagtggac ggaggacagt gtaaaaaccc    140386
gcgaggttgt cagggacgcg gaggtaagga agccgctaga gggcgtcatt ctcccgtcaa    140446
cggcgccgcg ccagcgccag cgcgattcca gcgtccctcg caaagatcga ggcgctcact    140506
tcgggagagt tggcggcagc cgcgccggcg cgcaaggcgg ccaggtattc gcgacggcgc    140566
atctccgatt gcgggactct ccccgtcccg acgcagaaaa gactctgcac gtaaatcgag    140626
tcgtacaaac acgcttcgcg gcacggccga gggtgccaca agcagcacca gtgcccggcc    140686
gccaggagag accggaggt ctctcgctcg gcggacgcga ggtcggccgg caggtgtcgg    140746
gacagccagg ataacagttc tttctcgatc acgaaacgca tattctcgct ctgcatggta    140806
cggctctcgt cctcgaagcg gtcaccgtcc agagagtcga gccagaaatc gccctcgatc    140866
ccttccattg cctcctctaa ttctcccaac ccgttgccgt tattcgggtc agtggggag    140926 ttggcgacgc tctccgtcga cgcccaccgc ggcctcaaac ctaggccgcg cgtcgcccgg    140986
ctggccccca gaaaagccga acgtagccgt tcgttggcag caatcagcgc gttgcggcgg    141046
tctctcgctg acgtgaactc tccgtaaccg tccttgagtt cggacgatat ctcgactaac    141106
tcgcgccaga gccgcgaggc gatccgaatg cacgggtcta ccgagtcggc cgactccgac    141166
gaggcgacag cggcaccttg ccgcctgcgc tcgccacgag gtaccgcgtg cgcagtaatg    141226
tgatcgctgt ccatcagcgc cagcgggtag cacccgtcga gcatgttttc catttaggga    141286
tgtgtctaga ggagagcggt ccgggcggtc tactgcggtt gtgctgggcc gagttggacg    141346
gctacggatt gcgccgggcg tgaaggggg ggggcggcg ggatgtccgg cggtcgcaaa    141406
```

```
ggggcgcgcg tccgcttctg cgtgaaggct gagcgggaaa gaagttctgg atgagaatgg   141466
atcgagcggg caataaatgt ccagagtagg ggggtgggag ggagggggag gttctgcccc   141526
gcgtctcctc tatctgctcg tcgaggcctc ggccttgcgt cgccgtgcag gggtcgaggc   141586
cgcttcttct tttttacttc tctcctcgga ttcctcgtca gaggaagaag aaaatgacaa   141646
cctccgtctt ttaagagtgc gcctacccgc cctggcggcc gaagccttcc gtgggtcttt   141706
gcggggtgcc gcgcaccgca ataacgcacg gacgcggggg atagcaaatg gcggcggcgc   141766
cggagagctg tcgtcaataa agtctaagtc agattgcgtg ggctctgact cggtggagct   141826
gtgtcccgtg tcctcctcgc ccaagtccac tccccggcac ccaggctgct cttcctccga   141886
ctccgggtcg ctccagctcc tcccgcgtgc cggttcttcg tcctccgata cgtccgaaaa   141946
gaaaaacttc tgggagagct cttcgggatc ccagggaagc tgctctgctg actttccgcg   142006
gggcgacgga taggtctctt ctggcaaggg agagggatca ctcgacaaag gactgtggct   142066
catatcttgc gcactgggtc ttatttactc gtgttgtctt tccgcaggga atgcgcggtt   142126
cgagtaggcc gtggtttgcg gccgttctcg gataagcaca aaatatcgcc ctactcgtgt   142186
gtcaaaaagg aaaagtctta atgggctgtg aagtgatctg gagatcaaag cggcactctc   142246
tttgagaagt ctcttctcga gactctctcg agtcctaatg ttaataactc tggcagaggc   142306
gcttcgttac tgacgaagct tctgtgcatt tatacgtgac gccacgctaa caaggaagcg   142366
ccgcgcaatt tgctcacggt tgggcgtagc tctgtcctcg agcgcacgcg aaaaattctc   142426
gtctcatttc cccttaccac accacaccaa acactggtag taaaatcgca taatgcaccc   142486
caacgtcgga aacacagccc gagacgatgt tgcttcttct ttagggcccc ctctttttta   142546
agctacaaaa tttgctttga ggccttttcc tttctttctt tctttcgcgt gtgattgacg   142606
ggggtttacg tgactacctt attagtcgtc tcatatgcac ggacacatca tgggctcagc   142666
gctattaccc taggccgctt gtaattcgtt gtctgtctac ctgtctgtca aattgtgact   142726
accacgtacc aactcctccc caaagttcta ccctttccct taaaaacaca tttaaaatgt   142786
caaaataccg atccttatat ttgcgtgtta tgttttcttt tgccttctag gattgattga   142846
attggaatga aacgcaaaat cttggaataa tgacggaacg cggatgcgaa gaatctacaa   142906
cgagacaggt caatattttt tcaaaaaagg tgttttatta aatctgctat accgctctta   142966
tattaaagaa actttttatt tattaaattg ttgttacccc ccaccgtaga gcaagaccgt   143026
gatgttcttt acgccctctt ctccggtcgt tgtgttgtcc atacatctcg tcttccctca   143086
gcgctgcccg caaatggttc aacgtatgtc ggttggttga ctatgtccta atatcacttc   143146
aagtttggcg cgcggacaaa atttaaactc aatattctcg cgccatattc cattacaaaa   143206
cgcgtgacct cgacaaaatt cgggaaaatc taacagcatt ctatcttgga gaatacgctc   143266
ttgcgacaga ccgtgggaaa aaattagaaa atttacccac ggaccccagt cccgctttgc   143326
cattttagga aaatgttgga ccctcggtgc gaacgtgacg taggtgggtg ccacccacat   143386
catgtaaatt aggtcacggg gtaggattcc ggctccgcga ttggttatga ggcccctaaa   143446
gcaaacattc gcactccagt atttaatata ttagggaaaa cctaatatat taaatactgg   143506
agtgcgaatg tttgctttag gggcctcata accaatcgcg gagccggaat cctacccgt    143566
gacctaattt acatgatgtg ggtggcaccc acctacgtca cgttcgcacc gagggtcctg   143626
catcccctt ccagccaatg agctgtgact tgcatcttcg ggcactgcat aaaagaacga    143686
tccaggtcgc tgtccccgca tatagcggga ccatcgggtc ctgctcggat taccccagga   143746
agaggggaga agatttcata ctgggggcac aatgggatgg gtcattgtct tctcacatga   143806
```

```
gcaacccgaa aatcccccg ccgatgcctc cagaccacgc cgacgcaggc tccgtttaaa 143866 gccatgcact gtcccagatg gggatgggtc gccgatcgga gaggcttgtc ctcacgatac 143926 acacgacccg ggtcgagcac cccctcgac ccccgaccct gaatgtgatc gggaagtgat 143986 attcggcggg atgaactcat ccggaggctg cgtgaccgat actctccaag acatcgcggg 144046 ttaaaaatac tctacgaaag ctcatgttcg agtttacctg acccagaaaa taaggaccca 144106 acaaagtcga ttgtcgtgaa gagctagtta acactgaacc gccataggcg ggtttgcact 144166 ttatgaattt ttgtttttac ttgagccgtt cggcatgtgc cgggctcact actttatttg 144226 ctctttaata gggccgctga gttgtttggg cccaccgacg tgcaggttat cggcttcgtt 144286 gcccttgctt attgcataca tattgcatac tttcatatta ctgctacgac tgcgttgtaa 144346 caccgtcagt taacacgatt actgggtaga tccagtatgg atgtattacg cgcatgtata 144406 tagcccgtac cttgatatta taccggctat tgcaactcgt gctttgtttc gagcgcatct 144466 gctaagcctg cggctgcttc cacgcgcaga taactggttt tagtcccacg ggcaatccga 144526 cataggtgcg tttcctaaaa gaaacctgta gagacagtgc cttgacccc cgacatatat 144586 atctggaagt gtatttgcga ttcaccggcg aatcggcaag tctcctgcgg agaggctcct 144646 gcgattactt ccagatccgc gtaagaaaat tacaggaacg tttgtaaatc gcaaaccaga 144706 ttgcgaacta tattcccgag catggacctt ctcgccatat ctctcaaaag aagaaaagtg 144766 ccctgcaaat acagaacgca tcccgagatt caaaatttgc gattcgtgca tcccgagcgg 144826 caaatgtctc aataaagtaa ttatgtgttc ccgcgaacta ctcgcgtgga acatggaacc 144886 aagcttttgc gttgtctgaa ttttttattt aggctgggtt agaggggtgg ctagaagata 144946 ataatctttc gtggaaaatt gctagagatt agaacacaca agtaacacaa gtgctcacgg 145006 tgatatttac acatgtcaac tctcccatat ggggatcttt tttctgtcac aacttccttg 145066 gcactcccag gaagcgtgac ccatgtgctt tccttggcat tcaaaataaa cttcactgct 145126 tcccggtgtg gccaataacg tgcaagcgag cgtgtttctc gggtaatatc aatgccaaca 145186 aaacacgcgt gacctttcta gagtaggcac acacccggc accgaattgc acgcacctgt 145246 ggacacaagc aatgtattgt tttgttatct tcgtcatctg ttctacagta ggctcaggtt 145306 tgtttattat gttggctcat aaaaaatgcc ggaagttcct ggtacggtaa tggtatgctg 145366 ggcgcatggc atgcattggc tatggcacac cggaactgga aatacgctcg ctaacgatat 145426 gcaggccgca tgggcgccat tggatctgaa ttatatcatg cctcaataca aatgccatac 145486 ccaaccaac tgcacaagac cgaggggttg actctccaaa gttctttctt caccgttgt 145546 aaatcgcaaa ccagattgcg aactatattc ccgagcatgg accttctcgc catatctctc 145606 aaaagaagaa aagtgccctg caaatacaga acgcatcccg agattcaaaa tttgcgattc 145666 gtgcatcccg agcggcaaat gtctcaataa agtaattatg tgttcccgcg aactactcgc 145726 gtggaacatg gaaccaagct tttgcgttgt ctgaattttt tatttaggct gggttagagg 145786 ggtggctaga agataataat ctttcgtgga aaattgctag agattagaac acacaagtaa 145846 cacaagtgct cacggtgata tttacacatg tcaactctcc catatgggga tcttttttct 145906 gtcacaactt ccttggcact cccaggaagc gtgacccatg tgcttccctt ggcattcaaa 145966 ataaacttca ctgcttcccg gtgtggccaa taacgtgcaa gcgagcgtgt ttctcgggta 146026 atatcaatgc caacaaaaca cgcgtgacct ttctagagta ggcacacacc ccggcaccga 146086 attgcacgca cctgtggaca caagcaatgt attgttttgt tatcttcgtc atctgttcta 146146
```

```
cagtaggctc aggtttgttt attatgttgg ctcataaaaa atgccggaag ttcctggtac  146206
ggtaatggta tgctgggcgc atggcatgca ttggctatgg cacaccggaa ctggaaatac  146266
gctcgctaac gatatgcagg ccgcatgggc gccattggtt ctgaattata tcatgcctca  146326
atacaaatgc catacccaaa ccaactgcac aagaccgagg ggttgactct ccaaagttct  146386
ttcttcaccg tttgtaaatc gcaaaccaga ttgcgaacta tattcccgag catggacctt  146446
ctcgccatat ctctcaaaag aagaaaagtg ccctgcaaat acagaacgca tcccgagatt  146506
caaaatttgc gattcgtgca tcccgagcgg caaatgtctc aataaagtaa ttatgtgttc  146566
ccgcgaacta ctcgcgtgga acatggaacc aagcttttgc gttgtctgaa ttttttattt  146626
aggctgggtt agaggggtgg ctagaagata ataatctttc gtggaaaatt gctagagatt  146686
agaacacaca agtaacacaa gtgctcacgg tgatatttac acatgtcaac tctcccatat  146746
ggggatcttt tttctgtcac aacttccttg gcactcccag gaagcgtgac ccatgtgctt  146806
tccttggcat tcaaaataaa cttcactgct tcccggtgtg gccaataacg tgcaagcgag  146866
cgtgtttctc gggtaatatc aatgccaaca aaacacgcgt gacctttcta gagtaggcac  146926
acaccccggc accgaattgc acgcacctgt ggacacaagc aatgtattgt tttgttatct  146986
tcgtcatctg ttctacagta ggctcaggtt tgtttattat gttggctcat aaaaaatgcc  147046
ggaagttcct ggtacggtaa tggtatgctg ggcgcatggc atgcattggc tatggcacac  147106
cggaactgga aatacgctcg ctaacgatat gcaggccgca tgggcgccat ggatctgaa   147166 ttatatcatg cctcaataca aatgccatac ccaaaccaac tgcacaagac cgaggggttg  147226
actctccaaa gttctttctt caccgtttgt aaatcgcaaa ccagattgcg aactatattc  147286
ccgagcatgg accttctcgc catatctctc aaaagaagaa aagtgccctg caaatacaga  147346
acgcatcccg agattcaaaa tttgcgattc gtgcatcccg agcggcaaat gtctcaataa  147406
agtaattatg tgttcccgcg aactactcgc gtggaacatg gaaccaagct tttgcgttgt  147466
ctgaattttt tatttaggct gggttagagg ggtggctaga agataataat ctttcgtgga  147526
aaattgctag agattagaac acacaagtaa cacaagtgct cacggtgata tttacacatg  147586
tcaactctcc catatgggga tcttttttct gtcacaactt ccttggcact cccaggaagc  147646
gtgacccatg tgctttcctt ggcattcaaa ataaacttca ctgcttcccg gtgtggccaa  147706
taacgtgcaa gcgagcgtgt ttctcgggta atatcaatgc caacaaaaca cgcgtgacct  147766
ttctagagta ggcacacacc ccggcaccga attgcacgca cctgtggaca caagcaatgt  147826
attgttttgt tatcttcgtc atctgttcta cagtaggctc aggtttgttt attatgttgg  147886
ctcataaaaa atgccggaag ttcctggtac ggtaatggta tgctgggcgc atggcatgca  147946
ttggctatgg cacaccggaa ctggaaatac gctcgctaac gatatgcagg ccgcatgggc  148006
gccattggtt ctgaattata tcatgcctca atacaaatgc catacccaaa ccaactgcac  148066
aagaccgagg ggttgactct ccaaagttct ttcttcacaa caccttttgct gaaacctacc  148126 cagcgtggaa aggacctctt cgcaaaacgt aagtcatgaa accaatattc tgttataaat  148186
tttggggtgg gattaggtgg gctgtcatta tttgagggga ccacgaaata tccttttgca  148246
tggggtatcg tgcaaaaata tgactgtggg cttcgaataa ttcccccata cagtcaagag  148306
tatgggctgc tgttatggat gaacatgaag cgcacaaaac gataatccac ttctttagca  148366
tgtattgctg ttccaaaatt gtgcctatgg ttgcggagct ttattgtgct ctgcattgcg  148426
gggacgaaaa taaacaggcc aacgcgagaa acggagggtt tcgagagtcg cgcatcttta  148486
ttttttctgt tactactccc caccagaaag cttcacgttt cttccaactt ctgcacaaaa  148546
```

```
cttacgtaac cttgtcactc gggtcttgtt ctgcaggatt ctggaaatcg ctagtccttc    148606
cactagcatt ctatcatgtc ctctgattcc tcgacgccga gtaatttggc cgctccaatt    148666
gttgatgagt cgggattctc aactggcccg ccctcagatc tatttacctt tttgcgcgcc    148726
gataagagtg ggcgctacga ttctttgggt tctcccatcc cgaaccctcc aaacgcacct    148786
acctgtgaga ccactactga tagcttttcg tacagcacgc cacctctttt ttccagcgag    148846
gacgagctct ttcactctgt catcgctgag aatgcggccc aagacgcggc caagacgtg    148906 gacgggcgag aaatgtctct ccgcgacctt atagcgatgt taaacgacat ggatcccgaa    148966
aacataaact ctatagaacc gtgtccgaac gctaccagtg atgtcgtggc actagatatt    149026
aacgtggata ccgatcagcc cggagtttat acggtcatcg actcgctcgc acatccctgc    149086
gaaactccca tggagcagca gcacgttgaa tgcccgtgtc cattacctgc agtagagaaa    149146
acaaccgctg tgaggcgtca agaagtggtg aggaagtcag agagagtggc cagatctcgt    149206
tcgcgacgcg ccgtggcgcg atctttgagc aaccggcgcc ccgtcccttc gccgcagagg    149266
accagcaaag accgtctccc caagcgaggg aagagggaat tttcgaagaa gatgggcccg    149326
agccaccttt cctcttcctc ctcttcctcc tcttcctcat tctcgctgtc agggaggagg    149386
ggacgtctcg cccgaaggct ggaaagcgcg ggaagtgaaa aatccgccga aagccccgac    149446
cgggactctg cccaattagt gctacctgga gaatgtcccg atgtcgcgct agagccactc    149506
tggcgagttt tgagggagtg ggtcgaaacg gacggtacag acgggtcggt tcagtcagta    149566
accgcgccta cggagctccc agacctaggc cgcggcatta ccctgaatgt actctcacga    149626
gcgttggccg tcgacctcca tagttccgag gctcgcgttt ttgttccaga agctattatc    149686
ccgtccccac ccagtagagg acaagtatat catggaagtg gctatagaca gtctttggtc    149746
gatgacccgc aggttcggga ggccgcggcc gaattccatg ccaatccgaa atcagcttcc    149806
gtgtatctcg aagagtacgg gatgccagtg aacagttag agcgccttgt ggaggagttc    149866
atggtccagc ccctgtcgcg cgtttcgtat gggtatggcg gccccaagct gagcccacgt    149926
gacaaacggc tctgcgaact gtgcgctctc cgcggtccgg gttcttccga gggaggattg    149986
tctcgttctg cggtgccgac gtgcctcccg cacgtagcgc acgccatgcg tgatggccgt    150046
gtgtcattag ctctgccgca ccttaccgag ctcgtacgcg tgtgccgccg ctatgaccat    150106
ccgcagaaaa cttacctgtt ggcggctctt aggagagcgt tgtcccgtt tgtatttcca    150166 ggagcggccg tggatcctac ggcggcgtct gcttctgggg accaccctgt actcgttggc    150226
gccaggcgaa tagcgcgtgc cacgagggag ctggaagccg cagcgaaaga gccacctgcg    150286
gcaaccccgg aaaaactttc ctcttcggcg ctattgcgcc atactagaac ttgcattgtt    150346
gctgccgcag atctcatggc ggcgcttact gctatagact gcccaccagt tacaataaac    150406
cccgccaagc gtcgcccgga tctgtatcaa gcactctcga gggcgcccaa aacagtcttt    150466
acgtgggagc gcgccatgcg ctactgcgcg gcttcgctat ggagtcgcct cgtcataggg    150526
tccctgccgc tgccatctac cgatgatgtc actcttcttg tagaagccat ggaagctgcc    150586
gtgggcgtgc ttggctgctc cgacgagggt gacgtgcggc cttcaattgc ctacgcggcc    150646
tctggttgga ggatgatcgc taccatgcta ggagatgatt ccgcgcccgg cagcgagcac    150706
gtcacggacg attgtcccgc agatgatgac acccaccacc atgacaggcg caaaagacga    150766
ggcggccggc ggagcacttg ccggtacgac ctacctcctg gcactcccga tcgcgcggcc    150826
cacctcctac tctacgggag tcctggcggc ggcaacggag cagagccttc ggctgcccaa    150886
```

```
gaatctcccg ccaaccnctg gcccagagct ccaccgtgcg atgaacagga gccattatct 150946
gtgtcaccgt acgggcccga acccgaccgc cctccagatg atgactttga gacccgtaaa 151006
ggtctgaaaa gaaagtcatc tgaagatcac gcggacccga tcccagaagg caacgcgact 151066
aaaaaaacat gtggcctcca gggcttacca gattcattac ctccagcggt tccagaaaca 151126
gatagagaca acctcctcct ttcgccatgc cccataactc ccagggtcc accatgtccg 151186
ccccgagaag aaccgcaaga accacaatcc ccgtcctttc acatttccga gataggtgag 151246
gccctgtttc attctacccc aatcagccct accatcctgt tcgcaccgga gggtttcatc 151306
ccgaaccaag gggatgttta ccgtccccat ggcaaaaact gggcgttgc gctctccgca 151366
ggggagccat acgtgcccgc ccatcgcgcg cgtcctgctt tggagcggct cgcgaactat 151426
ttgcgcgggt tgagcagcgg tccggcggga agctattccg cgaccggacc cgcagattgg 151486
ctacctgctt ttgcgaggga cccagtagcc ctggggagt tttgcaagag gatttcaccc 151546
gtgaacagag gggggcgctg cgtcttagag gagcggcttt cctggacgtt gcgacatccg 151606
gctgacaaaa tctatgacct catcattctt gtctcagaac gtgccccggg cgaattttta 151666
gaacgcgcgt acgcctacgc ggccctctgc ggacgtgcct gcatgccggg cggtgcctgt 151726
tggcagaat cgtggacacg cggggagtat ccctatatcc ctcccgacga gaagacccg 151786
ggccgcagcg tggccattct ctgtacgaca gaccttggat acgccggggc ggtagaatgg 151846
atgcttgagc gcgctctcag tacatctggg gcgcatgcg tggtcgtaga tgctaggat 151906
cccggggacg aggattcccg ctcgggtccg cgcataccta ccgggcggag gggtgttgtc 151966
tatgcccgga ctagccccc gtcgcacgct taccttgtaa aactgtttac cggtccggcg 152026
gccgaacggt tggaacgggg tgggctcaat gtaggtcacg tagtaatgga caggcgactc 152086
actgtctcat ggcccctcag cgttgggaag accgacaacg acgatgaggg tacaggagac 152146
agagagaagt gtcctcccgt taagcacccc ttcctcactc acgtaactct caggagatta 152206
cgcgacgttg ctcgtgccat ggatgccggg tggagccact ccgaaatcgg aaaagcttca 152266
gccgtcttgt atccgtacat ggcccagccc catgtgggcg ccggggcgat ccgccatgt 152326
ccggaccttt ccgagtccag ttccactatg cattcttctt cgtcgtcttc ctcttcctca 152386
tgctcctcgt cgtcgtcttc ttcagactcc agctcatctg aagaagacgg ggacgagaag 152446
aacgagaaag aagatcgtga gcgcgccgga ggtggaaagc ggcgcggccg ccagcgcctc 152506
ccgattcggg accgcgtgta ccgtggccgg gactaccgcg tgcgcactcc ctgtgctgat 152566
attgtgggag gcacttctgc ttcctttagg gccgtcgctg cgtggggggg ggacacggta 152626
attcccgccc tccctctcgc agcgtcctgg tccgatccca gcaaaattcc acaggaagtt 152686
ctccgcatca tctccgatta ttacccggat gcgccagggg cgcgggcgcg tcggaacccg 152746
cttcacgtgg aaggactagc gcttatgcgt gccagaaatc ccgcccctct cgcattgcta 152806
cttggtgacg actattccca ttatcacact ccccgcaatc ggtccccaat gtgttgttgc 152866
tggagtgctc cgcggggagc aacgccagag tcacccagat gcaccggaca cacgcgcacc 152926
aggcgcccaa ggctaaccgt ctcctcaggg agggggaaa ctagaaccct tgtacccaga 152986
ttagactctt cagaggatag gcggtcgcgt caacgccata gacgcatgac taactaccct 153046
ctaccgcatc ccactgtcac tgaccctggg tggtaaccgt ggtttccgtt attaacttaa 153106
cttattaaaa cttttttgtac aattacttc tggttgcgtg ctcattcttt tgctagtcgg 153166
agcttgtcag ccaccgacga cttgtagaaa agaccgggg aaatgatcta gccccgttga 153226
ctttagcttt gctgaacatt ctacccgtgc ggccatggag tgatattaga aaaggggacga 153286
```

```
gaatggggc  aagtacgaat  atcgggagga  ggcggaacga  ggtgttaagt  aatgcacttg  153346
aatatttaat  tcgttcattt  tgatacataa  gatccacgga  agcttgtaat  gctggccggc  153406
agcattatta  ctattgcaag  cgccgatata  aaaatcgcaa  tcaaaatact  agattgtcta  153466
gtattgcctg  ctctgacgga  cgtaacgtct  ctgtagggcg  ttcgccaggt  cattcaggaa  153526
cgacttcatc  aaatacgaat  cctccactgt  tatagggcac  ggtgcctgta  ataaatagga  153586
gatacaatgt  tagactcgtc  atgcgaccaa  taaggaccgc  gtgagcacgg  agacaaaaga  153646
tgtctcggag  atactgtgct  gcgcgttaga  tagtctcttc  aaagtacaga  atgcgcgatg  153706
ctgccattat  cttaccttgc  gagagctacc  gccattactg  acagaattca  gcacgtaata  153766
caaattgacg  tagagcccct  gcagttttt   gtgacactgt  tggtgtttca  aaatgaccga  153826
aagggattgg  cacaactctt  cagtttcgtt  tagacgctgc  aggaaaagca  agattcgtta  153886
ataaaccgcc  gagcagatta  ttgggcaggg  tagacctaag  caaaaaatct  acatttttaa  153946 tctgggcta   gcgcgcggcc  ggcctccagg  gcattgccgt  tgagaacatg  tgacaaatga  154006
gctggctttt  actcaccgtg  tcggacgtaa  agatgttcgg  aactcttcta  ccgtcgcagg  154066
aacccttata  aggaaacgag  agagcctaca  gttatgaacg  tgaacataga  ctgaatagcc  154126
gtacatagtt  acaagaccg   tgcaggcatg  tcagcatggt  ccaacgagaa  tgagttgcct  154186
tacgtccttc  tgcacacggt  gcagtattct  gatgctctcc  gccagtaact  tcaagggtgc  154246
cgcgcgtata  ctgcgagcat  ccccgactcc  aagtagtaac  accagtaacg  ccagtgcggc  154306
ggacaatgga  ggcttcgact  tgccaggcat  tcccaccgcg  cgcaaccgcc  gccgcgaaac  154366
ttctccccta  gttctccctc  tgggttcttc  cctaaggata  cactgccacc  atttatatag  154426
ctttacgtgg  cgggaaagcc  ctagccccca  ctatacccgg  aagcggctac  actagagccc  154486
ttgcaagagc  agaaaatttt  cccgccgtgg  gttgcgcgtg  aacaacttac  cagaacgaga  154546 attttttgaaa cctctgagac  tcacagcacg  tgcttacgaa  taccagaaac  tgggagcacg  154606
gtgcttccgc  gacactctac  aaagataagt  gcgggcacag  ttaggtgcta  ctgcgcttag  154666
ctaagtgctt  aacctgagta  gcacctaatt  gcggccttag  gccaaggtgt  cgttacccgg  154726
atagctttca  catcgatagc  gcgtattacc  ttcggcctga  caactgtcag  ctacccaacc  154786
gctctgtctt  ctttcaatcc  ttgactatta  taactcgcgg  taaccggccg  tggccacata  154846
gtgaggcggt  tatacggaat  aagaccccc   cccccgggc   cttcacgttc  gtgtccgttc  154906
ttgccagtga  gcgttgctgg  aaatcgaaaa  ttccagtgtg  gcgcttattg  tgcaagaacc  154966
acgggcgtga  cctgtatgac  tactgagcaa  agcacctcgc  gctgccgcga  aacttacaaa  155026
cggggcgaac  tgcgtgacga  ttctgtgatc  gcgcttcgag  gtccagtcgg  agcccaccgg  155086
tgcccacctg  aacctttca   gctccggaaa  aggctaaact  ggaaaatcta  gtagaactag  155146
tttcacggct  gcccgcgctg  accgtttgct  ctccacgggt  ggaagaactt  ggggggggg   155206 gttggcggac  gctggcgttt  gatgtcgggc  cgtcaagtat  ctcgcaaccc  cagaacctgt  155266
ccagcatcta  atagtagggg  tcggacatga  aaccacaagg  gattggaagg  gcgggagca   155326 ctcaggggac  tgggaggga   cgggtcggag  aaaaccgcgg  accaccagtg  cacacaccct  155386
gcatccttgg  ctgctcatat  atagccccc   cccgcaaaac  accccccgg   gtttattgcc  155446 gacgacgggg  ctgtggagc                                                 155465
```

What is claimed is:

1. A method of producing a live attenuated infectious laryngotracheitis virus (ILTV), the method comprising serially passaging the ILTV in culture for at least 15 serial passages at a temperature of at least 25° C. and no greater than 35° C.

2. The method of claim 1 wherein ILTV is passaged for at least 30 serial passages.

3. The method of claim 1 wherein the ILTV is passaged in culture at a temperature of from 28° C. to 31° C.

4. The method of claim 2 wherein the ILTV is passaged in culture at a temperature of from 28° C. to 31° C.

* * * * *